United States Patent
Taggi

(10) Patent No.: US 9,743,667 B2
(45) Date of Patent: Aug. 29, 2017

(54) SUBSTITUTED BENZENE FUNGICIDES

(71) Applicant: E I DU PONT DE NEMOURS AND COMPANY, Wilmington, DE (US)

(72) Inventor: Andrew Edmund Taggi, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/812,083

(22) Filed: Jul. 29, 2015

(65) Prior Publication Data

US 2015/0335023 A1 Nov. 26, 2015

Related U.S. Application Data

(62) Division of application No. 14/325,432, filed on Jul. 8, 2014, now Pat. No. 9,198,433, which is a division of application No. 12/593,360, filed as application No. PCT/US2008/004443 on Apr. 3, 2008, now Pat. No. 8,822,521.

(60) Provisional application No. 61/008,425, filed on Dec. 19, 2007, provisional application No. 60/921,600, filed on Apr. 3, 2007.

(51) Int. Cl.

| | |
|---|---|
| *A01N 55/00* | (2006.01) |
| *C07C 271/08* | (2006.01) |
| *A01N 47/10* | (2006.01) |
| *A01N 47/24* | (2006.01) |
| *A01N 43/56* | (2006.01) |
| *A01N 47/12* | (2006.01) |
| *C07D 231/02* | (2006.01) |
| *A61K 31/415* | (2006.01) |
| *C07D 231/10* | (2006.01) |
| *C07F 7/10* | (2006.01) |
| *C07D 231/12* | (2006.01) |
| *C07D 239/26* | (2006.01) |
| *C07D 417/04* | (2006.01) |
| *C07D 249/06* | (2006.01) |

(52) U.S. Cl.
CPC .............. *A01N 55/00* (2013.01); *A01N 43/56* (2013.01); *A01N 47/10* (2013.01); *A01N 47/12* (2013.01); *A01N 47/24* (2013.01); *A61K 31/415* (2013.01); *C07C 271/08* (2013.01); *C07D 231/02* (2013.01); *C07D 231/10* (2013.01); *C07D 231/12* (2013.01); *C07D 239/26* (2013.01); *C07D 249/06* (2013.01); *C07D 417/04* (2013.01); *C07F 7/10* (2013.01); *A01N 2300/00* (2013.01)

(58) Field of Classification Search
None
See application file for complete search history.

(56) References Cited

U.S. PATENT DOCUMENTS

| | | | |
|---|---|---|---|
| 3,519,615 | A | 7/1970 | Wolfrum |
| 3,642,813 | A | 2/1972 | Kirchmayr |
| 3,948,932 | A | 4/1976 | Buckler et al. |
| 5,032,165 | A | 7/1991 | Miura et al. |
| 5,262,412 | A | 11/1993 | Ashton et al. |
| 5,928,999 | A | 7/1999 | von dem Bussche-Hunnefeld et al. |
| 6,054,412 | A | 4/2000 | Zagar et al. |
| 6,812,229 | B1 | 11/2004 | Ozaki et al. |
| 7,776,791 | B2 | 8/2010 | Fischer et al. |
| 8,822,521 | B2 | 9/2014 | Taggi et al. |
| 2003/0050477 | A1 | 3/2003 | Zagar |
| 2004/0077597 | A1 | 4/2004 | Bretschneider et al. |
| 2005/0165005 | A1 | 7/2005 | Genevois-Borella et al. |
| 2006/0166829 | A1 | 7/2006 | Fischer et al. |

FOREIGN PATENT DOCUMENTS

| | | |
|---|---|---|
| DE | 4305279 A1 | 8/1994 |
| DE | 4417837 A1 | 11/1995 |
| DE | 10326386 A1 | 12/2004 |
| EP | 0443059 A1 | 8/1991 |
| EP | 0609099 A | 8/1994 |

(Continued)

OTHER PUBLICATIONS

M. T. Cocco et al.,"Phytotoxic Activity in Pyrazole Derivatives", Farmaco Societa Chimica Italiana, 1985, vol. 40, pp. 272-284.

(Continued)

*Primary Examiner* — Samantha Shterengarts
(74) *Attorney, Agent, or Firm* — Charlene Gross Sternberg

(57) ABSTRACT

Disclosed are compounds of Formula 1, including all geometric and stereoisomers, N-oxides, and salts thereof,

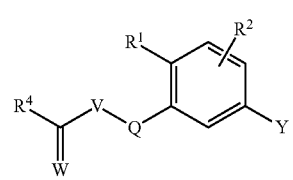

wherein
W is O or S;
V is a direct bond or $NR^3$;
Q is or $CR^{6a}R^{6b}$, O, $NR^7$, C=N—O—$R^7$ or C(=O);
Y is —C($R^5$)=N—O—$(CR^{8a}R^{8b})_p$—X—$(CR^{9a}R^{9b})_q$—Si$R^{10a}R^{10b}R^{10c}$; or a phenyl ring substituted as defined in the disclosure; or Z; and
$R^1$, $R^2$, $R^3$, $R^4$, $R^5$, $R^{6a}$, $R^{6b}$, $R^7$, $R^{8a}$, $R^{8b}$, $R^{9a}$, $R^{9b}$, $R^{10a}$, $R^{10b}$, $R^{10c}$, Z, p and q are as defined in the disclosure.
Also disclosed are compositions containing the compounds of Formula 1 and methods for controlling plant disease caused by a fungal pathogen comprising applying an effective amount of a compound or a composition of the invention.

12 Claims, No Drawings

(56) References Cited

FOREIGN PATENT DOCUMENTS

| | | |
|---|---|---|
| EP | 1070708 A1 | 1/2001 |
| EP | 1201648 A | 5/2002 |
| FR | 1534629 A | 7/1968 |
| JP | 56053662 A | 5/1981 |
| JP | 3/151367 A | 6/1991 |
| JP | 4/124178 A | 4/1992 |
| JP | 8092224 A | 4/1996 |
| JP | 1998500673 A | 1/1998 |
| JP | 2000219679 A | 8/2000 |
| JP | 2000273088 A | 10/2000 |
| JP | 2003096327 A | 4/2003 |
| JP | 2003313103 A | 11/2003 |
| JP | 2006514003 A | 4/2006 |
| WO | 92/02509 A1 | 2/1992 |
| WO | 92/06962 A1 | 4/1992 |
| WO | 96/01254 A1 | 1/1996 |
| WO | 98/27061 A1 | 6/1998 |
| WO | 9828269 A1 | 7/1998 |
| WO | 01/10825 A1 | 2/2001 |
| WO | 01/17355 A1 | 3/2001 |
| WO | 01/29006 A1 | 4/2001 |
| WO | 01/78723 A1 | 10/2001 |
| WO | 02/088097 A1 | 11/2002 |
| WO | 03/022214 A2 | 3/2003 |
| WO | 2004/037770 A1 | 5/2004 |
| WO | 2004/041161 A2 | 5/2004 |
| WO | 2004/093544 A1 | 11/2004 |
| WO | 2005/051917 A1 | 6/2005 |
| WO | 2005/051932 A1 | 6/2005 |
| WO | 2005/066139 A2 | 7/2005 |
| WO | 2005/110994 A2 | 11/2005 |
| WO | 2006/071940 A2 | 7/2006 |
| WO | 2007/047306 A1 | 4/2007 |
| WO | 2008/103277 A2 | 8/2008 |
| WO | 2008/104077 A1 | 9/2008 |
| ZA | 9711102 A | 8/1998 |

OTHER PUBLICATIONS

EPO Search Report.
European Search Report.
Chemical Abstracts Service Registry Columbus, OH, Accession No. RN 209959-91-1, Entered STN Aug. 16, 1998.

SUBSTITUTED BENZENE FUNGICIDES

This application is a divisional of application Ser. No. 14/325,432 filed Jul. 8, 2014, which is a divisional application of Ser. No. 12/593,360 filed Sep. 28, 2009, which is a national stage entry of PCT/US2008/004443, filed Apr. 4, 2008. PCT/US2008/004443 claims priority benefit from Provisional Applications 61/008,425, filed Dec. 19, 2007, and 60/921,600, filed Apr. 3, 2007.

FIELD OF THE INVENTION

This invention relates to certain benzene fungicides, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

World Patent Publication WO 2001/010825 discloses certain carbamate derivatives of Formula i as fungicides.

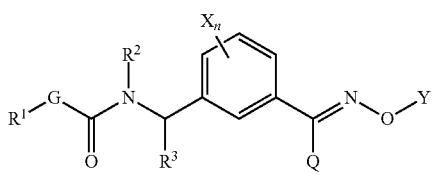

wherein, inter alia, $R^1$ is $C_1$-$C_6$ alkyl; G is O, S or $NR^4$; $R^2$ is H or $C_1$-$C_6$ alkyl; $R^3$ is H or $C_1$-$C_6$ alkyl; X is halogen; n is 0 to 4; Q is H or $C_1$-$C_6$ alkyl; and Y is $C_1$-$C_{10}$ alkyl.

World Patent Publication WO 2004/037770 discloses certain N-phenylhydrazine derivatives of Formula ii as fungicides and insecticides.

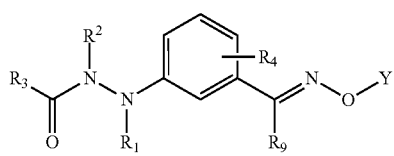

wherein, inter alia, each $R^1$ and $R^2$ is independently H or $C_1$-$C_6$ alkyl; $R^3$ is $C_1$-$C_6$ alkyl or $C_1$-$C_6$ alkoxy; $R^4$ is H or halogen; $R^9$ is H or $C_1$-$C_6$ alkyl; and Y is H or $C_1$-$C_6$ alkyl.

World Patent publication WO 2005/051932 discloses certain arylheterocycle derivatives of Formula iii as fungicides and insecticides.

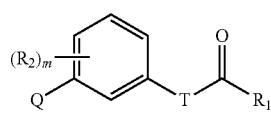

wherein, inter alia, $R_1$ is $C_1$-$C_6$ alkyl or $C_1$-$C_6$ alkoxy; $R_2$ is halogen; m is 0 to 4; T is a substituted C—N or N—N bridge; and Q is a N-heterocycle also containing as ring members selected from O and S.

SUMMARY OF THE INVENTION

This invention is directed to compounds of Formula 1 (including all geometric and stereoisomers), N-oxides, and salts thereof, agricultural compositions containing them and their use as fungicides:

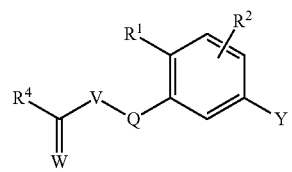

wherein
  each $R^1$ and $R^2$ is independently H, halogen, CN, $C_1$-$C_3$ alkyl, $C_1$-$C_3$ alkoxy, $C_1$-$C_3$ haloalkyl, $C_1$-$C_3$ haloalkoxy, $C_3$-$C_6$ cycloalkyl, $C_3$-$C_{15}$ trialkylsilyl or $C_3$-$C_{15}$ halotrialkylsilyl;
  V is a direct bond or $NR^3$;
  $R^3$ is H, $C_1$-$C_3$ alkyl, $C_3$-$C_6$ cycloalkyl, $C_1$-$C_3$ haloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;
  $R^4$ is H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_3$-$C_6$ cycloalkoxy, $C_1$-$C_6$ alkylamino, $C_1$-$C_6$ haloalkylamino, $C_2$-$C_8$ dialkylamino, $C_2$-$C_8$ halodialkylamino or $C_3$-$C_6$ cycloalkylamino;
  W is O or S;
  Q is $CR^{6a}R^{6b}$, O, $NR^7$, C(=N)—O—$R^7$ or C(=O);
  Y is —C($R^5$)=N—O—($CR^{8a}R^{8b})_p$—X—($CR^{9a}R^{9b})_q$—$SiR^{10a}R^{10b}R^{10c}$; or Z; or a phenyl ring substituted with one substituent selected from $C_1$-$C_5$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl and optionally substituted with up to four additional substituents independently selected from halogen, CN, $C_1$-$C_3$ alkyl, $C_1$-$C_3$ alkoxy, $C_1$-$C_3$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl; provided that when Y is a phenyl ring, then Q is O, $NR^7$, C=N—O—$R^7$ or C(=O);
  Z is a 5- or 6-membered heteroaromatic ring selected from Z-1 through Z-24

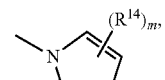

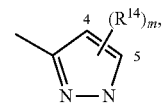

-continued

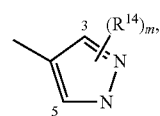 Z-3

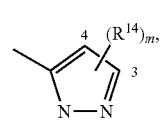 Z-4

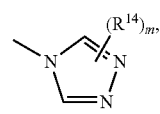 Z-5

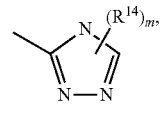 Z-6

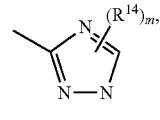 Z-7

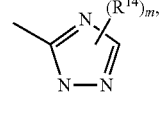 Z-8

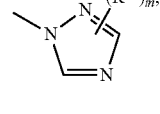 Z-9

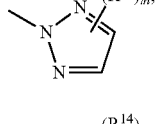 Z-10

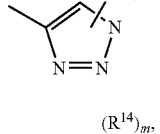 Z-11

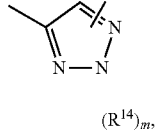 Z-12

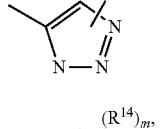 Z-13

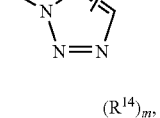 Z-14

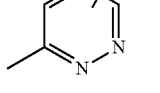 Z-15

-continued

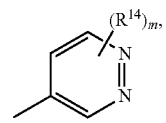 Z-16

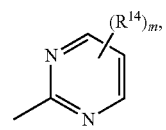 Z-17

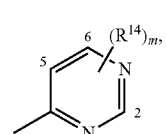 Z-18

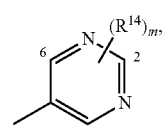 Z-19

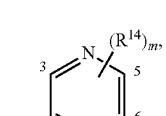 Z-20

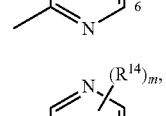 Z-21

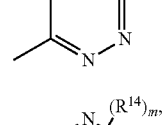 Z-22

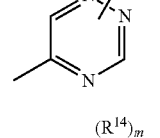 Z-23 or

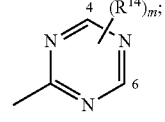 Z-24

$R^5$ is H, CN, $C_1$-$C_6$ alkyl, $C_3$-$C_6$ cycloalkyl, $C_1$-$C_6$ haloalkyl, $C_3$-$C_6$ halocycloalkyl, $C_3$-$C_{15}$ trialkylsilyl or $C_3$-$C_{15}$ halotrialkylsilyl;

$R^{6a}$ is H, OH, halogen, CN, $C_1$-$C_6$ alkyl, $C_1$-$C_6$ haloalkyl, $C_2$-$C_6$ alkoxyalkyl, $C_1$-$C_6$ alkoxy, $C_1$-$C_6$ haloalkoxy or $C_1$-$C_6$ alkylsulfonyl;

$R^{6b}$ is H, $C_1$-$C_6$ alkyl, $C_1$-$C_6$ haloalkyl, $C_2$-$C_6$ alkoxyalkyl, $C_1$-$C_6$ alkoxy or $C_1$-$C_6$ haloalkoxy; or $R^{6a}$ and $R^{6b}$ are taken together with the carbon atom to which they are attached to form a $C_3$-$C_6$ cycloalkyl ring or $C_3$-$C_6$ halocycloalkyl ring;

$R^7$ is H, $C_1$-$C_3$ alkyl, $C_1$-$C_3$ haloalkyl, $C_2$-$C_3$ alkylcarbonyl or $C_2$-$C_3$ haloalkylcarbonyl;

each $R^{8a}$ and $R^{9a}$ is independently H, OH, CN, halogen, $C_1$-$C_5$ alkyl, $C_1$-$C_5$ haloalkyl or $C_1$-$C_5$ alkoxy;

each $R^{8b}$ and $R^{9b}$ is independently H, CN, halogen, $C_1$-$C_5$ alkyl, $C_1$-$C_5$ haloalkyl or $C_1$-$C_5$ alkoxy; or each pair of $R^{8a}$ and $R^{8b}$ or $R^{9a}$ and $R^{9b}$ attached to the same carbon atom can be independently taken together with the carbon atom to which they are attached to form a $C_3$-$C_6$ cycloalkyl or $C_3$-$C_6$ halocycloalkyl ring; or each $R^{8a}$, $R^{8b}$, $R^{9a}$ or $R^{9b}$ can be independently taken together with a $R^{8a}$, $R^{8b}$, $R^{9a}$ or $R^{9b}$ attached to an adjacent carbon atom and the carbon atoms to which they are attached to form a $C_3$-$C_6$ cycloalkyl or $C_3$-$C_6$ halocycloalkyl ring;

each $R^{10a}$, $R^{10b}$ and $R^{10c}$ is independently $C_1$-$C_6$ alkyl, $C_1$-$C_6$ haloalkyl, $C_1$-$C_6$ alkoxy, $C_1$-$C_6$ haloalkoxy, $C_2$-$C_8$ alkoxyalkyl, $C_2$-$C_8$ haloalkoxyalkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_5$-$C_{10}$ alkylcycloalkylalkyl, $C_2$-$C_6$ haloalkenyl, $C_1$-$C_6$ alkylthio, $C_2$-$C_6$ alkylcarbonyl, $C_2$-$C_6$ alkoxycarbonyl, $C_4$-$C_{12}$ trialkylsilylalkyl or J;

each J is independently a phenyl ring; a 5- or 6-membered heteroaromatic ring; or an 8-, 9- or 10-membered fused bicyclic ring system, or a 3- to 6-membered nonaromatic carbocyclic or heterocyclic ring, said ring or ring system optionally including ring members selected from the group consisting of C(=O), C(=S), C(=NR$^{11}$), NR$^{11}$, SiR$^{12a}$R$^{12b}$ and S(=O)$_u$(=NR$^{11}$)$_z$, and each ring or ring system optionally substituted with up to 5 substituents independently selected from R$^{13}$; or two of $R^{10a}$, $R^{10b}$ or $R^{10c}$ are taken together with the silicon atom to which they are attached to form a saturated ring containing from 3 to 6 carbon atoms in addition to the silicon atom as ring members, the ring optionally substituted on carbon atoms with halogen;

X is a direct bond, O, NR$^{11}$, C(=O), C(=S) or C(=NR$^{11}$); or a phenyl ring, a 5- or 6-membered heteroaromatic ring or a 3- to 8-membered nonaromatic carbocyclic or heterocyclic ring, said ring optionally including ring members selected from the group consisting of C(=O), C(=S), C(=NR$^{11}$), NR$^{11}$, SiR$^{12a}$R$^{12b}$ and S(=O)$_u$(=NR$^{11}$)$_z$, and optionally substituted with up to 5 substituents independently selected from R$^{13}$;

each R$^{11}$ is independently H, CN, NH$_2$, OH, $C_1$-$C_6$ alkyl, $C_3$-$C_8$ cycloalkyl, $C_2$-$C_6$ alkylcarbonyl, $C_2$-$C_6$ haloalkylcarbonyl or $C_1$-$C_6$ alkoxy;

each R$^{12a}$ and R$^{12b}$ is independently $C_1$-$C_5$ alkyl, $C_2$-$C_5$ alkenyl, $C_2$-$C_5$ alkynyl, $C_3$-$C_8$ cycloalkyl, $C_3$-$C_6$ halocycloalkyl, $C_4$-$C_{10}$ cycloalkylalkyl, $C_4$-$C_7$ alkylcycloalkyl, $C_5$-$C_8$ alkylcycloalkylalkyl, $C_1$-$C_5$ haloalkyl, $C_1$-$C_5$ alkoxy or $C_1$-$C_5$ haloalkoxy;

each R$^{13}$ is independently halogen, $C_1$-$C_6$ alkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_1$-$C_6$ haloalkyl, $C_2$-$C_6$ haloalkenyl, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_6$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_3$-$C_{15}$ trialkylsilyl or $C_3$-$C_{15}$ halotrialkylsilyl;

each R$^{14}$ is independently H, halogen, cyano, hydroxy, amino, nitro, —CH(=O) or —C(=O)NH$_2$; or $C_1$-$C_6$ alkyl, $C_3$-$C_8$ cycloalkyl, $C_3$-$C_6$ halocycloalkyl, $C_2$-$C_6$ alkenyl, $C_2$-$C_6$ alkynyl, $C_1$-$C_6$ haloalkyl, $C_2$-$C_6$ alkylcarbonyl, $C_2$-$C_8$ alkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_2$-$C_8$ alkylcarbonyloxy, $C_4$-$C_{10}$ cycloalkylcarbonyloxy, $C_1$-$C_6$ alkylthio, $C_3$-$C_8$ cycloalkylthio, $C_1$-$C_6$ alkylsulfinyl, $C_1$-$C_6$ alkylsulfonyl, $C_3$-$C_8$ cycloalkylsulfonyl, $C_1$-$C_6$ alkylamino, $C_2$-$C_8$ dialkylamino, $C_3$-$C_8$ cycloalkylamino, $C_2$-$C_8$ alkylcarbonylamino, $C_1$-$C_6$ alkylsulfonylamino, $C_1$-$C_6$ alkylaminosulfonyl, $C_2$-$C_8$ dialkylaminosulfonyl, naphthalenyl or G$^A$, each optionally substituted with one or more substituents independently selected from the group consisting of halogen, cyano, hydroxy, amino, nitro, —CH(=O), —C(=O)OH, —C(=O)NH$_2$, —C(R$^{15}$)=N—O—R$^{16}$, —C(R$^{15}$)=N—R$^{16}$, $C_1$-$C_6$ alkyl, $C_3$-$C_8$ cycloalkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ halo alkylcarbonyloxy, $C_4$-$C_{10}$ cycloalkylcarbonyloxy, $C_1$-$C_6$ alkylthio, benzylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino and G$^B$;

G$^A$ is independently a phenyl ring, benzyl, benzyloxy, benzoyl, phenoxy or phenylsulfonyl or a 5- or 6-membered heteroaromatic ring;

each G$^B$ is independently a phenyl ring or a 5- or 6-membered heteroaromatic ring optionally substituted with one or more substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_1$-$C_6$ haloalkyl, $C_2$-$C_6$ haloalkenyl, cyano, nitro, $C_1$-$C_6$ alkoxy, $C_1$-$C_6$ haloalkoxy and $C_1$-$C_6$ alkylthio;

each R$^{15}$ is H, $C_1$-$C_3$ alkyl, $C_3$-$C_8$ cycloalkyl or $C_1$-$C_3$ haloalkyl;

each R$^{16}$ is H, $C_1$-$C_3$ alkyl, $C_1$-$C_3$ haloalkyl, $C_2$-$C_3$ alkylcarbonyl or $C_2$-$C_3$ haloalkylcarbonyl;

m is an integer from 1 to 3;

p and q are independently an integer from 0 to 5; provided that when p is 0, then X is other than O or NR$^{11}$; and u and z in each instance of S(=O)$_u$(=NR$^{11}$)$_z$ are independently 0, 1 or 2, provided that the sum of u and z in each instance of S(=O)$_u$(=NR$^{11}$)$_z$ is 0, 1 or 2.

More particularly, this invention relates to a compound of Formula 1 including all geometric and stereoisomers, an N-oxide or a salt thereof.

This invention also relates to a fungicidal composition comprising a fungicidally effective amount of a compound of the invention and at least one additional component selected from the group consisting of surfactants, solid diluents and liquid diluents.

This invention also relates to a fungicidal composition comprising (a) a compound of the invention and (b) at least one other fungicide (e.g., at least one other fungicide having the same or different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes straight-chain or branched alkoxy substitution on a straight-chain or branched alkoxy. Examples of "alkoxyalkoxy" include $CH_3OCH_2O$—, $CH_3OCH_2(CH_3O)CHCH_2O$— and $(CH_3)_2CHOCH_2CH_2O$—. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC≡CCH_2O$, $CH_3C≡CCH_2O$ and $CH_3C≡CCH_2CH_2O$.

"Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "Alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylamino" and "dialkylamino" and the like, are defined analogously to the above examples.

"Trialkylsilyl" includes 3 branched and/or straight-chain alkyl radicals attached to and linked through a silicon atom, such as trimethylsilyl, triethylsilyl and tert-butyldimethylsilyl.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom. Examples of "cycloalkylalkoxy" include cyclopropylmethoxy, cyclopentylethoxy, and other cycloalkyl moieties bonded to straight-chain or branched alkoxy groups.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3OC(=O)$—, $CH_3CH_2OC(=O)$—, $CH_3CH_2CH_2OC(=O)$—, $(CH_3)_2CHOC(=O)$— and the different butoxy- or pentoxycarbonyl isomers. Examples of "alkylaminocarbonyl" include $CH_3NHC(=O)$—, $CH_3CH_2NHC(=O)$—, $CH_3CH_2CH_2NHC(=O)$—, $(CH_3)_2CHNHC(=O)$— and the different butylamino- or pentylaminocarbonyl isomers. Examples of "dialkylaminocarbonyl" include $(CH_3)_2NC(=O)$—, $(CH_3CH_2)_2NC(=O)$—, $CH_3CH_2(CH_3)NC(=O)$—, $(CH_3)_2CHN(CH_3)C(=O)$— and $CH_3CH_2CH_2(CH_3)NC(=O)$—.

"Cycloalkylamino" denotes cycloalkyl linked through an amine group such as cyclopropylamino, cyclobutylamino, cyclopentylamino and cyclohexylamino.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$, $CF_3CH_2$— and $CF_3CCl_2$—. The terms "halocycloalkyl", "haloalkoxy", "haloalkylthio", "haloalkenyl", "haloalkenyloxy" and "haloalkynyloxy" and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. Examples of "haloalkenyl" include $(Cl)_2C=CHCH_2$— and $CF_3CH_2CH=CHCH_2$—. Examples of "halodialkylamino" include $CF_3(CH_3)N$—, $(CF_3)_2N$— and $CH_2Cl(CH_3)N$. Examples of "halotrialkylsilyl" include $CF_3(CH_3)_2Si$—, $(CF_3)_3Si$—, and $CH_2Cl(CH_3)_2Si$—.

The abbreviation "CN" means cyano.

The total number of carbon atoms in a substituent group is indicated by the "$C_i$-$C_j$" prefix where i and j are integers from 1 to 25. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., —$(CR^{8a}R^{8b})_p$—, p is 1, 2, 3, 4 or 5. Further, when the subscript indicates a range, e.g. $(R)_{i-j}$, then the number of substituents may be selected from the integers between i and j inclusive. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent J) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "ring member" refers to an atom (e.g., C, O, N or S) or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic.

The term "optionally substituted" in connection with $R^{10a}$, $R^{10b}$, $R^{10c}$, $R^{14}$, $G^B$, J and X refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other. Commonly, the number of optional substituents (when present) ranges from 1 to 3. When a range specified for the number of substituents (e.g., r being an integer from 0 to 4 in Exhibit 1) exceeds the number of positions available for substituents on a ring (e.g., 1 position available for $(R^v)_r$, on U-29 in Exhibit 3), the actual higher end of the range is recognized to be the number of available positions. The term "optionally substituted" means that the number of substituents can be zero. For example, the phrase "optionally substituted with up to 5 substituents independently selected from $R^{13}$" means that 0, 1, 2, 3, 4 or 5 substituents can be present (if number of potential connection points allows), and thus the number of $R^{13}$ substituents can be zero.

When J is a 3- to 6-membered nitrogen-containing heterocyclic ring, it may be attached to the remainder of Formula 1 though any available carbon or nitrogen ring atom, unless otherwise described.

As noted above, J can be (among others) a phenyl ring optionally substituted with one or more substituents selected from a group of substituents as defined in the Summary of Invention (i.e. $R^{13}$). An example of a phenyl ring optionally substituted with up to 5 substituents is the ring illustrated as U-1 in Exhibit 1, wherein $R^v$ is $R^{13}$ as defined in the Summary of the Invention for J and r is an integer from 0 to 5. Also, as noted above, J can be (among others) a 5- or 6-membered heteroaromatic ring, optionally substituted with one or more substituents selected from a group of substituents as defined in the Summary of Invention. Examples of a 5- or 6-membered heteroaromatic ring optionally substituted with from one or more substituents include the rings U-2 through U-61 illustrated in Exhibit 1 wherein $R^v$ is any substituent as defined in the Summary of the Invention for J (i.e. $R^{13}$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.
Exhibit 1
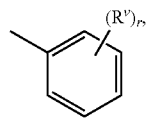 U-1
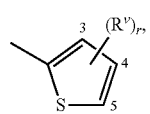 U-2
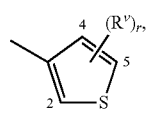 U-3
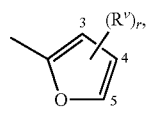 U-4
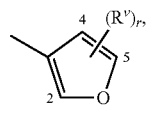 U-5
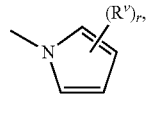 U-6
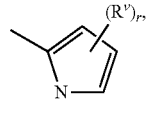 U-7
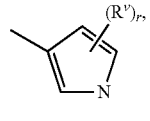 U-8
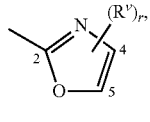 U-9
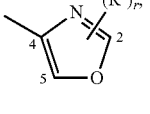 U-10
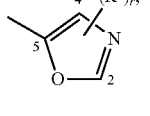 U-11
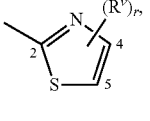 U-12
-continued
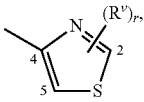 U-13
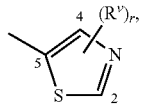 U-14
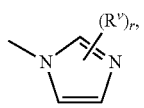 U-15
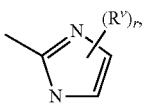 U-16
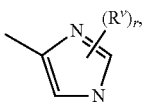 U-17
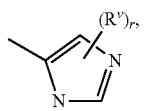 U-18
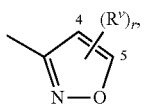 U-19
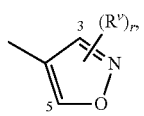 U-20
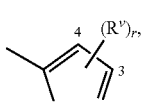 U-21
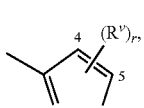 U-22
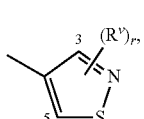 U-23
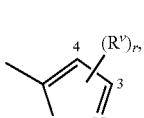 U-24
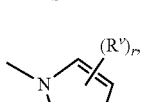 U-25

-continued

U-26, U-27, U-28, U-29, U-30, U-31, U-32, U-33, U-34, U-35, U-36, U-37, U-38

-continued

U-39, U-40, U-41, U-42, U-43, U-44, U-45, U-46, U-47, U-48, U-49, U-50

-continued

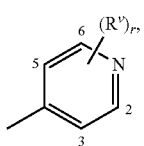 U-51

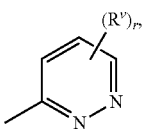 U-52

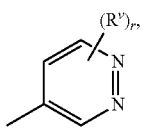 U-53

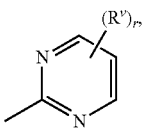 U-54

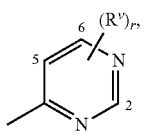 U-55

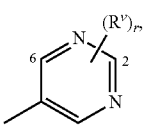 U-56

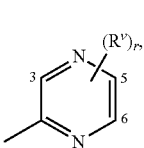 U-57

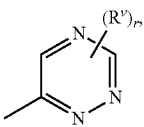 U-58

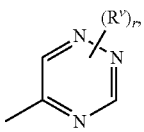 U-59 and U-60

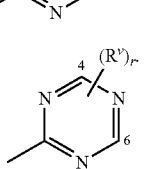 U-61

Examples of a 5- or 6-membered nonaromatic unsaturated heterocyclic ring include the rings G-1 through G-35 as illustrated in Exhibit 2, wherein in $R^v$ is $R^{13}$ as defined in the Summary of the Invention. The optional substituents corresponding to $R^v$ can be attached to any available carbon or nitrogen by replacing a hydrogen atom. For these G rings, r is typically an integer from 0 to 4, limited by the number of available positions on each G group. Note that when the attachment point on the G group is illustrated as floating, the G group can be attached to the remainder of Formula 1 through any available carbon or nitrogen of the G group by replacement of a hydrogen atom.

Note that when J comprises a ring selected from G-28 through G-35, $G^2$ is selected from O, S and N. Note that when $G^2$ is N, the nitrogen atom can complete its valence by substitution with either H or the substituents corresponding to $R^v$ as defined in the Summary of Invention for J (i.e. $R^{13}$).

Exibit 2

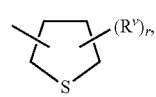 G-1

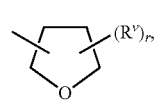 G-2

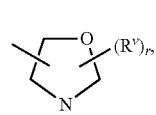 G-3

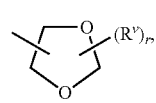 G-4

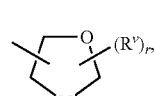 G-5

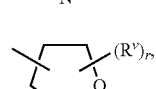 G-6

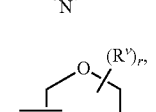 G-7

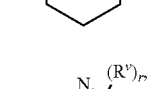 G-8

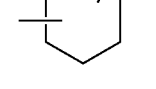 G-9

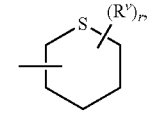 G-10

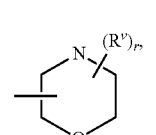

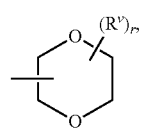 G-11
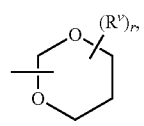 G-12
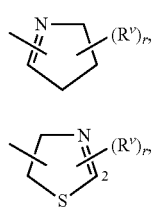 G-13
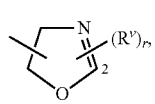 G-14
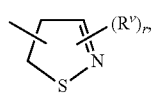 G-15
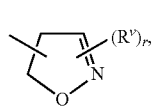 G-16
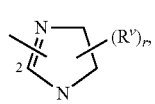 G-17
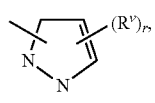 G-18
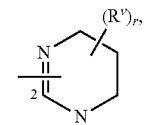 G-19
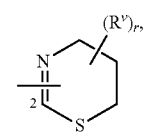 G-20
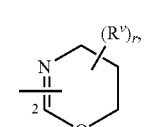 G-21
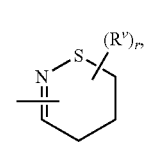 G-22
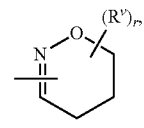 G-23
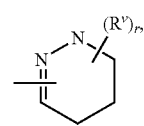 G-24
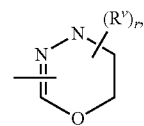 G-25
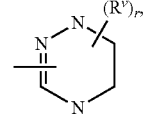 G-26
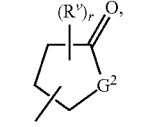 G-27
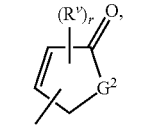 G-28
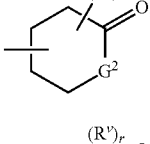 G-29
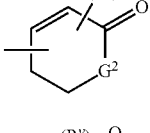 G-30
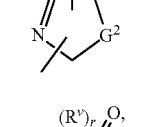 G-31
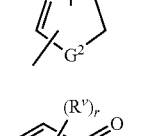 G-32
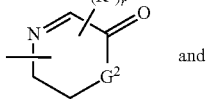 G-33
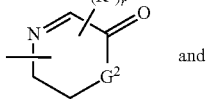 G-34
and

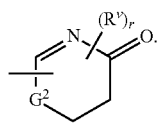
G-35

As noted above, J can be (among others) an 8-, 9- or 10-membered fused bicyclic ring system optionally substituted with one or more substituents selected from a group of substituents as defined in the Summary of Invention (i.e. $R^{13}$). Examples of 8-, 9- or 10-membered fused bicyclic ring system optionally substituted with up to 5 substituents include the rings U-81 through U-123 illustrated in Exhibit 3 wherein $R^v$ is any substituent as defined in the Summary of the Invention for J (i.e. $R^{13}$), and r is typically an integer from 0 to 5.

Exibit 3

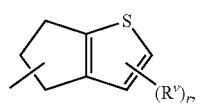 U-81

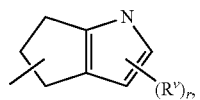 U-82

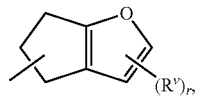 U-83

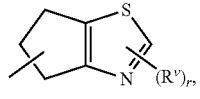 U-84

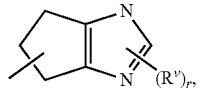 U-85

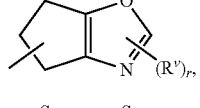 U-86

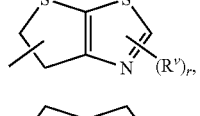 U-87

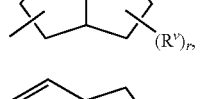 U-88

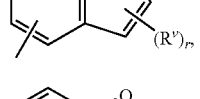 U-89

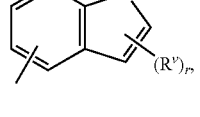 U-90

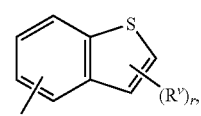 U-91

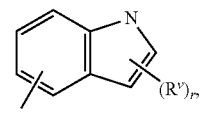 U-92

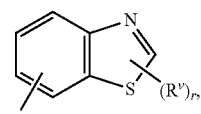 U-93

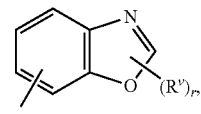 U-94

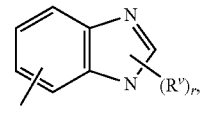 U-95

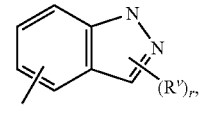 U-96

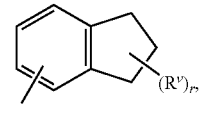 U-97

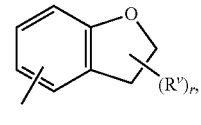 U-98

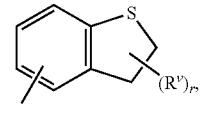 U-99

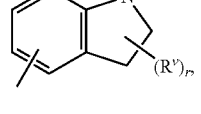 U-100

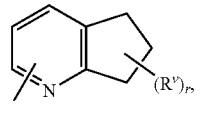 U-101

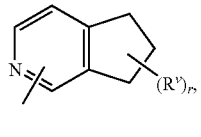 U-102

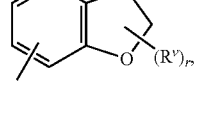 U-103

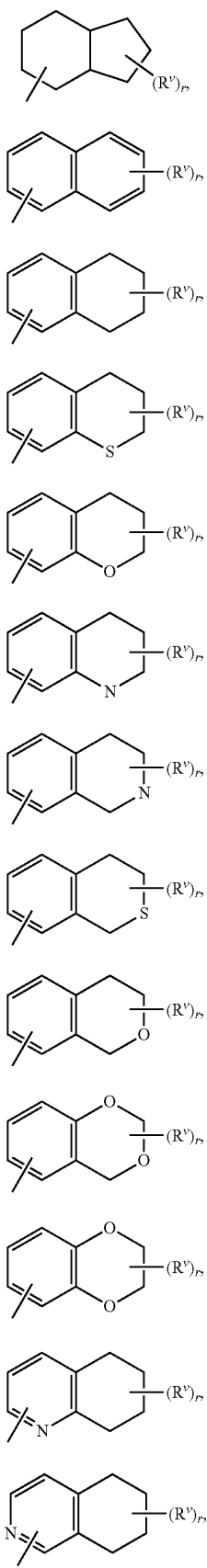

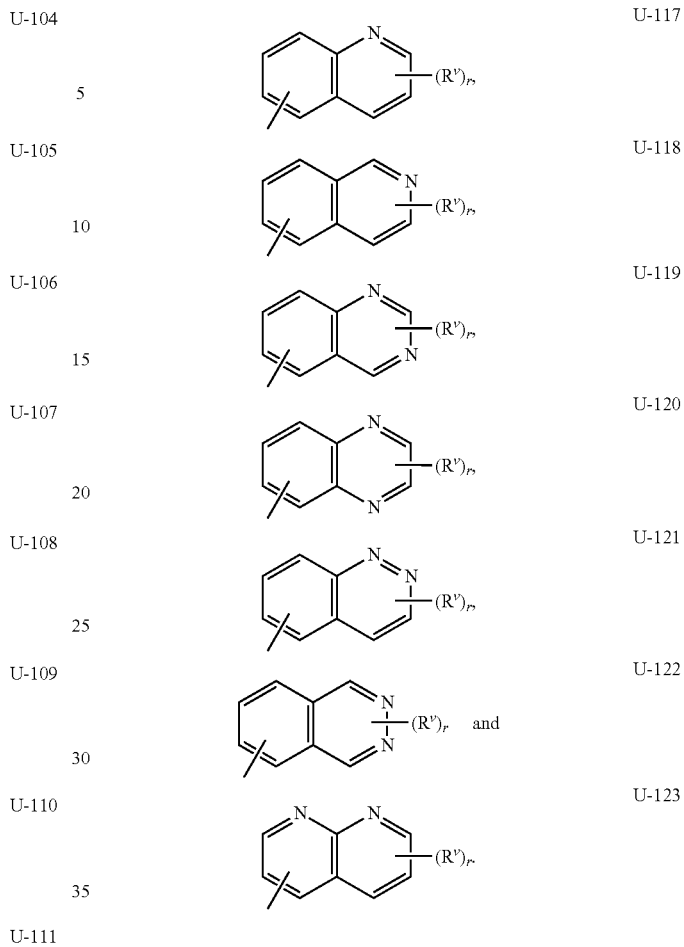

Although $R^v$ groups are shown in the structures U-1 through U-123, it is noted that they do not need to be present since they are optional substituents. The nitrogen atoms that require substitution to fill their valence are substituted with H or $R^v$. Note that when the point of attachment between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein $R^1$ is H, halogen, CN, $C_1$-$C_3$ alkyl, $C_1$-$C_3$ alkoxy, $C_1$-$C_3$ haloalkyl, $C_1$-$C_3$ haloalkoxy, $C_3$-$C_4$ cycloalkyl, $C_3$-$C_6$ trialkylsilyl or $C_3$-$C_6$ halotrialkylsilyl.

Embodiment 1a

A compound of Embodiment 1 wherein $R^1$ is halogen, CN, $C_1$-$C_2$ alkyl, $C_1$-$C_2$ alkoxy, $C_1$-$C_2$ haloalkyl or $C_1$-$C_2$ haloalkoxy.

Embodiment 1b

A compound of Embodiment 1a wherein $R^1$ is halogen, CN, $C_1$-$C_2$ alkyl or $C_1$-$C_2$ haloalkyl.

Embodiment 1c

A compound of Embodiment 1b wherein $R^1$ is F, Cl, Br, CN, methyl or $C_1$ haloalkyl.

Embodiment 1d

A compound of Embodiment 1c wherein $R^1$ is Cl or methyl.

Embodiment 2

A compound of Formula 1 wherein $R^2$ is H, halogen, CN, $C_1$-$C_3$ alkyl, $C_1$-$C_3$ alkoxy or $C_1$-$C_3$ haloalkyl.

Embodiment 2a

A compound of Embodiment 2 wherein $R^2$ is H, halogen, CN, methyl or trifluoromethyl.

Embodiment 2b

A compound of Embodiment 2a wherein $R^2$ is H or halogen.

Embodiment 2c

A compound of Embodiment 2b wherein $R^2$ is H, F or Cl.

Embodiment 2d

A compound of Embodiment 2c wherein $R^2$ is H.

Embodiment 3

A compound of Formula 1 wherein $R^3$ is H, $C_1$-$C_2$ alkyl, $C_1$-$C_2$ haloalkyl, $C_2$-$C_3$ alkylcarbonyl or $C_2$-$C_3$ haloalkylcarbonyl.

Embodiment 3a

A compound of Embodiment 3 wherein $R^3$ is H, $C_1$-$C_2$ alkyl or $C_1$-$C_2$ haloalkyl.

Embodiment 3b

A compound of Embodiment 3a wherein $R^3$ is H.

Embodiment 4

A compound of Formula 1 wherein $R^4$ is $C_1$-$C_2$ alkoxy, $C_1$-$C_2$ haloalkoxy, $C_3$-$C_4$ cycloalkoxy, $C_1$-$C_2$ alkylamino, $C_1$-$C_2$ haloalkylamino, $C_2$-$C_4$ dialkylamino, $C_2$-$C_4$ halodialkylamino or $C_3$-$C_4$ cycloalkylamino.

Embodiment 4a

A compound of Embodiment 4 wherein $R^4$ is $C_1$-$C_2$ alkoxy, $C_1$-$C_2$ haloalkoxy, $C_1$-$C_2$ alkylamino or $C_2$-$C_4$ dialkylamino.

Embodiment 4b

A compound of Embodiment 4a wherein $R^4$ is $C_1$-$C_2$ alkoxy or $C_1$-$C_2$ haloalkoxy.

Embodiment 4c

A compound of Embodiment 4b wherein $R^4$ is methoxy.

Embodiment 5

A compound of Formula 1 wherein W is O.

Embodiment 6

A compound of Formula 1 wherein W is S.

Embodiment 7

A compound of Formula 1 wherein Q is $CR^{6a}R^{6b}$, O, $NR^7$ or C=N—O—$R^7$.

Embodiment 7a

A compound of Formula 1 wherein Q is $CR^{6a}R^{6b}$ or $NR^7$.

Embodiment 7b

A compound of Formula 1 wherein Q is O or $NR^7$.

Embodiment 7c

A compound of Formula 1 wherein Q is $CR^{6a}R^{6b}$.

Embodiment 7d

A compound of Formula 1 wherein Q is $NR^7$.

Embodiment 7e

A compound of Formula 1 wherein Q is C=N—O—$R^7$.

Embodiment 7f

A compound of Formula 1 wherein $R^{6a}$ and $R^{6b}$ are independently H, halogen, CN, $C_1$-$C_3$ alkyl or $C_1$-$C_3$ haloalkyl.

Embodiment 7g

A compound of Embodiment 7f wherein $R^{6a}$ and $R^{6b}$ are independently H, F, CN or methyl.

Embodiment 7h

A compound of Embodiment 7g wherein $R^{6a}$ and $R^{6b}$ are H.

Embodiment 8

A compound of Formula 1 wherein $R^7$ is H, $C_1$-$C_2$ alkyl, $C_1$-$C_2$ haloalkyl, $C_2$-$C_3$ alkylcarbonyl or $C_2$-$C_3$ haloalkylcarbonyl.

Embodiment 9

A compound of Embodiment 8 wherein $R^7$ is H, methyl, $C_1$-$C_3$ haloalkyl, acetyl or haloacetyl.

Embodiment 10

A compound of Embodiment 9 wherein $R^7$ is H.

Embodiment 11

A compound of Formula 1 wherein Y is —C($R^5$)=N—O—$(CR^{8a}R^{8b})_p$—X—$(CR^{9a}R^{9b})_q$—$SiR^{10a}R^{10b}R^{10c}$.

Embodiment 11a

A compound of Formula 1 wherein p is 0.

Embodiment 12

A compound of Formula 1 wherein Y is a phenyl ring substituted with one substituent selected from $C_1$-$C_5$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl and optionally substituted with up to four additional substituents independently selected from halogen, CN, $C_1$-$C_3$ alkyl, $C_1$-$C_3$ alkoxy, $C_1$-$C_3$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl.

Embodiment 13

A compound of Embodiment 12 wherein Y is a phenyl ring substituted with one additional substituent selected from $C_1$-$C_3$ haloalkoxy, $C_3$-$C_9$ trialkylsilyl, $C_3$-$C_9$ halotrialkylsilyl, $C_4$-$C_{12}$ trialkylsilylalkyl and $C_4$-$C_{12}$ trialkylsilylalkoxy, and optionally substituted with up to four additional substituents independently selected from halogen, CN, $C_1$-$C_3$ alkyl, $C_1$-$C_3$ alkoxy and $C_1$-$C_3$ haloalkoxy.

Embodiment 14

A compound of Embodiment 13 wherein Y is a phenyl ring substituted with one additional substituent selected from $C_1$-$C_3$ haloalkoxy or $C_3$-$C_6$ trialkylsilyl, and optionally substituted with up to four additional substituents independently selected from halogen and $C_1$-$C_3$ alkyl.

Embodiment 15

A compound of Embodiment 14 wherein Y is a phenyl ring substituted with one additional substituent selected from $C_1$-$C_3$ haloalkoxy and $C_3$-$C_6$ trialkylsilyl.

Embodiment 16

A compound of Formula 1 wherein Y is Z.

Embodiment 16a

A compound of Embodiment 16 wherein Z is Z-1, Z-2, Z-3, Z-4, Z-6, Z-7, Z-8, Z-9, Z-11, Z-12, Z-18 or Z-24.

Embodiment 16b

A compound of Embodiment 16a wherein each $R^{14}$ is independently halogen, $C_1$-$C_6$ alkyl, $C_3$-$C_8$ cycloalkyl, $C_1$-$C_6$ haloalkyl, $C_1$-$C_6$ haloalkoxy, or $G^4$ each optionally substituted with one or more substituents independently selected from the group halogen, cyano, hydroxy, amino, nitro, —CH(=O), —C(=O)OH, —C(=O)$NH_2$, C($R^{15}$)

=N—O—R$^{16}$, C(R$^{15}$)=N—R$^{16}$, C$_1$-C$_6$ alkyl, C$_3$-C$_8$ cycloalkyl, C$_2$-C$_6$ alkenyl, C$_2$-C$_6$ alkynyl, C$_1$-C$_6$ haloalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ haloalkoxy, C$_3$-C$_8$ cycloalkoxy and C$_3$-C$_{10}$ trialkylsilyl.

Embodiment 16c

A compound of Embodiment 16b wherein each G$^A$ is independently phenyl, benzyl or 5- or 6-membered heteroaromatic ring, each optionally substituted with one or more substituents independently selected from the group halogen, —CH(=O), —C(R$^{15}$)=N—O—R$^{16}$, C(R$^{15}$)=N—R$^{16}$, C$_1$-C$_6$ alkyl, C$_3$-C$_8$ cycloalkyl, C$_1$-C$_6$ haloalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ haloalkoxy, C$_3$-C$_8$ cycloalkoxy and C$_3$-C$_{10}$ trialkylsilyl.

Embodiment 16d

A compound of Embodiment 16c wherein each G$^A$ is independently phenyl or 1,2,4-thiadiazole each optionally substituted with one or more substituents independently selected from the group halogen, C$_1$-C$_6$ alkyl, C$_3$-C$_8$ cycloalkyl, C$_1$-C$_6$ haloalkyl, C$_2$-C$_8$ alkylcarbonyl, C$_2$-C$_8$ haloalkylcarbonyl, C$_1$-C$_6$ alkoxy, C$_1$-C$_6$ haloalkoxy, C$_3$-C$_8$ cycloalkoxy and C$_3$-C$_{10}$ trialkylsilyl.

Embodiment 16e

A compound of Embodiment 16a wherein Q is CR$^{6a}$R$^{6b}$.

Embodiment 17

A compound of Formula 1 wherein R$^5$ is C$_1$-C$_3$ alkyl or C$_1$-C$_3$ haloalkyl.

Embodiment 17a

A compound of Embodiment 17 wherein R$^5$ is C$_1$-C$_3$ alkyl.

Embodiment 17b

A compound of Embodiment 17a wherein R$^5$ is methyl.

Embodiment 18

A compound of Embodiment 17 wherein R$^5$ is C$_1$-C$_3$ haloalkyl.

Embodiment 19

A compound of Formula 1 wherein p and q are independently an integer from 0 to 3.

Embodiment 20

A compound of Formula 1 wherein each R$^{8a}$ and R$^{9a}$ is independently H, OH, CN, halogen, C$_1$-C$_5$ alkyl, C$_1$-C$_5$ haloalkyl or C$_1$-C$_5$ alkoxy.

Embodiment 21

A compound of Embodiment 20 wherein each R$^{8a}$ and R$^{9a}$ is independently H, halogen, C$_1$-C$_3$ alkyl, C$_1$-C$_3$ haloalkyl or C$_1$-C$_3$ alkoxy.

Embodiment 22

A compound of Formula 1 wherein each R$^{10a}$, R$^{10b}$ and R$^{10c}$ is independently C$_1$-C$_6$ alkyl, C$_1$-C$_6$ haloalkyl, C$_2$-C$_8$ alkoxyalkyl, C$_2$-C$_8$ haloalkoxyalkyl, C$_3$-C$_6$ cycloalkyl, C$_5$-C$_{10}$ alkylcycloalkylalkyl or J.

Embodiment 22a

A compound of Formula 1 wherein J is independently a phenyl ring, or a 5- or 6-membered heteroaromatic ring, or a 3- to 6-membered nonaromatic carbocyclic or heterocyclic ring, each optionally including ring members selected from the group consisting of C(=O), C(=S), C(=NR$^{11}$), NR$^{11}$, SiR$^{12a}$R$^{12b}$ and S(=O)$_u$(=NR$^{11}$)$_z$; each ring optionally substituted with up to 5 substituents independently selected from R$^{13}$.

Embodiment 23

A compound of Embodiment 22 wherein each R$^{10a}$, R$^{10b}$ and R$^{10c}$ is independently C$_1$-C$_6$ alkyl, C$_1$-C$_6$ haloalkyl, C$_2$-C$_8$ alkoxyalkyl, C$_2$-C$_8$ haloalkoxyalkyl, C$_3$-C$_6$ cycloalkyl or C$_5$-C$_{10}$ alkylcycloalkylalkyl.

Embodiment 24

A compound of Formula 1 wherein X is a direct bond, O or C(=O); or a phenyl ring; or a 5- or 6-membered heteroaromatic ring or a 3- to 6-membered nonaromatic carbocyclic or heterocyclic ring, each optionally including ring members selected from the group consisting of C(=O), C(=S), C(=NR$^{11}$), NR$^{11}$, SiR$^{12a}$R$^{12b}$ or S(=O)$_u$(=NR$^{11}$)$_z$; each ring optionally substituted with up to 3 substituents independently selected from R$^{13}$.

Embodiment 24a

A compound of Formula 1 wherein X is a direct bond.

Embodiment 25

A compound of Formula 1 wherein each R$^{11}$ is independently H, CN, C$_1$-C$_6$ alkyl, C$_3$-C$_{10}$ cycloalkyl, C$_2$-C$_6$ alkylcarbonyl or C$_2$-C$_6$ haloalkylcarbonyl.

Embodiment 26

A compound of Formula 1 wherein each R$^{12a}$ and R$^{12b}$ is independently C$_1$-C$_5$ alkyl or C$_1$-C$_5$ haloalkyl.

Embodiment 27

A compound of Formula 1 wherein each R$^{13}$ is independently halogen, C$_1$-C$_6$ alkyl, C$_3$-C$_6$ cycloalkyl, C$_3$-C$_6$ halocycloalkyl, C$_4$-C$_7$ alkylcycloalkyl, C$_1$-C$_6$ haloalkyl, cyano, C$_1$-C$_6$ alkoxy, C$_1$-C$_6$ haloalkoxy, C$_1$-C$_6$ alkylthio, C$_2$-C$_6$ alkylcarbonyl, C$_2$-C$_6$ alkoxycarbonyl, C$_2$-C$_6$ alkylaminocarbonyl or C$_3$-C$_6$ dialkylaminocarbonyl.

Embodiment 28

A compound of Embodiment 27 wherein each $R^{13}$ is independently halogen, $C_1$-$C_6$ alkyl, $C_3$-$C_6$ cycloalkyl, $C_1$-$C_6$ haloalkyl, cyano, $C_1$-$C_6$ alkoxy, or $C_1$-$C_6$ haloalkoxy.

Embodiment 29

A compound of Formula 1 wherein V is $NR^3$.

Embodiment 30

A compound of Formula 1 wherein V is a direct bond and Q C(=N)—O—$R^7$ or C(=O).

Embodiment 31

A compound of Formula 1 wherein
V is other than a direct bond;
$R^3$ and $R^4$ are other than $C_3$-$C_6$ cycloalkyl;
$R^5$ is other than $C_3$-$C_6$ halocycloalkyl;
Q is other than C=N—O—$R'^7$;
Y is other than Z; and
$R^{14}$ is other than $C_3$-$C_6$ halocycloalkyl, $C_1$-$C_6$ haloalkyl, $C_1$-$C_6$ haloalkoxy, $C_3$-$C_8$ halocycloalkoxy.

Embodiment 32

A compound of Formula 1 wherein
V is other than a direct bond;
$R^5$ is other than $C_3$-$C_6$ halocycloalky; and
$R^{14}$ is other than $C_3$-$C_6$ halocycloalkyl, $C_1$-$C_6$ haloalkyl, $C_1$-$C_6$ haloalkoxy, $C_3$-$C_8$ halocycloalkoxy.

Embodiments of this invention, including Embodiments 1-32 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-32 above as well as any other embodiments described herein, and any combination thereof, pertain to the compositions and methods of the present invention.

Combinations of Embodiments 1-32 are illustrated by:

Embodiment A

A compound of Formula 1 wherein
$R^1$ is halogen, CN, $C_1$-$C_2$ alkyl, $C_1$-$C_2$ alkoxy, $C_1$-$C_2$ haloalkyl, or $C_1$-$C_2$ haloalkoxy;
$R^2$ is H, halogen, CN, methyl or trifluoromethyl;
V is $NR^3$;
$R^3$ is H, $C_1$-$C_2$ alkyl, $C_1$-$C_2$ haloalkyl, $C_2$-$C_3$ alkylcarbonyl or $C_2$-$C_3$ haloalkylcarbonyl;
$R^4$ is $C_1$-$C_2$ alkoxy, $C_1$-$C_2$ haloalkoxy, $C_1$-$C_2$ alkylamino or $C_2$-$C_4$ dialkylamino;
W is O;
Q is $CR^{6a}R^{6b}$, C=N—O—$R^7$, O or $NR^7$;
$R^5$ is $C_1$-$C_3$ alkyl or $C_1$-$C_3$ haloalkyl; and
Y is —C($R^5$)=N—O—($CR^{8a}R^{8b}$)$_p$—X—($CR^{9a}R^{9b}$)$_q$—Si$R^{10a}R^{10b}R^{10c}$.

Embodiment A1

A compound of Embodiment A wherein
$R^1$ is F, Cl, Br, CN, methyl or $C_1$ haloalkyl;
$R^2$ is H, F or Cl;
$R^3$ is H, $C_1$-$C_2$ alkyl or $C_1$-$C_2$ haloalkyl;
$R^4$ is $C_1$-$C_2$ alkoxy or $C_1$-$C_2$ haloalkoxy;
Q is $CR^{6a}R^{6b}$ or $NR^7$;
$R^5$ is $C_1$-$C_3$ alkyl;
p is 0; and
X is direct bond.

Embodiment A2

A compound of Embodiment A1 wherein
$R^1$ is Cl or methyl;
$R^2$ is H;
$R^3$ is H;
$R^4$ is methoxy;
Q is $CR^{6a}R^{6b}$; and
$R^5$ is methyl.

Embodiment B

A compound of Formula 1 wherein
$R^1$ is halogen, CN, $C_1$-$C_2$ alkyl, $C_1$-$C_2$ alkoxy, $C_1$-$C_2$ haloalkyl or $C_1$-$C_2$ haloalkoxy;
$R^2$ is H, halogen, CN, methyl or trifluoromethyl;
V is $NR^3$;
$R^3$ is H, $C_1$-$C_2$ alkyl, $C_1$-$C_2$ haloalkyl, $C_2$-$C_3$ alkylcarbonyl or $C_2$-$C_3$ haloalkylcarbonyl;
$R^4$ is $C_1$-$C_2$ alkoxy, $C_1$-$C_2$ haloalkoxy, $C_1$-$C_2$ alkylamino or $C_2$-$C_4$ dialkylamino;
W is O;
Q is O or $NR^7$; and
Y is a phenyl ring substituted with one substituent selected from $C_1$-$C_5$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl and optionally substituted with up to four additional substituents independently selected from halogen, CN, $C_1$-$C_3$ alkyl, $C_1$-$C_3$ alkoxy, $C_1$-$C_3$ haloalkoxy, $C_3$-$C_{15}$ trialkylsilyl, $C_3$-$C_{15}$ halotrialkylsilyl, $C_4$-$C_{20}$ trialkylsilylalkyl, $C_4$-$C_{20}$ trialkylsilylalkoxy and $C_5$-$C_{25}$ trialkylsilylalkoxyalkyl.

Embodiment B1

A compound of Embodiment B wherein
$R^1$ is halogen, CN, $C_1$-$C_2$ alkyl or $C_1$-$C_2$ haloalkyl;
$R^2$ is H or halogen;
$R^3$ is H, $C_1$-$C_2$ alkyl or $C_1$-$C_2$ haloalkyl;
$R^4$ is $C_1$-$C_2$ alkoxy or $C_1$-$C_2$ haloalkoxy;
Q is $NR^7$;
$R^5$ is $C_1$-$C_3$ alkyl; and
Y is a phenyl ring substituted with one additional substituent selected from $C_1$-$C_3$ haloalkoxy, $C_3$-$C_9$ trialkylsilyl, $C_3$-$C_9$ halotrialkylsilyl, $C_4$-$C_{12}$ trialkylsilylalkyl and $C_4$-$C_{12}$ trialkylsilylalkoxy, and optionally substituted with up to four additional substituents independently selected from halogen, CN, $C_1$-$C_3$ alkyl, $C_1$-$C_3$ alkoxy and $C_1$-$C_3$ haloalkoxy.

Embodiment B2

A compound of Embodiment B1 wherein
$R^1$ is Cl or methyl;
$R^2$ is H;
$R^3$ is H;
$R^4$ is methoxy;
$R^5$ is methyl; and
Y is a phenyl ring with one substituent selected from $C_1$-$C_3$ haloalkoxy and $C_3$-$C_6$ trialkylsilyl.

Embodiment C

A compound of Formula 1 wherein
$R^1$ is halogen, CN, $C_1$-$C_2$ alkyl, $C_1$-$C_2$ alkoxy, $C_1$-$C_2$ haloalkyl or $C_1$-$C_2$ haloalkoxy;
$R^2$ is H, halogen, CN, methyl or trifluoromethyl;
$R^3$ is H, $C_1$-$C_2$ alkyl, $C_1$-$C_2$ haloalkyl, $C_2$-$C_3$ alkylcarbonyl or $C_2$-$C_3$ haloalkylcarbonyl;
$R^4$ is $C_1$-$C_2$ alkoxy, $C_1$-$C_2$ haloalkoxy, $C_1$-$C_2$ alkylamino or $C_2$-$C_4$ dialkylamino;
W is O;
Q is $CR^{6a}R^{6b}$, O, C=N—O—$R^7$ or $NR^7$; and
Y is Z.

Embodiment C1

A compound of Embodiment C wherein
$R^1$ is halogen, CN, $C_1$-$C_2$ alkyl or $C_1$-$C_2$ haloalkyl;
$R^2$ is H or halogen;
$R^3$ is H, $C_1$-$C_2$ alkyl or $C_1$-$C_2$ haloalkyl;
$R^4$ is $C_1$-$C_2$ alkoxy or $C_1$-$C_2$ haloalkoxy;
$R^5$ is $C_1$-$C_3$ alkyl; and
Y is Z-1, Z-2, Z-3, Z-4, Z-6, Z-7, Z-8, Z-9, Z-11, Z-12, Z-18 or Z-24.

Embodiment C2

A compound of Embodiment C1 wherein each $R^{14}$ is independently $C_1$-$C_6$ alkyl, $C_3$-$C_8$ cycloalkyl, $C_1$-$C_6$ haloalkyl, $C_1$-$C_6$ haloalkoxy, or $G^A$ each optionally substituted with one or more substituents independently selected from the group halogen, cyano, hydroxy, amino, nitro, —CH(=O), —C(=O)OH, —C(=O)NH$_2$, $C(R^{15})$=N—O—$R^{16}$, $C(R^{15})$=N—$R^{16}$, $C_1$-$C_6$ alkyl, $C_3$-$C_8$ cycloalkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy and $C_3$-$C_{10}$ trialkylsilyl.

Embodiment C3

A compound of Embodiment C2 wherein each $G^A$ is independently phenyl, benzyl or 5- or 6-membered heteroaromatic ring, each optionally substituted with one or more substituents independently selected from the group halogen, —CH(=O), —$C(R^{15})$=N—O—$R^{16}$, $C(R^{15})$=N—$R^{16}$, $C_1$-$C_6$ alkyl, $C_3$-$C_8$ cycloalkyl, $C_1$-$C_6$ haloalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy and $C_3$-$C_{10}$ trialkylsilyl.

Embodiment C4

A compound of Embodiment C3 wherein each $G^A$ is independently phenyl or 1,2,4-thiadiazole each optionally substituted with one or more substituents independently selected from the group halogen, $C_1$-$C_6$ alkyl, $C_3$-$C_8$ cycloalkyl, $C_1$-$C_6$ haloalkyl, $C_2$-$C_8$ alkylcarbonyl, $C_2$-$C_8$ haloalkylcarbonyl, $C_1$-$C_6$ alkoxy, $C_1$-$C_6$ haloalkoxy, $C_3$-$C_8$ cycloalkoxy and $C_3$-$C_{10}$ trialkylsilyl.

Embodiment C5

A compound of Embodiment C wherein Q is $CR^{6a}R^{6b}$.

Embodiment C6

A compound of Embodiment C wherein
V is $NR^3$.

Embodiment C

A compound of Embodiment C wherein
V is $NR^3$; and
Q is C=N—O—$R^7$.

Specific embodiments include compounds of Formula 1 selected from the group consisting of:
methyl N-[[2-chloro-5-[1-[[2-(trimethylsilyl)ethoxy]imino]ethyl]phenyl]-methyl]carbamate,
methyl N-[[2-chloro-5-[1-[[2-(trimethylsilyl)propoxy]imino]ethyl]phenyl]-methyl]carbamate,
methyl 2-[4-chloro-3'-(trifluoromethoxy)[1,1'-biphenyl]-3-yl]hydrazinecarboxylate,
methyl N-[[2-chloro-5-[1-[[(trimethylsilyl)methoxy]imino]ethyl]phenyl]-methyl]carbamate,
methyl N-[[2-chloro-5-[1-[[(ethyldimethylsilyl)methoxy]imino]ethyl]phenyl]-methyl]carbamate;
methyl N-[[2-chloro-5-[1-(4-chlorophenyl)-1H-pyrazol-3-yl]phenyl]methyl]carbamate;
methyl N-[[2-chloro-5-[1-(4-methoxyphenyl)-1H-pyrazol-3-yl]phenyl]methyl]carbamate;
methyl N-[[5-[1-(4-acetylphenyl)-1H-pyrazol-3-yl]-2-chlorophenyl]methyl]carbamate;
methyl N-[[2-chloro-5-[1-[3-(trimethylsilyl)propyl]-1H-pyrazol-3-yl]phenyl]methyl]carbamate; and
methyl N-[[2-chloro-5-[1-[4-methylphenyl)methyl]-1H-pyrazol-3-yl]phenyl]methyl]carbamate.

This invention provides a fungicidal composition comprising a compound of Formula 1 (including all geometric and stereoisomers, N-oxides, and salts thereof), and at least one other fungicide. Of note as embodiments of such compositions are compositions comprising a compound corresponding to any of the compound embodiments described above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note, as embodiments of such compositions, are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all geometric and stereoisomers, N-oxides, and salts thereof). Of note as embodiment of such methods are methods comprising applying a fungicidally effective amount of a compound corresponding to any of the compound embodiments describe above. Of particular note are embodiments where the compounds are applied as compositions of this invention.

One or more of the following methods and variations as described in Schemes 1-21 can be used to prepare the compounds of Formula 1. The definitions of $R^1$, $R^2$, $R^3$, $R^4$, $R^5$, $R^{6a}$, $R^{6b}$, $R^{8a}$, $R^{8b}$, $R^{9a}$, $R^{9b}$, $R^{10a}$, $R^{10b}$, $R^{10c}$, $R^{14}$, $G^A$, W, Q, X, Y, p and q in the compounds of Formulae 1-30 below are as defined above in the Summary of the Invention unless otherwise noted. Compounds of Formulae 1a-1m are various subsets of Formula 1, and all substituents for Formulae 1a-1m are as defined above for Formula 1 unless otherwise noted. Formulae 2a, 2b and 2c are subsets of Formula 2, Formula 6a is a subset of Formula 6, Formula 8a is a subset of Formula 8 and Formula 10a is a subset of Formula 10.

As shown in Scheme 1 certain compounds of Formula 1a, (Formula 1 wherein V is $NR^3$ and Y is —$C(R^5)$=N—O—$(CR^{8a}R^{8b})_p$—X—$(CR^{9a}R^{9b})_q$—$SiR^{10a}R^{10b}R^{10c}$), can be prepared by first reacting a compound of Formula 2 with hydroxylamine at temperatures ranging from about 50 to about 100° C. in a lower alkanol solvent such as methanol or ethanol, which can optionally containing water. The resulting oxime of Formula 3 can then be alkylated with a terminal alkyl halide of Formula 4 wherein $T^A$ is —$(CR^{8a}R^{8b})_p$—X—$(CR^{9a}R^{9b})_q$—$SiR^{10a}R^{10b}R^{10c}$ and $X^1$ is a leaving group such as halide (i.e. Cl, Br, I) in a polar aprotic solvent such as N,N-dimethylformamide in the presence of an inorganic base such as potassium carbonate or sodium hydride at temperatures ranging from about 50 to about 120° C. The method of Scheme 1 is illustrated in Example 2.

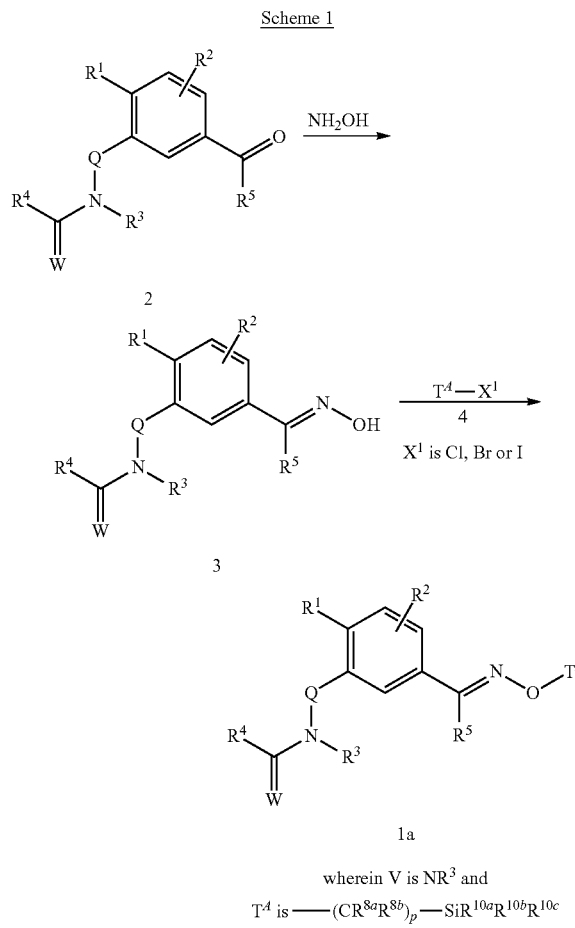

Alternatively, compounds of Formula 1a can be prepared by reacting a hydroxylamine derivative of Formula 5 or salt thereof with a compound of Formula 2 in a lower alkanol solvent at temperatures ranging from about 50 to about 100° C. as shown in Scheme 2. For a reference illustrating this type of reaction see, for example, de Lijser et al., *J. Organic Chem.* 2004, 69, 3057-3067. The method of Scheme 2 is also illustrated in Example 1.

For a general reference for the synthesis of compounds of Formula 5 see Kikugawa et al., *Organic Preparations and Procedures International*, 1994, 26(1), 111-113.

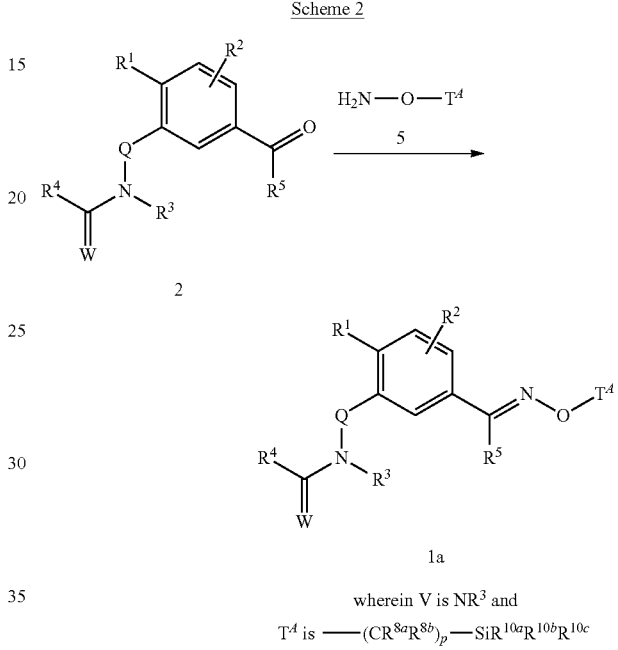

Compounds of Formula 1b (Formula 1 wherein V is $NR^3$) wherein Y is a substituted phenyl ring or a 5- or 6-membered heteroaromatic ring can be prepared by the well known Suzuki reaction via Pd-catalyzed cross-coupling of an aromatic iodide or bromide of Formula 6a (Formula 6, shown in Scheme 5, wherein $X^2$ is Br or I) with a substituted phenyl or heteroaromatic boronic acid of Formula 7 as shown in Scheme 3. For typical Suzuki reactions conditions see, for example, Suzuki et al., *Chemical Review*, 1995, 95, 2457-2483. A wide variety of catalysts are useful for this type of transformation; particularly useful as a catalyst is tetrakis (triphenylphosphine)palladium(0). Solvents such as tetrahydrofuran, acetonitrile, diethyl ether and dioxane are suitable. The boronic acids of Formula 7 are either commercially available or can be prepared by known methods. Other coupling procedures offer a number of alternatives for introduction of a substituted phenyl group onto Formula 1, including coupling methods published by Heck, Stille and Kumada. Also see, for example, Zificsak et al., *Tetrahedron*, 2004, 60, 8991-9016. Compounds of Formula 1b wherein Y is a N-linked heteroaromatic ring can be prepared via a palladium cross-coupling reaction using compounds of Formula 7a. For leading references see, for example, Buchwald et al., *Accounts of Chemical Research*, 1998, 31(12), 805-818 and Hartwig, *Angew. Chem. Int. Ed.*, 1998, 37, 2046-2067.

Scheme 3

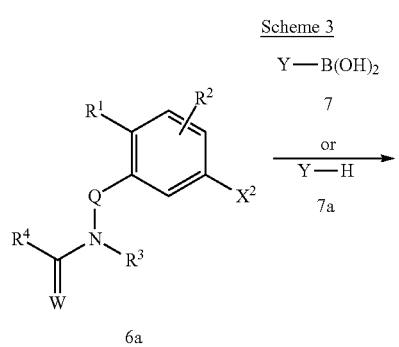

wherein $X^2$ is Br or I

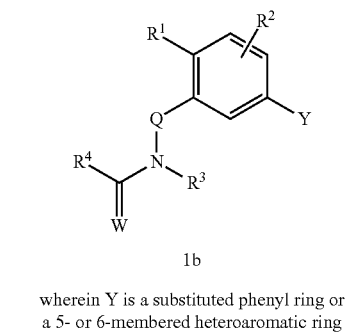

wherein Y is a substituted phenyl ring or a 5- or 6-membered heteroaromatic ring As shown in Scheme 4, compounds of Formula 2 can be prepared by reacting a substituted amine of Formula 8 with an acid chloride of Formula 9 in the presence of a base such as triethylamine or pyridine. The reaction can be carried out without solvent other than the compounds of Formulae 6a, 9 and the base or in an aprotic solvent such as dichloromethane, chloroform, diethyl ether or tetrahydrofuran at temperatures ranging from about 0 to about 50° C. For a related reference see European Patent Publication EP 1586552. For a general synthesis of compounds of Formula 9, see *Advanced Organic Synthesis*, 4th Edition, Wiley & Sons 1992, 437, and references cited therein. For synthesis of a compound of Formula 2 wherein Q is $NR^7$ and $R^7$ is H see World Patent Publication WO 2004/037770, and also see Step B of Example 1.

Scheme 4

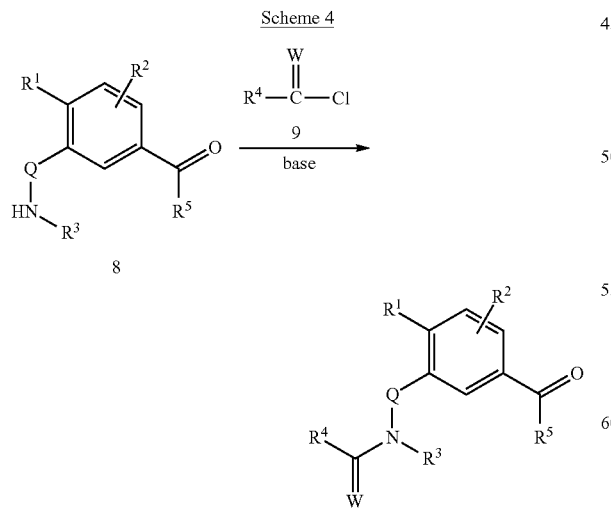

Additionally, compounds of Formula 2a (Formula 2 wherein $R^5$ is $CH_3$) can be prepared from compounds of Formula 6 by reaction with acetic anhydride in the presence of a palladium catalysis as shown in Scheme 5. For a reference illustrating the method of Scheme 5 see, for example, Cacchi et al., *Organic Letters* 2003, 5(3), 289-291.

Scheme 5

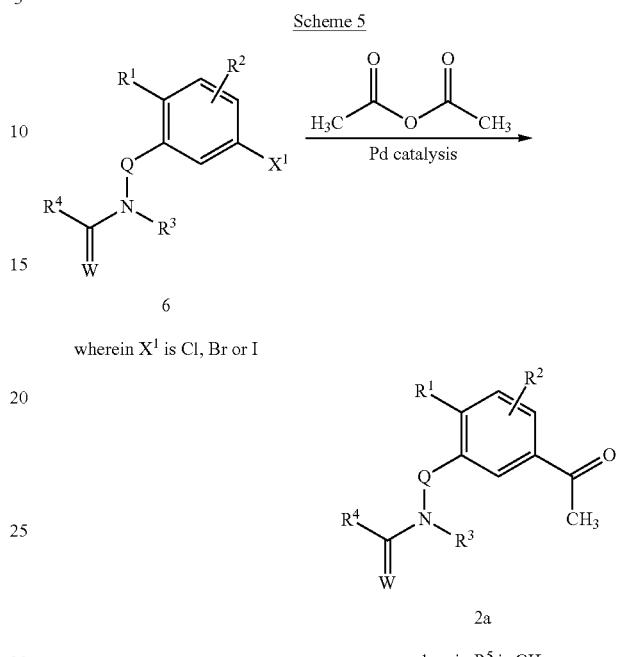

wherein $X^1$ is Cl, Br or I wherein $R^5$ is $CH_3$

As shown in Scheme 6, compounds of Formula 6 can be prepared from amines of Formula 10 by a method analogous to Scheme 4. Also, U.S. Pat. No. 6,313,071 describes the method of Scheme 6 when Q is $CH_2$. Additionally, U.S. Pat. No. 6,313,071 describes an alternative method for preparing certain compounds of Formula 6 when Q is $CH_2$, involving first preparing an isocyanate from the amine of Formula 10 and then reacting the isocyanate with a compound of Formula $R^4H$ wherein $R^4$ is alkoxy or alkylamino to provide a compound of Formula 6. For synthesis of a compound of Formula 6 wherein Q is $NR^7$ and $R^7$ is H see Step C of Example 1.

Scheme 6

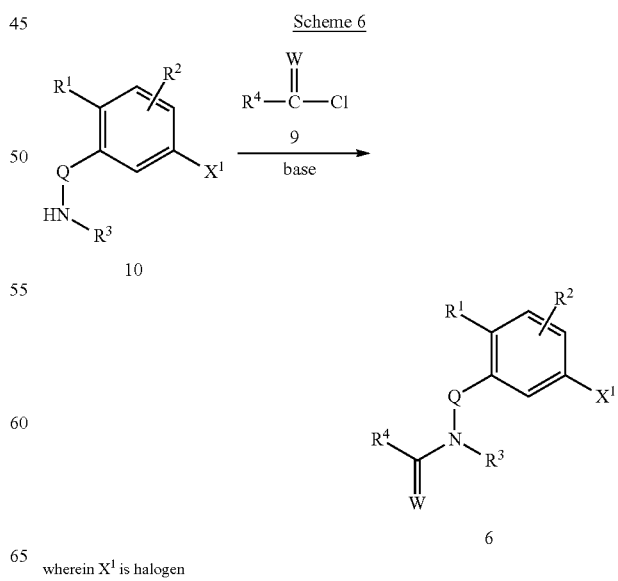

wherein $X^1$ is halogen

Compounds of Formula 8a (Formula 8 wherein Q is $CR^{6a}R^{6b}$) can be prepared by a simple three-step procedure from amines of Formula 11 as outlined in Scheme 7. The amines of Formula 11 are known or can be easily synthesized by general methods known to one skilled in the art. In the first step, an amine of Formula 11 is reacted with acetic anhydride with or without an aprotic solvent such as dichloromethane, chloroform, diethyl ether or tetrahydrofuran at temperatures ranging from about 0 to about 100° C., in the presence of a base such as triethylamine or pyridine with or without a nucleophilic catalyst such as 4-dimethylaminopyridine to provide a compound of Formula 12. The compound of Formula 12 can then be reacted according to Friedel-Crafts conditions to provide a compound of Formula 2b (Formula 2 wherein Q is $CR^{6a}R^{6b}$) which can then be deprotected to yield a compound of Formula 8a. For typical reactions conditions see, European Patent Publication EP 1586552.

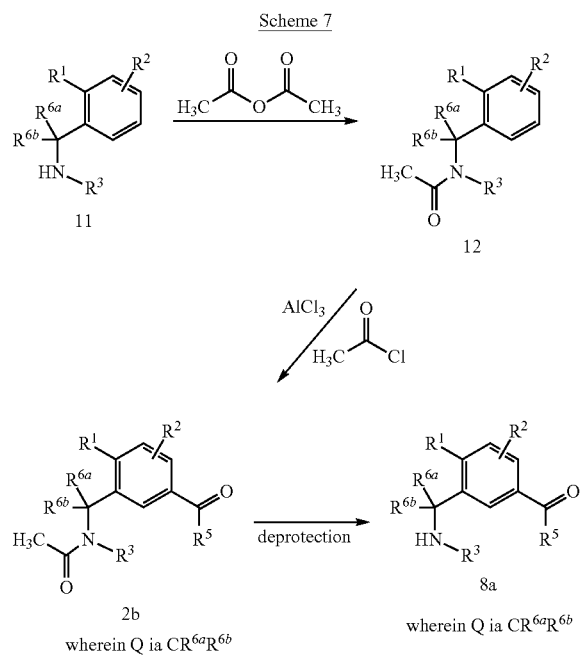

Scheme 7

Compounds of Formula 10 are known or can be easily synthesized by general methods known to one skilled in the art. For example, compounds of Formula 10a (Formula 10 wherein Q is O and $R^3$ is H) can be prepared from simple fluorobenzene derivatives of Formula 14 as shown in Scheme 8. The reaction of a compound of Formula 14 with a acetohydroxamate of Formula 15 is typically carried out in a polar aprotic solvent such as N,N-dimethylformamide in the presence of a suitable base such as potassium tert-butoxide or sodium hydride at temperatures ranging from about −10 to 120° C. The resulting compound of Formula 16 can then be deprotected using a strong acid such as perchloric acid at temperatures ranging from about −10 to about 40° C. to give a compound of Formula 10a (for a relevant reference see, for example, Kikugawa et al., Organic Preparations and Procedures International 1997, 29(5), 594-600).

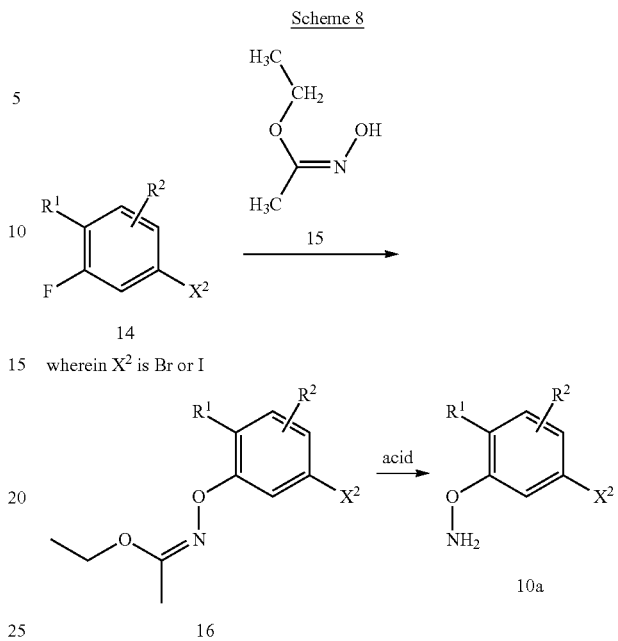

Scheme 8 wherein $X^2$ is Br or I

Compounds of Formula 1c (Formula 1 wherein V is $NR^3$ and Q is C(=O)) wherein Y is a substituted phenyl ring or a 5- or 6-membered heteroaromatic ring can be prepared according to the method of Scheme 9. In the first step of the method of Scheme 9 a compound of Formula 18 is reacted with a suitable base such as sodium hydride or potassium tert-butoxide in a solvent such as tetrahydrofuran or N,N-dimethylformamide and then reacted with a compound of Formula 17, which is either commercially available or readily prepared from the corresponding carboxylic acid by known procedures, at temperatures ranging from about −10 to about 40° C. to yield a compound of Formula 6a. Compounds of Formula 1c can then be prepared by Suzuki reaction coupling procedures using a substituted phenyl or heteroaromatic boronic acid of Formula 7 via Pd-catalyzed cross-coupling of the aromatic iodide or bromide compound of Formula 6a (for reaction conditions see, for example, Suzuki, et al., Chemical Review, 1995, 95, 2457-2483). Compounds of Formula 1c wherein Y is a N-linked heteroaromatic ring can be prepared via a palladium cross-coupling reaction using compounds of Formula 7a. For leading references see, for example, Buchwald et al., Accounts of Chemical Research, 1998, 31(12), 805-818 and Hartwig, Angew. Chem. Int. Ed., 1998, 37, 2046-2067. For a general synthesis of compounds of Formulae 17 and 18 see, for example, Advanced Organic Synthesis, 4th Edition, Wiley & Sons 1992, 417-418, and 437.

Scheme 9

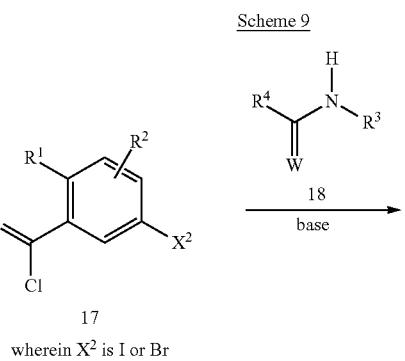

wherein $X^2$ is I or Br

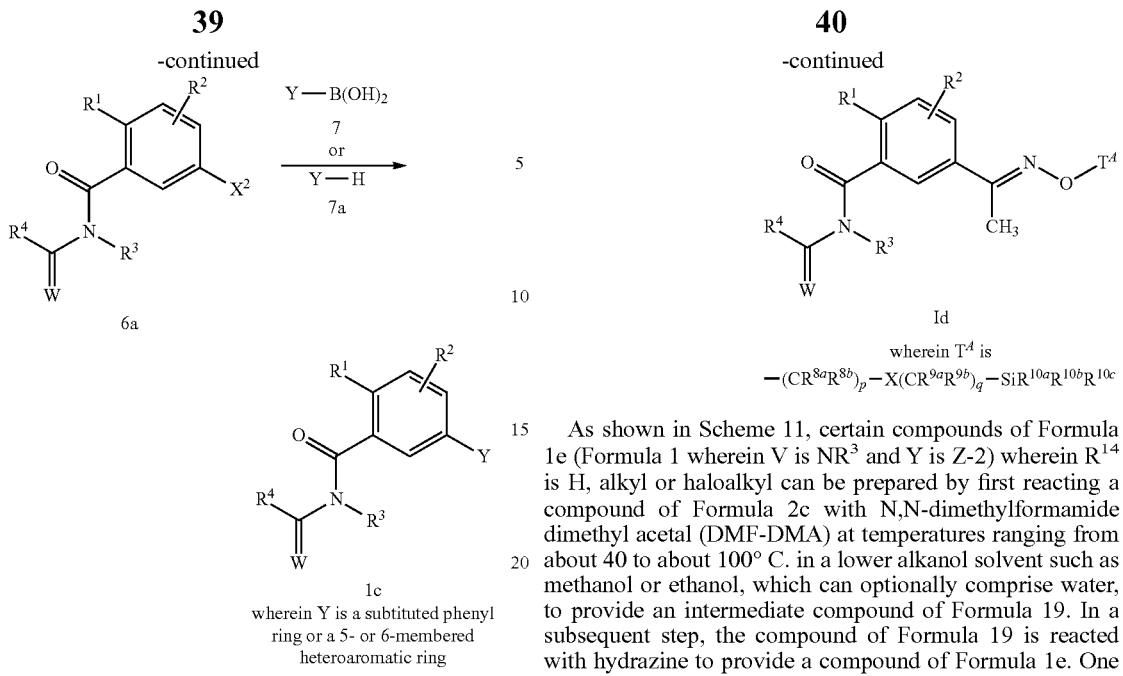

Compounds of Formula 1d (Formula 1 wherein Y is wherein is —C(R⁵)=N—O—(CR⁸ᵃR⁸ᵇ)ₚ—X—(CR⁹ᵃR⁹ᵇ)_q—SiR¹⁰ᵃR¹⁰ᵇR¹⁰ᶜ and R⁵ is CH₃) can be prepared as shown in Scheme 10. The method first involves reacting a compound of Formula 6a with a vinyl ether of Formula 19 in the presence of a palladium catalysis according to the general procedures reported in the literature (see, for example, Xiao et al., *J. Organic Chem.* 2006, 71, 7467-7470) to give a compound of Formula 2a. The compound of Formula 2a can then be converted to a compound of Formula 1d according to the method of Scheme 1 or 2.

As shown in Scheme 11, certain compounds of Formula 1e (Formula 1 wherein V is NR³ and Y is Z-2) wherein R¹⁴ is H, alkyl or haloalkyl can be prepared by first reacting a compound of Formula 2c with N,N-dimethylformamide dimethyl acetal (DMF-DMA) at temperatures ranging from about 40 to about 100° C. in a lower alkanol solvent such as methanol or ethanol, which can optionally comprise water, to provide an intermediate compound of Formula 19. In a subsequent step, the compound of Formula 19 is reacted with hydrazine to provide a compound of Formula 1e. One skilled in the art will recognize that there are other methods for performing transformations of this type, for example, the method described by Barrett et al., *Bioorganic and Medicinal Chemistry Letters* 2005, 15, 3540-3546. The method of Scheme 11 is illustrated in Steps A and B of Example 4.

As shown in Scheme 12, certain compounds of Formula 1f (Formula 1 wherein V is NR³ and Y is Z-2) wherein R¹⁴ is H, alkyl or haloalkyl and $G^4$ is an optionally substituted phenyl ring, benzyl ring or a 5- or 6-membered heteroaromatic can be prepared from a compound of Formula 1e by reaction with a compound of Formula $7^{a'}$. The reaction is optionally run in the presence of a catalyst, typically comprising palladium or copper. For leading references see Buchwald et al., *Accounts of Chemical Research*, 1998, 31(12), 805-818. Alternatively, compounds of Formula 1f can be prepared by reacting a compound of Formula 1e with a boronic acid of Formula 7' in the presence of a suitable copper salt to provide compounds of Formula 1f. For leading references see Chan et al., in *Boronic Acids*, 205-240, D. G. Hall, Ed., Wiley-VCH. Example 5 illustrates the method of Scheme 12 for the preparation of a compound of Formula 1f from Formula 1e using a boronic acid of Formula 7'. Also, Example 5, Example 6, and Step B of Example 8 illustrate the method of Scheme 12 using a compound of Formula $7^{a'}$.

Scheme 12

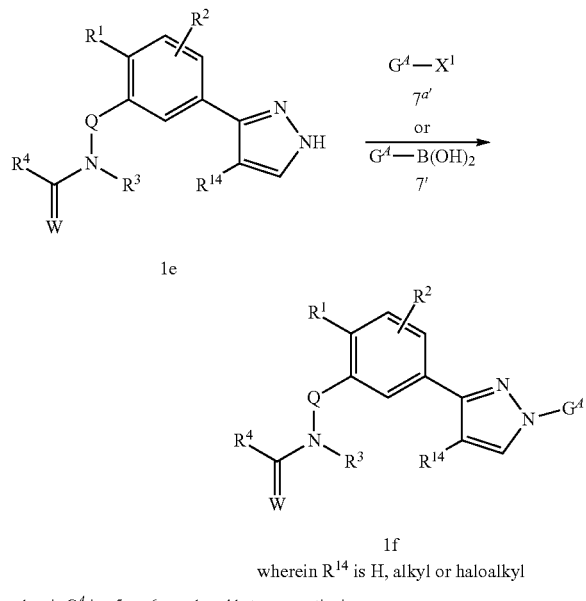

1e 1f
wherein $R^{14}$ is H, alkyl or haloalkyl
wherein $G^4$ is a 5- or 6-membered heteroaromatic ring Certain compounds of Formula 1g (Formula 1 wherein V is $NR^3$ and Y is Z-18) can be prepared by reacting a compound of Formula 19 with an amidine of Formula 20 in the presence of a suitable alkoxide base such as potassium tert-butoxide or alkali hydride base such as sodium hydride at a temperature ranging from about 50 to about 100° C. in a lower alkanol solvent (e.g., methanol or ethanol) to provide a compound of Formula 1g.

Scheme 13

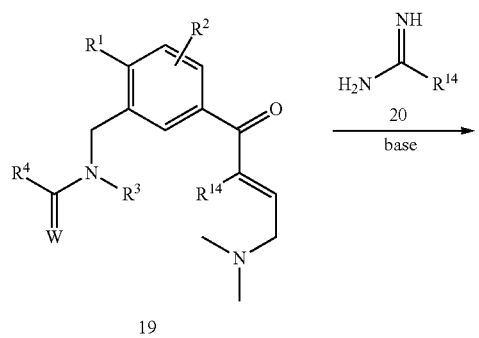

19

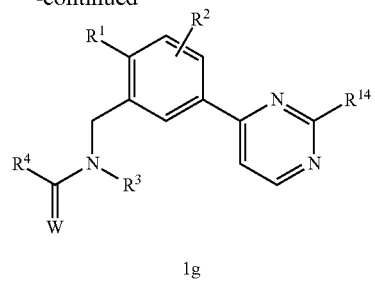

1g

Compounds of Formula 1h (Formula 1 wherein V is $NR^3$ and Y is Z-11, Z-12 or Z-13) wherein $R^{14}$ is H can be prepared in three-step synthesis starting from a compound Formula 6a as outlined in Scheme 14.

In step 1 of Scheme 14, trimethylsilyl substituted alkynes of Formula 20 are obtained by contacting a compound of Formula 6a with ethynyltrimethylsilane in the presence of a suitable palladium catalyst (such as, for example, tetrakis(triphenylphosphine)palladium or dichlorobis(triphenylphosphine)palladium) and in the presence of a suitable copper catalyst (such, as for example, copper(I) iodide). In this method the mole ratio of ethynyltrimethylsilane to the compound of Formula 6a is typically from about 1.1 to about 5, and the mole ratios of the palladium catalyst and the copper catalyst to the compound of Formula 6a are each about 0.005 to about 0.1. The reaction is preferably run in the presence of a suitable amine base such as, for example, an amine base comprising triethylamine, N,N-diisopropylethylamine, diethylamine or piperidine. The reaction is preferably conducted in the presence of a solvent. However, in some cases the reaction can be carried out without solvent other than the compound of Formula 6a, the ethynyltrimethylsilane and the amine base. But a preferred procedure involves use of a suitable solvent including, for example, tetrahydrofuran, toluene or N,N-dimethylformamide. Further preferred as a solvent is a mixture of the suitable solvent with the amine base. When the solvent comprises the amine base or a combination of the amine base and the suitable solvent, the amine base is typically in large stoichiometric excess relative to the compound of Formula 6a. For an example illustrating the method Scheme 14 for the preparation of a compound of Formula 20 see Step C of Example 9.

In step 2 of Scheme 14, removal of the trimethylsilane group to give an alkyne of Formula 21 is achieved by treating a compound Formula 20 with an alkali metal hydroxide or carbonate such as potassium hydroxide, sodium hydroxide or potassium carbonate in methanol or ethanol. Typically the mole ratio of the base to the compound of Formula 20 is from about 0.001 to about 5. The reaction is preferably conducted in a suitable organic solvent. Typically, the method is most satisfactorily conducted at a temperature ranging from about 0° C. to the reflux temperature of the solvent, and most preferably from about 25 to 30° C. Alternatively, other disilylating conditions known in the art can be used, such as treatment with tetrabutylammonium fluoride in solvents such as tetrahydrofuran and chloroform (optimally comprising water). For an example illustrating the method of Scheme 14 for the preparation of a compound of Formula 21 see Step D of Example 9.

In step 3 of Scheme 14, compounds of Formula 1h are prepared by reacting alkynes of Formula 21 with a suitable source of azide ions and in the presence of at least one copper(I) salt. Suitable azide sources include, for example, sodium azide and trimethylsilyl azide. The mole ratio of the azide source relative to the compound of Formula 21 is typically from about 1 to about 3. In the present method, suitable copper(I) salts comprise one or more compounds selected from the group consisting of copper(I) iodide, copper(I) bromide and copper(I) chloride. Alternatively, a copper(II) salt can be used in combination with a mild reducing agent, for example copper(II) sulfate with sodium ascorbate. The mole ratio of the copper(I) salt to the compound of Formula 21 is typically from about 0.05 to about 0.2. The reaction is typically run in a solvent such as N,N-dimethylformamide, tetrahydrofuran, methanol, tert-butanol, dimethyl sulfoxide (optionally comprising water), at temperatures from about 25 to 100° C. The use of lower boiling solvents can in some cases necessitate the need for elevated pressure to facilitate running the reaction at temperatures higher then the normal boiling point of the solvent. For leading references describing the method of step 3 of Scheme 14 see Jin et al., *European J. Organic Chem.* 2004, 3789-3791; Anderson et al., *Synlett* 2005, 2941-2947; and Weinreb et al., *Tetrahedron Letters* 2006, 47, 3035-3038. For an example illustrating the method of Scheme 14 for the preparation of a compound of Formula 1h see Step E of Example 9.

amount ranging from about 1 to 10 molar equivalents. Optimum results are usually obtained when the reaction is run in a polar solvent such as N,N-dimethylformamide, tetrahydrofuran, acetone, 2-butanone or dimethyl sulfoxide, at temperatures ranging from about 0° C. to 150° C. (depending on the solvent). Typically these reaction conditions provide a mixture of N-alkylated triazole isomers of Formula 1i, which can be purified by chromatography. For representative procedures see Caliendo et al., *European Journal of Pharmaceutical Sciences*, 2002, 16, 15-28; Seto et al., *Bioorganic & Medicinal Chemistry* 2005, 13, 363-386; and Fray et al., *J. Medicinal Chemistry* 2001, 44, 1951-1962. Also, Example 11 illustrates the method of Scheme 15 for the preparation of a compound of Formula 1h wherein $R^{14}$ is 4-methylbenzyl.

Compounds of Formula 1h can also be N-arylated to provide certain compounds of Formula 1i wherein $R^{14}$ is an optionally substituted N-phenyl ring. This can be accomplished by reacting a compound of Formula 1h with a phenyl iodide, bromide or chloride in the presence of iron(III) acetylacetonate (Fe(acac)$_3$), copper oxide and cesium carbonate in N,N-dimethylformamide at temperatures ranging from about 25 to about 150° C. as described by Taillefer et al., *Angew. Chem. Int. Ed.* 2007, 46, 934-936. Typically mixtures of regioisomers of Formula 1i are obtained from

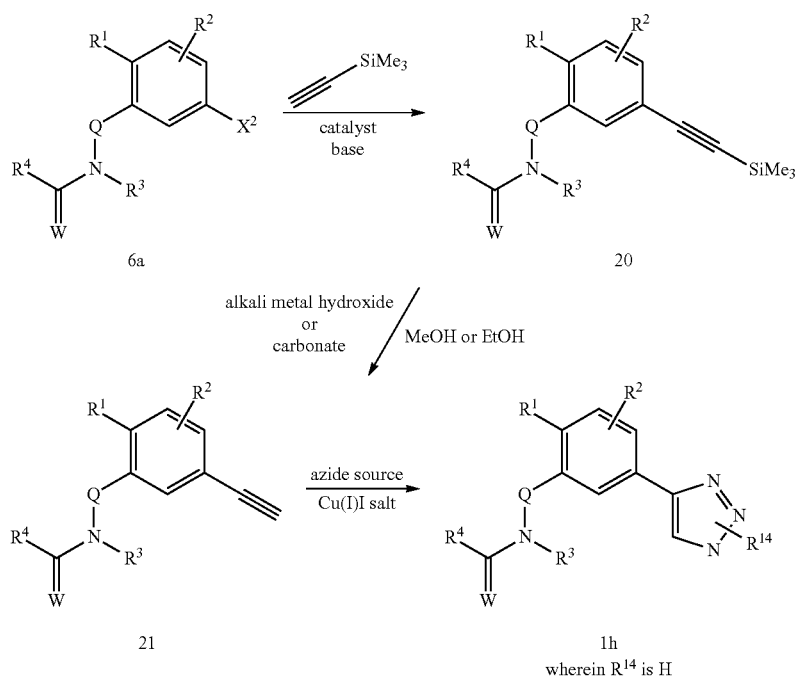

As depicted in Scheme 15, compounds of the Formula 1h are useful as intermediates for preparing compounds of Formula 1i (Formula 1 wherein V is $NR^3$ and Y is Z-11, Z-12 or Z-13) wherein $R^{14}$ is other than H. For example, compounds of Formula 1i wherein $R^{14}$ is an optionally substituted N-alkyl group can be obtained by treating a compound of Formula 1h with an alkylating agent, typically in amount ranging from about 1 to about 10 molar equivalents relative to the compound of Formula 1h. The reaction is preferably run in the presence of a base such as potassium carbonate, sodium hydride or potassium tert-butoxide typically in an these reactions. Purification of the regioisomers is achieved by chromatography. For representative procedures see Beauchard et al., *Tetrahedron* 2006, 62, 1895-1903. Also Example 10 illustrates the method of Scheme 15 when $R^{14}$ is 4-chlorophenyl.

Certain compounds of Formula 1i wherein $R^{14}$ is cyano can be prepared by reacting a compound of Formula 1h with cyanogen bromide in the presence of a base such a sodium hydride in solvents such as tetrahydrofuran or N,N-dimethylformamide. For representative procedures see Nakajima et al., *J. Organic Chem.* 1978, 43(13), 2693-2696.

Certain compounds of Formula 1i wherein $R^{14}$ is Cl can be prepared by reacting a compound of Formula 1h with sodium hypochlorite in acetic acid using procedures analogous to those described by Canada et al., *Heterocycles* 1985, 23(9), 2225-2228.

The formation of compounds of Formula 1i wherein $R^{14}$ is OH can be achieved by reacting a compound of Formula 1h with an oxidizing agent such as hydrogen peroxide or m-chlorobenzoic acid (MCPBA) using procedures analogous to those described by Uhlmann et al., *J. Organic Chem.*, 1997, 62, 9177-9181 and Begtrup et al., *Journal of the Chemical Society, Perkin Transactions* 1, (3) 1995, 243-247, respectively. Additionally, representative procedures illustrating methods for preparing certain compounds of Formula 1i wherein $R^{14}$ is an optionally substituted carbonyl group are described in *Chemistry of Heterocyclic Compounds* 1984, 20, 1392-1393. Representative procedures for the formation of compounds of Formula 1i wherein $R^{14}$ is an alkenyl group are disclosed in Taillefer et al., *Chemistry—A European Journal* 2006, 12(20), 5301-5313.

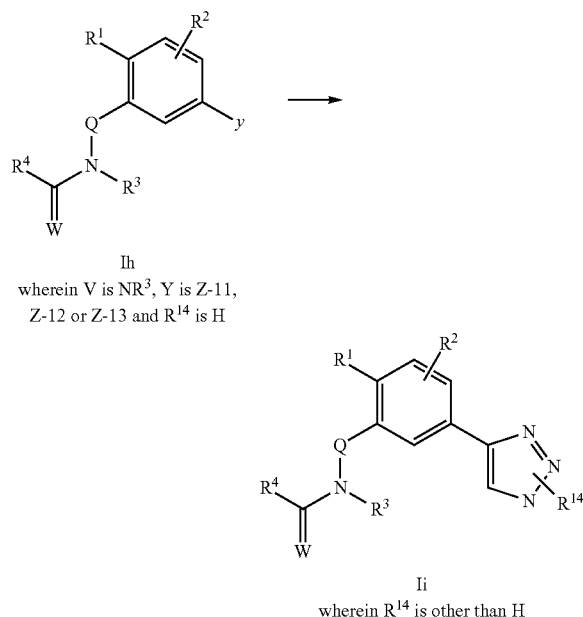

As shown in Scheme 16, certain compounds of Formula 1j (Formula 1 wherein Q is $CH_2$ and V is $NR^3$) wherein Z is Z-1 or Z-7 substituted with $R^{14}$ and $R^{14}$ is other than H can be prepared by brominating a compound of Formula 22 using a brominating agent such as N-bromosuccinimide (NBS) or bromine. Bromination methods of this type are well documented in the chemical literature. For leading references see, for example, Song et al., *Synthetic Communications* 2007, 37(19), 3311-3317; Andrus et al., *Organic Letters* 2007, 9(23), 4865-4868; *Organic & Biomolecular Chemistry* 2007, 5(16), 2555-2559; Piazzi et al., *Journal of Medicinal Chemistry* 2007, 50(17), 4250-4254 and Zhao et al., *Journal of Agricultural and Food Chemistry* 2007, 55(14), 5697-5700. Also, U.S. Pat. No. 6,313,071 provides an example relevant to the bromination method of Scheme 16. Additionally, Step A of Example 15 illustrates the bromination method of Scheme 16.

In the second step, treatment of the benzyl bromide of Formula 23 with potassium cyanate or sodium cyanate and a compound of Formula $R^4H$ wherein $R^4$ is an alkoxy or alkylamino group provides compounds of Formula 1j. The reaction is typically carried out in a solvent such as N,N-dimethylformamide at temperatures ranging from about room temperature to 100° C. according to the procedure described in U.S. Pat. No. 6,313,071, also Step B of Example 15 illustrates the method of Scheme 16.

In a subsequent step, compounds of Formula 1j wherein W is O are converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

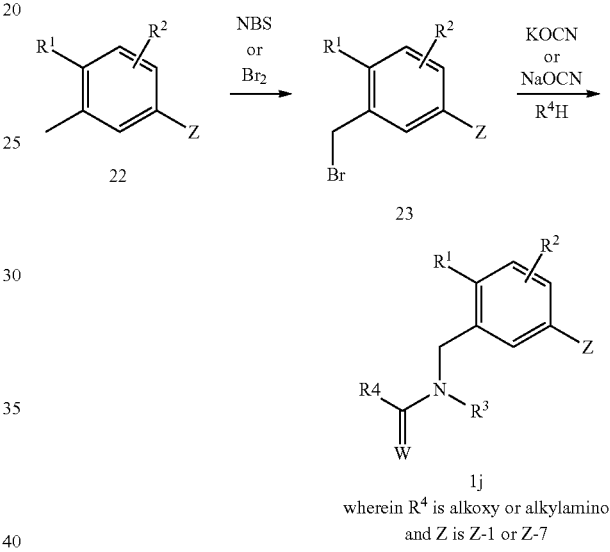

Compounds of Formula 22 wherein Z is Z-1 are either commercially available or can be prepared by known methods. As illustrated in Scheme 17, compounds of Formula 22a (Formula 22 wherein Z is Z-7) can be prepared by treating a compound of Formula 24 with an oxidizing agent such as hydrogen peroxide or silver carbonate according to the procedures taught by Paulvannan et al., *Tetrahedron* 2000, 56(41), 8071-8076 and Buzykin et al., *Synthesis* 1993, (1), 59-61.

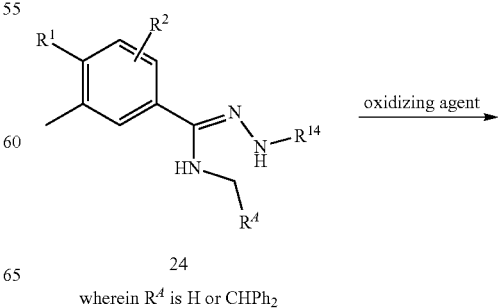

-continued

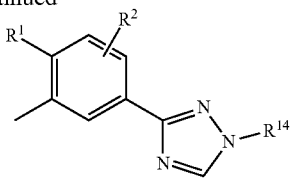

22a wherein R⁴ is other than H

As shown in Scheme 18, a compound of Formula 24 can be prepared by reacting a compound of Formula 25 with methylamine or 2,2-diphenylethylamine according to the procedure given in Paulvannan et al., *Tetrahedron* 2000, 56(41), 8071-8076 and Buzykin et al., *Synthesis* 1993, (1) 59-61.

Scheme 18

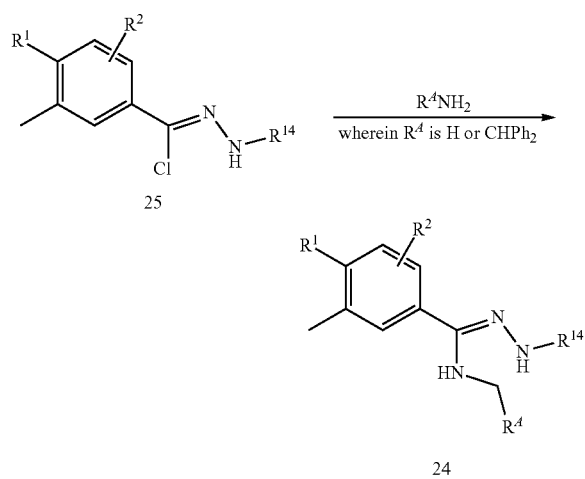

In the method of Scheme 19, a compound of Formula 25 is prepared by first reacting a an aldehyde of Formula 26 with a hydrazine of Formula 27 to provide the intermediate compound of Formula 28. For leading reference teaching this method see *Tetrahedron* 2000, 56(41), 8071-8076; Lebedev et al., *J. Organic Chemistry* 2005, 70(2), 596-602 and Halley et al., *Synthetic Communications* 1997, 27(7), 1199-1207. In a subsequent step the compound of Formula 28 is chlorinated using a chlorinating agent such N-chlorosuccinimide (NCS). For references relevant to this type of chlorination see Paulvannan et al., *Tetrahedron* 2000, 56(41), 8071-8076; Patel et al., *Tetrahedron* 1996, 52(2), 661-668 and Chen et al., *Chemistry Letters* 1998 (2), 285-288. Compounds of Formula 26 can be prepared by methods well documented in the chemistry art, and many are commercially available.

Scheme 19

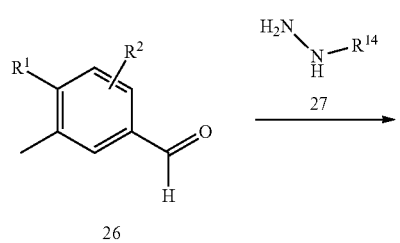

-continued

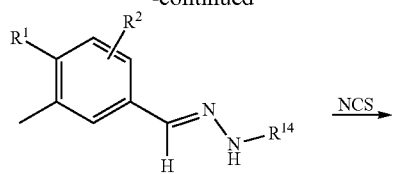

28

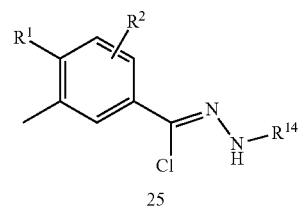

25

As shown in Scheme 20, certain compounds of Formula 1k (Formula 1 wherein Q is C(=O) and V is a direct bond) wherein W is O can be prepared according to the method disclosed in World Patent Publication WO 99/28305 and by Walker, *Chimia* 2003, 57(11), 675-679. Reaction conditions for the method of Scheme 20 for the preparation of a compound of Formula 1k are also illustrated in Step D of Example 12. Compounds of Formula 1k are useful intermediates for preparing certain compounds of Formula 1m (Formula 1 wherein Q is C(=N)—OR⁷ and V is a direct bond) wherein W is O. For leading references relevant to this type of reaction see, for example, World Patent Publication WO 99/28305 and by Walker, *Chimia* 2003, 57(11), 675-679. Also, the method of Scheme 20 for the preparation of a compound of Formula 1m is illustrated in Example 13.

Scheme 20

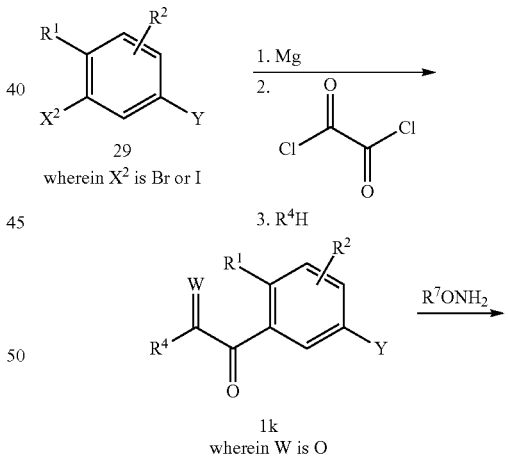

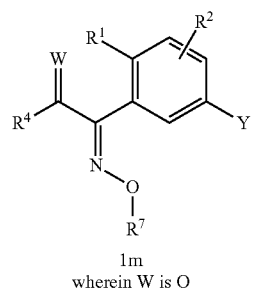

1m
wherein W is O

Alternatively, a compound of Formula 1m can also be prepared as shown in Scheme 21. The method of Scheme 21 is described in World Patent Publication WO 99/28305 and by Walker, *Chimia* 2003, 57(11), 675-679.

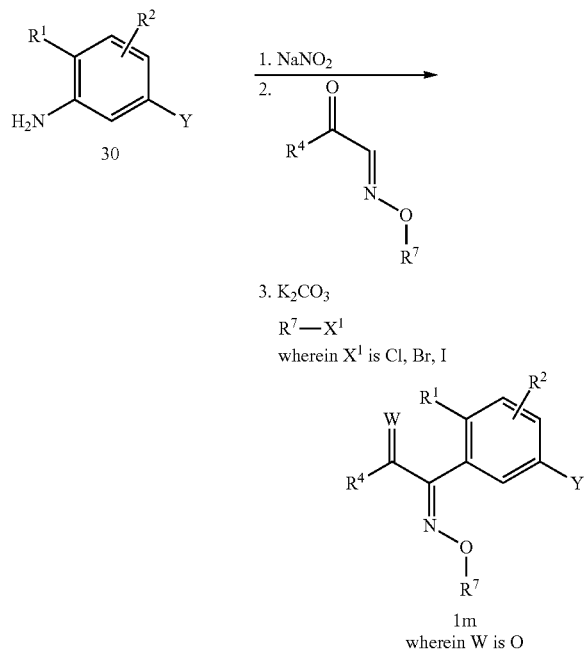

Scheme 21 wherein W is O

One skilled in the art will recognize that certain compounds of Formula 1m wherein $R^4$ is an alkoxy group can be converted to the corresponding alkylamino compound by treatment of Formula 1m with an amine of Formula $R^4NH_2$. For this type of transformation, one or more equivalents of the amine (i.e. $R^4NH_2$) can be used relative to Formula 1m. Alternatively, one equivalent of the amine and an acid scavenger (e.g., triethylamine) can be used. The reaction can be run with or without solvent, including using the amine as the solvent, at temperatures ranging between about room temperature and the normal boiling point of the solvent. It is understood by one skilled in the art, that when the amine is used as a solvent it will be in large stoichiometric excess relative to the compound of Formula 1m (Example 14 illustrates this method).

Additionally, one skilled in the art will recognize that compounds of Formula 1m wherein W is O can be converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "dd" means doublet of doublets, and "br s" means broad singlet Example 1

Preparation of methyl N-[[2-chloro-5-[1-[[2-(trimethylsilyl)ethoxy]imino]ethyl]phenyl]-methyl]carbamate A solution of methyl N-[(5-acetyl-2-chlorophenyl)methyl]acetamide (0.15 g, 0.62 mmol) (prepared according the method given in European Patent Publication EP 1586552) and 3-trimethylsilylethylhydroxylamine hydrochloride (0.21 g, 1.2 mmol) in ethanol (20 mL) was heated at refluxed overnight. The ethanol was then removed under reduced pressure, and the residual oil was purified by medium pressure liquid chromatography (0 to 100% gradient of ethyl acetate in hexanes as eluant) to yield the title compound, a compound of the present invention, as a clear oil (0.20 g).

$^1$H NMR (CDCl$_3$): δ 7.66 (br s, 1H), 7.51 (m, 1H), 7.34 (d, 1H), 5.21 (br s, 1H), 4.46 (d, 2H), 4.28 (m, 2H), 3.69 (s, 3H), 2.20 (s, 3H), 1.09 (m, 2H), 0.06 (s, 9H).

Example 2

Preparation of methyl N-[[2-chloro-5-[1-[[2-(trimethylsilyl)propoxy]imino]ethyl]phenyl]-methyl]carbamate To a solution of methyl N-[(5-acetyl-2-chlorophenyl)methyl]acetamide (0.5 g, 2.1 mmol) (prepared according the method given in European Patent Publication EP 1586552) in ethanol (10 mL) was added an aqueous solution hydroxylamine (50% by wt) (0.82 g, 12.4 mmol). The reaction mixture was heated at refluxed overnight, and then concentrated to provide methyl N-[[2-chloro-5-[1-(hydroxyimino)ethyl]phenyl]methyl]carbamate as a white solid, which was used without purification. To N,N-dimethylformamide (5.0 mL) was added methyl N-[[2-chloro-5-[1-(hydroxyimino)ethyl]phenyl]methyl]carbamate (0.28 g, 1.1 mmol), 3-(chloropropyl)trimethylsilane (0.33 g, 2.2 mmol) and potassium carbonate (0.45 g, 3.3 mmol). This reaction mixture was then heated at 100° C. overnight, and then concentrated under reduced pressure. The resulting oil was purified by medium pressure liquid chromatography (0 to 100% gradient of ethyl acetate in hexanes as eluant) to yield the title compound, a compound of the present invention, as a clear oil. (0.22 g).

$^1$H NMR (CDCl$_3$): δ 7.66 (br s, 1H), 7.52 (m, 1H), 7.35 (m, 1H), 5.18 (m, 1H), 4.46 (d, 2H), 4.14 (m, 2H), 3.69 (s, 3H), 2.21 (s, 3H), 1.71 (m, 2H), 0.54 (m, 2H), 0.01 (m, 9H).

Example 3

Preparation of methyl 2-[4-chloro-3'-(trifluoromethoxy)[1,1'-biphenyl]-3-yl]hydrazine carboxylate Step A: Preparation of 5-bromo-2-chlorophenylhydrazine hydrochloride A suspension of 5-bromo-2-chloroaniline (23 g, 0.11 mol) in concentrated hydrochloric acid (150 mL) and water (90 mL) was cooled in an ice/salt bath. A solution of sodium nitrite (8 g, 0.11 mol) in water (50 mL) was added dropwise to the reaction mixture while maintaining the temperature below 4° C. After stirring for 30 minutes the suspension was transferred via cannula to a solution of SnCl$_2$ dihydrate in concentrated hydrochloric acid (170 mL) and cooled to 5° C. The resulting thick suspension was stirred for 2 h at 5° C. and the solid was isolated via filtration. The solid was air dried and then further dried by adding chlorobutane (500 mL) and refluxing using a Dean-Stark condenser. After cooling, the solid was isolated by filtration to afford the title compound as an off-white solid (35.3 g).

$^1$H NMR (CD$_3$COCD$_3$): δ 10.25 (br s, 1H), 8.32 (br s, 2H) 7.38 (d, 1H), 7.30 (d, 1H), 7.16 (dd, 1H).

Step B Preparation of methyl 2-(5-bromo-2-chlorophenyl)hydrazine carboxylate

To a mixture of 2-(5-bromo-2-chlorophenyl) hydrazine carboxylic acid methyl ester (i.e. the product of Step A) (2.1 g, 8 mmol) and methyl chloroformate (1 mL, 13 mmol) in tetrahydrofuran at 0° C. was added N,N-diisopropylethylamine (4 mL, 24 mmol). The reaction mixture was allowed to slowly warm to room temperature and was stirred for three days. Ethyl acetate and water were added. The layers were separated, and the aqueous layer was extracted with ethyl acetate. The combined organic layers were washed with water and a solution of saturated aqueous sodium chloride and dried. The solvent was removed under reduced pressure to afford the title compound as a pale yellow solid (1.4 g).

$^1$H NMR (CDCl$_3$): δ 7.13 (d, 1H), 7.08 (d, 1H), 7.16 (dd, 1H), 6.60 (br s, 1H), 6.23 (br s, 1H), 3.29 (s, 3H).

Step C Preparation of methyl 2-[4-chloro-3'-(trifluoromethoxy)[1,1'-biphenyl]-3-yl]hydrazine carboxylate A mixture of methyl 2-(5-bromo-2-chlorophenyl)hydrazine carboxylate (i.e. the product of Step B) (1.27 g, 4.5 mmol), [3-(trifluoromethoxy)phenyl]boronic acid (1.85 g, 9 mmol), cesium carbonate (2.9 g, 9 mmol), tris(dibenzylideneacetone)dipalladium (0.18 g, 0.2 mmol) and triphenylphosphine (1.2 g, 4.5 mmol) in toluene (60 mL) and methanol (60 mL) was heated at refluxed for 24 h. After cooling, the reaction mixture was taken up in diethyl ether and washed with water. After drying over sodium sulfate, the solvent was removed under reduced pressure. The residue was purified by flash chromatography using 25% ethyl acetate in hexanes as eluant to afford a solid material (1.3 g), which was a mixture of starting material and the title compound.

The solid material was dissolved in toluene (50 mL) and methanol (50 mL), and then [3-(trifluoromethoxy)phenyl] boronic acid (0.82 g, 4 mmol), cesium carbonate (2.6 g, 8 mmol), tris(dibenzylideneacetone)dipalladium (0.18 g, 0.2 mmol) and triphenylphosphine (0.52 g, 2 mmol) were added. The reaction mixture was heated at reflux for three days. After cooling, the reaction mixture was taken up in diethyl ether and washed with water. After drying over sodium sulfate, the solvent was removed under reduced pressure. The residue was purified by flash chromatography (75 to 100% gradient of dichloromethane in 1-chlorobutane as eluant) to afford an oily solid (0.67 g). The oily solid was triturated with hexanes to afford the title compound, a compound of the present invention, as a white solid (0.475 g) melting at 98-100° C.

$^1$H NMR (CDCl$_3$): δ 7.45 (m, 2H), 7.35 (m, 2H), 7.20 (m, 1H), 7.11 (d, 1H), 7.02 (dd, 1H), 6.55 (br s, 1H), 6.32 (br s, 1H), 3.78 (s, 3H).

Example 4

Preparation of methyl N-[[2-chloro-5-(1H-pyrazol-3-yl)phenyl]methyl]carbamate

Step A: Preparation of methyl N-[[2-chloro-5-[3-(dimethylamino)-1-oxo-2-propen-1-yl]phenyl] methyl]carbamate A solution of methyl N-[(5-acetyl-2-chlorophenyl) methyl]acetamide (3.5 g, 14.5 mmol) (prepared by the method given in European Patent Publication EP 1586552) in N,N-dimethylformamide dimethyl acetal (5.36 g, 43.5 mmol) was added to toluene (35 mL). The reaction mixture was heated at reflux overnight and then concentrated under reduced pressure. The resulting residue was dissolved in ethyl acetate and washed with water (4×). The organic layer was dried over magnesium sulfate, filtered and concentrated to provide the crude product as an oil (4.14 g), which was used without further purification.

Step B Preparation of methyl N-[[2-chloro-5-(1H-pyrazol-3-yl)phenyl]methyl]carbamate To a solution of methyl N-[[2-chloro-5-[3-(dimethylamino)-1-oxo-2-propen-1-yl]phenyl]methyl]carbamate (i.e. the product of Step A) (4.14 g, 13.9 mmol) in methanol (80 mL) was added hydrazine hydrate (0.771 g, 15.4 mmol). The reaction mixture was stirred at room temperature for 2 days. The reaction mixture was filtered and the solid collected was dried under reduced pressure to provide the title compound, a compound of the present invention, as a solid (3.26 g).

$^1$H NMR (DMSO-d$_6$): δ 12.95 (br s, 1H), 7.80 (d, 2H), 7.70 (m, 1H), 7.44 (d, 1H), 6.69 (m, 1H), 4.30 (d, 2H), 3.58 (s, 3H).

Example 5

Preparation of methyl N-[[2-chloro-5-[1-(4-chlorophenyl)-1H-pyrazol-3-yl]phenyl]methyl]-carbamate To a mixture of methyl N-[[2-chloro-5-(1H-pyrazol-3-yl) phenyl]methyl]carbamate (i.e. the product of Step B, Example 4) (0.2 g, 0.75 mmol), trans-N,N'-dimethylcyclohexane-1,2-diamine (0.043 g, 0.3 mmol), copper(I) iodide (0.03 g, 0.15 mmol) and potassium carbonate (–325 mesh) (0.622 g, 4.5 mmol) in dioxane (4 mL) was added 1-chloro-4-iodobenzene (0.27 g, 1.13 mmol). The reaction mixture heated at reflux overnight and then concentrated under reduced pressure. The resulting residue was purified by medium pressure liquid chromatography (0 to 100% gradient of ethyl acetate in hexanes as eluant) to provide the title compound, a compound of the present invention, as a solid (0.156 g) melting at 151-153° C.

$^1$H NMR (CDCl$_3$): δ 7.92 (m, 2H), 7.77 (m, 1H), 7.71 (m, 2H), 7.43 (m, 3H), 6.76 (d, 1H), 5.21 (br s, 1H), 4.52 (d, 2H), 3.70 (s, 3H).

Example 6

Preparation of methyl N-[[2-chloro-5-[1-[[3-(trifluoromethoxy)phenyl]methyl]-1H-pyrazol-3-yl]phenyl]methyl]carbamate A mixture of methyl N-[[2-chloro-5-(1H-pyrazol-3-yl)phenyl]methyl]carbamate (i.e. the product of Step B, Example 4) (0.2 g, 0.75 mmol), 1-(bromomethyl)-3-(trifluoromethoxy)benzene (0.765 g, 3.0 mmol) and potassium carbonate (–325 mesh, 0.829 g, 6.0 mmol) in N,N-dimethylformamide (4 mL) was heated at 100° C. overnight and then concentrated under reduced pressure. The resulting residue was purified by medium pressure liquid chromatography (0 to 100% gradient of ethyl acetate in hexanes as eluant) to provide the title compound, a compound of the present invention, as a solid (0.178 g).

$^1$H NMR (CDCl$_3$): δ 7.92 (m, 2H), 7.81 (s, 1H), 7.67 (m, 1H), 7.39 (m, 3H), 7.15 (t, 2H), 7.08 (s, 1H), 6.59 (d, 1H), 5.36 (s, 2H), 5.20 (br s, 1H), 4.49 (d, 2H), 3.69 (s, 3H).

Example 7

Preparation of methyl N-[[2-chloro-5-[2-(4-methylphenyl)-4-pyrimidinyl]phenyl]methyl]-carbamate To mixture of methyl N-[[2-chloro-5-[3-(dimethylamino)-1-oxo-2-propen-1-yl]phenyl]-methyl]carbamate (i.e. the product of Step A, Example 4) (0.43 g, 1.44 mmol), 4-methylbenzamidine hydrochloride (0.74 g, 4.33 mmol) and sodium hydride (0.14 g, 5.8 mmol) at 0° C. was slowly added methanol (5 mL). The reaction mixture was heated at reflux overnight. A solution of saturated ammonium chloride was added to the reaction mixture, and the mixture was concentrated under reduced pressure. The resulting residue was dissolved in ethyl acetate, washed with saturated aqueous sodium carbonate, dried over magnesium sulfate, filtered and concentrated under reduced pressure. The resulting residue was purified by medium pressure liquid chromatography (0 to 100% gradient of ethyl acetate in hexanes as eluant) to provide the title compound, a compound of the present invention, as a solid (0.160 g).

$^1$H NMR (CDCl$_3$): δ 7.92 (m, 2H), 8.81 (d, 1H), 8.44 (d, 2H), 8.21 (br s, 1H), 7.15 (t, 2H), 7.08 (s, 1H), 6.59 (d, 1H), 5.36 (s, 2H), 5.20 (br s, 1H), 4.49 (d, 2H), 3.69 (s, 3H).

Example 8

Preparation of methyl N-[[2-chloro-5-[1-[3-(1-methylethyl)-1,2,4-thiadiazol-5-yl]-1H-pyrazol-3-yl]phenyl]methyl]carbamate Step A: Preparation of 5-chloro-3-(1-methylethyl)-1,2,4-thiadiazole To a mixture of 2-methyl propanimidamide hydrochloride (5.0 g, 40.8 mmol), trichloromethanesulfonyl chloride (7.14 g, 38.4 mmol) in methylene chloride (200 mL) at 0° C. was added dropwise an aqueous solution of sodium hydroxide (50%, 9.9 mL) over 20 minutes. The reaction mixture was stirred for 2 h at 0° C. and then was allowed to warm to room temperature, and stirred for an additional 3 h. Ice was added to the reaction mixture, the mixture was separated, and the aqueous layer was extracted with methylene chloride (3×25 mL). The combined organic extracts were dried over magnesium sulfate, filtered and concentrated under reduced pressure. The resulting residue was purified by medium pressure liquid chromatography (0 to 100% gradient of ethyl acetate in hexanes as eluant) to provide the title compound as a oil (3.8 g).

Step B Preparation of methyl N-[[2-chloro-5-[1-[3-(1-methylethyl)-1,2,4-thiadiazol-5-yl]-1H-pyrazol-3-yl]phenyl]methyl]carbamate A mixture of methyl N-[[2-chloro-5-(1H-pyrazol-3-yl)phenyl]methyl]carbamate (i.e. the product of Step B, Example 4) (0.02 g, 0.75 mmol), 5-chloro-3-(1-methylethyl)-1,2,4-thiadiazole (i.e. the product of Step A) (0.61 g, 3.75 mmol) and potassium carbonate (0.25 g, 1.5 mmol) in N-methyl-2-pyrrolidinone (2.5 mL) was heated in a Biotage Creator XM microwave apparatus at 165° C. for 15 minutes. The reaction mixture was poured into water (60 mL), and the aqueous mixture was extracted with ethyl acetate (2×50 mL). The combined organic extracts were washed with water, dried over magnesium sulfate, filtered and concentrated under reduced pressure. The resulting residue was purified by medium pressure liquid chromatography (0 to 100% gradient of ethyl acetate in hexanes as eluant) to provide the title compound, a compound of the present invention, as a solid (0.5 g).

$^1$H NMR (DMSO-d$_6$): δ 8.22 (d, 1H), 7.79 (s, 2H), 7.63 (d, 1H), 7.38 (d, 1H), 6.74 (d, 1H), 5.42 (br s, 2H), 4.42 (d, 2H), 3.67 (s, 3H), 3.18 (m, 1H), 1.37 (d, 6H).

Example 9

Preparation of methyl N-[[2-chloro-5-(1H-1,2,3-triazol-5-yl)phenyl]methyl]carbamate Step A: Preparation of 2-(bromomethyl)-1-chloro-4-iodobenzene To a mixture of 2-chloro-5-iodotoluene (4.07 g, 16.12 mmol), N-bromosuccinimide (3.16 g, 17.73 mmol) in dichloromethane (258 mL) and water (258 mL) was added 2,2'-azodiisobutyronitrile (0.132 g, 0.81 mmol). The reaction mixture was irradiated with a halogen sun lamp (150 watt) for 2 h and then cooled to room temperature. The two-phase reaction mixture was separated, and the aqueous layer was extracted with dichloromethane (50 mL). The combined organic layers were washed with water (2×150 mL), dried over magnesium sulfate, filtered and concentrated under reduced pressure to provide the title compound as an orange oil (5.20 g).

$^1$H NMR (CDCl$_3$): δ 7.76 (d, 1H), 7.58 (d, 1H), 7.11 (d, 1H), 4.49 (s, 2H).

Step B Preparation of methyl [(2-chloro-5-iodo-phenyl)methyl]carbamate

To a mixture of potassium carbonate (4.30 g, 53.3 mmol) in N,N-dimethylformamide (47 mL) and methanol (5 mL) at 50° C. was added a solution of 2-(bromomethyl)-1-chloro- 4-iodobenzene (i.e. the product of Step A) (5.20 g, 15.7 mmol) in N,N-dimethylformamide (10 mL). The reaction mixture was heated at 110° C. for 1 h and then cooled to room temperature. The reaction mixture was partitioned between diethyl ether (200 mL) and water (200 mL), the organic layer was separated, washed with water (3×50 mL), dried over magnesium sulfate, filtered and concentrated under reduced pressure to provide the title compound as a yellow oil (4.32 g).

$^1$H NMR (CDCl$_3$): δ 7.58 (apparent d, 1H), 7.79 (s, 2H), 7.10-7.03 (m, 2H), 5.18 (br s, 1H), 4.40 (d, 2H), 3.71 (s, 3H).

Step C Preparation of methyl N-[[2-chloro-5-[2-(trimethylsilyl)ethynyl]-phenyl]methyl]carbamate A mixture methyl [(2-chloro-5-iodo-phenyl)methyl]carbamate (i.e. the product of Step B) (3.0 g, 9.2 mmol), ethynyltrimethylsilane (1.94 mL, 13.8 mmol), bis(triphenylphosphine)palladium(II) dichloride (0.032 g, 0.05 mmol), copper(I) iodide (0.018 g, 0.09 mmol), triphenylphosphine (0.024 g, 0.09 mmol) in tetrahydrofuran (18 mL) and triethylamine (18 mL) was stirred at room temperature for 30 minutes. The reaction mixture was concentrated onto silica gel (7 g) and then purified by medium pressure liquid chromatography (0 to 25% gradient of ethyl acetate in hexanes as eluant) to provide the title compound as an oil (1.37 g).

$^1$H NMR (CDCl$_3$): δ 7.47 (d, 1H), 7.33-7.22 (m, 2H), 5.16 (br s, 1H), 4.41 (d, 2H), 3.69 (s, 3H), 0.24 (s, 9H).

Step D Preparation of methyl N-[(2-chloro-5-ethynylphenyl)methyl]carbamate

To a solution of methyl N-[[2-chloro-5-[2-(trimethylsilyl) ethynyl]phenyl]methyl]-carbamate (i.e. the product of Step C) (1.37 g, 4.6 mmol) in methanol (28 mL) was added potassium hydroxide (2.3 mL, 1M in methanol). The reaction mixture was stirred at room temperature for 18 h, and then concentrated. The resulting residue was partitioned between ethyl acetate and water, the organic layer was separated, washed with water, dried over magnesium sulfate, filtered and concentrated under reduced pressure to provide the title compound as a brown oil (0.90 g).

$^1$H NMR (CDCl$_3$): δ 7.52 (br s, 1H), 7.38-7.30 (m, 2H), 5.15 (br s, 1H), 4.42 (br d, 2H), 3.70 (s, 3H), 3.11 (s, 1H).

Step E Preparation of methyl N-[[2-chloro-5-(1H-1,2,3-triazol-5-yl)phenyl]methyl]-carbamate To a solution of methyl N-[(2-chloro-5-ethynylphenyl) methyl]carbamate (i.e. the product of Step D) (0.43 g, 1.92 mmol) in N,N-dimethylformamide (3.9 mL) and methanol (0.4 mL) was added trimethylsilyl azide (0.38 mL, 2.89 mmol) and copper(I) iodide (0.019 g, 0.1 mmol). The reaction mixture was heated in a CEM Discover microwave apparatus at 100° C. for 8 h and then allowed to cool to room temperature. The reaction mixture was partitioned between ethyl acetate and aqueous sodium chloride, the layers were separated and the aqueous layer was extracted with ethyl acetate (2×). The combined organic layers were washed with water (3×), dried over magnesium sulfate, filtered and concentrated under reduced pressure to provide the title compound, a compound of the present invention, as a brown solid (0.30 g).

$^1$H NMR (CDCl$_3$): δ 7.94 (s, 1H), 7.83 (s, 1H), 7.70 (d, 1H), 7.42 (d, 1H), 5.28 (br s, 1H), 4.50 (d, 2H), 3.71 (s, 3H).

Example 10

Preparation of methyl N-[[2-chloro-5-[2-(4-chlorophenyl)-2H-1,2,3-triazol-4-yl]phenyl]methyl]carbamate and methyl N-[[2-chloro-5-[1-(4-chlorophenyl)-1H-1,2,3-triazol-4-yl]phenyl]methyl]carbamate A mixture of methyl N-[[2-chloro-5-(1H-1,2,3-triazol-5-yl)phenyl]methyl]carbamate (i.e. the product of Step E, Example 9) (0.53 g, 2.0 mmol), 1-chloro-4-iodobenzene (0.57 g, 2.4 mmol), iron(III) acetylacetonate (0.21 g, 0.6 mmol), copper(II) oxide (0.016 g, 0.2 mmol) and cesium carbonate (1.29 g, 4.0 mmol) in N,N-dimethylformamide (4 mL) was heated at 110° C. for 14 h and then concentrated under reduced pressure. The resulting residue was suspended in ethanol and then concentrated onto silica gel (2 g). The silica gel mixture was purified by flash column chromatography using a Supelco (division of Sigma-Aldrich Co., 595 North Harrison Road, Bellefonte, Pa. 16823, U.S.A.) tube prepacked with 10 g of silica gel (50 μm particle diameter, 70 Å pore size) and 3:1 hexanes-ethyl acetate as eluant to provide methyl N-[[2-chloro-5-[2-(4-chlorophenyl)-2H-1,2,3-triazol-4-yl]phenyl]methyl]carbamate, a compound of the present invention, as a beige solid (0.105 g)

$^1$H NMR (CDCl$_3$): δ 8.08 (d, 2H), 8.04 (s, 1H), 7.96 (br s, 1H), 7.75 (dd, 1H), 7.48-7.44 (m, 3H), 5.25 (br s, 1H), 4.51 (d, 2H), 3.71 (s, 3H).

Also obtained was methyl N-[[2-chloro-5-[1-(4-chlorophenyl)-1H-1,2,3-triazol-4-yl]phenyl]methyl]carbamate, a compound of the present invention, as a brown oil (0.10 g)

$^1$H NMR (CDCl$_3$): δ 8.20 (s, 1H), 7.89 (s, 1H), 7.83 (d, 1H), 7.74 (d, 2H), 7.53 (d, 2H), 5.24 (br s, 1H), 4.52 (d, 2H), 3.70 (s, 3H).

Example 11

Preparation of methyl N-[[2-chloro-5-[2-[(4-methylphenyl)methyl-2H-1,2,3-triazol-4-yl]phenyl]methyl] carbamate and methyl N-[[2-chloro-5-[1-[(4-methylphenyl)methyl-2H-1,2,3-triazol-4-yl]phenyl] methyl]carbamate A mixture of methyl N-[[2-chloro-5-(1H-1,2,3-triazol-5-yl)phenyl]methyl]carbamate (i.e. the product of Step E, Example 9) (0.24, 0.9 mmol), 4-methylbenzyl bromide (0.17 g, 1.1 mmol) and potassium carbonate (0.25 g, 1.8 mmol) in N,N-dimethylformamide (4.5 mL) was heated at 100° C. for 24 h. The reaction mixture was allowed to cool and then partitioned between diethyl ether (50 mL) and water (30 mL). The organic layer was separated, washed with water (3×), dried over magnesium sulfate, filtered and concentrated under reduced pressure. The resulting residue was dissolved in ethyl acetate and ethanol (2:1 mixture) and concentrated onto silica gel, and then purified by flash column chromatography using 5 g of silica gel (0 to 50% gradient of ethyl acetate in hexanes as eluant) to provide methyl N-[[2-chloro-5-[2-[(4-methylphenyl)methyl-2H-1,2, 3-triazol-4-yl]phenyl]methyl]carbamate, a compound of the present invention, as a colorless oil (0.11 g)

$^1$H NMR (CDCl$_3$): δ 7.82 (s, 1H), 7.79 (br s, 1H), 7.61 (d, 1H), 7.38 (d, 1H), 7.24 (d, 2H), 7.13 (d, 2H), 5.56 (s, 2H), 5.23 (br s, 1H), 4.48 (d, 2H), 3.69 (s, 3H), 2.32 (s, 3H).

Also obtained was methyl N-[[2-chloro-5-[1-[(4-methylphenyl)methyl-2H-1,2,3-triazol-4-yl]phenyl]methyl]carbamate, a compound of the present invention, as a colorless oil (0.10 g)

$^1$H NMR (CDCl$_3$): δ 7.77 (s, 1H), 7.72 (d, 1H), 7.65 (s, 1H), 7.39 (d, 1H), 7.21 (s, 4H), 5.52 (s, 2H), 5.21 (br s, 3H), 4.41 (d, 2H), 3.67 (2, 3H), 2.36 (s, 3H).

Example 12

Preparation of methyl 2-methyl-α-oxo-5-[1-[3-(trifluoromethyl)phenyl]-1H-pyrazol-3-yl]benzeneacetate

Step A: Preparation of 1-(3-bromo-4-methyl)-3-(dimethylamino)-2-propen-1-one A solution of 3'-bromo-4'-methylacetophenone (15 g, 70.4 mmol) in N,N-dimethylformamide dimethyl acetal (130 mL, 985 mmol) was heated at reflux overnight. The reaction mixture was cooled to room temperature and concentrated under reduced pressure. The resulting oil (20.2 g) was crystallized from hexanes to obtain the title compound as a yellow solid (15.97 g).

$^1$H NMR (CDCl$_3$): δ 8.0 (s, 1H), 7.8 (d, 1H), 7.7 (d, 1H), 7.2 (d, 1H), 5.6 (d, 1H), 3.1 (br s, 3H), 2.9 (br s, 3H).

Step B Preparation of 3-(3-bromo-4-methylphenyl)-1H-pyrazole

To a solution of 1-(3-bromo-4-methyl)-3-(dimethylamino)-2-propen-1-one (i.e. the product of Step A) (15.97 g, 59.57 mmol) in ethanol (150 mL) was added hydrazine monohydrate (14.4 mL, 299 mmol). The reaction mixture was heated at reflux for 2 h, cooled to room temperature and concentrated under reduced pressure. The resulting solid was diluted with hexanes and filtered to provide the title compound as a white solid (13.95 g).

$^1$H NMR (CDCl$_3$): δ 7.9 (s, 1H), 7.62 (d, 1H), 7.6 (d, 1H), 7.2 (d, 1H), 6.5 (d, 1H), 2.41 (s, 3H).

Step C Preparation of 3-(3-bromo-4-methylphenyl)-1-[3-(trifluoromethyl)phenyl]-1H-pyrazole To a stirred solution of 3-(3-bromo-4-methylphenyl)-1H-pyrazole (i.e. the product of Step B) (5.0 g, 21.09 mmol) in p-dioxane (19 mL) under a nitrogen atmosphere was added 3-iodobenzotrifluoride (5.75 g, 21.11 mmol), copper(I) iodide (0.05 g, 0.262 mmol), trans-1,2-diaminocyclohexane (253.5 μL, 2.10 mmol) and potassium carbonate (6.1 g, 44.14 mmol). The reaction mixture was heated at 100° C. overnight, cooled to room temperature and diluted with water and ethyl acetate. The resulting mixture was separated, and the aqueous layer was extracted with ethyl acetate (3×). The combined organic layers were washed with hydrochloric acid (1N), saturated aqueous sodium chloride, dried over magnesium sulfate, filtered and concentrated under reduced pressure to provide a solid (9 g). Hexanes were added to the solid, and the mixture was filtered to obtain the title compound as a solid (6.4 g).

$^1$H NMR (CDCl$_3$): δ 8.08 (s, 1H), 8.0 (s, 2H), 7.99 (s, 1H), 7.7 (d, 1H), 7.6-7.5 (m, 2H), 7.3 (d, 1H), 6.7 (d, 1H), 2.4 (s, 3H).

Step D Preparation of methyl 2-methyl-α-oxo-5-[1-[3-(trifluoromethyl)phenyl]-1H-pyrazol-3-yl]benzeneacetate To a mixture of magnesium turnings (0.17 g, 6.98 mmol) and 1,2-dibromoethane (2 drops) in tetrahydrofuran (0.5 mL) under a nitrogen atmosphere was added dropwise a solution of 3-(3-bromo-4-methylphenyl)-1-[3-(trifluoromethyl)phenyl]-1H-pyrazole (i.e. the product of Step C) (2.0 g, 5.25 mmol) in tetrahydrofuran (3.5 mL). After about 2% of the total volume of the 3-(3-bromo-4-methylphenyl)-1-[3-(trifluoromethyl)phenyl]-1H-pyrazole solution had been added, the addition was stopped and iodine (catalytic amount) was added to the reaction mixture. The remaining 3-(3-bromo-4-methylphenyl)-1-[3-(trifluoromethyl)-phenyl]-1H-pyrazole solution was then added to the reaction mixture over 1 h while heating at reflux. Heating was continued for an additional 45 minutes, and then the reaction mixture was cooled to room temperature. The reaction mixture was added via an addition funnel to a solution of oxalyl chloride (0.508 mL, 5.82 mmol) in tetrahydrofuran (6 mL) at −65° C. Stirring was continued for 2 h at −65° C., and then methanol (1.17 mL) was added to the reaction mixture, and the mixture was allowed to warm to room temperature and stirred for 2 h. The reaction mixture was diluted with saturated aqueous ammonium chloride (4 mL) and water (8 mL) and then extracted with ethyl acetate (2×). The combined organic layers were washed with saturated aqueous sodium chloride, dried over magnesium sulfate, filtered and concentrated under reduced pressure to give an oil. The oil was purified by medium pressure liquid chromatography (0 to 20% gradient of ethyl acetate in hexanes as eluant) to provide an oil (0.31 g). The oil was crystallized from hexanes-diethyl ether to provide the title compound, a compound of the present invention, as a solid (200 mg).

$^1$H NMR (CDCl$_3$): δ 8.2 (s, 1H), 8.1-8.0 (m, 3H), 7.9 (d, 1H), 7.6-7.5 (m, 2H), 7.4 (d, 1H), 6.8 (d, 1H), 4.0 (s, 3H), 2.6 (s, 3H).

Example 13

Preparation of methyl α-(methoxyimino)-2-methyl-5-[1-[3-(trifluoromethyl)phenyl]-1H-pyrazol-3-yl]benzeneacetamide A mixture of methyl 2-methyl-α-oxo-5-[1-[3-(trifluoromethyl)phenyl]-1H-pyrazol-3-yl]benzeneacetate (i.e. the product of Step D, Example 12) (0.184 g, 0.475 mmol) and O-methylhydroxylamine hydrochloride (0.048 g, 0.57 mmol) in methanol (2 mL) under a nitrogen atmosphere was heated to reflux overnight. The reaction mixture was cooled to room temperature, diluted with water and dichloromethane, the layers were separated, and the aqueous layer was extracted with dichloromethane. The combined organic layers were washed with saturated aqueous sodium chloride, dried over magnesium sulfate, filtered and concentrated under reduced pressure to give a solid (0.21 g). The solid was purified by flash column chromatography using a Bond Elute® tube (manufactured by Varian) prepacked with 5 g of silica gel (50 μm particle diameter, 70 Å pore size) and 0 to 20% gradient of ethyl acetate in hexanes as eluent to provide a solid (180 mg). Hexanes and diethyl ether were added to the solid, and the mixture was filtered to provide the title compound, a compound of the present invention, as a white solid (120 mg).

$^1$H NMR (CDCl$_3$): δ 8.0 (s, 1H), 7.99 (d, 1H), 7.8 (d, 1H), 7.63 (s, 1H), 7.6-7.5 (m, 2H), 7.3 (d, 1H), 6.7 (d, 1H), 4.07 (s, 3H), 3.89 (s, 3H), 2.23 (s, 3H).

Example 14

Preparation of α-(methoxyimino)-N,2-dimethyl-5-[1-[3-(trifluoromethyl)phenyl]-1H-pyrazol-3-yl]benzeneacetamide To a solution of methyl α-(methoxyimino)-2-methyl-5-[1-[3-(trifluoromethyl)phenyl]-1H-pyrazol-3-yl]benzeneacetamide (i.e. the product of Example 13) (0.062 g, 0.149 mmol) in tetrahydrofuran (2 mL) under a nitrogen atmosphere was added methylamine (33% by weight in ethanol). The reaction mixture was stirred overnight at room temperature and then concentrated under reduced pressure to leave a solid. Hexanes and diethyl ether were added to the solid, and the mixture was filtered to obtain the title compound, a compound of the present invention, as a white solid (56 mg).

$^1$H NMR (CDCl$_3$): δ 8.0 (s, 1H), 7.99 (d, 1H), 7.9 (d, 1H), 7.8 (d, 1H), 7.63 (s, 1H), 7.6-7.5 (m, 2H), 7.3 (d, 1H), 7.3 (d, 1H), 6.7 (d, 1H), 3.89 (s, 3H), 2.9 (d, 3H), 2.2 (s, 3H).

Example 15

Preparation of methyl N-[[2-chloro-5-[3-(4-chlorophenyl)-1H-pyrazol-1-yl]phenyl]methyl]-carbamate Step A: 1-(3-methyl-4-chlorophenyl)-3-(3-chlorophenyl)-1H-pyrazole A mixture of 3-(3-chlorophenyl)-1H-pyrazole (5.3 g, 29.8 mmol) (prepared according to the method given in European Patent Publication EP 538156), salicylaldoxime (0.58 g, 4.25 mmol), 5-bromo-2-chlorotoluene (2.8 g, 21.3 mmol), copper oxide (0.15 g, 1.06 mmol) and cesium carbonate (11.8 g, 36.2 mmol) in 20 mL of N,N-dimethylformamide was heated at 140° C. overnight and then allowed to cool to room temperature. The resulting suspension was filtered and the filtrate was concentrated under reduce pressure. The resulting residue was purified by medium pressure liquid chromatography (2 to 10% gradient of ethyl acetate in hexanes as eluant) to give the title compound as a white solid (1.4 g).

$^1$H NMR (CDCl$_3$): δ 7.92-7.30 (m, 8H), 6.78 (s, 1H), 2.46 (s, 3H).

Step B Preparation of 1-(3-bromomethyl-4-chlorophenyl)-3-(3-chlorophenyl)-1H-pyrazole A mixture of 1-(3-methyl-4-chlorophenyl)-3-(3-chlorophenyl)-1H-pyrazole (i.e. the product of Step A) (1.7 g, 5.61 mmol), N-bromosuccinimide (1.1 g, 6.17 mmol) and benzoyl peroxide (30 mg, 0.12 mmol) in 100 mL of carbon tetrachloride was irradiated with a sun lamp for 4 hours. The reaction mixture was concentrated under reduced pressure and the residue was purified by medium pressure liquid chromatography (10 to 20% gradient of ethyl acetate in hexanes as eluant) to give the title compound as a white solid (0.37 g).

$^1$H NMR (CDCl$_3$): δ 7.98-7.30 (m, 8H), 6.79 (s, 1H), 4.65 (s, 2H).

Step C Preparation of methyl N-[[2-chloro-5-[3-(4-chlorophenyl)-1H-pyrazol-1-yl]phenyl]methyl]carbamate A mixture of 1-(3-bromomethyl-4-chlorophenyl)-3-(3-chlorophenyl)-1H-pyrazole (i.e. the product of Step B) (0.37 g, 0.97 mmol) and potassium cyanate (0.16 g, 1.94 mmol) in 3 mL of methanol and 6 mL of N,N-dimethylformamide was heated at 100° C. for 4 hours. After cooling, the solvent was then removed under reduced pressure and the residue was purified by medium pressure liquid chromatography (20 to 40% gradient of ethyl acetate in hexanes as eluant) to afford the title compound, a compound of the present invention, as a tan solid (0.24 g) melting at 127-130° C.

$^1$H NMR (CDCl$_3$): δ 7.98-7.30 (m, 8H), 6.78 (s, 1H), 5.25 (m, 1H), 4.53 (d, 2H), 3.72 (s, 3H).

By the procedures described herein together with methods known in the art, the following compounds of Tables 1 to 10 can be prepared. The following abbreviations are used in the Tables which follow: i means iso, c means cyclo, n means normal, s means secondary, t means tertiary, Ac means acetyl, Me means methyl, Et means ethyl, Pr means propyl, OMe means methoxy, CN means cyano, and Ph means phenyl. Substituents on benzyl are attached to the phenyl ring of the benzyl, and locant numbers for the substituents are relative to the phenyl position bonded to the methylene component of benzyl. In Tables 1-3 the left end of the moieties listed for V$^1$ are bonded to O and the right end is bonded to Si in the depicted molecular structures. In Tables 1-3, V$^a$ through V$^h$ have the following meanings as defined below in Exhibit 4.

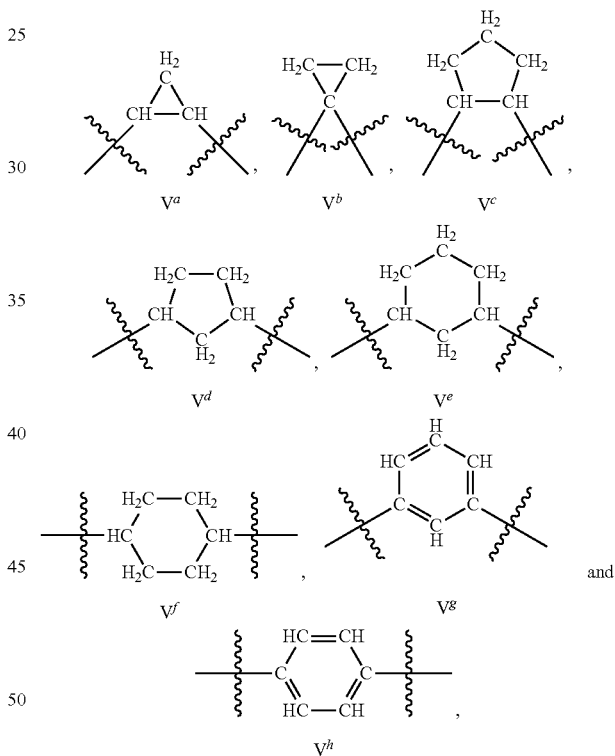

Exhibit 4

TABLE 1

| R$^1$ | V$^1$ | R$^{10a}$ | R$^{10b}$ | R$^{10c}$ | R$^1$ | V$^1$ | R$^{10a}$ | R$^{10b}$ | R$^{10c}$ |
|---|---|---|---|---|---|---|---|---|---|
| Cl | —CH$_2$— | Me | Me | Me | F | —CH$_2$— | Me | Me | Me |
| Cl | —CH$_2$CH$_2$— | Me | Me | Me | F | —CH$_2$CH$_2$— | Me | Me | Me |

TABLE 1-continued

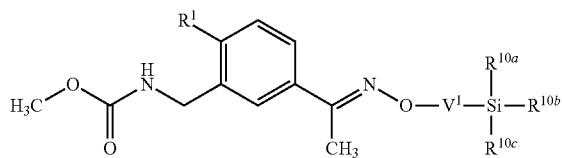

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂CH₂CH₂— | Me | Me | Me | F | —CH₂CH₂CH₂— | Me | Me | Me |
| Cl | —CH₂CH₂CH₂CH₂— | Me | Me | Me | F | —CH₂CH₂CH₂CH₂— | Me | Me | Me |
| Cl | —CH₂OCH₂CH₂— | Me | Me | Me | F | —CH₂OCH₂CH₂— | Me | Me | Me |
| Cl | —CH₂CH₂OCH₂— | Me | Me | Me | F | —CH₂CH₂OCH₂— | Me | Me | Me |
| Cl | —CH₂C(=O)CH₂CH₂— | Me | Me | Me | F | —CH₂C(=O)CH₂CH₂— | Me | Me | Me |
| Cl | —CH₂CH₂C(=O)CH₂— | Me | Me | Me | F | —CH₂CH₂C(=O)CH₂— | Me | Me | Me |
| Cl | —CH₂C(=S)CH₂CH₂— | Me | Me | Me | F | —CH₂C(=S)CH₂CH₂— | Me | Me | Me |
| Cl | —CH₂CH₂C(=S)CH₂— | Me | Me | Me | F | —CH₂CH₂C(=S)CH₂— | Me | Me | Me |
| Cl | —CH₂C(=O)CH₂— | Me | Me | Me | F | —CH₂C(=O)CH₂— | Me | Me | Me |
| Cl | —CH₂C(=S)CH₂— | Me | Me | Me | F | —CH₂C(=S)CH₂— | Me | Me | Me |
| Cl | —CH(Me)— | Me | Me | Me | F | —CH(Me)— | Me | Me | Me |
| Cl | —CH(OMe)— | Me | Me | Me | F | —CH(OMe)— | Me | Me | Me |
| Cl | —CH(Me)CH₂— | Me | Me | Me | F | —CH(Me)CH₂— | Me | Me | Me |
| Cl | —CH₂CH(Me)— | Me | Me | Me | F | —CH₂CH(Me)— | Me | Me | Me |
| Cl | —CH₂CH(OMe)— | Me | Me | Me | F | —CH₂CH(OMe)— | Me | Me | Me |
| Cl | —CH(Me)CH₂CH₂— | Me | Me | Me | F | —CH(Me)CH₂CH₂— | Me | Me | Me |
| Cl | —CH₂CH(Me)CH₂— | Me | Me | Me | F | —CH₂CH(Me)CH₂— | Me | Me | Me |
| Cl | —CH₂CH₂CH(Me)— | Me | Me | Me | F | —CH₂CH₂CH(Me)— | Me | Me | Me |
| Cl | —CH(Et)— | Me | Me | Me | F | —CH(Et)— | Me | Me | Me |
| Cl | —CH(Et)CH₂— | Me | Me | Me | F | —CH(Et)CH₂— | Me | Me | Me |
| Cl | —CH₂CH(Et)— | Me | Me | Me | F | —CH₂CH(Et)— | Me | Me | Me |
| Cl | —CH(Et)CH₂CH₂— | Me | Me | Me | F | —CH(Et)CH₂CH₂— | Me | Me | Me |
| Cl | —CH₂CH(Et)CH₂— | Me | Me | Me | F | —CH₂CH(Et)CH₂— | Me | Me | Me |
| Cl | —CH₂CH₂CH(Et)— | Me | Me | Me | F | —CH₂CH₂CH(Et)— | Me | Me | Me |
| Cl | —CH(OCF₃)— | Me | Me | Me | F | —CH(OCF₃)— | Me | Me | Me |
| Cl | —CH(CF₃)— | Me | Me | Me | F | —CH(CF₃)— | Me | Me | Me |
| Cl | —CH₂CF₂CH₂— | Me | Me | Me | F | —CH₂CF₂CH₂— | Me | Me | Me |
| Cl | —CH₂CHFCH₂— | Me | Me | Me | F | —CH₂CHFCH₂— | Me | Me | Me |
| Cl | —CH₂CF₂— | Me | Me | Me | F | —CH₂CF₂— | Me | Me | Me |
| Cl | —CH₂CHF— | Me | Me | Me | F | —CH₂CHF— | Me | Me | Me |
| Cl | —CH(CN)— | Me | Me | Me | F | —CH(CN)— | Me | Me | Me |
| Cl | Vᵃ | Me | Me | Me | F | Vᵃ | Me | Me | Me |
| Cl | Vᵇ | Me | Me | Me | F | Vᵇ | Me | Me | Me |
| Cl | Vᶜ | Me | Me | Me | F | Vᶜ | Me | Me | Me |
| Cl | Vᵈ | Me | Me | Me | F | Vᵈ | Me | Me | Me |
| Cl | Vᵉ | Me | Me | Me | F | Vᵉ | Me | Me | Me |
| Cl | Vᶠ | Me | Me | Me | F | Vᶠ | Me | Me | Me |
| Cl | Vᵍ | Me | Me | Me | F | Vᵍ | Me | Me | Me |
| Cl | Vʰ | Me | Me | Me | F | Vʰ | Me | Me | Me |
| Cl | —CH₂OC(=O)CH₂— | Me | Me | Me | F | —CH₂OC(=O)CH₂— | Me | Me | Me |
| Cl | —CH₂C(=O)CH₂— | Me | Me | Me | F | —CH₂C(=O)CH₂— | Me | Me | Me |
| Cl | —CH₂C(=O)— | Me | Me | Me | F | —CH₂C(=O)— | Me | Me | Me |
| Cl | —CH₂— | Me | Me | Et | F | —CH₂— | Me | Me | Et |
| Cl | —CH₂CH₂— | Me | Me | Et | F | —CH₂CH₂— | Me | Me | Et |
| Cl | —CH₂CH₂CH₂— | Me | Me | Et | F | —CH₂CH₂CH₂— | Me | Me | Et |
| Cl | —CH₂CH₂CH₂CH₂— | Me | Me | Et | F | —CH₂CH₂CH₂CH₂— | Me | Me | Et |
| Cl | —CH₂OCH₂CH₂— | Me | Me | Et | F | —CH₂OCH₂CH₂— | Me | Me | Et |
| Cl | —CH₂CH₂OCH₂— | Me | Me | Et | F | —CH₂CH₂OCH₂— | Me | Me | Et |
| Cl | —CH₂C(=O)CH₂CH₂— | Me | Me | Et | F | —CH₂C(=O)CH₂CH₂— | Me | Me | Et |
| Cl | —CH₂CH₂C(=O)CH₂— | Me | Me | Et | F | —CH₂CH₂C(=O)CH₂— | Me | Me | Et |
| Cl | —CH₂C(=S)CH₂CH₂— | Me | Me | Et | F | —CH₂C(=S)CH₂CH₂— | Me | Me | Et |
| Cl | —CH₂CH₂C(=S)CH₂— | Me | Me | Et | F | —CH₂CH₂C(=S)CH₂— | Me | Me | Et |
| Cl | —CH₂C(=O)CH₂— | Me | Me | Et | F | —CH₂C(=O)CH₂— | Me | Me | Et |
| Cl | —CH₂C(=S)CH₂— | Me | Me | Et | F | —CH₂C(=S)CH₂— | Me | Me | Et |
| Cl | —CH(Me)— | Me | Me | Et | F | —CH(Me)— | Me | Me | Et |
| Cl | —CH(OMe)— | Me | Me | Et | F | —CH(OMe)— | Me | Me | Et |
| Cl | —CH(Me)CH₂— | Me | Me | Et | F | —CH(Me)CH₂— | Me | Me | Et |
| Cl | —CH₂CH(Me)— | Me | Me | Et | F | —CH₂CH(Me)— | Me | Me | Et |
| Cl | —CH₂CH(OMe)— | Me | Me | Et | F | —CH₂CH(OMe)— | Me | Me | Et |
| Cl | —CH(Me)CH₂CH₂— | Me | Me | Et | F | —CH(Me)CH₂CH₂— | Me | Me | Et |
| Cl | —CH₂CH(Me)CH₂— | Me | Me | Et | F | —CH₂CH(Me)CH₂— | Me | Me | Et |
| Cl | —CH₂CH₂CH(Me)— | Me | Me | Et | F | —CH₂CH₂CH(Me)— | Me | Me | Et |
| Cl | —CH(Et)— | Me | Me | Et | F | —CH(Et)— | Me | Me | Et |
| Cl | —CH(Et)CH₂— | Me | Me | Et | F | —CH(Et)CH₂— | Me | Me | Et |
| Cl | —CH₂CH(Et)— | Me | Me | Et | F | —CH₂CH(Et)— | Me | Me | Et |
| Cl | —CH(Et)CH₂CH₂— | Me | Me | Et | F | —CH(Et)CH₂CH₂— | Me | Me | Et |
| Cl | —CH₂CH(Et)CH₂— | Me | Me | Et | F | —CH₂CH(Et)CH₂— | Me | Me | Et |
| Cl | —CH₂CH₂CH(Et)— | Me | Me | Et | F | —CH₂CH₂CH(Et)— | Me | Me | Et |
| Cl | —CH(OCF₃)— | Me | Me | Et | F | —CH(OCF₃)— | Me | Me | Et |

TABLE 1-continued

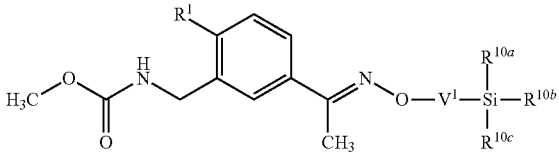

| R$^1$ | V$^1$ | R$^{10a}$ | R$^{10b}$ | R$^{10c}$ | R$^1$ | V$^1$ | R$^{10a}$ | R$^{10b}$ | R$^{10c}$ |
|---|---|---|---|---|---|---|---|---|---|
| Cl | —CH(CF$_3$)— | Me | Me | Et | F | —CH(CF$_3$)— | Me | Me | Et |
| Cl | —CH$_2$CF$_2$CH$_2$— | Me | Me | Et | F | —CH$_2$CF$_2$CH$_2$— | Me | Me | Et |
| Cl | —CH$_2$CHFCH$_2$— | Me | Me | Et | F | —CH$_2$CHFCH$_2$— | Me | Me | Et |
| Cl | —CH$_2$CF$_2$— | Me | Me | Et | F | —CH$_2$CF$_2$— | Me | Me | Et |
| Cl | —CH$_2$CHF— | Me | Me | Et | F | —CH$_2$CHF— | Me | Me | Et |
| Cl | —CH(CN)— | Me | Me | Et | F | —CH(CN)— | Me | Me | Et |
| Cl | V$^a$ | Me | Me | Et | F | V$^a$ | Me | Me | Et |
| Cl | V$^b$ | Me | Me | Et | F | V$^b$ | Me | Me | Et |
| Cl | V$^c$ | Me | Me | Et | F | V$^c$ | Me | Me | Et |
| Cl | V$^d$ | Me | Me | Et | F | V$^d$ | Me | Me | Et |
| Cl | V$^e$ | Me | Me | Et | F | V$^e$ | Me | Me | Et |
| Cl | V$^f$ | Me | Me | Et | F | V$^f$ | Me | Me | Et |
| Cl | V$^g$ | Me | Me | Et | F | V$^g$ | Me | Me | Et |
| Cl | V$^h$ | Me | Me | Et | F | V$^h$ | Me | Me | Et |
| Cl | —CH$_2$OC(=O)CH$_2$— | Me | Me | Et | F | —CH$_2$OC(=O)CH$_2$— | Me | Me | Et |
| Cl | —CH$_2$C(=O)CH$_2$— | Me | Me | Et | F | —CH$_2$C(=O)CH$_2$— | Me | Me | Et |
| Cl | —CH$_2$C(=O)— | Me | Me | Et | F | —CH$_2$C(=O)— | Me | Me | Et |
| Cl | —CH$_2$— | Me | Et | Et | F | —CH$_2$— | Me | Et | Et |
| Cl | —CH$_2$CH$_2$— | Me | Et | Et | F | —CH$_2$CH$_2$— | Me | Et | Et |
| Cl | —CH$_2$CH$_2$CH$_2$— | Me | Et | Et | F | —CH$_2$CH$_2$CH$_2$— | Me | Et | Et |
| Cl | —CH$_2$CH$_2$CH$_2$CH$_2$— | Me | Et | Et | F | —CH$_2$CH$_2$CH$_2$CH$_2$— | Me | Et | Et |
| Cl | —CH$_2$OCH$_2$CH$_2$— | Me | Et | Et | F | —CH$_2$OCH$_2$CH$_2$— | Me | Et | Et |
| Cl | —CH$_2$CH$_2$OCH$_2$— | Me | Et | Et | F | —CH$_2$CH$_2$OCH$_2$— | Me | Et | Et |
| Cl | —CH$_2$C(=O)CH$_2$CH$_2$— | Me | Et | Et | F | —CH$_2$C(=O)CH$_2$CH$_2$— | Me | Et | Et |
| Cl | —CH$_2$CH$_2$C(=O)CH$_2$— | Me | Et | Et | F | —CH$_2$CH$_2$C(=O)CH$_2$— | Me | Et | Et |
| Cl | —CH$_2$C(=S)CH$_2$CH$_2$— | Me | Et | Et | F | —CH$_2$C(=S)CH$_2$CH$_2$— | Me | Et | Et |
| Cl | —CH$_2$CH$_2$C(=S)CH$_2$— | Me | Et | Et | F | —CH$_2$CH$_2$C(=S)CH$_2$— | Me | Et | Et |
| Cl | —CH$_2$C(=O)CH$_2$— | Me | Et | Et | F | —CH$_2$C(=O)CH$_2$— | Me | Et | Et |
| Cl | —CH$_2$C(=S)CH$_2$— | Me | Et | Et | F | —CH$_2$C(=S)CH$_2$— | Me | Et | Et |
| Cl | —CH(Me)— | Me | Et | Et | F | —CH(Me)— | Me | Et | Et |
| Cl | —CH(OMe)— | Me | Et | Et | F | —CH(OMe)— | Me | Et | Et |
| Cl | —CH(Me)CH$_2$— | Me | Et | Et | F | —CH(Me)CH$_2$— | Me | Et | Et |
| Cl | —CH$_2$CH(Me)— | Me | Et | Et | F | —CH$_2$CH(Me)— | Me | Et | Et |
| Cl | —CH$_2$CH(OMe)— | Me | Et | Et | F | —CH$_2$CH(OMe)— | Me | Et | Et |
| Cl | —CH(Me)CH$_2$CH$_2$— | Me | Et | Et | F | —CH(Me)CH$_2$CH$_2$— | Me | Et | Et |
| Cl | —CH$_2$CH(Me)CH$_2$— | Me | Et | Et | F | —CH$_2$CH(Me)CH$_2$— | Me | Et | Et |
| Cl | —CH$_2$CH$_2$CH(Me)— | Me | Et | Et | F | —CH$_2$CH$_2$CH(Me)— | Me | Et | Et |
| Cl | —CH(Et)— | Me | Et | Et | F | —CH(Et)— | Me | Et | Et |
| Cl | —CH(Et)CH$_2$— | Me | Et | Et | F | —CH(Et)CH$_2$— | Me | Et | Et |
| Cl | —CH$_2$CH(Et)— | Me | Et | Et | F | —CH$_2$CH(Et)— | Me | Et | Et |
| Cl | —CH(Et)CH$_2$CH$_2$— | Me | Et | Et | F | —CH(Et)CH$_2$CH$_2$— | Me | Et | Et |
| Cl | —CH$_2$CH(Et)CH$_2$— | Me | Et | Et | F | —CH$_2$CH(Et)CH$_2$— | Me | Et | Et |
| Cl | —CH$_2$CH$_2$CH(Et)— | Me | Et | Et | F | —CH$_2$CH$_2$CH(Et)— | Me | Et | Et |
| Cl | —CH(OCF$_3$)— | Me | Et | Et | F | —CH(OCF$_3$)— | Me | Et | Et |
| Cl | —CH(CF$_3$)— | Me | Et | Et | F | —CH(CF$_3$)— | Me | Et | Et |
| Cl | —CH$_2$CF$_2$CH$_2$— | Me | Et | Et | F | —CH$_2$CF$_2$CH$_2$— | Me | Et | Et |
| Cl | —CH$_2$CHFCH$_2$— | Me | Et | Et | F | —CH$_2$CHFCH$_2$— | Me | Et | Et |
| Cl | —CH$_2$CF$_2$— | Me | Et | Et | F | —CH$_2$CF$_2$— | Me | Et | Et |
| Cl | —CH$_2$CHF— | Me | Et | Et | F | —CH$_2$CHF— | Me | Et | Et |
| Cl | —CH(CN)— | Me | Et | Et | F | —CH(CN)— | Me | Et | Et |
| Cl | V$^a$ | Me | Et | Et | F | V$^a$ | Me | Et | Et |
| Cl | V$^b$ | Me | Et | Et | F | V$^b$ | Me | Et | Et |
| Cl | V$^c$ | Me | Et | Et | F | V$^c$ | Me | Et | Et |
| Cl | V$^d$ | Me | Et | Et | F | V$^d$ | Me | Et | Et |
| Cl | V$^e$ | Me | Et | Et | F | V$^e$ | Me | Et | Et |
| Cl | V$^f$ | Me | Et | Et | F | V$^f$ | Me | Et | Et |
| Cl | V$^g$ | Me | Et | Et | F | V$^g$ | Me | Et | Et |
| Cl | V$^h$ | Me | Et | Et | F | V$^h$ | Me | Et | Et |
| Cl | —CH$_2$OC(=O)CH$_2$— | Me | Et | Et | F | —CH$_2$OC(=O)CH$_2$— | Me | Et | Et |
| Cl | —CH$_2$C(=O)CH$_2$— | Me | Et | Et | F | —CH$_2$C(=O)CH$_2$— | Me | Et | Et |
| Cl | —CH$_2$C(=O)— | Me | Et | Et | F | —CH$_2$C(=O)— | Me | Et | Et |
| Cl | —CH$_2$— | Et | Et | Et | F | —CH$_2$— | Et | Et | Et |
| Cl | —CH$_2$CH$_2$— | Et | Et | Et | F | —CH$_2$CH$_2$— | Et | Et | Et |
| Cl | —CH$_2$CH$_2$CH$_2$— | Et | Et | Et | F | —CH$_2$CH$_2$CH$_2$— | Et | Et | Et |
| Cl | —CH$_2$CH$_2$CH$_2$CH$_2$— | Et | Et | Et | F | —CH$_2$CH$_2$CH$_2$CH$_2$— | Et | Et | Et |
| Cl | —CH$_2$OCH$_2$CH$_2$— | Et | Et | Et | F | —CH$_2$OCH$_2$CH$_2$— | Et | Et | Et |
| Cl | —CH$_2$CH$_2$OCH$_2$— | Et | Et | Et | F | —CH$_2$CH$_2$OCH$_2$— | Et | Et | Et |
| Cl | —CH$_2$C(=O)CH$_2$CH$_2$— | Et | Et | Et | F | —CH$_2$C(=O)CH$_2$CH$_2$— | Et | Et | Et |
| Cl | —CH$_2$CH$_2$C(=O)CH$_2$— | Et | Et | Et | F | —CH$_2$CH$_2$C(=O)CH$_2$— | Et | Et | Et |

TABLE 1-continued

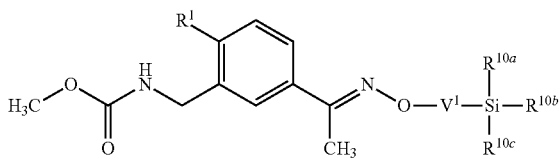

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH$_2$C(=S)CH$_2$CH$_2$— | Et | Et | Et | F | —CH$_2$C(=S)CH$_2$CH$_2$— | Et | Et | Et |
| Cl | —CH$_2$CH$_2$C(=S)CH$_2$— | Et | Et | Et | F | —CH$_2$CH$_2$C(=S)CH$_2$— | Et | Et | Et |
| Cl | —CH$_2$C(=O)CH$_2$— | Et | Et | Et | F | —CH$_2$C(=O)CH$_2$— | Et | Et | Et |
| Cl | —CH$_2$C(=S)CH$_2$— | Et | Et | Et | F | —CH$_2$C(=S)CH$_2$— | Et | Et | Et |
| Cl | —CH(Me)— | Et | Et | Et | F | —CH(Me)— | Et | Et | Et |
| Cl | —CH(OMe)— | Et | Et | Et | F | —CH(OMe)— | Et | Et | Et |
| Cl | —CH(Me)CH$_2$— | Et | Et | Et | F | —CH(Me)CH$_2$— | Et | Et | Et |
| Cl | —CH$_2$CH(Me)— | Et | Et | Et | F | —CH$_2$CH(Me)— | Et | Et | Et |
| Cl | —CH$_2$CH(OMe)— | Et | Et | Et | F | —CH$_2$CH(OMe)— | Et | Et | Et |
| Cl | —CH(Me)CH$_2$CH$_2$— | Et | Et | Et | F | —CH(Me)CH$_2$CH$_2$— | Et | Et | Et |
| Cl | —CH$_2$CH(Me)CH$_2$— | Et | Et | Et | F | —CH$_2$CH(Me)CH$_2$— | Et | Et | Et |
| Cl | —CH$_2$CH$_2$CH(Me)— | Et | Et | Et | F | —CH$_2$CH$_2$CH(Me)— | Et | Et | Et |
| Cl | —CH(Et)— | Et | Et | Et | F | —CH(Et)— | Et | Et | Et |
| Cl | —CH(Et)CH$_2$— | Et | Et | Et | F | —CH(Et)CH$_2$— | Et | Et | Et |
| Cl | —CH$_2$CH(Et)— | Et | Et | Et | F | —CH$_2$CH(Et)— | Et | Et | Et |
| Cl | —CH(Et)CH$_2$CH$_2$— | Et | Et | Et | F | —CH(Et)CH$_2$CH$_2$— | Et | Et | Et |
| Cl | —CH$_2$CH(Et)CH$_2$— | Et | Et | Et | F | —CH$_2$CH(Et)CH$_2$— | Et | Et | Et |
| Cl | —CH$_2$CH$_2$CH(Et)— | Et | Et | Et | F | —CH$_2$CH$_2$CH(Et)— | Et | Et | Et |
| Cl | —CH(OCF$_3$)— | Et | Et | Et | F | —CH(OCF$_3$)— | Et | Et | Et |
| Cl | —CH(CF$_3$)— | Et | Et | Et | F | —CH(CF$_3$)— | Et | Et | Et |
| Cl | —CH$_2$CF$_2$CH$_2$— | Et | Et | Et | F | —CH$_2$CF$_2$CH$_2$— | Et | Et | Et |
| Cl | —CH$_2$CHFCH$_2$— | Et | Et | Et | F | —CH$_2$CHFCH$_2$— | Et | Et | Et |
| Cl | —CH$_2$CF$_2$— | Et | Et | Et | F | —CH$_2$CF$_2$— | Et | Et | Et |
| Cl | —CH$_2$CHF— | Et | Et | Et | F | —CH$_2$CHF— | Et | Et | Et |
| Cl | —CH(CN)— | Et | Et | Et | F | —CH(CN)— | Et | Et | Et |
| Cl | $V^a$ | Et | Et | Et | F | $V^a$ | Et | Et | Et |
| Cl | $V^b$ | Et | Et | Et | F | $V^b$ | Et | Et | Et |
| Cl | $V^c$ | Et | Et | Et | F | $V^c$ | Et | Et | Et |
| Cl | $V^d$ | Et | Et | Et | F | $V^d$ | Et | Et | Et |
| Cl | $V^e$ | Et | Et | Et | F | $V^e$ | Et | Et | Et |
| Cl | $V^f$ | Et | Et | Et | F | $V^f$ | Et | Et | Et |
| Cl | $V^g$ | Et | Et | Et | F | $V^g$ | Et | Et | Et |
| Cl | $V^h$ | Et | Et | Et | F | $V^h$ | Et | Et | Et |
| Cl | —CH$_2$OC(=O)CH$_2$— | Et | Et | Et | F | —CH$_2$OC(=O)CH$_2$— | Et | Et | Et |
| Cl | —CH$_2$C(=O)CH$_2$— | Et | Et | Et | F | —CH$_2$C(=O)CH$_2$— | Et | Et | Et |
| Cl | —CH$_2$C(=O)— | Et | Et | Et | F | —CH$_2$C(=O)— | Et | Et | Et |
| Cl | —CH$_2$— | Me | Me | i-Pr | F | —CH$_2$— | Me | Me | i-Pr |
| Cl | —CH$_2$CH$_2$— | Me | Me | i-Pr | F | —CH$_2$CH$_2$— | Me | Me | i-Pr |
| Cl | —CH$_2$CH$_2$CH$_2$— | Me | Me | i-Pr | F | —CH$_2$CH$_2$CH$_2$— | Me | Me | i-Pr |
| Cl | —CH$_2$CH$_2$CH$_2$CH$_2$— | Me | Me | i-Pr | F | —CH$_2$CH$_2$CH$_2$CH$_2$— | Me | Me | i-Pr |
| Cl | —CH$_2$OCH$_2$CH$_2$— | Me | Me | i-Pr | F | —CH$_2$OCH$_2$CH$_2$— | Me | Me | i-Pr |
| Cl | —CH$_2$CH$_2$OCH$_2$— | Me | Me | i-Pr | F | —CH$_2$CH$_2$OCH$_2$— | Me | Me | i-Pr |
| Cl | —CH$_2$C(=O)CH$_2$CH$_2$— | Me | Me | i-Pr | F | —CH$_2$C(=O)CH$_2$CH$_2$— | Me | Me | i-Pr |
| Cl | —CH$_2$CH$_2$C(=O)CH$_2$— | Me | Me | i-Pr | F | —CH$_2$CH$_2$C(=O)CH$_2$— | Me | Me | i-Pr |
| Cl | —CH$_2$C(=S)CH$_2$CH$_2$— | Me | Me | i-Pr | F | —CH$_2$C(=S)CH$_2$CH$_2$— | Me | Me | i-Pr |
| Cl | —CH$_2$CH$_2$C(=S)CH$_2$— | Me | Me | i-Pr | F | —CH$_2$CH$_2$C(=S)CH$_2$— | Me | Me | i-Pr |
| Cl | —CH$_2$C(=O)CH$_2$— | Me | Me | i-Pr | F | —CH$_2$C(=O)CH$_2$— | Me | Me | i-Pr |
| Cl | —CH$_2$C(=S)CH$_2$— | Me | Me | i-Pr | F | —CH$_2$C(=S)CH$_2$— | Me | Me | i-Pr |
| Cl | —CH(Me)— | Me | Me | i-Pr | F | —CH(Me)— | Me | Me | i-Pr |
| Cl | —CH(OMe)— | Me | Me | i-Pr | F | —CH(OMe)— | Me | Me | i-Pr |
| Cl | —CH(Me)CH$_2$— | Me | Me | i-Pr | F | —CH(Me)CH$_2$— | Me | Me | i-Pr |
| Cl | —CH$_2$CH(Me)— | Me | Me | i-Pr | F | —CH$_2$CH(Me)— | Me | Me | i-Pr |
| Cl | —CH$_2$CH(OMe)— | Me | Me | i-Pr | F | —CH$_2$CH(OMe)— | Me | Me | i-Pr |
| Cl | —CH(Me)CH$_2$CH$_2$— | Me | Me | i-Pr | F | —CH(Me)CH$_2$CH$_2$— | Me | Me | i-Pr |
| Cl | —CH$_2$CH(Me)CH$_2$— | Me | Me | i-Pr | F | —CH$_2$CH(Me)CH$_2$— | Me | Me | i-Pr |
| Cl | —CH$_2$CH$_2$CH(Me)— | Me | Me | i-Pr | F | —CH$_2$CH$_2$CH(Me)— | Me | Me | i-Pr |
| Cl | —CH(Et)— | Me | Me | i-Pr | F | —CH(Et)— | Me | Me | i-Pr |
| Cl | —CH(Et)CH$_2$— | Me | Me | i-Pr | F | —CH(Et)CH$_2$— | Me | Me | i-Pr |
| Cl | —CH$_2$CH(Et)— | Me | Me | i-Pr | F | —CH$_2$CH(Et)— | Me | Me | i-Pr |
| Cl | —CH(Et)CH$_2$CH$_2$— | Me | Me | i-Pr | F | —CH(Et)CH$_2$CH$_2$— | Me | Me | i-Pr |
| Cl | —CH$_2$CH(Et)CH$_2$— | Me | Me | i-Pr | F | —CH$_2$CH(Et)CH$_2$— | Me | Me | i-Pr |
| Cl | —CH$_2$CH$_2$CH(Et)— | Me | Me | i-Pr | F | —CH$_2$CH$_2$CH(Et)— | Me | Me | i-Pr |
| Cl | —CH(OCF$_3$)— | Me | Me | i-Pr | F | —CH(OCF$_3$)— | Me | Me | i-Pr |
| Cl | —CH(CF$_3$)— | Me | Me | i-Pr | F | —CH(CF$_3$)— | Me | Me | i-Pr |
| Cl | —CH$_2$CF$_2$CH$_2$— | Me | Me | i-Pr | F | —CH$_2$CF$_2$CH$_2$— | Me | Me | i-Pr |
| Cl | —CH$_2$CHFCH$_2$— | Me | Me | i-Pr | F | —CH$_2$CHFCH$_2$— | Me | Me | i-Pr |
| Cl | —CH$_2$CF$_2$— | Me | Me | i-Pr | F | —CH$_2$CF$_2$— | Me | Me | i-Pr |
| Cl | —CH$_2$CHF— | Me | Me | i-Pr | F | —CH$_2$CHF— | Me | Me | i-Pr |
| Cl | —CH(CN)— | Me | Me | i-Pr | F | —CH(CN)— | Me | Me | i-Pr |

TABLE 1-continued

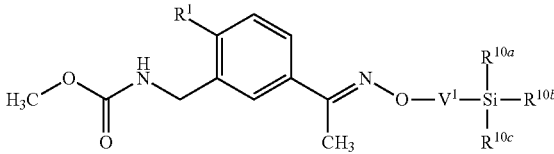

| R$^1$ | V$^1$ | R$^{10a}$ | R$^{10b}$ | R$^{10c}$ | R$^1$ | V$^1$ | R$^{10a}$ | R$^{10b}$ | R$^{10c}$ |
|---|---|---|---|---|---|---|---|---|---|
| Cl | V$^a$ | Me | Me | i-Pr | F | V$^a$ | Me | Me | i-Pr |
| Cl | V$^b$ | Me | Me | i-Pr | F | V$^b$ | Me | Me | i-Pr |
| Cl | V$^c$ | Me | Me | i-Pr | F | V$^c$ | Me | Me | i-Pr |
| Cl | V$^d$ | Me | Me | i-Pr | F | V$^d$ | Me | Me | i-Pr |
| Cl | V$^e$ | Me | Me | i-Pr | F | V$^e$ | Me | Me | i-Pr |
| Cl | V$^f$ | Me | Me | i-Pr | F | V$^f$ | Me | Me | i-Pr |
| Cl | V$^g$ | Me | Me | i-Pr | F | V$^g$ | Me | Me | i-Pr |
| Cl | V$^h$ | Me | Me | i-Pr | F | V$^h$ | Me | Me | i-Pr |
| Cl | —CH$_2$OC(=O)CH$_2$— | Me | Me | i-Pr | F | —CH$_2$OC(=O)CH$_2$— | Me | Me | i-Pr |
| Cl | —CH$_2$C(=O)CH$_2$— | Me | Me | i-Pr | F | —CH$_2$C(=O)CH$_2$— | Me | Me | i-Pr |
| Cl | —CH$_2$C(=O)— | Me | Me | i-Pr | F | —CH$_2$C(=O)— | Me | Me | i-Pr |
| Cl | —CH$_2$— | Me | Et | i-Pr | F | —CH$_2$— | Me | Et | i-Pr |
| Cl | —CH$_2$CH$_2$— | Me | Et | i-Pr | F | —CH$_2$CH$_2$— | Me | Et | i-Pr |
| Cl | —CH$_2$CH$_2$CH$_2$— | Me | Et | i-Pr | F | —CH$_2$CH$_2$CH$_2$— | Me | Et | i-Pr |
| Cl | —CH$_2$CH$_2$CH$_2$CH$_2$— | Me | Et | i-Pr | F | —CH$_2$CH$_2$CH$_2$CH$_2$— | Me | Et | i-Pr |
| Cl | —CH$_2$OCH$_2$CH$_2$— | Me | Et | i-Pr | F | —CH$_2$OCH$_2$CH$_2$— | Me | Et | i-Pr |
| Cl | —CH$_2$CH$_2$OCH$_2$— | Me | Et | i-Pr | F | —CH$_2$CH$_2$OCH$_2$— | Me | Et | i-Pr |
| Cl | —CH$_2$C(=O)CH$_2$CH$_2$— | Me | Et | i-Pr | F | —CH$_2$C(=O)CH$_2$CH$_2$— | Me | Et | i-Pr |
| Cl | —CH$_2$C(=S)CH$_2$CH$_2$— | Me | Et | i-Pr | F | —CH$_2$C(=S)CH$_2$CH$_2$— | Me | Et | i-Pr |
| Cl | —CH$_2$CH$_2$C(=S)CH$_2$— | Me | Et | i-Pr | F | —CH$_2$CH$_2$C(=S)CH$_2$— | Me | Et | i-Pr |
| Cl | —CH$_2$CH$_2$C(=S)CH$_2$— | Me | Et | i-Pr | F | —CH$_2$CH$_2$C(=S)CH$_2$— | Me | Et | i-Pr |
| Cl | —CH$_2$C(=O)CH$_2$— | Me | Et | i-Pr | F | —CH$_2$C(=O)CH$_2$— | Me | Et | i-Pr |
| Cl | —CH$_2$C(=S)CH$_2$— | Me | Et | i-Pr | F | —CH$_2$C(=S)CH$_2$— | Me | Et | i-Pr |
| Cl | —CH(Me)— | Me | Et | i-Pr | F | —CH(Me)— | Me | Et | i-Pr |
| Cl | —CH(OMe)— | Me | Et | i-Pr | F | —CH(OMe)— | Me | Et | i-Pr |
| Cl | —CH(Me)CH$_2$— | Me | Et | i-Pr | F | —CH(Me)CH$_2$— | Me | Et | i-Pr |
| Cl | —CH$_2$CH(Me)— | Me | Et | i-Pr | F | —CH$_2$CH(Me)— | Me | Et | i-Pr |
| Cl | —CH$_2$CH(OMe)— | Me | Et | i-Pr | F | —CH$_2$CH(OMe)— | Me | Et | i-Pr |
| Cl | —CH(Me)CH$_2$CH$_2$— | Me | Et | i-Pr | F | —CH(Me)CH$_2$CH$_2$— | Me | Et | i-Pr |
| Cl | —CH$_2$CH(Me)CH$_2$— | Me | Et | i-Pr | F | —CH$_2$CH(Me)CH$_2$— | Me | Et | i-Pr |
| Cl | —CH$_2$CH$_2$CH(Me)— | Me | Et | i-Pr | F | —CH$_2$CH$_2$CH(Me)— | Me | Et | i-Pr |
| Cl | —CH(Et)— | Me | Et | i-Pr | F | —CH(Et)— | Me | Et | i-Pr |
| Cl | —CH(Et)CH$_2$— | Me | Et | i-Pr | F | —CH(Et)CH$_2$— | Me | Et | i-Pr |
| Cl | —CH$_2$CH(Et)— | Me | Et | i-Pr | F | —CH$_2$CH(Et)— | Me | Et | i-Pr |
| Cl | —CH(Et)CH$_2$CH$_2$— | Me | Et | i-Pr | F | —CH(Et)CH$_2$CH$_2$— | Me | Et | i-Pr |
| Cl | —CH$_2$CH(Et)CH$_2$— | Me | Et | i-Pr | F | —CH$_2$CH(Et)CH$_2$— | Me | Et | i-Pr |
| Cl | —CH$_2$CH$_2$CH(Et)— | Me | Et | i-Pr | F | —CH$_2$CH$_2$CH(Et)— | Me | Et | i-Pr |
| Cl | —CH(OCF$_3$)— | Me | Et | i-Pr | F | —CH(OCF$_3$)— | Me | Et | i-Pr |
| Cl | —CH(CF$_3$)— | Me | Et | i-Pr | F | —CH(CF$_3$)— | Me | Et | i-Pr |
| Cl | —CH$_2$CF$_2$CH$_2$— | Me | Et | i-Pr | F | —CH$_2$CF$_2$CH$_2$— | Me | Et | i-Pr |
| Cl | —CH$_2$CHFCH$_2$— | Me | Et | i-Pr | F | —CH$_2$CHFCH$_2$— | Me | Et | i-Pr |
| Cl | —CH$_2$CF$_2$— | Me | Et | i-Pr | F | —CH$_2$CF$_2$— | Me | Et | i-Pr |
| Cl | —CH$_2$CHF— | Me | Et | i-Pr | F | —CH$_2$CHF— | Me | Et | i-Pr |
| Cl | —CH(CN)— | Me | Et | i-Pr | F | —CH(CN)— | Me | Et | i-Pr |
| Cl | V$^a$ | Me | Et | i-Pr | F | V$^a$ | Me | Et | i-Pr |
| Cl | V$^b$ | Me | Et | i-Pr | F | V$^b$ | Me | Et | i-Pr |
| Cl | V$^c$ | Me | Et | i-Pr | F | V$^c$ | Me | Et | i-Pr |
| Cl | V$^d$ | Me | Et | i-Pr | F | V$^d$ | Me | Et | i-Pr |
| Cl | V$^e$ | Me | Et | i-Pr | F | V$^e$ | Me | Et | i-Pr |
| Cl | V$^f$ | Me | Et | i-Pr | F | V$^f$ | Me | Et | i-Pr |
| Cl | V$^g$ | Me | Et | i-Pr | F | V$^g$ | Me | Et | i-Pr |
| Cl | V$^h$ | Me | Et | i-Pr | F | V$^h$ | Me | Et | i-Pr |
| Cl | —CH$_2$OC(=O)CH$_2$— | Me | Et | i-Pr | F | —CH$_2$OC(=O)CH$_2$— | Me | Et | i-Pr |
| Cl | —CH$_2$C(=O)CH$_2$— | Me | Et | i-Pr | F | —CH$_2$C(=O)CH$_2$— | Me | Et | i-Pr |
| Cl | —CH$_2$C(=O)— | Me | Et | i-Pr | F | —CH$_2$C(=O)— | Me | Et | i-Pr |
| Cl | —CH$_2$— | Me | Me | Ph | F | —CH$_2$— | Me | Me | Ph |
| Cl | —CH$_2$CH$_2$— | Me | Me | Ph | F | —CH$_2$CH$_2$— | Me | Me | Ph |
| Cl | —CH$_2$CH$_2$CH$_2$— | Me | Me | Ph | F | —CH$_2$CH$_2$CH$_2$— | Me | Me | Ph |
| Cl | —CH$_2$CH$_2$CH$_2$CH$_2$— | Me | Me | Ph | F | —CH$_2$CH$_2$CH$_2$CH$_2$— | Me | Me | Ph |
| Cl | —CH$_2$OCH$_2$CH$_2$— | Me | Me | Ph | F | —CH$_2$OCH$_2$CH$_2$— | Me | Me | Ph |
| Cl | —CH$_2$CH$_2$OCH$_2$— | Me | Me | Ph | F | —CH$_2$CH$_2$OCH$_2$— | Me | Me | Ph |
| Cl | —CH$_2$C(=O)CH$_2$CH$_2$— | Me | Me | Ph | F | —CH$_2$C(=O)CH$_2$CH$_2$— | Me | Me | Ph |
| Cl | —CH$_2$C(=O)CH$_2$— | Me | Me | Ph | F | —CH$_2$C(=O)CH$_2$— | Me | Me | Ph |
| Cl | —CH$_2$C(=S)CH$_2$CH$_2$— | Me | Me | Ph | F | —CH$_2$C(=S)CH$_2$CH$_2$— | Me | Me | Ph |
| Cl | —CH$_2$CH$_2$C(=S)CH$_2$— | Me | Me | Ph | F | —CH$_2$CH$_2$C(=S)CH$_2$— | Me | Me | Ph |
| Cl | —CH$_2$C(=O)CH$_2$— | Me | Me | Ph | F | —CH$_2$C(=O)CH$_2$— | Me | Me | Ph |
| Cl | —CH$_2$C(=S)CH$_2$— | Me | Me | Ph | F | —CH$_2$C(=S)CH$_2$— | Me | Me | Ph |
| Cl | —CH(Me)— | Me | Me | Ph | F | —CH(Me)— | Me | Me | Ph |
| Cl | —CH(OMe)— | Me | Me | Ph | F | —CH(OMe)— | Me | Me | Ph |

TABLE 1-continued

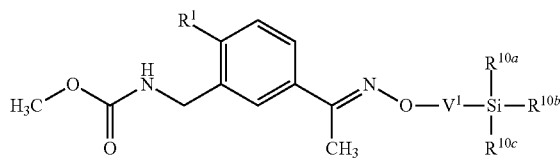

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH(Me)CH₂— | Me | Me | Ph | F | —CH(Me)CH₂— | Me | Me | Ph |
| Cl | —CH₂CH(Me)— | Me | Me | Ph | F | —CH₂CH(Me)— | Me | Me | Ph |
| Cl | —CH₂CH(OMe)— | Me | Me | Ph | F | —CH₂CH(OMe)— | Me | Me | Ph |
| Cl | —CH(Me)CH₂CH₂— | Me | Me | Ph | F | —CH(Me)CH₂CH₂— | Me | Me | Ph |
| Cl | —CH₂CH(Me)CH₂— | Me | Me | Ph | F | —CH₂CH(Me)CH₂— | Me | Me | Ph |
| Cl | —CH₂CH₂CH(Me)— | Me | Me | Ph | F | —CH₂CH₂CH(Me)— | Me | Me | Ph |
| Cl | —CH(Et)— | Me | Me | Ph | F | —CH(Et)— | Me | Me | Ph |
| Cl | —CH(Et)CH₂— | Me | Me | Ph | F | —CH(Et)CH₂— | Me | Me | Ph |
| Cl | —CH₂CH(Et)— | Me | Me | Ph | F | —CH₂CH(Et)— | Me | Me | Ph |
| Cl | —CH(Et)CH₂CH₂— | Me | Me | Ph | F | —CH(Et)CH₂CH₂— | Me | Me | Ph |
| Cl | —CH₂CH(Et)CH₂— | Me | Me | Ph | F | —CH₂CH(Et)CH₂— | Me | Me | Ph |
| Cl | —CH₂CH₂CH(Et)— | Me | Me | Ph | F | —CH₂CH₂CH(Et)— | Me | Me | Ph |
| Cl | —CH(OCF₃)— | Me | Me | Ph | F | —CH(OCF₃)— | Me | Me | Ph |
| Cl | —CH(CF₃)— | Me | Me | Ph | F | —CH(CF₃)— | Me | Me | Ph |
| Cl | —CH₂CF₂CH₂— | Me | Me | Ph | F | —CH₂CF₂CH₂— | Me | Me | Ph |
| Cl | —CH₂CHFCH₂— | Me | Me | Ph | F | —CH₂CHFCH₂— | Me | Me | Ph |
| Cl | —CH₂CF₂— | Me | Me | Ph | F | —CH₂CF₂— | Me | Me | Ph |
| Cl | —CH₂CHF— | Me | Me | Ph | F | —CH₂CHF— | Me | Me | Ph |
| Cl | —CH(CN)— | Me | Me | Ph | F | —CH(CN)— | Me | Me | Ph |
| Cl | Vᵃ | Me | Me | Ph | F | Vᵃ | Me | Me | Ph |
| Cl | Vᵇ | Me | Me | Ph | F | Vᵇ | Me | Me | Ph |
| Cl | Vᶜ | Me | Me | Ph | F | Vᶜ | Me | Me | Ph |
| Cl | Vᵈ | Me | Me | Ph | F | Vᵈ | Me | Me | Ph |
| Cl | Vᵉ | Me | Me | Ph | F | Vᵉ | Me | Me | Ph |
| Cl | Vᶠ | Me | Me | Ph | F | Vᶠ | Me | Me | Ph |
| Cl | Vᵍ | Me | Me | Ph | F | Vᵍ | Me | Me | Ph |
| Cl | Vʰ | Me | Me | Ph | F | Vʰ | Me | Me | Ph |
| Cl | —CH₂OC(=O)CH₂— | Me | Me | Ph | F | —CH₂OC(=O)CH₂— | Me | Me | Ph |
| Cl | —CH₂C(=O)CH₂— | Me | Me | Ph | F | —CH₂C(=O)CH₂— | Me | Me | Ph |
| Cl | —CH₂C(=O)— | Me | Me | Ph | F | —CH₂C(=O)— | Me | Me | Ph |
| Cl | —CH₂— | Me | Me | 4-Cl—Ph | F | —CH₂— | Me | Me | 4-Cl—Ph |
| Cl | —CH₂CH₂— | Me | Me | 4-Cl—Ph | F | —CH₂CH₂— | Me | Me | 4-Cl—Ph |
| Cl | —CH₂CH₂CH₂— | Me | Me | 4-Cl—Ph | F | —CH₂CH₂CH₂— | Me | Me | 4-Cl—Ph |
| Cl | —CH₂CH₂CH₂CH₂— | Me | Me | 4-Cl—Ph | F | —CH₂CH₂CH₂CH₂— | Me | Me | 4-Cl—Ph |
| Cl | —CH₂OCH₂CH₂— | Me | Me | 4-Cl—Ph | F | —CH₂OCH₂CH₂— | Me | Me | 4-Cl—Ph |
| Cl | —CH₂CH₂OCH₂— | Me | Me | 4-Cl—Ph | F | —CH₂CH₂OCH₂— | Me | Me | 4-Cl—Ph |
| Cl | —CH₂C(=O)CH₂CH₂— | Me | Me | 4-Cl—Ph | F | —CH₂C(=O)CH₂CH₂— | Me | Me | 4-Cl—Ph |
| Cl | —CH₂C(=S)CH₂CH₂— | Me | Me | 4-Cl—Ph | F | —CH₂C(=S)CH₂CH₂— | Me | Me | 4-Cl—Ph |
| Cl | —CH₂CH₂C(=S)CH₂— | Me | Me | 4-Cl—Ph | F | —CH₂CH₂C(=S)CH₂— | Me | Me | 4-Cl—Ph |
| Cl | —CH₂CH₂C(=S)CH₂— | Me | Me | 4-Cl—Ph | F | —CH₂CH₂C(=S)CH₂— | Me | Me | 4-Cl—Ph |
| Cl | —CH₂C(=O)CH₂— | Me | Me | 4-Cl—Ph | F | —CH₂C(=O)CH₂— | Me | Me | 4-Cl—Ph |
| Cl | —CH₂C(=S)CH₂— | Me | Me | 4-Cl—Ph | F | —CH₂C(=S)CH₂— | Me | Me | 4-Cl—Ph |
| Cl | —CH(Me)— | Me | Me | 4-Cl—Ph | F | —CH(Me)— | Me | Me | 4-Cl—Ph |
| Cl | —CH(OMe)— | Me | Me | 4-Cl—Ph | F | —CH(OMe)— | Me | Me | 4-Cl—Ph |
| Cl | —CH(Me)CH₂— | Me | Me | 4-Cl—Ph | F | —CH(Me)CH₂— | Me | Me | 4-Cl—Ph |
| Cl | —CH₂CH(Me)— | Me | Me | 4-Cl—Ph | F | —CH₂CH(Me)— | Me | Me | 4-Cl—Ph |
| Cl | —CH₂CH(OMe)— | Me | Me | 4-Cl—Ph | F | —CH₂CH(OMe)— | Me | Me | 4-Cl—Ph |
| Cl | —CH(Me)CH₂CH₂— | Me | Me | 4-Cl—Ph | F | —CH(Me)CH₂CH₂— | Me | Me | 4-Cl—Ph |
| Cl | —CH₂CH(Me)CH₂— | Me | Me | 4-Cl—Ph | F | —CH₂CH(Me)CH₂— | Me | Me | 4-Cl—Ph |
| Cl | —CH₂CH₂CH(Me)— | Me | Me | 4-Cl—Ph | F | —CH₂CH₂CH(Me)— | Me | Me | 4-Cl—Ph |
| Cl | —CH(Et)— | Me | Me | 4-Cl—Ph | F | —CH(Et)— | Me | Me | 4-Cl—Ph |
| Cl | —CH(Et)CH₂— | Me | Me | 4-Cl—Ph | F | —CH(Et)CH₂— | Me | Me | 4-Cl—Ph |
| Cl | —CH₂CH(Et)— | Me | Me | 4-Cl—Ph | F | —CH₂CH(Et)— | Me | Me | 4-Cl—Ph |
| Cl | —CH(Et)CH₂CH₂— | Me | Me | 4-Cl—Ph | F | —CH(Et)CH₂CH₂— | Me | Me | 4-Cl—Ph |
| Cl | —CH₂CH(Et)CH₂— | Me | Me | 4-Cl—Ph | F | —CH₂CH(Et)CH₂— | Me | Me | 4-Cl—Ph |
| Cl | —CH₂CH₂CH(Et)— | Me | Me | 4-Cl—Ph | F | —CH₂CH₂CH(Et)— | Me | Me | 4-Cl—Ph |
| Cl | —CH(OCF₃)— | Me | Me | 4-Cl—Ph | F | —CH(OCF₃)— | Me | Me | 4-Cl—Ph |
| Cl | —CH(CF₃)— | Me | Me | 4-Cl—Ph | F | —CH(CF₃)— | Me | Me | 4-Cl—Ph |
| Cl | —CH₂CF₂CH₂— | Me | Me | 4-Cl—Ph | F | —CH₂CF₂CH₂— | Me | Me | 4-Cl—Ph |
| Cl | —CH₂CHFCH₂— | Me | Me | 4-Cl—Ph | F | —CH₂CHFCH₂— | Me | Me | 4-Cl—Ph |
| Cl | —CH₂CF₂— | Me | Me | 4-Cl—Ph | F | —CH₂CF₂— | Me | Me | 4-Cl—Ph |
| Cl | —CH₂CHF— | Me | Me | 4-Cl—Ph | F | —CH₂CHF— | Me | Me | 4-Cl—Ph |
| Cl | —CH(CN)— | Me | Me | 4-Cl—Ph | F | —CH(CN)— | Me | Me | 4-Cl—Ph |
| Cl | Vᵃ | Me | Me | 4-Cl—Ph | F | Vᵃ | Me | Me | 4-Cl—Ph |
| Cl | Vᵇ | Me | Me | 4-Cl—Ph | F | Vᵇ | Me | Me | 4-Cl—Ph |
| Cl | Vᶜ | Me | Me | 4-Cl—Ph | F | Vᶜ | Me | Me | 4-Cl—Ph |
| Cl | Vᵈ | Me | Me | 4-Cl—Ph | F | Vᵈ | Me | Me | 4-Cl—Ph |
| Cl | Vᵉ | Me | Me | 4-Cl—Ph | F | Vᵉ | Me | Me | 4-Cl—Ph |
| Cl | Vᶠ | Me | Me | 4-Cl—Ph | F | Vᶠ | Me | Me | 4-Cl—Ph |

TABLE 1-continued

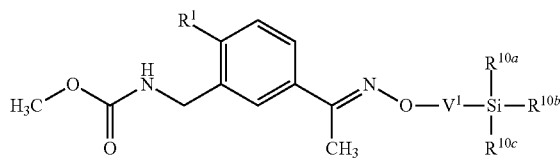

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | Vᵍ | Me | Me | 4-Cl—Ph | F | Vᵍ | Me | Me | 4-Cl—Ph |
| Cl | Vʰ | Me | Me | 4-Cl—Ph | F | Vʰ | Me | Me | 4-Cl—Ph |
| Cl | —CH₂OC(=O)CH₂— | Me | Me | 4-Cl—Ph | F | —CH₂OC(=O)CH₂— | Me | Me | 4-Cl—Ph |
| Cl | —CH₂C(=O)CH₂— | Me | Me | 4-Cl—Ph | F | —CH₂C(=O)CH₂— | Me | Me | 4-Cl—Ph |
| Cl | —CH₂C(=O)— | Me | Me | 4-Cl—Ph | F | —CH₂C(=O)— | Me | Me | 4-Cl—Ph |
| Cl | —CH₂— | Me | Me | 3-Cl—Ph | F | —CH₂— | Me | Me | 3-Cl—Ph |
| Cl | —CH₂CH₂— | Me | Me | 3-Cl—Ph | F | —CH₂CH₂— | Me | Me | 3-Cl—Ph |
| Cl | —CH₂CH₂CH₂— | Me | Me | 3-Cl—Ph | F | —CH₂CH₂CH₂— | Me | Me | 3-Cl—Ph |
| Cl | —CH₂CH₂CH₂CH₂— | Me | Me | 3-Cl—Ph | F | —CH₂CH₂CH₂CH₂— | Me | Me | 3-Cl—Ph |
| Cl | —CH₂OCH₂CH₂— | Me | Me | 3-Cl—Ph | F | —CH₂OCH₂CH₂— | Me | Me | 3-Cl—Ph |
| Cl | —CH₂CH₂OCH₂— | Me | Me | 3-Cl—Ph | F | —CH₂CH₂OCH₂— | Me | Me | 3-Cl—Ph |
| Cl | —CH₂C(=O)CH₂CH₂— | Me | Me | 3-Cl—Ph | F | —CH₂C(=O)CH₂CH₂— | Me | Me | 3-Cl—Ph |
| Cl | —CH₂CH₂C(=O)CH₂— | Me | Me | 3-Cl—Ph | F | —CH₂CH₂C(=O)CH₂— | Me | Me | 3-Cl—Ph |
| Cl | —CH₂C(=S)CH₂CH₂— | Me | Me | 3-Cl—Ph | F | —CH₂C(=S)CH₂CH₂— | Me | Me | 3-Cl—Ph |
| Cl | —CH₂CH₂C(=S)CH₂— | Me | Me | 3-Cl—Ph | F | —CH₂CH₂C(=S)CH₂— | Me | Me | 3-Cl—Ph |
| Cl | —CH₂C(=O)CH₂— | Me | Me | 3-Cl—Ph | F | —CH₂C(=O)CH₂— | Me | Me | 3-Cl—Ph |
| Cl | —CH₂C(=S)CH₂— | Me | Me | 3-Cl—Ph | F | —CH₂C(=S)CH₂— | Me | Me | 3-Cl—Ph |
| Cl | —CH(Me)— | Me | Me | 3-Cl—Ph | F | —CH(Me)— | Me | Me | 3-Cl—Ph |
| Cl | —CH(OMe)— | Me | Me | 3-Cl—Ph | F | —CH(OMe)— | Me | Me | 3-Cl—Ph |
| Cl | —CH(Me)CH₂— | Me | Me | 3-Cl—Ph | F | —CH(Me)CH₂— | Me | Me | 3-Cl—Ph |
| Cl | —CH₂CH(Me)— | Me | Me | 3-Cl—Ph | F | —CH₂CH(Me)— | Me | Me | 3-Cl—Ph |
| Cl | —CH₂CH(OMe)— | Me | Me | 3-Cl—Ph | F | —CH₂CH(OMe)— | Me | Me | 3-Cl—Ph |
| Cl | —CH(Me)CH₂CH₂— | Me | Me | 3-Cl—Ph | F | —CH(Me)CH₂CH₂— | Me | Me | 3-Cl—Ph |
| Cl | —CH₂CH(Me)CH₂— | Me | Me | 3-Cl—Ph | F | —CH₂CH(Me)CH₂— | Me | Me | 3-Cl—Ph |
| Cl | —CH₂CH₂CH(Me)— | Me | Me | 3-Cl—Ph | F | —CH₂CH₂CH(Me)— | Me | Me | 3-Cl—Ph |
| Cl | —CH(Et)— | Me | Me | 3-Cl—Ph | F | —CH(Et)— | Me | Me | 3-Cl—Ph |
| Cl | —CH(Et)CH₂— | Me | Me | 3-Cl—Ph | F | —CH(Et)CH₂— | Me | Me | 3-Cl—Ph |
| Cl | —CH₂CH(Et)— | Me | Me | 3-Cl—Ph | F | —CH₂CH(Et)— | Me | Me | 3-Cl—Ph |
| Cl | —CH(Et)CH₂CH₂— | Me | Me | 3-Cl—Ph | F | —CH(Et)CH₂CH₂— | Me | Me | 3-Cl—Ph |
| Cl | —CH₂CH(Et)CH₂— | Me | Me | 3-Cl—Ph | F | —CH₂CH(Et)CH₂— | Me | Me | 3-Cl—Ph |
| Cl | —CH₂CH₂CH(Et)— | Me | Me | 3-Cl—Ph | F | —CH₂CH₂CH(Et)— | Me | Me | 3-Cl—Ph |
| Cl | —CH(OCF₃)— | Me | Me | 3-Cl—Ph | F | —CH(OCF₃)— | Me | Me | 3-Cl—Ph |
| Cl | —CH(CF₃)— | Me | Me | 3-Cl—Ph | F | —CH(CF₃)— | Me | Me | 3-Cl—Ph |
| Cl | —CH₂CF₂CH₂— | Me | Me | 3-Cl—Ph | F | —CH₂CF₂CH₂— | Me | Me | 3-Cl—Ph |
| Cl | —CH₂CHFCH₂— | Me | Me | 3-Cl—Ph | F | —CH₂CHFCH₂— | Me | Me | 3-Cl—Ph |
| Cl | —CH₂CF₂— | Me | Me | 3-Cl—Ph | F | —CH₂CF₂— | Me | Me | 3-Cl—Ph |
| Cl | —CH₂CHF— | Me | Me | 3-Cl—Ph | F | —CH₂CHF— | Me | Me | 3-Cl—Ph |
| Cl | —CH(CN)— | Me | Me | 3-Cl—Ph | F | —CH(CN)— | Me | Me | 3-Cl—Ph |
| Cl | Vᵃ | Me | Me | 3-Cl—Ph | F | Vᵃ | Me | Me | 3-Cl—Ph |
| Cl | Vᵇ | Me | Me | 3-Cl—Ph | F | Vᵇ | Me | Me | 3-Cl—Ph |
| Cl | Vᶜ | Me | Me | 3-Cl—Ph | F | Vᶜ | Me | Me | 3-Cl—Ph |
| Cl | Vᵈ | Me | Me | 3-Cl—Ph | F | Vᵈ | Me | Me | 3-Cl—Ph |
| Cl | Vᵉ | Me | Me | 3-Cl—Ph | F | Vᵉ | Me | Me | 3-Cl—Ph |
| Cl | Vᶠ | Me | Me | 3-Cl—Ph | F | Vᶠ | Me | Me | 3-Cl—Ph |
| Cl | Vᵍ | Me | Me | 3-Cl—Ph | F | Vᵍ | Me | Me | 3-Cl—Ph |
| Cl | Vʰ | Me | Me | 3-Cl—Ph | F | Vʰ | Me | Me | 3-Cl—Ph |
| Cl | —CH₂OC(=O)CH₂— | Me | Me | 3-Cl—Ph | F | —CH₂OC(=O)CH₂— | Me | Me | 3-Cl—Ph |
| Cl | —CH₂C(=O)CH₂— | Me | Me | 3-Cl—Ph | F | —CH₂C(=O)CH₂— | Me | Me | 3-Cl—Ph |
| Cl | —CH₂C(=O)— | Me | Me | 3-Cl—Ph | F | —CH₂C(=O)— | Me | Me | 3-Cl—Ph |
| Cl | —CH₂— | Me | Me | 2-Cl—Ph | F | —CH₂— | Me | Me | 2-Cl—Ph |
| Cl | —CH₂CH₂— | Me | Me | 2-Cl—Ph | F | —CH₂CH₂— | Me | Me | 2-Cl—Ph |
| Cl | —CH₂CH₂CH₂— | Me | Me | 2-Cl—Ph | F | —CH₂CH₂CH₂— | Me | Me | 2-Cl—Ph |
| Cl | —CH₂CH₂CH₂CH₂— | Me | Me | 2-Cl—Ph | F | —CH₂CH₂CH₂CH₂— | Me | Me | 2-Cl—Ph |
| Cl | —CH₂OCH₂CH₂— | Me | Me | 2-Cl—Ph | F | —CH₂OCH₂CH₂— | Me | Me | 2-Cl—Ph |
| Cl | —CH₂CH₂OCH₂— | Me | Me | 2-Cl—Ph | F | —CH₂CH₂OCH₂— | Me | Me | 2-Cl—Ph |
| Cl | —CH₂C(=O)CH₂CH₂— | Me | Me | 2-Cl—Ph | F | —CH₂C(=O)CH₂CH₂— | Me | Me | 2-Cl—Ph |
| Cl | —CH₂CH₂C(=O)CH₂— | Me | Me | 2-Cl—Ph | F | —CH₂CH₂C(=O)CH₂— | Me | Me | 2-Cl—Ph |
| Cl | —CH₂C(=S)CH₂CH₂— | Me | Me | 2-Cl—Ph | F | —CH₂C(=S)CH₂CH₂— | Me | Me | 2-Cl—Ph |
| Cl | —CH₂CH₂C(=S)CH₂— | Me | Me | 2-Cl—Ph | F | —CH₂CH₂C(=S)CH₂— | Me | Me | 2-Cl—Ph |
| Cl | —CH₂C(=O)CH₂— | Me | Me | 2-Cl—Ph | F | —CH₂C(=O)CH₂— | Me | Me | 2-Cl—Ph |
| Cl | —CH₂C(=S)CH₂— | Me | Me | 2-Cl—Ph | F | —CH₂C(=S)CH₂— | Me | Me | 2-Cl—Ph |
| Cl | —CH(Me)— | Me | Me | 2-Cl—Ph | F | —CH(Me)— | Me | Me | 2-Cl—Ph |
| Cl | —CH(OMe)— | Me | Me | 2-Cl—Ph | F | —CH(OMe)— | Me | Me | 2-Cl—Ph |
| Cl | —CH(Me)CH₂— | Me | Me | 2-Cl—Ph | F | —CH(Me)CH₂— | Me | Me | 2-Cl—Ph |
| Cl | —CH₂CH(Me)— | Me | Me | 2-Cl—Ph | F | —CH₂CH(Me)— | Me | Me | 2-Cl—Ph |
| Cl | —CH₂CH(OMe)— | Me | Me | 2-Cl—Ph | F | —CH₂CH(OMe)— | Me | Me | 2-Cl—Ph |
| Cl | —CH(Me)CH₂CH₂— | Me | Me | 2-Cl—Ph | F | —CH(Me)CH₂CH₂— | Me | Me | 2-Cl—Ph |
| Cl | —CH₂CH(Me)CH₂— | Me | Me | 2-Cl—Ph | F | —CH₂CH(Me)CH₂— | Me | Me | 2-Cl—Ph |
| Cl | —CH₂CH₂CH(Me)— | Me | Me | 2-Cl—Ph | F | —CH₂CH₂CH(Me)— | Me | Me | 2-Cl—Ph |

TABLE 1-continued

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH(Et)— | Me | Me | 2-Cl—Ph | F | —CH(Et)— | Me | Me | 2-Cl—Ph |
| Cl | —CH(Et)CH$_2$— | Me | Me | 2-Cl—Ph | F | —CH(Et)CH$_2$— | Me | Me | 2-Cl—Ph |
| Cl | —CH$_2$CH(Et)— | Me | Me | 2-Cl—Ph | F | —CH$_2$CH(Et)— | Me | Me | 2-Cl—Ph |
| Cl | —CH(Et)CH$_2$CH$_2$— | Me | Me | 2-Cl—Ph | F | —CH(Et)CH$_2$CH$_2$— | Me | Me | 2-Cl—Ph |
| Cl | —CH$_2$CH(Et)CH$_2$— | Me | Me | 2-Cl—Ph | F | —CH$_2$CH(Et)CH$_2$— | Me | Me | 2-Cl—Ph |
| Cl | —CH$_2$CH$_2$CH(Et)— | Me | Me | 2-Cl—Ph | F | —CH$_2$CH$_2$CH(Et)— | Me | Me | 2-Cl—Ph |
| Cl | —CH(OCF$_3$)— | Me | Me | 2-Cl—Ph | F | —CH(OCF$_3$)— | Me | Me | 2-Cl—Ph |
| Cl | —CH(CF$_3$)— | Me | Me | 2-Cl—Ph | F | —CH(CF$_3$)— | Me | Me | 2-Cl—Ph |
| Cl | —CH$_2$CF$_2$CH$_2$— | Me | Me | 2-Cl—Ph | F | —CH$_2$CF$_2$CH$_2$— | Me | Me | 2-Cl—Ph |
| Cl | —CH$_2$CHFCH$_2$— | Me | Me | 2-Cl—Ph | F | —CH$_2$CHFCH$_2$— | Me | Me | 2-Cl—Ph |
| Cl | —CH$_2$CF$_2$— | Me | Me | 2-Cl—Ph | F | —CH$_2$CF$_2$— | Me | Me | 2-Cl—Ph |
| Cl | —CH$_2$CHF— | Me | Me | 2-Cl—Ph | F | —CH$_2$CHF— | Me | Me | 2-Cl—Ph |
| Cl | —CH(CN)— | Me | Me | 2-Cl—Ph | F | —CH(CN)— | Me | Me | 2-Cl—Ph |
| Cl | V$^a$ | Me | Me | 2-Cl—Ph | F | V$^a$ | Me | Me | 2-Cl—Ph |
| Cl | V$^b$ | Me | Me | 2-Cl—Ph | F | V$^b$ | Me | Me | 2-Cl—Ph |
| Cl | V$^c$ | Me | Me | 2-Cl—Ph | F | V$^c$ | Me | Me | 2-Cl—Ph |
| Cl | V$^d$ | Me | Me | 2-Cl—Ph | F | V$^d$ | Me | Me | 2-Cl—Ph |
| Cl | V$^e$ | Me | Me | 2-Cl—Ph | F | V$^e$ | Me | Me | 2-Cl—Ph |
| Cl | V$^f$ | Me | Me | 2-Cl—Ph | F | V$^f$ | Me | Me | 2-Cl—Ph |
| Cl | V$^g$ | Me | Me | 2-Cl—Ph | F | V$^g$ | Me | Me | 2-Cl—Ph |
| Cl | V$^h$ | Me | Me | 2-Cl—Ph | F | V$^h$ | Me | Me | 2-Cl—Ph |
| Cl | —CH$_2$OC(=O)CH$_2$— | Me | Me | 2-Cl—Ph | F | —CH$_2$OC(=O)CH$_2$— | Me | Me | 2-Cl—Ph |
| Cl | —CH$_2$C(=O)CH$_2$— | Me | Me | 2-Cl—Ph | F | —CH$_2$C(=O)CH$_2$— | Me | Me | 2-Cl—Ph |
| Cl | —CH$_2$C(=O)— | Me | Me | 2-Cl—Ph | F | —CH$_2$C(=O)— | Me | Me | 2-Cl—Ph |
| Cl | —CH$_2$— | Me | Me | c-Pr | F | —CH$_2$— | Me | Me | c-Pr |
| Cl | —CH$_2$CH$_2$— | Me | Me | c-Pr | F | —CH$_2$CH$_2$— | Me | Me | c-Pr |
| Cl | —CH$_2$CH$_2$CH$_2$— | Me | Me | c-Pr | F | —CH$_2$CH$_2$CH$_2$— | Me | Me | c-Pr |
| Cl | —CH$_2$CH$_2$CH$_2$CH$_2$— | Me | Me | c-Pr | F | —CH$_2$CH$_2$CH$_2$CH$_2$— | Me | Me | c-Pr |
| Cl | —CH$_2$OCH$_2$CH$_2$— | Me | Me | c-Pr | F | —CH$_2$OCH$_2$CH$_2$— | Me | Me | c-Pr |
| Cl | —CH$_2$CH$_2$OCH$_2$— | Me | Me | c-Pr | F | —CH$_2$CH$_2$OCH$_2$— | Me | Me | c-Pr |
| Cl | —CH$_2$C(=O)CH$_2$CH$_2$— | Me | Me | c-Pr | F | —CH$_2$C(=O)CH$_2$CH$_2$— | Me | Me | c-Pr |
| Cl | —CH$_2$CH$_2$C(=O)CH$_2$— | Me | Me | c-Pr | F | —CH$_2$CH$_2$C(=O)CH$_2$— | Me | Me | c-Pr |
| Cl | —CH$_2$C(=S)CH$_2$CH$_2$— | Me | Me | c-Pr | F | —CH$_2$C(=S)CH$_2$CH$_2$— | Me | Me | c-Pr |
| Cl | —CH$_2$CH$_2$C(=S)CH$_2$— | Me | Me | c-Pr | F | —CH$_2$CH$_2$C(=S)CH$_2$— | Me | Me | c-Pr |
| Cl | —CH$_2$C(=O)CH$_2$— | Me | Me | c-Pr | F | —CH$_2$C(=O)CH$_2$— | Me | Me | c-Pr |
| Cl | —CH$_2$C(=S)CH$_2$— | Me | Me | c-Pr | F | —CH$_2$C(=S)CH$_2$— | Me | Me | c-Pr |
| Cl | —CH(Me)— | Me | Me | c-Pr | F | —CH(Me)— | Me | Me | c-Pr |
| Cl | —CH(OMe)— | Me | Me | c-Pr | F | —CH(OMe)— | Me | Me | c-Pr |
| Cl | —CH(Me)CH$_2$— | Me | Me | c-Pr | F | —CH(Me)CH$_2$— | Me | Me | c-Pr |
| Cl | —CH$_2$CH(Me)— | Me | Me | c-Pr | F | —CH$_2$CH(Me)— | Me | Me | c-Pr |
| Cl | —CH$_2$CH(OMe)— | Me | Me | c-Pr | F | —CH$_2$CH(OMe)— | Me | Me | c-Pr |
| Cl | —CH(Me)CH$_2$CH$_2$— | Me | Me | c-Pr | F | —CH(Me)CH$_2$CH$_2$— | Me | Me | c-Pr |
| Cl | —CH$_2$CH(Me)CH$_2$— | Me | Me | c-Pr | F | —CH$_2$CH(Me)CH$_2$— | Me | Me | c-Pr |
| Cl | —CH$_2$CH$_2$CH(Me)— | Me | Me | c-Pr | F | —CH$_2$CH$_2$CH(Me)— | Me | Me | c-Pr |
| Cl | —CH(Et)— | Me | Me | c-Pr | F | —CH(Et)— | Me | Me | c-Pr |
| Cl | —CH(Et)CH$_2$— | Me | Me | c-Pr | F | —CH(Et)CH$_2$— | Me | Me | c-Pr |
| Cl | —CH$_2$CH(Et)— | Me | Me | c-Pr | F | —CH$_2$CH(Et)— | Me | Me | c-Pr |
| Cl | —CH(Et)CH$_2$CH$_2$— | Me | Me | c-Pr | F | —CH(Et)CH$_2$CH$_2$— | Me | Me | c-Pr |
| Cl | —CH$_2$CH(Et)CH$_2$— | Me | Me | c-Pr | F | —CH$_2$CH(Et)CH$_2$— | Me | Me | c-Pr |
| Cl | —CH$_2$CH$_2$CH(Et)— | Me | Me | c-Pr | F | —CH$_2$CH$_2$CH(Et)— | Me | Me | c-Pr |
| Cl | —CH(OCF$_3$)— | Me | Me | c-Pr | F | —CH(OCF$_3$)— | Me | Me | c-Pr |
| Cl | —CH(CF$_3$)— | Me | Me | c-Pr | F | —CH(CF$_3$)— | Me | Me | c-Pr |
| Cl | —CH$_2$CF$_2$CH$_2$— | Me | Me | c-Pr | F | —CH$_2$CF$_2$CH$_2$— | Me | Me | c-Pr |
| Cl | —CH$_2$CHFCH$_2$— | Me | Me | c-Pr | F | —CH$_2$CHFCH$_2$— | Me | Me | c-Pr |
| Cl | —CH$_2$CF$_2$— | Me | Me | c-Pr | F | —CH$_2$CF$_2$— | Me | Me | c-Pr |
| Cl | —CH$_2$CHF— | Me | Me | c-Pr | F | —CH$_2$CHF— | Me | Me | c-Pr |
| Cl | —CH(CN)— | Me | Me | c-Pr | F | —CH(CN)— | Me | Me | c-Pr |
| Cl | V$^a$ | Me | Me | c-Pr | F | V$^a$ | Me | Me | c-Pr |
| Cl | V$^b$ | Me | Me | c-Pr | F | V$^b$ | Me | Me | c-Pr |
| Cl | V$^c$ | Me | Me | c-Pr | F | V$^c$ | Me | Me | c-Pr |
| Cl | V$^d$ | Me | Me | c-Pr | F | V$^d$ | Me | Me | c-Pr |
| Cl | V$^e$ | Me | Me | c-Pr | F | V$^e$ | Me | Me | c-Pr |
| Cl | V$^f$ | Me | Me | c-Pr | F | V$^f$ | Me | Me | c-Pr |
| Cl | V$^g$ | Me | Me | c-Pr | F | V$^g$ | Me | Me | c-Pr |
| Cl | V$^h$ | Me | Me | c-Pr | F | V$^h$ | Me | Me | c-Pr |
| Cl | —CH$_2$OC(=O)CH$_2$— | Me | Me | c-Pr | F | —CH$_2$OC(=O)CH$_2$— | Me | Me | c-Pr |
| Cl | —CH$_2$C(=O)CH$_2$— | Me | Me | c-Pr | F | —CH$_2$C(=O)CH$_2$— | Me | Me | c-Pr |
| Cl | —CH$_2$C(=O)— | Me | Me | c-Pr | F | —CH$_2$C(=O)— | Me | Me | c-Pr |
| Me | —CH$_2$— | Me | Me | Me | Me | —CH$_2$— | Me | Me | Et |

TABLE 1-continued

Structure: methyl carbamate-NH-CH2-[benzene with R¹]-C(CH3)=N-O-V¹-Si(R^10a)(R^10b)(R^10c)

| R¹ | V¹ | R^10a | R^10b | R^10c | R¹ | V¹ | R^10a | R^10b | R^10c |
|---|---|---|---|---|---|---|---|---|---|
| Me | —CH₂CH₂— | Me | Me | Me | Me | —CH₂CH₂— | Me | Me | Et |
| Me | —CH₂CH₂CH₂— | Me | Me | Me | Me | —CH₂CH₂CH₂— | Me | Me | Et |
| Me | —CH₂CH₂CH₂CH₂— | Me | Me | Me | Me | —CH₂CH₂CH₂CH₂— | Me | Me | Et |
| Me | —CH₂OCH₂CH₂— | Me | Me | Me | Me | —CH₂OCH₂CH₂— | Me | Me | Et |
| Me | —CH₂CH₂OCH₂— | Me | Me | Me | Me | —CH₂CH₂OCH₂— | Me | Me | Et |
| Me | —CH₂C(=O)CH₂CH₂— | Me | Me | Me | Me | —CH₂C(=O)CH₂CH₂— | Me | Me | Et |
| Me | —CH₂CH₂C(=O)CH₂— | Me | Me | Me | Me | —CH₂CH₂C(=O)CH₂— | Me | Me | Et |
| Me | —CH₂C(=S)CH₂CH₂— | Me | Me | Me | Me | —CH₂C(=S)CH₂CH₂— | Me | Me | Et |
| Me | —CH₂CH₂C(=S)CH₂— | Me | Me | Me | Me | —CH₂CH₂C(=S)CH₂— | Me | Me | Et |
| Me | —CH₂C(=O)CH₂— | Me | Me | Me | Me | —CH₂C(=O)CH₂— | Me | Me | Et |
| Me | —CH₂C(=S)CH₂— | Me | Me | Me | Me | —CH₂C(=S)CH₂— | Me | Me | Et |
| Me | —CH(Me)— | Me | Me | Me | Me | —CH(Me)— | Me | Me | Et |
| Me | —CH(OMe)— | Me | Me | Me | Me | —CH(OMe)— | Me | Me | Et |
| Me | —CH(Me)CH₂— | Me | Me | Me | Me | —CH(Me)CH₂— | Me | Me | Et |
| Me | —CH₂CH(Me)— | Me | Me | Me | Me | —CH₂CH(Me)— | Me | Me | Et |
| Me | —CH₂CH(OMe)— | Me | Me | Me | Me | —CH₂CH(OMe)— | Me | Me | Et |
| Me | —CH(Me)CH₂CH₂— | Me | Me | Me | Me | —CH(Me)CH₂CH₂— | Me | Me | Et |
| Me | —CH₂CH(Me)CH₂— | Me | Me | Me | Me | —CH₂CH(Me)CH₂— | Me | Me | Et |
| Me | —CH₂CH₂CH(Me)— | Me | Me | Me | Me | —CH₂CH₂CH(Me)— | Me | Me | Et |
| Me | —CH(Et)— | Me | Me | Me | Me | —CH(Et)— | Me | Me | Et |
| Me | —CH(Et)CH₂— | Me | Me | Me | Me | —CH(Et)CH₂— | Me | Me | Et |
| Me | —CH₂CH(Et)— | Me | Me | Me | Me | —CH₂CH(Et)— | Me | Me | Et |
| Me | —CH(Et)CH₂CH₂— | Me | Me | Me | Me | —CH(Et)CH₂CH₂— | Me | Me | Et |
| Me | —CH₂CH(Et)CH₂— | Me | Me | Me | Me | —CH₂CH(Et)CH₂— | Me | Me | Et |
| Me | —CH₂CH₂CH(Et)— | Me | Me | Me | Me | —CH₂CH₂CH(Et)— | Me | Me | Et |
| Me | —CH(OCF₃)— | Me | Me | Me | Me | —CH(OCF₃)— | Me | Me | Et |
| Me | —CH(CF₃)— | Me | Me | Me | Me | —CH(CF₃)— | Me | Me | Et |
| Me | —CH₂CF₂CH₂— | Me | Me | Me | Me | —CH₂CF₂CH₂— | Me | Me | Et |
| Me | —CH₂CHFCH₂— | Me | Me | Me | Me | —CH₂CHFCH₂— | Me | Me | Et |
| Me | —CH₂CF₂— | Me | Me | Me | Me | —CH₂CF₂— | Me | Me | Et |
| Me | —CH₂CHF— | Me | Me | Me | Me | —CH₂CHF— | Me | Me | Et |
| Me | —CH(CN)— | Me | Me | Me | Me | —CH(CN)— | Me | Me | Et |
| Me | V^a | Me | Me | Me | Me | V^a | Me | Me | Et |
| Me | V^b | Me | Me | Me | Me | V^b | Me | Me | Et |
| Me | V^c | Me | Me | Me | Me | V^c | Me | Me | Et |
| Me | V^d | Me | Me | Me | Me | V^d | Me | Me | Et |
| Me | V^e | Me | Me | Me | Me | V^e | Me | Me | Et |
| Me | V^f | Me | Me | Me | Me | V^f | Me | Me | Et |
| Me | V^g | Me | Me | Me | Me | V^g | Me | Me | Et |
| Me | V^h | Me | Me | Me | Me | V^h | Me | Me | Et |
| Me | —CH₂OC(=O)CH₂— | Me | Me | Me | Me | —CH₂OC(=O)CH₂— | Me | Me | Et |
| Me | —CH₂C(=O)CH₂— | Me | Me | Me | Me | —CH₂C(=O)CH₂— | Me | Me | Et |
| Me | —CH₂C(=O)— | Me | Me | Me | Me | —CH₂C(=O)— | Me | Me | Et |
| Me | —CH₂— | Me | Et | Et | Me | —CH₂— | Et | Et | Et |
| Me | —CH₂CH₂— | Me | Et | Et | Me | —CH₂CH₂— | Et | Et | Et |
| Me | —CH₂CH₂CH₂— | Me | Et | Et | Me | —CH₂CH₂CH₂— | Et | Et | Et |
| Me | —CH₂CH₂CH₂CH₂— | Me | Et | Et | Me | —CH₂CH₂CH₂CH₂— | Et | Et | Et |
| Me | —CH₂OCH₂CH₂— | Me | Et | Et | Me | —CH₂OCH₂CH₂— | Et | Et | Et |
| Me | —CH₂CH₂OCH₂— | Me | Et | Et | Me | —CH₂CH₂OCH₂— | Et | Et | Et |
| Me | —CH₂C(=O)CH₂CH₂— | Me | Et | Et | Me | —CH₂C(=O)CH₂CH₂— | Et | Et | Et |
| Me | —CH₂CH₂C(=O)CH₂— | Me | Et | Et | Me | —CH₂CH₂C(=O)CH₂— | Et | Et | Et |
| Me | —CH₂C(=S)CH₂CH₂— | Me | Et | Et | Me | —CH₂C(=S)CH₂CH₂— | Et | Et | Et |
| Me | —CH₂CH₂C(=S)CH₂— | Me | Et | Et | Me | —CH₂CH₂C(=S)CH₂— | Et | Et | Et |
| Me | —CH₂C(=O)CH₂— | Me | Et | Et | Me | —CH₂C(=O)CH₂— | Et | Et | Et |
| Me | —CH₂C(=S)CH₂— | Me | Et | Et | Me | —CH₂C(=S)CH₂— | Et | Et | Et |
| Me | —CH(Me)— | Me | Et | Et | Me | —CH(Me)— | Et | Et | Et |
| Me | —CH(OMe)— | Me | Et | Et | Me | —CH(OMe)— | Et | Et | Et |
| Me | —CH(Me)CH₂— | Me | Et | Et | Me | —CH(Me)CH₂— | Et | Et | Et |
| Me | —CH₂CH(Me)— | Me | Et | Et | Me | —CH₂CH(Me)— | Et | Et | Et |
| Me | —CH₂CH(OMe)— | Me | Et | Et | Me | —CH₂CH(OMe)— | Et | Et | Et |
| Me | —CH(Me)CH₂CH₂— | Me | Et | Et | Me | —CH(Me)CH₂CH₂— | Et | Et | Et |
| Me | —CH₂CH(Me)CH₂— | Me | Et | Et | Me | —CH₂CH(Me)CH₂— | Et | Et | Et |
| Me | —CH₂CH₂CH(Me)— | Me | Et | Et | Me | —CH₂CH₂CH(Me)— | Et | Et | Et |
| Me | —CH(Et)— | Me | Et | Et | Me | —CH(Et)— | Et | Et | Et |
| Me | —CH(Et)CH₂— | Me | Et | Et | Me | —CH(Et)CH₂— | Et | Et | Et |
| Me | —CH₂CH(Et)— | Me | Et | Et | Me | —CH₂CH(Et)— | Et | Et | Et |
| Me | —CH(Et)CH₂CH₂— | Me | Et | Et | Me | —CH(Et)CH₂CH₂— | Et | Et | Et |
| Me | —CH₂CH(Et)CH₂— | Me | Et | Et | Me | —CH₂CH(Et)CH₂— | Et | Et | Et |
| Me | —CH₂CH₂CH(Et)— | Me | Et | Et | Me | —CH₂CH₂CH(Et)— | Et | Et | Et |

TABLE 1-continued

Structure:
$$H_3C-O-C(=O)-N(H)-CH_2-\text{[2-}R^1\text{-phenyl-5-]}-C(CH_3)=N-O-V^1-Si(R^{10a})(R^{10b})(R^{10c})$$

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Me | —CH(OCF$_3$)— | Me | Et | Et | Me | —CH(OCF$_3$)— | Et | Et | Et |
| Me | —CH(CF$_3$)— | Me | Et | Et | Me | —CH(CF$_3$)— | Et | Et | Et |
| Me | —CH$_2$CF$_2$CH$_2$— | Me | Et | Et | Me | —CH$_2$CF$_2$CH$_2$— | Et | Et | Et |
| Me | —CH$_2$CHFCH$_2$— | Me | Et | Et | Me | —CH$_2$CHFCH$_2$— | Et | Et | Et |
| Me | —CH$_2$CF$_2$— | Me | Et | Et | Me | —CH$_2$CF$_2$— | Et | Et | Et |
| Me | —CH$_2$CHF— | Me | Et | Et | Me | —CH$_2$CHF— | Et | Et | Et |
| Me | —CH(CN)— | Me | Et | Et | Me | —CH(CN)— | Et | Et | Et |
| Me | $V^a$ | Me | Et | Et | Me | $V^a$ | Et | Et | Et |
| Me | $V^b$ | Me | Et | Et | Me | $V^b$ | Et | Et | Et |
| Me | $V^c$ | Me | Et | Et | Me | $V^c$ | Et | Et | Et |
| Me | $V^d$ | Me | Et | Et | Me | $V^d$ | Et | Et | Et |
| Me | $V^e$ | Me | Et | Et | Me | $V^e$ | Et | Et | Et |
| Me | $V^f$ | Me | Et | Et | Me | $V^f$ | Et | Et | Et |
| Me | $V^g$ | Me | Et | Et | Me | $V^g$ | Et | Et | Et |
| Me | $V^h$ | Me | Et | Et | Me | $V^h$ | Et | Et | Et |
| Me | —CH$_2$OC(=O)CH$_2$— | Me | Et | Et | Me | —CH$_2$OC(=O)CH$_2$— | Et | Et | Et |
| Me | —CH$_2$C(=O)CH$_2$— | Me | Et | Et | Me | —CH$_2$C(=O)CH$_2$— | Et | Et | Et |
| Me | —CH$_2$C(=O)— | Me | Et | Et | Me | —CH$_2$C(=O)— | Et | Et | Et |
| Me | —CH$_2$— | Me | Me | i-Pr | Me | —CH$_2$— | Me | Et | i-Pr |
| Me | —CH$_2$CH$_2$— | Me | Me | i-Pr | Me | —CH$_2$CH$_2$— | Me | Et | i-Pr |
| Me | —CH$_2$CH$_2$CH$_2$— | Me | Me | i-Pr | Me | —CH$_2$CH$_2$CH$_2$— | Me | Et | i-Pr |
| Me | —CH$_2$CH$_2$CH$_2$CH$_2$— | Me | Me | i-Pr | Me | —CH$_2$CH$_2$CH$_2$CH$_2$— | Me | Et | i-Pr |
| Me | —CH$_2$OCH$_2$CH$_2$— | Me | Me | i-Pr | Me | —CH$_2$OCH$_2$CH$_2$— | Me | Et | i-Pr |
| Me | —CH$_2$CH$_2$OCH$_2$— | Me | Me | i-Pr | Me | —CH$_2$CH$_2$OCH$_2$— | Me | Et | i-Pr |
| Me | —CH$_2$C(=O)CH$_2$CH$_2$— | Me | Me | i-Pr | Me | —CH$_2$C(=O)CH$_2$CH$_2$— | Me | Et | i-Pr |
| Me | —CH$_2$CH$_2$C(=O)CH$_2$— | Me | Me | i-Pr | Me | —CH$_2$CH$_2$C(=O)CH$_2$— | Me | Et | i-Pr |
| Me | —CH$_2$C(=S)CH$_2$CH$_2$— | Me | Me | i-Pr | Me | —CH$_2$C(=S)CH$_2$CH$_2$— | Me | Et | i-Pr |
| Me | —CH$_2$CH$_2$C(=S)CH$_2$— | Me | Me | i-Pr | Me | —CH$_2$CH$_2$C(=S)CH$_2$— | Me | Et | i-Pr |
| Me | —CH$_2$C(=O)CH$_2$— | Me | Me | i-Pr | Me | —CH$_2$C(=O)CH$_2$— | Me | Et | i-Pr |
| Me | —CH$_2$C(=S)CH$_2$— | Me | Me | i-Pr | Me | —CH$_2$C(=S)CH$_2$— | Me | Et | i-Pr |
| Me | —CH(Me)— | Me | Me | i-Pr | Me | —CH(Me)— | Me | Et | i-Pr |
| Me | —CH(OMe)— | Me | Me | i-Pr | Me | —CH(OMe)— | Me | Et | i-Pr |
| Me | —CH(Me)CH$_2$— | Me | Me | i-Pr | Me | —CH(Me)CH$_2$— | Me | Et | i-Pr |
| Me | —CH$_2$CH(Me)— | Me | Me | i-Pr | Me | —CH$_2$CH(Me)— | Me | Et | i-Pr |
| Me | —CH$_2$CH(OMe)— | Me | Me | i-Pr | Me | —CH$_2$CH(OMe)— | Me | Et | i-Pr |
| Me | —CH(Me)CH$_2$CH$_2$— | Me | Me | i-Pr | Me | —CH(Me)CH$_2$CH$_2$— | Me | Et | i-Pr |
| Me | —CH$_2$CH(Me)CH$_2$— | Me | Me | i-Pr | Me | —CH$_2$CH(Me)CH$_2$— | Me | Et | i-Pr |
| Me | —CH$_2$CH$_2$CH(Me)— | Me | Me | i-Pr | Me | —CH$_2$CH$_2$CH(Me)— | Me | Et | i-Pr |
| Me | —CH(Et)— | Me | Me | i-Pr | Me | —CH(Et)— | Me | Et | i-Pr |
| Me | —CH(Et)CH$_2$— | Me | Me | i-Pr | Me | —CH(Et)CH$_2$— | Me | Et | i-Pr |
| Me | —CH$_2$CH(Et)— | Me | Me | i-Pr | Me | —CH$_2$CH(Et)— | Me | Et | i-Pr |
| Me | —CH(Et)CH$_2$CH$_2$— | Me | Me | i-Pr | Me | —CH(Et)CH$_2$CH$_2$— | Me | Et | i-Pr |
| Me | —CH$_2$CH(Et)CH$_2$— | Me | Me | i-Pr | Me | —CH$_2$CH(Et)CH$_2$— | Me | Et | i-Pr |
| Me | —CH$_2$CH$_2$CH(Et)— | Me | Me | i-Pr | Me | —CH$_2$CH$_2$CH(Et)— | Me | Et | i-Pr |
| Me | —CH(OCF$_3$)— | Me | Me | i-Pr | Me | —CH(OCF$_3$)— | Me | Et | i-Pr |
| Me | —CH(CF$_3$)— | Me | Me | i-Pr | Me | —CH(CF$_3$)— | Me | Et | i-Pr |
| Me | —CH$_2$CF$_2$CH$_2$— | Me | Me | i-Pr | Me | —CH$_2$CF$_2$CH$_2$— | Me | Et | i-Pr |
| Me | —CH$_2$CHFCH$_2$— | Me | Me | i-Pr | Me | —CH$_2$CHFCH$_2$— | Me | Et | i-Pr |
| Me | —CH$_2$CF$_2$— | Me | Me | i-Pr | Me | —CH$_2$CF$_2$— | Me | Et | i-Pr |
| Me | —CH$_2$CHF— | Me | Me | i-Pr | Me | —CH$_2$CHF— | Me | Et | i-Pr |
| Me | —CH(CN)— | Me | Me | i-Pr | Me | —CH(CN)— | Me | Et | i-Pr |
| Me | $V^a$ | Me | Me | i-Pr | Me | $V^a$ | Me | Et | i-Pr |
| Me | $V^b$ | Me | Me | i-Pr | Me | $V^b$ | Me | Et | i-Pr |
| Me | $V^c$ | Me | Me | i-Pr | Me | $V^c$ | Me | Et | i-Pr |
| Me | $V^d$ | Me | Me | i-Pr | Me | $V^d$ | Me | Et | i-Pr |
| Me | $V^e$ | Me | Me | i-Pr | Me | $V^e$ | Me | Et | i-Pr |
| Me | $V^f$ | Me | Me | i-Pr | Me | $V^f$ | Me | Et | i-Pr |
| Me | $V^g$ | Me | Me | i-Pr | Me | $V^g$ | Me | Et | i-Pr |
| Me | $V^h$ | Me | Me | i-Pr | Me | $V^h$ | Me | Et | i-Pr |
| Me | —CH$_2$OC(=O)CH$_2$— | Me | Me | i-Pr | Me | —CH$_2$OC(=O)CH$_2$— | Me | Et | i-Pr |
| Me | —CH$_2$C(=O)CH$_2$— | Me | Me | i-Pr | Me | —CH$_2$C(=O)CH$_2$— | Me | Et | i-Pr |
| Me | —CH$_2$C(=O)— | Me | Me | i-Pr | Me | —CH$_2$C(=O)— | Me | Et | i-Pr |
| Me | —CH$_2$— | Me | Me | Ph | Me | —CH$_2$— | Me | Me | 4-Cl—Ph |
| Me | —CH$_2$CH$_2$— | Me | Me | Ph | Me | —CH$_2$CH$_2$— | Me | Me | 4-Cl—Ph |
| Me | —CH$_2$CH$_2$CH$_2$— | Me | Me | Ph | Me | —CH$_2$CH$_2$CH$_2$— | Me | Me | 4-Cl—Ph |
| Me | —CH$_2$CH$_2$CH$_2$CH$_2$— | Me | Me | Ph | Me | —CH$_2$CH$_2$CH$_2$CH$_2$— | Me | Me | 4-Cl—Ph |
| Me | —CH$_2$OCH$_2$CH$_2$— | Me | Me | Ph | Me | —CH$_2$OCH$_2$CH$_2$— | Me | Me | 4-Cl—Ph |
| Me | —CH$_2$CH$_2$OCH$_2$— | Me | Me | Ph | Me | —CH$_2$CH$_2$OCH$_2$— | Me | Me | 4-Cl—Ph |
| Me | —CH$_2$C(=O)CH$_2$CH$_2$— | Me | Me | Ph | Me | —CH$_2$C(=O)CH$_2$CH$_2$— | Me | Me | 4-Cl—Ph |

TABLE 1-continued

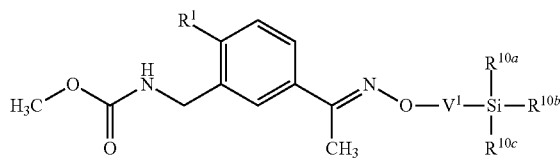

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | —CH₂CH₂C(=O)CH₂— | Me | Me | Ph | Me | —CH₂CH₂C(=O)CH₂— | Me | Me | 4-Cl—Ph |
| Me | —CH₂C(=S)CH₂CH₂— | Me | Me | Ph | Me | —CH₂C(=S)CH₂CH₂— | Me | Me | 4-Cl—Ph |
| Me | —CH₂CH₂C(=S)CH₂— | Me | Me | Ph | Me | —CH₂CH₂C(=S)CH₂— | Me | Me | 4-Cl—Ph |
| Me | —CH₂C(=O)CH₂— | Me | Me | Ph | Me | —CH₂C(=O)CH₂— | Me | Me | 4-Cl—Ph |
| Me | —CH₂C(=S)CH₂— | Me | Me | Ph | Me | —CH₂C(=S)CH₂— | Me | Me | 4-Cl—Ph |
| Me | —CH(Me)— | Me | Me | Ph | Me | —CH(Me)— | Me | Me | 4-Cl—Ph |
| Me | —CH(OMe)— | Me | Me | Ph | Me | —CH(OMe)— | Me | Me | 4-Cl—Ph |
| Me | —CH(Me)CH₂— | Me | Me | Ph | Me | —CH(Me)CH₂— | Me | Me | 4-Cl—Ph |
| Me | —CH₂CH(Me)— | Me | Me | Ph | Me | —CH₂CH(Me)— | Me | Me | 4-Cl—Ph |
| Me | —CH₂CH(OMe)— | Me | Me | Ph | Me | —CH₂CH(OMe)— | Me | Me | 4-Cl—Ph |
| Me | —CH(Me)CH₂CH₂— | Me | Me | Ph | Me | —CH(Me)CH₂CH₂— | Me | Me | 4-Cl—Ph |
| Me | —CH₂CH(Me)CH₂— | Me | Me | Ph | Me | —CH₂CH(Me)CH₂— | Me | Me | 4-Cl—Ph |
| Me | —CH₂CH₂CH(Me)— | Me | Me | Ph | Me | —CH₂CH₂CH(Me)— | Me | Me | 4-Cl—Ph |
| Me | —CH(Et)— | Me | Me | Ph | Me | —CH(Et)— | Me | Me | 4-Cl—Ph |
| Me | —CH(Et)CH₂— | Me | Me | Ph | Me | —CH(Et)CH₂— | Me | Me | 4-Cl—Ph |
| Me | —CH₂CH(Et)— | Me | Me | Ph | Me | —CH₂CH(Et)— | Me | Me | 4-Cl—Ph |
| Me | —CH(Et)CH₂CH₂— | Me | Me | Ph | Me | —CH(Et)CH₂CH₂— | Me | Me | 4-Cl—Ph |
| Me | —CH₂CH(Et)CH₂— | Me | Me | Ph | Me | —CH₂CH(Et)CH₂— | Me | Me | 4-Cl—Ph |
| Me | —CH₂CH₂CH(Et)— | Me | Me | Ph | Me | —CH₂CH₂CH(Et)— | Me | Me | 4-Cl—Ph |
| Me | —CH(OCF₃)— | Me | Me | Ph | Me | —CH(OCF₃)— | Me | Me | 4-Cl—Ph |
| Me | —CH(CF₃)— | Me | Me | Ph | Me | —CH(CF₃)— | Me | Me | 4-Cl—Ph |
| Me | —CH₂CF₂CH₂— | Me | Me | Ph | Me | —CH₂CF₂CH₂— | Me | Me | 4-Cl—Ph |
| Me | —CH₂CHFCH₂— | Me | Me | Ph | Me | —CH₂CHFCH₂— | Me | Me | 4-Cl—Ph |
| Me | —CH₂CF₂— | Me | Me | Ph | Me | —CH₂CF₂— | Me | Me | 4-Cl—Ph |
| Me | —CH₂CHF— | Me | Me | Ph | Me | —CH₂CHF— | Me | Me | 4-Cl—Ph |
| Me | —CH(CN)— | Me | Me | Ph | Me | —CH(CN)— | Me | Me | 4-Cl—Ph |
| Me | Vᵃ | Me | Me | Ph | Me | Vᵃ | Me | Me | 4-Cl—Ph |
| Me | Vᵇ | Me | Me | Ph | Me | Vᵇ | Me | Me | 4-Cl—Ph |
| Me | Vᶜ | Me | Me | Ph | Me | Vᶜ | Me | Me | 4-Cl—Ph |
| Me | Vᵈ | Me | Me | Ph | Me | Vᵈ | Me | Me | 4-Cl—Ph |
| Me | Vᵉ | Me | Me | Ph | Me | Vᵉ | Me | Me | 4-Cl—Ph |
| Me | Vᶠ | Me | Me | Ph | Me | Vᶠ | Me | Me | 4-Cl—Ph |
| Me | Vᵍ | Me | Me | Ph | Me | Vᵍ | Me | Me | 4-Cl—Ph |
| Me | Vʰ | Me | Me | Ph | Me | Vʰ | Me | Me | 4-Cl—Ph |
| Me | —CH₂OC(=O)CH₂— | Me | Me | Ph | Me | —CH₂OC(=O)CH₂— | Me | Me | 4-Cl—Ph |
| Me | —CH₂C(=O)CH₂— | Me | Me | Ph | Me | —CH₂C(=O)CH₂— | Me | Me | 4-Cl—Ph |
| Me | —CH₂C(=O)— | Me | Me | Ph | Me | —CH₂C(=O)— | Me | Me | 4-Cl—Ph |
| Me | —CH₂— | Me | Me | 3-Cl—Ph | Me | —CH₂— | Me | Me | 2-Cl—Ph |
| Me | —CH₂CH₂— | Me | Me | 3-Cl—Ph | Me | —CH₂CH₂— | Me | Me | 2-Cl—Ph |
| Me | —CH₂CH₂CH₂— | Me | Me | 3-Cl—Ph | Me | —CH₂CH₂CH₂— | Me | Me | 2-Cl—Ph |
| Me | —CH₂CH₂CH₂CH₂— | Me | Me | 3-Cl—Ph | Me | —CH₂CH₂CH₂CH₂— | Me | Me | 2-Cl—Ph |
| Me | —CH₂OCH₂CH₂— | Me | Me | 3-Cl—Ph | Me | —CH₂OCH₂CH₂— | Me | Me | 2-Cl—Ph |
| Me | —CH₂CH₂OCH₂— | Me | Me | 3-Cl—Ph | Me | —CH₂CH₂OCH₂— | Me | Me | 2-Cl—Ph |
| Me | —CH₂C(=O)CH₂CH₂— | Me | Me | 3-Cl—Ph | Me | —CH₂C(=O)CH₂CH₂— | Me | Me | 2-Cl—Ph |
| Me | —CH₂CH₂C(=O)CH₂— | Me | Me | 3-Cl—Ph | Me | —CH₂CH₂C(=O)CH₂— | Me | Me | 2-Cl—Ph |
| Me | —CH₂C(=S)CH₂CH₂— | Me | Me | 3-Cl—Ph | Me | —CH₂C(=S)CH₂CH₂— | Me | Me | 2-Cl—Ph |
| Me | —CH₂CH₂C(=S)CH₂— | Me | Me | 3-Cl—Ph | Me | —CH₂CH₂C(=S)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=S)CH₂— | Me | Me | 3-Cl—Ph | Me | —CH₂C(=S)CH₂— | Me | Me | 2-Cl—Ph |
| Me | —CH(Me)— | Me | Me | 3-Cl—Ph | Me | —CH(Me)— | Me | Me | 2-Cl—Ph |
| Me | —CH(OMe)— | Me | Me | 3-Cl—Ph | Me | —CH(OMe)— | Me | Me | 2-Cl—Ph |
| Me | —CH(Me)CH₂— | Me | Me | 3-Cl—Ph | Me | —CH(Me)CH₂— | Me | Me | 2-Cl—Ph |
| Me | —CH₂CH(Me)— | Me | Me | 3-Cl—Ph | Me | —CH₂CH(Me)— | Me | Me | 2-Cl—Ph |
| Me | —CH₂CH(OMe)— | Me | Me | 3-Cl—Ph | Me | —CH₂CH(OMe)— | Me | Me | 2-Cl—Ph |
| Me | —CH(Me)CH₂CH₂— | Me | Me | 3-Cl—Ph | Me | —CH(Me)CH₂CH₂— | Me | Me | 2-Cl—Ph |
| Me | —CH₂CH(Me)CH₂— | Me | Me | 3-Cl—Ph | Me | —CH₂CH(Me)CH₂— | Me | Me | 2-Cl—Ph |
| Me | —CH₂CH₂CH(Me)— | Me | Me | 3-Cl—Ph | Me | —CH₂CH₂CH(Me)— | Me | Me | 2-Cl—Ph |
| Me | —CH(Et)— | Me | Me | 3-Cl—Ph | Me | —CH(Et)— | Me | Me | 2-Cl—Ph |
| Me | —CH(Et)CH₂— | Me | Me | 3-Cl—Ph | Me | —CH(Et)CH₂— | Me | Me | 2-Cl—Ph |
| Me | —CH₂CH(Et)— | Me | Me | 3-Cl—Ph | Me | —CH₂CH(Et)— | Me | Me | 2-Cl—Ph |
| Me | —CH(Et)CH₂CH₂— | Me | Me | 3-Cl—Ph | Me | —CH(Et)CH₂CH₂— | Me | Me | 2-Cl—Ph |
| Me | —CH₂CH(Et)CH₂— | Me | Me | 3-Cl—Ph | Me | —CH₂CH(Et)CH₂— | Me | Me | 2-Cl—Ph |
| Me | —CH₂CH₂CH(Et)— | Me | Me | 3-Cl—Ph | Me | —CH₂CH₂CH(Et)— | Me | Me | 2-Cl—Ph |
| Me | —CH(OCF₃)— | Me | Me | 3-Cl—Ph | Me | —CH(OCF₃)— | Me | Me | 2-Cl—Ph |
| Me | —CH(CF₃)— | Me | Me | 3-Cl—Ph | Me | —CH(CF₃)— | Me | Me | 2-Cl—Ph |
| Me | —CH₂CF₂CH₂— | Me | Me | 3-Cl—Ph | Me | —CH₂CF₂CH₂— | Me | Me | 2-Cl—Ph |
| Me | —CH₂CHFCH₂— | Me | Me | 3-Cl—Ph | Me | —CH₂CHFCH₂— | Me | Me | 2-Cl—Ph |
| Me | —CH₂CF₂— | Me | Me | 3-Cl—Ph | Me | —CH₂CF₂— | Me | Me | 2-Cl—Ph |
| Me | —CH₂CHF— | Me | Me | 3-Cl—Ph | Me | —CH₂CHF— | Me | Me | 2-Cl—Ph |

TABLE 1-continued

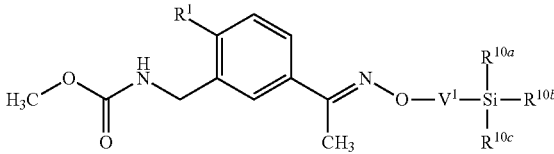

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | —CH(CN)— | Me | Me | 3-Cl—Ph | Me | —CH(CN)— | Me | Me | 2-Cl—Ph |
| Me | Vᵃ | Me | Me | 3-Cl—Ph | Me | Vᵃ | Me | Me | 2-Cl—Ph |
| Me | Vᵇ | Me | Me | 3-Cl—Ph | Me | Vᵇ | Me | Me | 2-Cl—Ph |
| Me | Vᶜ | Me | Me | 3-Cl—Ph | Me | Vᶜ | Me | Me | 2-Cl—Ph |
| Me | Vᵈ | Me | Me | 3-Cl—Ph | Me | Vᵈ | Me | Me | 2-Cl—Ph |
| Me | Vᵉ | Me | Me | 3-Cl—Ph | Me | Vᵉ | Me | Me | 2-Cl—Ph |
| Me | Vᶠ | Me | Me | 3-Cl—Ph | Me | Vᶠ | Me | Me | 2-Cl—Ph |
| Me | Vᵍ | Me | Me | 3-Cl—Ph | Me | Vᵍ | Me | Me | 2-Cl—Ph |
| Me | Vʰ | Me | Me | 3-Cl—Ph | Me | Vʰ | Me | Me | 2-Cl—Ph |
| Me | —CH₂OC(=O)CH₂— | Me | Me | 3-Cl—Ph | Me | —CH₂OC(=O)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=O)— | Me | Me | 3-Cl—Ph | Me | —CH₂C(=O)— | Me | Me | 2-Cl—Ph |
| Me | —CH₂— | Me | Me | c-Pr | Me | —CH₂CH(Et)— | Me | Me | c-Pr |
| Me | —CH₂CH₂— | Me | Me | c-Pr | Me | —CH(Et)CH₂CH₂— | Me | Me | c-Pr |
| Me | —CH₂CH₂CH₂— | Me | Me | c-Pr | Me | —CH₂CH(Et)CH₂— | Me | Me | c-Pr |
| Me | —CH₂CH₂CH₂CH₂— | Me | Me | c-Pr | Me | —CH₂CH₂CH(Et)— | Me | Me | c-Pr |
| Me | —CH₂OCH₂CH₂— | Me | Me | c-Pr | Me | —CH(OCF₃)— | Me | Me | c-Pr |
| Me | —CH₂CH₂OCH₂— | Me | Me | c-Pr | Me | —CH(CF₃)— | Me | Me | c-Pr |
| Me | —CH₂C(=O)CH₂CH₂— | Me | Me | c-Pr | Me | —CH₂CF₂CH₂— | Me | Me | c-Pr |
| Me | —CH₂CH₂C(=O)CH₂— | Me | Me | c-Pr | Me | —CH₂CHFCH₂— | Me | Me | c-Pr |
| Me | —CH₂C(=S)CH₂CH₂— | Me | Me | c-Pr | Me | —CH₂CF₂— | Me | Me | c-Pr |
| Me | —CH₂CH₂C(=S)CH₂— | Me | Me | c-Pr | Me | —CH₂CHF— | Me | Me | c-Pr |
| Me | —CH₂C(=O)CH₂— | Me | Me | c-Pr | Me | —CH(CN)— | Me | Me | c-Pr |
| Me | —CH₂C(=S)CH₂— | Me | Me | c-Pr | Me | Vᵃ | Me | Me | c-Pr |
| Me | —CH(Me)— | Me | Me | c-Pr | Me | Vᵇ | Me | Me | c-Pr |
| Me | —CH(OMe)— | Me | Me | c-Pr | Me | Vᶜ | Me | Me | c-Pr |
| Me | —CH(Me)CH₂— | Me | Me | c-Pr | Me | Vᵈ | Me | Me | c-Pr |
| Me | —CH₂CH(Me)— | Me | Me | c-Pr | Me | Vᵉ | Me | Me | c-Pr |
| Me | —CH₂CH(OMe)— | Me | Me | c-Pr | Me | Vᶠ | Me | Me | c-Pr |
| Me | —CH(Me)CH₂CH₂— | Me | Me | c-Pr | Me | Vᵍ | Me | Me | c-Pr |
| Me | —CH₂CH(Me)CH₂— | Me | Me | c-Pr | Me | Vʰ | Me | Me | c-Pr |
| Me | —CH₂CH₂CH(Me)— | Me | Me | c-Pr | Me | —CH₂OC(=O)CH₂— | Me | Me | c-Pr |
| Me | —CH(Et)— | Me | Me | c-Pr | Me | —CH₂C(=O)CH₂— | Me | Me | c-Pr |
| Me | —CH(Et)CH₂— | Me | Me | c-Pr | Me | —CH₂C(=O)— | Me | Me | c-Pr |

TABLE 2

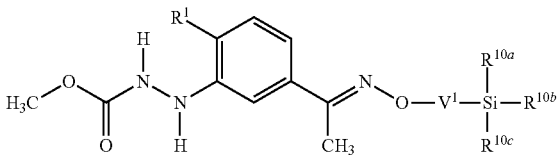

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂— | Me | Me | Me | F | —CH₂— | Me | Me | Me |
| Cl | —CH₂CH₂— | Me | Me | Me | F | —CH₂CH₂— | Me | Me | Me |
| Cl | —CH₂CH₂CH₂— | Me | Me | Me | F | —CH₂CH₂CH₂— | Me | Me | Me |
| Cl | —CH₂CH₂CH₂CH₂— | Me | Me | Me | F | —CH₂CH₂CH₂CH₂— | Me | Me | Me |
| Cl | —CH₂OCH₂CH₂— | Me | Me | Me | F | —CH₂OCH₂CH₂— | Me | Me | Me |
| Cl | —CH₂CH₂OCH₂— | Me | Me | Me | F | —CH₂CH₂OCH₂— | Me | Me | Me |
| Cl | —CH₂C(=O)CH₂CH₂— | Me | Me | Me | F | —CH₂C(=O)CH₂CH₂— | Me | Me | Me |
| Cl | —CH₂CH₂C(=O)CH₂— | Me | Me | Me | F | —CH₂CH₂C(=O)CH₂— | Me | Me | Me |
| Cl | —CH₂C(=S)CH₂CH₂— | Me | Me | Me | F | —CH₂C(=S)CH₂CH₂— | Me | Me | Me |
| Cl | —CH₂CH₂C(=S)CH₂— | Me | Me | Me | F | —CH₂CH₂C(=S)CH₂— | Me | Me | Me |
| Cl | —CH₂C(=O)CH₂— | Me | Me | Me | F | —CH₂C(=O)CH₂— | Me | Me | Me |
| Cl | —CH₂C(=S)CH₂— | Me | Me | Me | F | —CH₂C(=S)CH₂— | Me | Me | Me |
| Cl | —CH(Me)— | Me | Me | Me | F | —CH(Me)— | Me | Me | Me |
| Cl | —CH(OMe)— | Me | Me | Me | F | —CH(OMe)— | Me | Me | Me |
| Cl | —CH(Me)CH₂— | Me | Me | Me | F | —CH(Me)CH₂— | Me | Me | Me |
| Cl | —CH₂CH(Me)— | Me | Me | Me | F | —CH₂CH(Me)— | Me | Me | Me |
| Cl | —CH₂CH(OMe)— | Me | Me | Me | F | —CH₂CH(OMe)— | Me | Me | Me |
| Cl | —CH(Me)CH₂CH₂— | Me | Me | Me | F | —CH(Me)CH₂CH₂— | Me | Me | Me |
| Cl | —CH₂CH(Me)CH₂— | Me | Me | Me | F | —CH₂CH(Me)CH₂— | Me | Me | Me |
| Cl | —CH₂CH₂CH(Me)— | Me | Me | Me | F | —CH₂CH₂CH(Me)— | Me | Me | Me |

TABLE 2-continued

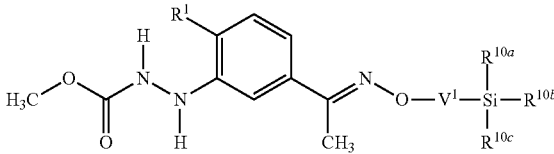

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH(Et)— | Me | Me | Me | F | —CH(Et)— | Me | Me | Me |
| Cl | —CH(Et)CH$_2$— | Me | Me | Me | F | —CH(Et)CH$_2$— | Me | Me | Me |
| Cl | —CH$_2$CH(Et)— | Me | Me | Me | F | —CH$_2$CH(Et)— | Me | Me | Me |
| Cl | —CH(Et)CH$_2$CH$_2$— | Me | Me | Me | F | —CH(Et)CH$_2$CH$_2$— | Me | Me | Me |
| Cl | —CH$_2$CH(Et)CH$_2$— | Me | Me | Me | F | —CH$_2$CH(Et)CH$_2$— | Me | Me | Me |
| Cl | —CH$_2$CH$_2$CH(Et)— | Me | Me | Me | F | —CH$_2$CH$_2$CH(Et)— | Me | Me | Me |
| Cl | —CH(OCF$_3$)— | Me | Me | Me | F | —CH(OCF$_3$)— | Me | Me | Me |
| Cl | —CH(CF$_3$)— | Me | Me | Me | F | —CH(CF$_3$)— | Me | Me | Me |
| Cl | —CH$_2$CF$_2$CH$_2$— | Me | Me | Me | F | —CH$_2$CF$_2$CH$_2$— | Me | Me | Me |
| Cl | —CH$_2$CHFCH$_2$— | Me | Me | Me | F | —CH$_2$CHFCH$_2$— | Me | Me | Me |
| Cl | —CH$_2$CF$_2$— | Me | Me | Me | F | —CH$_2$CF$_2$— | Me | Me | Me |
| Cl | —CH$_2$CHF— | Me | Me | Me | F | —CH$_2$CHF— | Me | Me | Me |
| Cl | —CH(CN)— | Me | Me | Me | F | —CH(CN)— | Me | Me | Me |
| Cl | $V^a$ | Me | Me | Me | F | $V^a$ | Me | Me | Me |
| Cl | $V^b$ | Me | Me | Me | F | $V^b$ | Me | Me | Me |
| Cl | $V^c$ | Me | Me | Me | F | $V^c$ | Me | Me | Me |
| Cl | $V^d$ | Me | Me | Me | F | $V^d$ | Me | Me | Me |
| Cl | $V^e$ | Me | Me | Me | F | $V^e$ | Me | Me | Me |
| Cl | $V^f$ | Me | Me | Me | F | $V^f$ | Me | Me | Me |
| Cl | $V^g$ | Me | Me | Me | F | $V^g$ | Me | Me | Me |
| Cl | $V^h$ | Me | Me | Me | F | $V^h$ | Me | Me | Me |
| Cl | —CH$_2$OC(=O)CH$_2$— | Me | Me | Me | F | —CH$_2$OC(=O)CH$_2$— | Me | Me | Me |
| Cl | —CH$_2$C(=O)CH$_2$— | Me | Me | Me | F | —CH$_2$C(=O)CH$_2$— | Me | Me | Me |
| Cl | —CH$_2$C(=O)— | Me | Me | Me | F | —CH$_2$C(=O)— | Me | Me | Me |
| Cl | —CH$_2$— | Me | Me | Et | F | —CH$_2$— | Me | Me | Et |
| Cl | —CH$_2$CH$_2$— | Me | Me | Et | F | —CH$_2$CH$_2$— | Me | Me | Et |
| Cl | —CH$_2$CH$_2$CH$_2$— | Me | Me | Et | F | —CH$_2$CH$_2$CH$_2$— | Me | Me | Et |
| Cl | —CH$_2$CH$_2$CH$_2$CH$_2$— | Me | Me | Et | F | —CH$_2$CH$_2$CH$_2$CH$_2$— | Me | Me | Et |
| Cl | —CH$_2$OCH$_2$CH$_2$— | Me | Me | Et | F | —CH$_2$OCH$_2$CH$_2$— | Me | Me | Et |
| Cl | —CH$_2$CH$_2$OCH$_2$— | Me | Me | Et | F | —CH$_2$CH$_2$OCH$_2$— | Me | Me | Et |
| Cl | —CH$_2$C(=O)CH$_2$CH$_2$— | Me | Me | Et | F | —CH$_2$C(=O)CH$_2$CH$_2$— | Me | Me | Et |
| Cl | —CH$_2$CH$_2$C(=O)CH$_2$— | Me | Me | Et | F | —CH$_2$CH$_2$C(=O)CH$_2$— | Me | Me | Et |
| Cl | —CH$_2$C(=S)CH$_2$CH$_2$— | Me | Me | Et | F | —CH$_2$C(=S)CH$_2$CH$_2$— | Me | Me | Et |
| Cl | —CH$_2$CH$_2$C(=S)CH$_2$— | Me | Me | Et | F | —CH$_2$CH$_2$C(=S)CH$_2$— | Me | Me | Et |
| Cl | —CH$_2$C(=O)CH$_2$— | Me | Me | Et | F | —CH$_2$C(=O)CH$_2$— | Me | Me | Et |
| Cl | —CH$_2$C(=S)CH$_2$— | Me | Me | Et | F | —CH$_2$C(=S)CH$_2$— | Me | Me | Et |
| Cl | —CH(Me)— | Me | Me | Et | F | —CH(Me)— | Me | Me | Et |
| Cl | —CH(OMe)— | Me | Me | Et | F | —CH(OMe)— | Me | Me | Et |
| Cl | —CH(Me)CH$_2$— | Me | Me | Et | F | —CH(Me)CH$_2$— | Me | Me | Et |
| Cl | —CH$_2$CH(Me)— | Me | Me | Et | F | —CH$_2$CH(Me)— | Me | Me | Et |
| Cl | —CH$_2$CH(OMe)— | Me | Me | Et | F | —CH$_2$CH(OMe)— | Me | Me | Et |
| Cl | —CH(Me)CH$_2$CH$_2$— | Me | Me | Et | F | —CH(Me)CH$_2$CH$_2$— | Me | Me | Et |
| Cl | —CH$_2$CH(Me)CH$_2$— | Me | Me | Et | F | —CH$_2$CH(Me)CH$_2$— | Me | Me | Et |
| Cl | —CH$_2$CH$_2$CH(Me)— | Me | Me | Et | F | —CH$_2$CH$_2$CH(Me)— | Me | Me | Et |
| Cl | —CH(Et)— | Me | Me | Et | F | —CH(Et)— | Me | Me | Et |
| Cl | —CH(Et)CH$_2$— | Me | Me | Et | F | —CH(Et)CH$_2$— | Me | Me | Et |
| Cl | —CH$_2$CH(Et)— | Me | Me | Et | F | —CH$_2$CH(Et)— | Me | Me | Et |
| Cl | —CH(Et)CH$_2$CH$_2$— | Me | Me | Et | F | —CH(Et)CH$_2$CH$_2$— | Me | Me | Et |
| Cl | —CH$_2$CH(Et)CH$_2$— | Me | Me | Et | F | —CH$_2$CH(Et)CH$_2$— | Me | Me | Et |
| Cl | —CH$_2$CH$_2$CH(Et)— | Me | Me | Et | F | —CH$_2$CH$_2$CH(Et)— | Me | Me | Et |
| Cl | —CH(OCF$_3$)— | Me | Me | Et | F | —CH(OCF$_3$)— | Me | Me | Et |
| Cl | —CH(CF$_3$)— | Me | Me | Et | F | —CH(CF$_3$)— | Me | Me | Et |
| Cl | —CH$_2$CF$_2$CH$_2$— | Me | Me | Et | F | —CH$_2$CF$_2$CH$_2$— | Me | Me | Et |
| Cl | —CH$_2$CHFCH$_2$— | Me | Me | Et | F | —CH$_2$CHFCH$_2$— | Me | Me | Et |
| Cl | —CH$_2$CF$_2$— | Me | Me | Et | F | —CH$_2$CF$_2$— | Me | Me | Et |
| Cl | —CH$_2$CHF— | Me | Me | Et | F | —CH$_2$CHF— | Me | Me | Et |
| Cl | —CH(CN)— | Me | Me | Et | F | —CH(CN)— | Me | Me | Et |
| Cl | $V^a$ | Me | Me | Et | F | $V^a$ | Me | Me | Et |
| Cl | $V^b$ | Me | Me | Et | F | $V^b$ | Me | Me | Et |
| Cl | $V^c$ | Me | Me | Et | F | $V^c$ | Me | Me | Et |
| Cl | $V^d$ | Me | Me | Et | F | $V^d$ | Me | Me | Et |
| Cl | $V^e$ | Me | Me | Et | F | $V^e$ | Me | Me | Et |
| Cl | $V^f$ | Me | Me | Et | F | $V^f$ | Me | Me | Et |
| Cl | $V^g$ | Me | Me | Et | F | $V^g$ | Me | Me | Et |
| Cl | $V^h$ | Me | Me | Et | F | $V^h$ | Me | Me | Et |
| Cl | —CH$_2$OC(=O)CH$_2$— | Me | Me | Et | F | —CH$_2$OC(=O)CH$_2$— | Me | Me | Et |
| Cl | —CH$_2$C(=O)CH$_2$— | Me | Me | Et | F | —CH$_2$C(=O)CH$_2$— | Me | Me | Et |
| Cl | —CH$_2$C(=O)— | Me | Me | Et | F | —CH$_2$C(=O)— | Me | Me | Et |
| Cl | —CH$_2$— | Me | Et | Et | F | —CH$_2$— | Me | Et | Et |

TABLE 2-continued

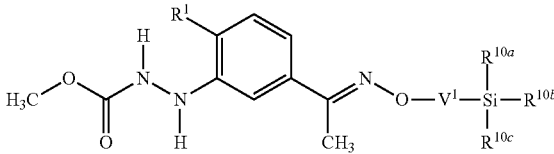

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH$_2$CH$_2$— | Me | Et | Et | F | —CH$_2$CH$_2$— | Me | Et | Et |
| Cl | —CH$_2$CH$_2$CH$_2$— | Me | Et | Et | F | —CH$_2$CH$_2$CH$_2$— | Me | Et | Et |
| Cl | —CH$_2$CH$_2$CH$_2$CH$_2$— | Me | Et | Et | F | —CH$_2$CH$_2$CH$_2$CH$_2$— | Me | Et | Et |
| Cl | —CH$_2$OCH$_2$CH$_2$— | Me | Et | Et | F | —CH$_2$OCH$_2$CH$_2$— | Me | Et | Et |
| Cl | —CH$_2$CH$_2$OCH$_2$— | Me | Et | Et | F | —CH$_2$CH$_2$OCH$_2$— | Me | Et | Et |
| Cl | —CH$_2$C(=O)CH$_2$CH$_2$— | Me | Et | Et | F | —CH$_2$C(=O)CH$_2$CH$_2$— | Me | Et | Et |
| Cl | —CH$_2$CH$_2$C(=O)CH$_2$— | Me | Et | Et | F | —CH$_2$CH$_2$C(=O)CH$_2$— | Me | Et | Et |
| Cl | —CH$_2$C(=S)CH$_2$CH$_2$— | Me | Et | Et | F | —CH$_2$C(=S)CH$_2$CH$_2$— | Me | Et | Et |
| Cl | —CH$_2$CH$_2$C(=S)CH$_2$— | Me | Et | Et | F | —CH$_2$CH$_2$C(=S)CH$_2$— | Me | Et | Et |
| Cl | —CH$_2$C(=O)CH$_2$— | Me | Et | Et | F | —CH$_2$C(=O)CH$_2$— | Me | Et | Et |
| Cl | —CH$_2$C(=S)CH$_2$— | Me | Et | Et | F | —CH$_2$C(=S)CH$_2$— | Me | Et | Et |
| Cl | —CH(Me)— | Me | Et | Et | F | —CH(Me)— | Me | Et | Et |
| Cl | —CH(OMe)— | Me | Et | Et | F | —CH(OMe)— | Me | Et | Et |
| Cl | —CH(Me)CH$_2$— | Me | Et | Et | F | —CH(Me)CH$_2$— | Me | Et | Et |
| Cl | —CH$_2$CH(Me)— | Me | Et | Et | F | —CH$_2$CH(Me)— | Me | Et | Et |
| Cl | —CH$_2$CH(OMe)— | Me | Et | Et | F | —CH$_2$CH(OMe)— | Me | Et | Et |
| Cl | —CH(Me)CH$_2$CH$_2$— | Me | Et | Et | F | —CH(Me)CH$_2$CH$_2$— | Me | Et | Et |
| Cl | —CH$_2$CH(Me)CH$_2$— | Me | Et | Et | F | —CH$_2$CH(Me)CH$_2$— | Me | Et | Et |
| Cl | —CH$_2$CH$_2$CH(Me)— | Me | Et | Et | F | —CH$_2$CH$_2$CH(Me)— | Me | Et | Et |
| Cl | —CH(Et)— | Me | Et | Et | F | —CH(Et)— | Me | Et | Et |
| Cl | —CH(Et)CH$_2$— | Me | Et | Et | F | —CH(Et)CH$_2$— | Me | Et | Et |
| Cl | —CH$_2$CH(Et)— | Me | Et | Et | F | —CH$_2$CH(Et)— | Me | Et | Et |
| Cl | —CH(Et)CH$_2$CH$_2$— | Me | Et | Et | F | —CH(Et)CH$_2$CH$_2$— | Me | Et | Et |
| Cl | —CH$_2$CH(Et)CH$_2$— | Me | Et | Et | F | —CH$_2$CH(Et)CH$_2$— | Me | Et | Et |
| Cl | —CH$_2$CH$_2$CH(Et)— | Me | Et | Et | F | —CH$_2$CH$_2$CH(Et)— | Me | Et | Et |
| Cl | —CH(OCF$_3$)— | Me | Et | Et | F | —CH(OCF$_3$)— | Me | Et | Et |
| Cl | —CH(CF$_3$)— | Me | Et | Et | F | —CH(CF$_3$)— | Me | Et | Et |
| Cl | —CH$_2$CF$_2$CH$_2$— | Me | Et | Et | F | —CH$_2$CF$_2$CH$_2$— | Me | Et | Et |
| Cl | —CH$_2$CHFCH$_2$— | Me | Et | Et | F | —CH$_2$CHFCH$_2$— | Me | Et | Et |
| Cl | —CH$_2$CF$_2$— | Me | Et | Et | F | —CH$_2$CF$_2$— | Me | Et | Et |
| Cl | —CH$_2$CHF— | Me | Et | Et | F | —CH$_2$CHF— | Me | Et | Et |
| Cl | —CH(CN)— | Me | Et | Et | F | —CH(CN)— | Me | Et | Et |
| Cl | $V^a$ | Me | Et | Et | F | $V^a$ | Me | Et | Et |
| Cl | $V^b$ | Me | Et | Et | F | $V^b$ | Me | Et | Et |
| Cl | $V^c$ | Me | Et | Et | F | $V^c$ | Me | Et | Et |
| Cl | $V^d$ | Me | Et | Et | F | $V^d$ | Me | Et | Et |
| Cl | $V^e$ | Me | Et | Et | F | $V^e$ | Me | Et | Et |
| Cl | $V^f$ | Me | Et | Et | F | $V^f$ | Me | Et | Et |
| Cl | $V^g$ | Me | Et | Et | F | $V^g$ | Me | Et | Et |
| Cl | $V^h$ | Me | Et | Et | F | $V^h$ | Me | Et | Et |
| Cl | —CH$_2$OC(=O)CH$_2$— | Me | Et | Et | F | —CH$_2$OC(=O)CH$_2$— | Me | Et | Et |
| Cl | —CH$_2$C(=O)CH$_2$— | Me | Et | Et | F | —CH$_2$C(=O)CH$_2$— | Me | Et | Et |
| Cl | —CH$_2$C(=O)— | Me | Et | Et | F | —CH$_2$C(=O)— | Me | Et | Et |
| Cl | —CH$_2$— | Et | Et | Et | F | —CH$_2$— | Et | Et | Et |
| Cl | —CH$_2$CH$_2$— | Et | Et | Et | F | —CH$_2$CH$_2$— | Et | Et | Et |
| Cl | —CH$_2$CH$_2$CH$_2$— | Et | Et | Et | F | —CH$_2$CH$_2$CH$_2$— | Et | Et | Et |
| Cl | —CH$_2$CH$_2$CH$_2$CH$_2$— | Et | Et | Et | F | —CH$_2$CH$_2$CH$_2$CH$_2$— | Et | Et | Et |
| Cl | —CH$_2$OCH$_2$CH$_2$— | Et | Et | Et | F | —CH$_2$OCH$_2$CH$_2$— | Et | Et | Et |
| Cl | —CH$_2$CH$_2$OCH$_2$— | Et | Et | Et | F | —CH$_2$CH$_2$OCH$_2$— | Et | Et | Et |
| Cl | —CH$_2$C(=O)CH$_2$CH$_2$— | Et | Et | Et | F | —CH$_2$C(=O)CH$_2$CH$_2$— | Et | Et | Et |
| Cl | —CH$_2$CH$_2$C(=O)CH$_2$— | Et | Et | Et | F | —CH$_2$CH$_2$C(=O)CH$_2$— | Et | Et | Et |
| Cl | —CH$_2$C(=S)CH$_2$CH$_2$— | Et | Et | Et | F | —CH$_2$C(=S)CH$_2$CH$_2$— | Et | Et | Et |
| Cl | —CH$_2$CH$_2$C(=S)CH$_2$— | Et | Et | Et | F | —CH$_2$CH$_2$C(=S)CH$_2$— | Et | Et | Et |
| Cl | —CH$_2$C(=O)CH$_2$— | Et | Et | Et | F | —CH$_2$C(=O)CH$_2$— | Et | Et | Et |
| Cl | —CH$_2$C(=S)CH$_2$— | Et | Et | Et | F | —CH$_2$C(=S)CH$_2$— | Et | Et | Et |
| Cl | —CH(Me)— | Et | Et | Et | F | —CH(Me)— | Et | Et | Et |
| Cl | —CH(OMe)— | Et | Et | Et | F | —CH(OMe)— | Et | Et | Et |
| Cl | —CH(Me)CH$_2$— | Et | Et | Et | F | —CH(Me)CH$_2$— | Et | Et | Et |
| Cl | —CH$_2$CH(Me)— | Et | Et | Et | F | —CH$_2$CH(Me)— | Et | Et | Et |
| Cl | —CH$_2$CH(OMe)— | Et | Et | Et | F | —CH$_2$CH(OMe)— | Et | Et | Et |
| Cl | —CH(Me)CH$_2$CH$_2$— | Et | Et | Et | F | —CH(Me)CH$_2$CH$_2$— | Et | Et | Et |
| Cl | —CH$_2$CH(Me)CH$_2$— | Et | Et | Et | F | —CH$_2$CH(Me)CH$_2$— | Et | Et | Et |
| Cl | —CH$_2$CH$_2$CH(Me)— | Et | Et | Et | F | —CH$_2$CH$_2$CH(Me)— | Et | Et | Et |
| Cl | —CH(Et)— | Et | Et | Et | F | —CH(Et)— | Et | Et | Et |
| Cl | —CH(Et)CH$_2$— | Et | Et | Et | F | —CH(Et)CH$_2$— | Et | Et | Et |
| Cl | —CH$_2$CH(Et)— | Et | Et | Et | F | —CH$_2$CH(Et)— | Et | Et | Et |
| Cl | —CH(Et)CH$_2$CH$_2$— | Et | Et | Et | F | —CH(Et)CH$_2$CH$_2$— | Et | Et | Et |
| Cl | —CH$_2$CH(Et)CH$_2$— | Et | Et | Et | F | —CH$_2$CH(Et)CH$_2$— | Et | Et | Et |
| Cl | —CH$_2$CH$_2$CH(Et)— | Et | Et | Et | F | —CH$_2$CH$_2$CH(Et)— | Et | Et | Et |

TABLE 2-continued

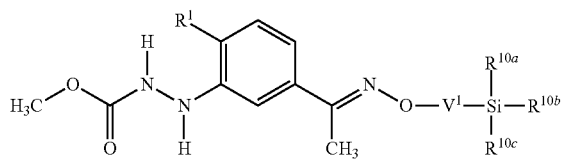

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH(OCF$_3$)— | Et | Et | Et | F | —CH(OCF$_3$)— | Et | Et | Et |
| Cl | —CH(CF$_3$)— | Et | Et | Et | F | —CH(CF$_3$)— | Et | Et | Et |
| Cl | —CH$_2$CF$_2$CH$_2$— | Et | Et | Et | F | —CH$_2$CF$_2$CH$_2$— | Et | Et | Et |
| Cl | —CH$_2$CHFCH$_2$— | Et | Et | Et | F | —CH$_2$CHFCH$_2$— | Et | Et | Et |
| Cl | —CH$_2$CF$_2$— | Et | Et | Et | F | —CH$_2$CF$_2$— | Et | Et | Et |
| Cl | —CH$_2$CHF— | Et | Et | Et | F | —CH$_2$CHF— | Et | Et | Et |
| Cl | —CH(CN)— | Et | Et | Et | F | —CH(CN)— | Et | Et | Et |
| Cl | V$^a$ | Et | Et | Et | F | V$^a$ | Et | Et | Et |
| Cl | V$^b$ | Et | Et | Et | F | V$^b$ | Et | Et | Et |
| Cl | V$^c$ | Et | Et | Et | F | V$^c$ | Et | Et | Et |
| Cl | V$^d$ | Et | Et | Et | F | V$^d$ | Et | Et | Et |
| Cl | V$^e$ | Et | Et | Et | F | V$^e$ | Et | Et | Et |
| Cl | V$^f$ | Et | Et | Et | F | V$^f$ | Et | Et | Et |
| Cl | V$^g$ | Et | Et | Et | F | V$^g$ | Et | Et | Et |
| Cl | V$^h$ | Et | Et | Et | F | V$^h$ | Et | Et | Et |
| Cl | —CH$_2$OC(=O)CH$_2$— | Et | Et | Et | F | —CH$_2$OC(=O)CH$_2$— | Et | Et | Et |
| Cl | —CH$_2$C(=O)CH$_2$— | Et | Et | Et | F | —CH$_2$C(=O)CH$_2$— | Et | Et | Et |
| Cl | —CH$_2$C(=O)— | Et | Et | Et | F | —CH$_2$C(=O)— | Et | Et | Et |
| Cl | —CH$_2$— | Me | Me | i-Pr | F | —CH$_2$— | Me | Me | i-Pr |
| Cl | —CH$_2$CH$_2$— | Me | Me | i-Pr | F | —CH$_2$CH$_2$— | Me | Me | i-Pr |
| Cl | —CH$_2$CH$_2$CH$_2$— | Me | Me | i-Pr | F | —CH$_2$CH$_2$CH$_2$— | Me | Me | i-Pr |
| Cl | —CH$_2$CH$_2$CH$_2$CH$_2$— | Me | Me | i-Pr | F | —CH$_2$CH$_2$CH$_2$CH$_2$— | Me | Me | i-Pr |
| Cl | —CH$_2$OCH$_2$CH$_2$— | Me | Me | i-Pr | F | —CH$_2$OCH$_2$CH$_2$— | Me | Me | i-Pr |
| Cl | —CH$_2$CH$_2$OCH$_2$— | Me | Me | i-Pr | F | —CH$_2$CH$_2$OCH$_2$— | Me | Me | i-Pr |
| Cl | —CH$_2$C(=O)CH$_2$CH$_2$— | Me | Me | i-Pr | F | —CH$_2$C(=O)CH$_2$CH$_2$— | Me | Me | i-Pr |
| Cl | —CH$_2$CH$_2$C(=O)CH$_2$— | Me | Me | i-Pr | F | —CH$_2$CH$_2$C(=O)CH$_2$— | Me | Me | i-Pr |
| Cl | —CH$_2$C(=S)CH$_2$CH$_2$— | Me | Me | i-Pr | F | —CH$_2$C(=S)CH$_2$CH$_2$— | Me | Me | i-Pr |
| Cl | —CH$_2$CH$_2$C(=S)CH$_2$— | Me | Me | i-Pr | F | —CH$_2$CH$_2$C(=S)CH$_2$— | Me | Me | i-Pr |
| Cl | —CH$_2$C(=O)CH$_2$— | Me | Me | i-Pr | F | —CH$_2$C(=O)CH$_2$— | Me | Me | i-Pr |
| Cl | —CH$_2$C(=S)CH$_2$— | Me | Me | i-Pr | F | —CH$_2$C(=S)CH$_2$— | Me | Me | i-Pr |
| Cl | —CH(Me)— | Me | Me | i-Pr | F | —CH(Me)— | Me | Me | i-Pr |
| Cl | —CH(OMe)— | Me | Me | i-Pr | F | —CH(OMe)— | Me | Me | i-Pr |
| Cl | —CH(Me)CH$_2$— | Me | Me | i-Pr | F | —CH(Me)CH$_2$— | Me | Me | i-Pr |
| Cl | —CH$_2$CH(Me)— | Me | Me | i-Pr | F | —CH$_2$CH(Me)— | Me | Me | i-Pr |
| Cl | —CH$_2$CH(OMe)— | Me | Me | i-Pr | F | —CH$_2$CH(OMe)— | Me | Me | i-Pr |
| Cl | —CH(Me)CH$_2$CH$_2$— | Me | Me | i-Pr | F | —CH(Me)CH$_2$CH$_2$— | Me | Me | i-Pr |
| Cl | —CH$_2$CH(Me)CH$_2$— | Me | Me | i-Pr | F | —CH$_2$CH(Me)CH$_2$— | Me | Me | i-Pr |
| Cl | —CH$_2$CH$_2$CH(Me)— | Me | Me | i-Pr | F | —CH$_2$CH$_2$CH(Me)— | Me | Me | i-Pr |
| Cl | —CH(Et)— | Me | Me | i-Pr | F | —CH(Et)— | Me | Me | i-Pr |
| Cl | —CH(Et)CH$_2$— | Me | Me | i-Pr | F | —CH(Et)CH$_2$— | Me | Me | i-Pr |
| Cl | —CH$_2$CH(Et)— | Me | Me | i-Pr | F | —CH$_2$CH(Et)— | Me | Me | i-Pr |
| Cl | —CH(Et)CH$_2$CH$_2$— | Me | Me | i-Pr | F | —CH(Et)CH$_2$CH$_2$— | Me | Me | i-Pr |
| Cl | —CH$_2$CH(Et)CH$_2$— | Me | Me | i-Pr | F | —CH$_2$CH(Et)CH$_2$— | Me | Me | i-Pr |
| Cl | —CH$_2$CH$_2$CH(Et)— | Me | Me | i-Pr | F | —CH$_2$CH$_2$CH(Et)— | Me | Me | i-Pr |
| Cl | —CH(OCF$_3$)— | Me | Me | i-Pr | F | —CH(OCF$_3$)— | Me | Me | i-Pr |
| Cl | —CH(CF$_3$)— | Me | Me | i-Pr | F | —CH(CF$_3$)— | Me | Me | i-Pr |
| Cl | —CH$_2$CF$_2$CH$_2$— | Me | Me | i-Pr | F | —CH$_2$CF$_2$CH$_2$— | Me | Me | i-Pr |
| Cl | —CH$_2$CHFCH$_2$— | Me | Me | i-Pr | F | —CH$_2$CHFCH$_2$— | Me | Me | i-Pr |
| Cl | —CH$_2$CF$_2$— | Me | Me | i-Pr | F | —CH$_2$CF$_2$— | Me | Me | i-Pr |
| Cl | —CH$_2$CHF— | Me | Me | i-Pr | F | —CH$_2$CHF— | Me | Me | i-Pr |
| Cl | —CH(CN)— | Me | Me | i-Pr | F | —CH(CN)— | Me | Me | i-Pr |
| Cl | V$^a$ | Me | Me | i-Pr | F | V$^a$ | Me | Me | i-Pr |
| Cl | V$^b$ | Me | Me | i-Pr | F | V$^b$ | Me | Me | i-Pr |
| Cl | V$^c$ | Me | Me | i-Pr | F | V$^c$ | Me | Me | i-Pr |
| Cl | V$^d$ | Me | Me | i-Pr | F | V$^d$ | Me | Me | i-Pr |
| Cl | V$^e$ | Me | Me | i-Pr | F | V$^e$ | Me | Me | i-Pr |
| Cl | V$^f$ | Me | Me | i-Pr | F | V$^f$ | Me | Me | i-Pr |
| Cl | V$^g$ | Me | Me | i-Pr | F | V$^g$ | Me | Me | i-Pr |
| Cl | V$^h$ | Me | Me | i-Pr | F | V$^h$ | Me | Me | i-Pr |
| Cl | —CH$_2$OC(=O)CH$_2$— | Me | Me | i-Pr | F | —CH$_2$OC(=O)CH$_2$— | Me | Me | i-Pr |
| Cl | —CH$_2$C(=O)CH$_2$— | Me | Me | i-Pr | F | —CH$_2$C(=O)CH$_2$— | Me | Me | i-Pr |
| Cl | —CH$_2$C(=O)— | Me | Me | i-Pr | F | —CH$_2$C(=O)— | Me | Me | i-Pr |
| Cl | —CH$_2$— | Me | Et | i-Pr | F | —CH$_2$— | Me | Et | i-Pr |
| Cl | —CH$_2$CH$_2$— | Me | Et | i-Pr | F | —CH$_2$CH$_2$— | Me | Et | i-Pr |
| Cl | —CH$_2$CH$_2$CH$_2$— | Me | Et | i-Pr | F | —CH$_2$CH$_2$CH$_2$— | Me | Et | i-Pr |
| Cl | —CH$_2$CH$_2$CH$_2$CH$_2$— | Me | Et | i-Pr | F | —CH$_2$CH$_2$CH$_2$CH$_2$— | Me | Et | i-Pr |
| Cl | —CH$_2$OCH$_2$CH$_2$— | Me | Et | i-Pr | F | —CH$_2$OCH$_2$CH$_2$— | Me | Et | i-Pr |
| Cl | —CH$_2$CH$_2$OCH$_2$— | Me | Et | i-Pr | F | —CH$_2$CH$_2$OCH$_2$— | Me | Et | i-Pr |
| Cl | —CH$_2$C(=O)CH$_2$CH$_2$— | Me | Et | i-Pr | F | —CH$_2$C(=O)CH$_2$CH$_2$— | Me | Et | i-Pr |

TABLE 2-continued

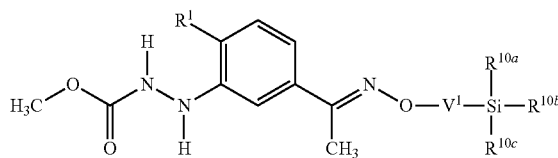

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH$_2$CH$_2$C(=O)CH$_2$— | Me | Et | i-Pr | F | —CH$_2$CH$_2$C(=O)CH$_2$— | Me | Et | i-Pr |
| Cl | —CH$_2$C(=S)CH$_2$CH$_2$— | Me | Et | i-Pr | F | —CH$_2$C(=S)CH$_2$CH$_2$— | Me | Et | i-Pr |
| Cl | —CH$_2$CH$_2$C(=S)CH$_2$— | Me | Et | i-Pr | F | —CH$_2$CH$_2$C(=S)CH$_2$— | Me | Et | i-Pr |
| Cl | —CH$_2$C(=O)CH$_2$— | Me | Et | i-Pr | F | —CH$_2$C(=O)CH$_2$— | Me | Et | i-Pr |
| Cl | —CH$_2$C(=S)CH$_2$— | Me | Et | i-Pr | F | —CH$_2$C(=S)CH$_2$— | Me | Et | i-Pr |
| Cl | —CH(Me)— | Me | Et | i-Pr | F | —CH(Me)— | Me | Et | i-Pr |
| Cl | —CH(OMe)— | Me | Et | i-Pr | F | —CH(OMe)— | Me | Et | i-Pr |
| Cl | —CH(Me)CH$_2$— | Me | Et | i-Pr | F | —CH(Me)CH$_2$— | Me | Et | i-Pr |
| Cl | —CH$_2$CH(Me)— | Me | Et | i-Pr | F | —CH$_2$CH(Me)— | Me | Et | i-Pr |
| Cl | —CH$_2$CH(OMe)— | Me | Et | i-Pr | F | —CH$_2$CH(OMe)— | Me | Et | i-Pr |
| Cl | —CH(Me)CH$_2$CH$_2$— | Me | Et | i-Pr | F | —CH(Me)CH$_2$CH$_2$— | Me | Et | i-Pr |
| Cl | —CH$_2$CH(Me)CH$_2$— | Me | Et | i-Pr | F | —CH$_2$CH(Me)CH$_2$— | Me | Et | i-Pr |
| Cl | —CH$_2$CH$_2$CH(Me)— | Me | Et | i-Pr | F | —CH$_2$CH$_2$CH(Me)— | Me | Et | i-Pr |
| Cl | —CH(Et)— | Me | Et | i-Pr | F | —CH(Et)— | Me | Et | i-Pr |
| Cl | —CH(Et)CH$_2$— | Me | Et | i-Pr | F | —CH(Et)CH$_2$— | Me | Et | i-Pr |
| Cl | —CH$_2$CH(Et)— | Me | Et | i-Pr | F | —CH$_2$CH(Et)— | Me | Et | i-Pr |
| Cl | —CH(Et)CH$_2$CH$_2$— | Me | Et | i-Pr | F | —CH(Et)CH$_2$CH$_2$— | Me | Et | i-Pr |
| Cl | —CH$_2$CH(Et)CH$_2$— | Me | Et | i-Pr | F | —CH$_2$CH(Et)CH$_2$— | Me | Et | i-Pr |
| Cl | —CH$_2$CH$_2$CH(Et)— | Me | Et | i-Pr | F | —CH$_2$CH$_2$CH(Et)— | Me | Et | i-Pr |
| Cl | —CH(OCF$_3$)— | Me | Et | i-Pr | F | —CH(OCF$_3$)— | Me | Et | i-Pr |
| Cl | —CH(CF$_3$)— | Me | Et | i-Pr | F | —CH(CF$_3$)— | Me | Et | i-Pr |
| Cl | —CH$_2$CF$_2$CH$_2$— | Me | Et | i-Pr | F | —CH$_2$CF$_2$CH$_2$— | Me | Et | i-Pr |
| Cl | —CH$_2$CHFCH$_2$— | Me | Et | i-Pr | F | —CH$_2$CHFCH$_2$— | Me | Et | i-Pr |
| Cl | —CH$_2$CF$_2$— | Me | Et | i-Pr | F | —CH$_2$CF$_2$— | Me | Et | i-Pr |
| Cl | —CH$_2$CHF— | Me | Et | i-Pr | F | —CH$_2$CHF— | Me | Et | i-Pr |
| Cl | —CH(CN)— | Me | Et | i-Pr | F | —CH(CN)— | Me | Et | i-Pr |
| Cl | $V^a$ | Me | Et | i-Pr | F | $V^a$ | Me | Et | i-Pr |
| Cl | $V^b$ | Me | Et | i-Pr | F | $V^b$ | Me | Et | i-Pr |
| Cl | $V^c$ | Me | Et | i-Pr | F | $V^c$ | Me | Et | i-Pr |
| Cl | $V^d$ | Me | Et | i-Pr | F | $V^d$ | Me | Et | i-Pr |
| Cl | $V^e$ | Me | Et | i-Pr | F | $V^e$ | Me | Et | i-Pr |
| Cl | $V^f$ | Me | Et | i-Pr | F | $V^f$ | Me | Et | i-Pr |
| Cl | $V^g$ | Me | Et | i-Pr | F | $V^g$ | Me | Et | i-Pr |
| Cl | $V^h$ | Me | Et | i-Pr | F | $V^h$ | Me | Et | i-Pr |
| Cl | —CH$_2$OC(=O)CH$_2$— | Me | Et | i-Pr | F | —CH$_2$OC(=O)CH$_2$— | Me | Et | i-Pr |
| Cl | —CH$_2$C(=O)CH$_2$— | Me | Et | i-Pr | F | —CH$_2$C(=O)CH$_2$— | Me | Et | i-Pr |
| Cl | —CH$_2$C(=O)— | Me | Et | i-Pr | F | —CH$_2$C(=O)— | Me | Et | i-Pr |
| Cl | —CH$_2$— | Me | Me | Ph | F | —CH$_2$— | Me | Me | Ph |
| Cl | —CH$_2$CH$_2$— | Me | Me | Ph | F | —CH$_2$CH$_2$— | Me | Me | Ph |
| Cl | —CH$_2$CH$_2$CH$_2$— | Me | Me | Ph | F | —CH$_2$CH$_2$CH$_2$— | Me | Me | Ph |
| Cl | —CH$_2$CH$_2$CH$_2$CH$_2$— | Me | Me | Ph | F | —CH$_2$CH$_2$CH$_2$CH$_2$— | Me | Me | Ph |
| Cl | —CH$_2$OCH$_2$CH$_2$— | Me | Me | Ph | F | —CH$_2$OCH$_2$CH$_2$— | Me | Me | Ph |
| Cl | —CH$_2$CH$_2$OCH$_2$— | Me | Me | Ph | F | —CH$_2$CH$_2$OCH$_2$— | Me | Me | Ph |
| Cl | —CH$_2$C(=O)CH$_2$CH$_2$— | Me | Me | Ph | F | —CH$_2$C(=O)CH$_2$CH$_2$— | Me | Me | Ph |
| Cl | —CH$_2$CH$_2$C(=O)CH$_2$— | Me | Me | Ph | F | —CH$_2$CH$_2$C(=O)CH$_2$— | Me | Me | Ph |
| Cl | —CH$_2$C(=S)CH$_2$CH$_2$— | Me | Me | Ph | F | —CH$_2$C(=S)CH$_2$CH$_2$— | Me | Me | Ph |
| Cl | —CH$_2$CH$_2$C(=S)CH$_2$— | Me | Me | Ph | F | —CH$_2$CH$_2$C(=S)CH$_2$— | Me | Me | Ph |
| Cl | —CH$_2$C(=O)CH$_2$— | Me | Me | Ph | F | —CH$_2$C(=O)CH$_2$— | Me | Me | Ph |
| Cl | —CH$_2$C(=S)CH$_2$— | Me | Me | Ph | F | —CH$_2$C(=S)CH$_2$— | Me | Me | Ph |
| Cl | —CH(Me)— | Me | Me | Ph | F | —CH(Me)— | Me | Me | Ph |
| Cl | —CH(OMe)— | Me | Me | Ph | F | —CH(OMe)— | Me | Me | Ph |
| Cl | —CH(Me)CH$_2$— | Me | Me | Ph | F | —CH(Me)CH$_2$— | Me | Me | Ph |
| Cl | —CH$_2$CH(Me)— | Me | Me | Ph | F | —CH$_2$CH(Me)— | Me | Me | Ph |
| Cl | —CH$_2$CH(OMe)— | Me | Me | Ph | F | —CH$_2$CH(OMe)— | Me | Me | Ph |
| Cl | —CH(Me)CH$_2$CH$_2$— | Me | Me | Ph | F | —CH(Me)CH$_2$CH$_2$— | Me | Me | Ph |
| Cl | —CH$_2$CH(Me)CH$_2$— | Me | Me | Ph | F | —CH$_2$CH(Me)CH$_2$— | Me | Me | Ph |
| Cl | —CH$_2$CH$_2$CH(Me)— | Me | Me | Ph | F | —CH$_2$CH$_2$CH(Me)— | Me | Me | Ph |
| Cl | —CH(Et)— | Me | Me | Ph | F | —CH(Et)— | Me | Me | Ph |
| Cl | —CH(Et)CH$_2$— | Me | Me | Ph | F | —CH(Et)CH$_2$— | Me | Me | Ph |
| Cl | —CH$_2$CH(Et)— | Me | Me | Ph | F | —CH$_2$CH(Et)— | Me | Me | Ph |
| Cl | —CH(Et)CH$_2$CH$_2$— | Me | Me | Ph | F | —CH(Et)CH$_2$CH$_2$— | Me | Me | Ph |
| Cl | —CH$_2$CH(Et)CH$_2$— | Me | Me | Ph | F | —CH$_2$CH(Et)CH$_2$— | Me | Me | Ph |
| Cl | —CH$_2$CH$_2$CH(Et)— | Me | Me | Ph | F | —CH$_2$CH$_2$CH(Et)— | Me | Me | Ph |
| Cl | —CH(OCF$_3$)— | Me | Me | Ph | F | —CH(OCF$_3$)— | Me | Me | Ph |
| Cl | —CH(CF$_3$)— | Me | Me | Ph | F | —CH(CF$_3$)— | Me | Me | Ph |
| Cl | —CH$_2$CF$_2$CH$_2$— | Me | Me | Ph | F | —CH$_2$CF$_2$CH$_2$— | Me | Me | Ph |
| Cl | —CH$_2$CHFCH$_2$— | Me | Me | Ph | F | —CH$_2$CHFCH$_2$— | Me | Me | Ph |
| Cl | —CH$_2$CF$_2$— | Me | Me | Ph | F | —CH$_2$CF$_2$— | Me | Me | Ph |
| Cl | —CH$_2$CHF— | Me | Me | Ph | F | —CH$_2$CHF— | Me | Me | Ph |

TABLE 2-continued

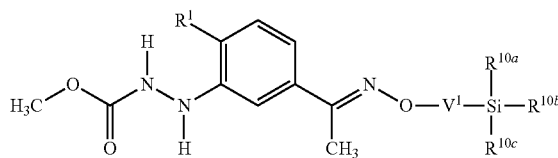

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH(CN)— | Me | Me | Ph | F | —CH(CN)— | Me | Me | Ph |
| Cl | $V^a$ | Me | Me | Ph | F | $V^a$ | Me | Me | Ph |
| Cl | $V^b$ | Me | Me | Ph | F | $V^b$ | Me | Me | Ph |
| Cl | $V^c$ | Me | Me | Ph | F | $V^c$ | Me | Me | Ph |
| Cl | $V^d$ | Me | Me | Ph | F | $V^d$ | Me | Me | Ph |
| Cl | $V^e$ | Me | Me | Ph | F | $V^e$ | Me | Me | Ph |
| Cl | $V^f$ | Me | Me | Ph | F | $V^f$ | Me | Me | Ph |
| Cl | $V^g$ | Me | Me | Ph | F | $V^g$ | Me | Me | Ph |
| Cl | $V^h$ | Me | Me | Ph | F | $V^h$ | Me | Me | Ph |
| Cl | —CH$_2$OC(=O)CH$_2$— | Me | Me | Ph | F | —CH$_2$OC(=O)CH$_2$— | Me | Me | Ph |
| Cl | —CH$_2$C(=O)CH$_2$— | Me | Me | Ph | F | —CH$_2$C(=O)CH$_2$— | Me | Me | Ph |
| Cl | —CH$_2$C(=O)— | Me | Me | Ph | F | —CH$_2$C(=O)— | Me | Me | Ph |
| Cl | —CH$_2$— | Me | Me | 4-Cl—Ph | F | —CH$_2$— | Me | Me | 4-Cl—Ph |
| Cl | —CH$_2$CH$_2$— | Me | Me | 4-Cl—Ph | F | —CH$_2$CH$_2$— | Me | Me | 4-Cl—Ph |
| Cl | —CH$_2$CH$_2$CH$_2$— | Me | Me | 4-Cl—Ph | F | —CH$_2$CH$_2$CH$_2$— | Me | Me | 4-Cl—Ph |
| Cl | —CH$_2$CH$_2$CH$_2$CH$_2$— | Me | Me | 4-Cl—Ph | F | —CH$_2$CH$_2$CH$_2$CH$_2$— | Me | Me | 4-Cl—Ph |
| Cl | —CH$_2$OCH$_2$CH$_2$— | Me | Me | 4-Cl—Ph | F | —CH$_2$OCH$_2$CH$_2$— | Me | Me | 4-Cl—Ph |
| Cl | —CH$_2$CH$_2$OCH$_2$— | Me | Me | 4-Cl—Ph | F | —CH$_2$CH$_2$OCH$_2$— | Me | Me | 4-Cl—Ph |
| Cl | —CH$_2$C(=O)CH$_2$CH$_2$— | Me | Me | 4-Cl—Ph | F | —CH$_2$C(=O)CH$_2$CH$_2$— | Me | Me | 4-Cl—Ph |
| Cl | —CH$_2$CH$_2$C(=O)CH$_2$— | Me | Me | 4-Cl—Ph | F | —CH$_2$CH$_2$C(=O)CH$_2$— | Me | Me | 4-Cl—Ph |
| Cl | —CH$_2$C(=S)CH$_2$CH$_2$— | Me | Me | 4-Cl—Ph | F | —CH$_2$C(=S)CH$_2$CH$_2$— | Me | Me | 4-Cl—Ph |
| Cl | —CH$_2$CH$_2$C(=S)CH$_2$— | Me | Me | 4-Cl—Ph | F | —CH$_2$CH$_2$C(=S)CH$_2$— | Me | Me | 4-Cl—Ph |
| Cl | —CH$_2$C(=O)CH$_2$— | Me | Me | 4-Cl—Ph | F | —CH$_2$C(=O)CH$_2$— | Me | Me | 4-Cl—Ph |
| Cl | —CH$_2$C(=S)CH$_2$— | Me | Me | 4-Cl—Ph | F | —CH$_2$C(=S)CH$_2$— | Me | Me | 4-Cl—Ph |
| Cl | —CH(Me)— | Me | Me | 4-Cl—Ph | F | —CH(Me)— | Me | Me | 4-Cl—Ph |
| Cl | —CH(OMe)— | Me | Me | 4-Cl—Ph | F | —CH(OMe)— | Me | Me | 4-Cl—Ph |
| Cl | —CH(Me)CH$_2$— | Me | Me | 4-Cl—Ph | F | —CH(Me)CH$_2$— | Me | Me | 4-Cl—Ph |
| Cl | —CH$_2$CH(Me)— | Me | Me | 4-Cl—Ph | F | —CH$_2$CH(Me)— | Me | Me | 4-Cl—Ph |
| Cl | —CH$_2$CH(OMe)— | Me | Me | 4-Cl—Ph | F | —CH$_2$CH(OMe)— | Me | Me | 4-Cl—Ph |
| Cl | —CH(Me)CH$_2$CH$_2$— | Me | Me | 4-Cl—Ph | F | —CH(Me)CH$_2$CH$_2$— | Me | Me | 4-Cl—Ph |
| Cl | —CH$_2$CH(Me)CH$_2$— | Me | Me | 4-Cl—Ph | F | —CH$_2$CH(Me)CH$_2$— | Me | Me | 4-Cl—Ph |
| Cl | —CH$_2$CH$_2$CH(Me)— | Me | Me | 4-Cl—Ph | F | —CH$_2$CH$_2$CH(Me)— | Me | Me | 4-Cl—Ph |
| Cl | —CH(Et)— | Me | Me | 4-Cl—Ph | F | —CH(Et)— | Me | Me | 4-Cl—Ph |
| Cl | —CH(Et)CH$_2$— | Me | Me | 4-Cl—Ph | F | —CH(Et)CH$_2$— | Me | Me | 4-Cl—Ph |
| Cl | —CH$_2$CH(Et)— | Me | Me | 4-Cl—Ph | F | —CH$_2$CH(Et)— | Me | Me | 4-Cl—Ph |
| Cl | —CH(Et)CH$_2$CH$_2$— | Me | Me | 4-Cl—Ph | F | —CH(Et)CH$_2$CH$_2$— | Me | Me | 4-Cl—Ph |
| Cl | —CH$_2$CH(Et)CH$_2$— | Me | Me | 4-Cl—Ph | F | —CH$_2$CH(Et)CH$_2$— | Me | Me | 4-Cl—Ph |
| Cl | —CH$_2$CH$_2$CH(Et)— | Me | Me | 4-Cl—Ph | F | —CH$_2$CH$_2$CH(Et)— | Me | Me | 4-Cl—Ph |
| Cl | —CH(OCF$_3$)— | Me | Me | 4-Cl—Ph | F | —CH(OCF$_3$)— | Me | Me | 4-Cl—Ph |
| Cl | —CH(CF$_3$)— | Me | Me | 4-Cl—Ph | F | —CH(CF$_3$)— | Me | Me | 4-Cl—Ph |
| Cl | —CH$_2$CF$_2$CH$_2$— | Me | Me | 4-Cl—Ph | F | —CH$_2$CF$_2$CH$_2$— | Me | Me | 4-Cl—Ph |
| Cl | —CH$_2$CHFCH$_2$— | Me | Me | 4-Cl—Ph | F | —CH$_2$CHFCH$_2$— | Me | Me | 4-Cl—Ph |
| Cl | —CH$_2$CF$_2$— | Me | Me | 4-Cl—Ph | F | —CH$_2$CF$_2$— | Me | Me | 4-Cl—Ph |
| Cl | —CH$_2$CHF— | Me | Me | 4-Cl—Ph | F | —CH$_2$CHF— | Me | Me | 4-Cl—Ph |
| Cl | —CH(CN)— | Me | Me | 4-Cl—Ph | F | —CH(CN)— | Me | Me | 4-Cl—Ph |
| Cl | $V^a$ | Me | Me | 4-Cl—Ph | F | $V^a$ | Me | Me | 4-Cl—Ph |
| Cl | $V^b$ | Me | Me | 4-Cl—Ph | F | $V^b$ | Me | Me | 4-Cl—Ph |
| Cl | $V^c$ | Me | Me | 4-Cl—Ph | F | $V^c$ | Me | Me | 4-Cl—Ph |
| Cl | $V^d$ | Me | Me | 4-Cl—Ph | F | $V^d$ | Me | Me | 4-Cl—Ph |
| Cl | $V^e$ | Me | Me | 4-Cl—Ph | F | $V^e$ | Me | Me | 4-Cl—Ph |
| Cl | $V^f$ | Me | Me | 4-Cl—Ph | F | $V^f$ | Me | Me | 4-Cl—Ph |
| Cl | $V^g$ | Me | Me | 4-Cl—Ph | F | $V^g$ | Me | Me | 4-Cl—Ph |
| Cl | $V^h$ | Me | Me | 4-Cl—Ph | F | $V^h$ | Me | Me | 4-Cl—Ph |
| Cl | —CH$_2$OC(=O)CH$_2$— | Me | Me | 4-Cl—Ph | F | —CH$_2$OC(=O)CH$_2$— | Me | Me | 4-Cl—Ph |
| Cl | —CH$_2$C(=O)CH$_2$— | Me | Me | 4-Cl—Ph | F | —CH$_2$C(=O)CH$_2$— | Me | Me | 4-Cl—Ph |
| Cl | —CH$_2$C(=O)— | Me | Me | 4-Cl—Ph | F | —CH$_2$C(=O)— | Me | Me | 4-Cl—Ph |
| Cl | —CH$_2$— | Me | Me | 3-Cl—Ph | F | —CH$_2$— | Me | Me | 3-Cl—Ph |
| Cl | —CH$_2$CH$_2$— | Me | Me | 3-Cl—Ph | F | —CH$_2$CH$_2$— | Me | Me | 3-Cl—Ph |
| Cl | —CH$_2$CH$_2$CH$_2$— | Me | Me | 3-Cl—Ph | F | —CH$_2$CH$_2$CH$_2$— | Me | Me | 3-Cl—Ph |
| Cl | —CH$_2$CH$_2$CH$_2$CH$_2$— | Me | Me | 3-Cl—Ph | F | —CH$_2$CH$_2$CH$_2$CH$_2$— | Me | Me | 3-Cl—Ph |
| Cl | —CH$_2$OCH$_2$CH$_2$— | Me | Me | 3-Cl—Ph | F | —CH$_2$OCH$_2$CH$_2$— | Me | Me | 3-Cl—Ph |
| Cl | —CH$_2$CH$_2$OCH$_2$— | Me | Me | 3-Cl—Ph | F | —CH$_2$CH$_2$OCH$_2$— | Me | Me | 3-Cl—Ph |
| Cl | —CH$_2$C(=O)CH$_2$CH$_2$— | Me | Me | 3-Cl—Ph | F | —CH$_2$C(=O)CH$_2$CH$_2$— | Me | Me | 3-Cl—Ph |
| Cl | —CH$_2$CH$_2$C(=O)CH$_2$— | Me | Me | 3-Cl—Ph | F | —CH$_2$CH$_2$C(=O)CH$_2$— | Me | Me | 3-Cl—Ph |
| Cl | —CH$_2$C(=S)CH$_2$CH$_2$— | Me | Me | 3-Cl—Ph | F | —CH$_2$C(=S)CH$_2$CH$_2$— | Me | Me | 3-Cl—Ph |
| Cl | —CH$_2$CH$_2$C(=S)CH$_2$— | Me | Me | 3-Cl—Ph | F | —CH$_2$CH$_2$C(=S)CH$_2$— | Me | Me | 3-Cl—Ph |
| Cl | —CH$_2$C(=O)CH$_2$— | Me | Me | 3-Cl—Ph | F | —CH$_2$C(=O)CH$_2$— | Me | Me | 3-Cl—Ph |
| Cl | —CH$_2$C(=S)CH$_2$— | Me | Me | 3-Cl—Ph | F | —CH$_2$C(=S)CH$_2$— | Me | Me | 3-Cl—Ph |
| Cl | —CH(Me)— | Me | Me | 3-Cl—Ph | F | —CH(Me)— | Me | Me | 3-Cl—Ph |

TABLE 2-continued

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH(OMe)— | Me | Me | 3-Cl—Ph | F | —CH(OMe)— | Me | Me | 3-Cl—Ph |
| Cl | —CH(Me)CH₂— | Me | Me | 3-Cl—Ph | F | —CH(Me)CH₂— | Me | Me | 3-Cl—Ph |
| Cl | —CH₂CH(Me)— | Me | Me | 3-Cl—Ph | F | —CH₂CH(Me)— | Me | Me | 3-Cl—Ph |
| Cl | —CH₂CH(OMe)— | Me | Me | 3-Cl—Ph | F | —CH₂CH(OMe)— | Me | Me | 3-Cl—Ph |
| Cl | —CH(Me)CH₂CH₂— | Me | Me | 3-Cl—Ph | F | —CH(Me)CH₂CH₂— | Me | Me | 3-Cl—Ph |
| Cl | —CH₂CH(Me)CH₂— | Me | Me | 3-Cl—Ph | F | —CH₂CH(Me)CH₂— | Me | Me | 3-Cl—Ph |
| Cl | —CH₂CH₂CH(Me)— | Me | Me | 3-Cl—Ph | F | —CH₂CH₂CH(Me)— | Me | Me | 3-Cl—Ph |
| Cl | —CH(Et)— | Me | Me | 3-Cl—Ph | F | —CH(Et)— | Me | Me | 3-Cl—Ph |
| Cl | —CH(Et)CH₂— | Me | Me | 3-Cl—Ph | F | —CH(Et)CH₂— | Me | Me | 3-Cl—Ph |
| Cl | —CH₂CH(Et)— | Me | Me | 3-Cl—Ph | F | —CH₂CH(Et)— | Me | Me | 3-Cl—Ph |
| Cl | —CH(Et)CH₂CH₂— | Me | Me | 3-Cl—Ph | F | —CH(Et)CH₂CH₂— | Me | Me | 3-Cl—Ph |
| Cl | —CH₂CH(Et)CH₂— | Me | Me | 3-Cl—Ph | F | —CH₂CH(Et)CH₂— | Me | Me | 3-Cl—Ph |
| Cl | —CH₂CH₂CH(Et)— | Me | Me | 3-Cl—Ph | F | —CH₂CH₂CH(Et)— | Me | Me | 3-Cl—Ph |
| Cl | —CH(OCF₃)— | Me | Me | 3-Cl—Ph | F | —CH(OCF₃)— | Me | Me | 3-Cl—Ph |
| Cl | —CH(CF₃)— | Me | Me | 3-Cl—Ph | F | —CH(CF₃)— | Me | Me | 3-Cl—Ph |
| Cl | —CH₂CF₂CH₂— | Me | Me | 3-Cl—Ph | F | —CH₂CF₂CH₂— | Me | Me | 3-Cl—Ph |
| Cl | —CH₂CHFCH₂— | Me | Me | 3-Cl—Ph | F | —CH₂CHFCH₂— | Me | Me | 3-Cl—Ph |
| Cl | —CH₂CF₂— | Me | Me | 3-Cl—Ph | F | —CH₂CF₂— | Me | Me | 3-Cl—Ph |
| Cl | —CH₂CHF— | Me | Me | 3-Cl—Ph | F | —CH₂CHF— | Me | Me | 3-Cl—Ph |
| Cl | —CH(CN)— | Me | Me | 3-Cl—Ph | F | —CH(CN)— | Me | Me | 3-Cl—Ph |
| Cl | Vᵃ | Me | Me | 3-Cl—Ph | F | Vᵃ | Me | Me | 3-Cl—Ph |
| Cl | Vᵇ | Me | Me | 3-Cl—Ph | F | Vᵇ | Me | Me | 3-Cl—Ph |
| Cl | Vᶜ | Me | Me | 3-Cl—Ph | F | Vᶜ | Me | Me | 3-Cl—Ph |
| Cl | Vᵈ | Me | Me | 3-Cl—Ph | F | Vᵈ | Me | Me | 3-Cl—Ph |
| Cl | Vᵉ | Me | Me | 3-Cl—Ph | F | Vᵉ | Me | Me | 3-Cl—Ph |
| Cl | Vᶠ | Me | Me | 3-Cl—Ph | F | Vᶠ | Me | Me | 3-Cl—Ph |
| Cl | Vᵍ | Me | Me | 3-Cl—Ph | F | Vᵍ | Me | Me | 3-Cl—Ph |
| Cl | Vʰ | Me | Me | 3-Cl—Ph | F | Vʰ | Me | Me | 3-Cl—Ph |
| Cl | —CH₂OC(=O)CH₂— | Me | Me | 3-Cl—Ph | F | —CH₂OC(=O)CH₂— | Me | Me | 3-Cl—Ph |
| Cl | —CH₂C(=O)CH₂— | Me | Me | 3-Cl—Ph | F | —CH₂C(=O)CH₂— | Me | Me | 3-Cl—Ph |
| Cl | —CH₂C(=O)— | Me | Me | 3-Cl—Ph | F | —CH₂C(=O)— | Me | Me | 3-Cl—Ph |
| Cl | —CH₂— | Me | Me | 2-Cl—Ph | F | —CH₂— | Me | Me | 2-Cl—Ph |
| Cl | —CH₂CH₂— | Me | Me | 2-Cl—Ph | F | —CH₂CH₂— | Me | Me | 2-Cl—Ph |
| Cl | —CH₂CH₂CH₂— | Me | Me | 2-Cl—Ph | F | —CH₂CH₂CH₂— | Me | Me | 2-Cl—Ph |
| Cl | —CH₂CH₂CH₂CH₂— | Me | Me | 2-Cl—Ph | F | —CH₂CH₂CH₂CH₂— | Me | Me | 2-Cl—Ph |
| Cl | —CH₂OCH₂CH₂— | Me | Me | 2-Cl—Ph | F | —CH₂OCH₂CH₂— | Me | Me | 2-Cl—Ph |
| Cl | —CH₂CH₂OCH₂— | Me | Me | 2-Cl—Ph | F | —CH₂CH₂OCH₂— | Me | Me | 2-Cl—Ph |
| Cl | —CH₂C(=O)CH₂CH₂— | Me | Me | 2-Cl—Ph | F | —CH₂C(=O)CH₂CH₂— | Me | Me | 2-Cl—Ph |
| Cl | —CH₂CH₂C(=O)CH₂— | Me | Me | 2-Cl—Ph | F | —CH₂CH₂C(=O)CH₂— | Me | Me | 2-Cl—Ph |
| Cl | —CH₂C(=S)CH₂CH₂— | Me | Me | 2-Cl—Ph | F | —CH₂C(=S)CH₂CH₂— | Me | Me | 2-Cl—Ph |
| Cl | —CH₂CH₂C(=S)CH₂— | Me | Me | 2-Cl—Ph | F | —CH₂CH₂C(=S)CH₂— | Me | Me | 2-Cl—Ph |
| Cl | —CH₂C(=O)CH₂— | Me | Me | 2-Cl—Ph | F | —CH₂C(=O)CH₂— | Me | Me | 2-Cl—Ph |
| Cl | —CH₂C(=S)CH₂— | Me | Me | 2-Cl—Ph | F | —CH₂C(=S)CH₂— | Me | Me | 2-Cl—Ph |
| Cl | —CH(Me)— | Me | Me | 2-Cl—Ph | F | —CH(Me)— | Me | Me | 2-Cl—Ph |
| Cl | —CH(OMe)— | Me | Me | 2-Cl—Ph | F | —CH(OMe)— | Me | Me | 2-Cl—Ph |
| Cl | —CH(Me)CH₂— | Me | Me | 2-Cl—Ph | F | —CH(Me)CH₂— | Me | Me | 2-Cl—Ph |
| Cl | —CH₂CH(Me)— | Me | Me | 2-Cl—Ph | F | —CH₂CH(Me)— | Me | Me | 2-Cl—Ph |
| Cl | —CH₂CH(OMe)— | Me | Me | 2-Cl—Ph | F | —CH₂CH(OMe)— | Me | Me | 2-Cl—Ph |
| Cl | —CH(Me)CH₂CH₂— | Me | Me | 2-Cl—Ph | F | —CH(Me)CH₂CH₂— | Me | Me | 2-Cl—Ph |
| Cl | —CH₂CH(Me)CH₂— | Me | Me | 2-Cl—Ph | F | —CH₂CH(Me)CH₂— | Me | Me | 2-Cl—Ph |
| Cl | —CH₂CH₂CH(Me)— | Me | Me | 2-Cl—Ph | F | —CH₂CH₂CH(Me)— | Me | Me | 2-Cl—Ph |
| Cl | —CH(Et)— | Me | Me | 2-Cl—Ph | F | —CH(Et)— | Me | Me | 2-Cl—Ph |
| Cl | —CH(Et)CH₂— | Me | Me | 2-Cl—Ph | F | —CH(Et)CH₂— | Me | Me | 2-Cl—Ph |
| Cl | —CH₂CH(Et)— | Me | Me | 2-Cl—Ph | F | —CH₂CH(Et)— | Me | Me | 2-Cl—Ph |
| Cl | —CH(Et)CH₂CH₂— | Me | Me | 2-Cl—Ph | F | —CH(Et)CH₂CH₂— | Me | Me | 2-Cl—Ph |
| Cl | —CH₂CH(Et)CH₂— | Me | Me | 2-Cl—Ph | F | —CH₂CH(Et)CH₂— | Me | Me | 2-Cl—Ph |
| Cl | —CH₂CH₂CH(Et)— | Me | Me | 2-Cl—Ph | F | —CH₂CH₂CH(Et)— | Me | Me | 2-Cl—Ph |
| Cl | —CH(OCF₃)— | Me | Me | 2-Cl—Ph | F | —CH(OCF₃)— | Me | Me | 2-Cl—Ph |
| Cl | —CH(CF₃)— | Me | Me | 2-Cl—Ph | F | —CH(CF₃)— | Me | Me | 2-Cl—Ph |
| Cl | —CH₂CF₂CH₂— | Me | Me | 2-Cl—Ph | F | —CH₂CF₂CH₂— | Me | Me | 2-Cl—Ph |
| Cl | —CH₂CHFCH₂— | Me | Me | 2-Cl—Ph | F | —CH₂CHFCH₂— | Me | Me | 2-Cl—Ph |
| Cl | —CH₂CF₂— | Me | Me | 2-Cl—Ph | F | —CH₂CF₂— | Me | Me | 2-Cl—Ph |
| Cl | —CH₂CHF— | Me | Me | 2-Cl—Ph | F | —CH₂CHF— | Me | Me | 2-Cl—Ph |
| Cl | —CH(CN)— | Me | Me | 2-Cl—Ph | F | —CH(CN)— | Me | Me | 2-Cl—Ph |
| Cl | Vᵃ | Me | Me | 2-Cl—Ph | F | Vᵃ | Me | Me | 2-Cl—Ph |
| Cl | Vᵇ | Me | Me | 2-Cl—Ph | F | Vᵇ | Me | Me | 2-Cl—Ph |
| Cl | Vᶜ | Me | Me | 2-Cl—Ph | F | Vᶜ | Me | Me | 2-Cl—Ph |
| Cl | Vᵈ | Me | Me | 2-Cl—Ph | F | Vᵈ | Me | Me | 2-Cl—Ph |
| Cl | Vᵉ | Me | Me | 2-Cl—Ph | F | Vᵉ | Me | Me | 2-Cl—Ph |

TABLE 2-continued

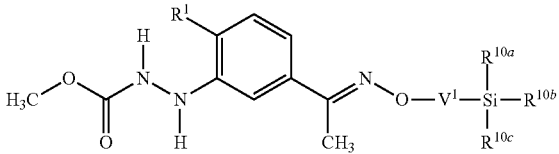

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | Vᶠ | Me | Me | 2-Cl—Ph | F | Vᶠ | Me | Me | 2-Cl—Ph |
| Cl | Vᵍ | Me | Me | 2-Cl—Ph | F | Vᵍ | Me | Me | 2-Cl—Ph |
| Cl | Vʰ | Me | Me | 2-Cl—Ph | F | Vʰ | Me | Me | 2-Cl—Ph |
| Cl | —CH₂OC(=O)CH₂— | Me | Me | 2-Cl—Ph | F | —CH₂OC(=O)CH₂— | Me | Me | 2-Cl—Ph |
| Cl | —CH₂C(=O)CH₂— | Me | Me | 2-Cl—Ph | F | —CH₂C(=O)CH₂— | Me | Me | 2-Cl—Ph |
| Cl | —CH₂C(=O)— | Me | Me | 2-Cl—Ph | F | —CH₂C(=O)— | Me | Me | 2-Cl—Ph |
| Cl | —CH₂— | Me | Me | c-Pr | F | —CH₂— | Me | Me | c-Pr |
| Cl | —CH₂CH₂— | Me | Me | c-Pr | F | —CH₂CH₂— | Me | Me | c-Pr |
| Cl | —CH₂CH₂CH₂— | Me | Me | c-Pr | F | —CH₂CH₂CH₂— | Me | Me | c-Pr |
| Cl | —CH₂CH₂CH₂CH₂— | Me | Me | c-Pr | F | —CH₂CH₂CH₂CH₂— | Me | Me | c-Pr |
| Cl | —CH₂OCH₂CH₂— | Me | Me | c-Pr | F | —CH₂OCH₂CH₂— | Me | Me | c-Pr |
| Cl | —CH₂CH₂OCH₂— | Me | Me | c-Pr | F | —CH₂CH₂OCH₂— | Me | Me | c-Pr |
| Cl | —CH₂C(=O)CH₂CH₂— | Me | Me | c-Pr | F | —CH₂C(=O)CH₂CH₂— | Me | Me | c-Pr |
| Cl | —CH₂CH₂C(=O)CH₂— | Me | Me | c-Pr | F | —CH₂CH₂C(=O)CH₂— | Me | Me | c-Pr |
| Cl | —CH₂C(=S)CH₂CH₂— | Me | Me | c-Pr | F | —CH₂C(=S)CH₂CH₂— | Me | Me | c-Pr |
| Cl | —CH₂CH₂C(=S)CH₂— | Me | Me | c-Pr | F | —CH₂CH₂C(=S)CH₂— | Me | Me | c-Pr |
| Cl | —CH₂C(=O)CH₂— | Me | Me | c-Pr | F | —CH₂C(=O)CH₂— | Me | Me | c-Pr |
| Cl | —CH₂C(=S)CH₂— | Me | Me | c-Pr | F | —CH₂C(=S)CH₂— | Me | Me | c-Pr |
| Cl | —CH(Me)— | Me | Me | c-Pr | F | —CH(Me)— | Me | Me | c-Pr |
| Cl | —CH(OMe)— | Me | Me | c-Pr | F | —CH(OMe)— | Me | Me | c-Pr |
| Cl | —CH(Me)CH₂— | Me | Me | c-Pr | F | —CH(Me)CH₂— | Me | Me | c-Pr |
| Cl | —CH₂CH(Me)— | Me | Me | c-Pr | F | —CH₂CH(Me)— | Me | Me | c-Pr |
| Cl | —CH₂CH(OMe)— | Me | Me | c-Pr | F | —CH₂CH(OMe)— | Me | Me | c-Pr |
| Cl | —CH(Me)CH₂CH₂— | Me | Me | c-Pr | F | —CH(Me)CH₂CH₂— | Me | Me | c-Pr |
| Cl | —CH₂CH(Me)CH₂— | Me | Me | c-Pr | F | —CH₂CH(Me)CH₂— | Me | Me | c-Pr |
| Cl | —CH₂CH₂CH(Me)— | Me | Me | c-Pr | F | —CH₂CH₂CH(Me)— | Me | Me | c-Pr |
| Cl | —CH(Et)— | Me | Me | c-Pr | F | —CH(Et)— | Me | Me | c-Pr |
| Cl | —CH(Et)CH₂— | Me | Me | c-Pr | F | —CH(Et)CH₂— | Me | Me | c-Pr |
| Cl | —CH₂CH(Et)— | Me | Me | c-Pr | F | —CH₂CH(Et)— | Me | Me | c-Pr |
| Cl | —CH(Et)CH₂CH₂— | Me | Me | c-Pr | F | —CH(Et)CH₂CH₂— | Me | Me | c-Pr |
| Cl | —CH₂CH(Et)CH₂— | Me | Me | c-Pr | F | —CH₂CH(Et)CH₂— | Me | Me | c-Pr |
| Cl | —CH₂CH₂CH(Et)— | Me | Me | c-Pr | F | —CH₂CH₂CH(Et)— | Me | Me | c-Pr |
| Cl | —CH(OCF₃)— | Me | Me | c-Pr | F | —CH(OCF₃)— | Me | Me | c-Pr |
| Cl | —CH(CF₃)— | Me | Me | c-Pr | F | —CH(CF₃)— | Me | Me | c-Pr |
| Cl | —CH₂CF₂CH₂— | Me | Me | c-Pr | F | —CH₂CF₂CH₂— | Me | Me | c-Pr |
| Cl | —CH₂CHFCH₂— | Me | Me | c-Pr | F | —CH₂CHFCH₂— | Me | Me | c-Pr |
| Cl | —CH₂CF₂— | Me | Me | c-Pr | F | —CH₂CF₂— | Me | Me | c-Pr |
| Cl | —CH₂CHF— | Me | Me | c-Pr | F | —CH₂CHF— | Me | Me | c-Pr |
| Cl | —CH(CN)— | Me | Me | c-Pr | F | —CH(CN)— | Me | Me | c-Pr |
| Cl | Vᵃ | Me | Me | c-Pr | F | Vᵃ | Me | Me | c-Pr |
| Cl | Vᵇ | Me | Me | c-Pr | F | Vᵇ | Me | Me | c-Pr |
| Cl | Vᶜ | Me | Me | c-Pr | F | Vᶜ | Me | Me | c-Pr |
| Cl | Vᵈ | Me | Me | c-Pr | F | Vᵈ | Me | Me | c-Pr |
| Cl | Vᵉ | Me | Me | c-Pr | F | Vᵉ | Me | Me | c-Pr |
| Cl | Vᶠ | Me | Me | c-Pr | F | Vᶠ | Me | Me | c-Pr |
| Cl | Vᵍ | Me | Me | c-Pr | F | Vᵍ | Me | Me | c-Pr |
| Cl | Vʰ | Me | Me | c-Pr | F | Vʰ | Me | Me | c-Pr |
| Cl | —CH₂OC(=O)CH₂— | Me | Me | c-Pr | F | —CH₂OC(=O)CH₂— | Me | Me | c-Pr |
| Cl | —CH₂C(=O)CH₂— | Me | Me | c-Pr | F | —CH₂C(=O)CH₂— | Me | Me | c-Pr |
| Cl | —CH₂C(=O)— | Me | Me | c-Pr | F | —CH₂C(=O)— | Me | Me | c-Pr |
| Me | —CH₂— | Me | Me | Me | Me | —CH₂— | Me | Me | Et |
| Me | —CH₂CH₂— | Me | Me | Me | Me | —CH₂CH₂— | Me | Me | Et |
| Me | —CH₂CH₂CH₂— | Me | Me | Me | Me | —CH₂CH₂CH₂— | Me | Me | Et |
| Me | —CH₂CH₂CH₂CH₂— | Me | Me | Me | Me | —CH₂CH₂CH₂CH₂— | Me | Me | Et |
| Me | —CH₂OCH₂CH₂— | Me | Me | Me | Me | —CH₂OCH₂CH₂— | Me | Me | Et |
| Me | —CH₂CH₂OCH₂— | Me | Me | Me | Me | —CH₂CH₂OCH₂— | Me | Me | Et |
| Me | —CH₂C(=O)CH₂CH₂— | Me | Me | Me | Me | —CH₂C(=O)CH₂CH₂— | Me | Me | Et |
| Me | —CH₂CH₂C(=O)CH₂— | Me | Me | Me | Me | —CH₂CH₂C(=O)CH₂— | Me | Me | Et |
| Me | —CH₂C(=S)CH₂CH₂— | Me | Me | Me | Me | —CH₂C(=S)CH₂CH₂— | Me | Me | Et |
| Me | —CH₂CH₂C(=S)CH₂— | Me | Me | Me | Me | —CH₂CH₂C(=S)CH₂— | Me | Me | Et |
| Me | —CH₂C(=O)CH₂— | Me | Me | Me | Me | —CH₂C(=O)CH₂— | Me | Me | Et |
| Me | —CH₂C(=S)CH₂— | Me | Me | Me | Me | —CH₂C(=S)CH₂— | Me | Me | Et |
| Me | —CH(Me)— | Me | Me | Me | Me | —CH(Me)— | Me | Me | Et |
| Me | —CH(OMe)— | Me | Me | Me | Me | —CH(OMe)— | Me | Me | Et |
| Me | —CH(Me)CH₂— | Me | Me | Me | Me | —CH(Me)CH₂— | Me | Me | Et |
| Me | —CH₂CH(Me)— | Me | Me | Me | Me | —CH₂CH(Me)— | Me | Me | Et |
| Me | —CH₂CH(OMe)— | Me | Me | Me | Me | —CH₂CH(OMe)— | Me | Me | Et |
| Me | —CH(Me)CH₂CH₂— | Me | Me | Me | Me | —CH(Me)CH₂CH₂— | Me | Me | Et |
| Me | —CH₂CH(Me)CH₂— | Me | Me | Me | Me | —CH₂CH(Me)CH₂— | Me | Me | Et |

TABLE 2-continued

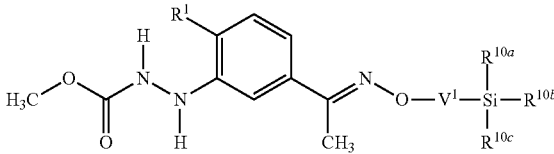

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Me | —CH₂CH₂CH(Me)— | Me | Me | Me | Me | —CH₂CH₂CH(Me)— | Me | Me | Et |
| Me | —CH(Et)— | Me | Me | Me | Me | —CH(Et)— | Me | Me | Et |
| Me | —CH(Et)CH₂— | Me | Me | Me | Me | —CH(Et)CH₂— | Me | Me | Et |
| Me | —CH₂CH(Et)— | Me | Me | Me | Me | —CH₂CH(Et)— | Me | Me | Et |
| Me | —CH(Et)CH₂CH₂— | Me | Me | Me | Me | —CH(Et)CH₂CH₂— | Me | Me | Et |
| Me | —CH₂CH(Et)CH₂— | Me | Me | Me | Me | —CH₂CH(Et)CH₂— | Me | Me | Et |
| Me | —CH₂CH₂CH(Et)— | Me | Me | Me | Me | —CH₂CH₂CH(Et)— | Me | Me | Et |
| Me | —CH(OCF₃)— | Me | Me | Me | Me | —CH(OCF₃)— | Me | Me | Et |
| Me | —CH(CF₃)— | Me | Me | Me | Me | —CH(CF₃)— | Me | Me | Et |
| Me | —CH₂CF₂CH₂— | Me | Me | Me | Me | —CH₂CF₂CH₂— | Me | Me | Et |
| Me | —CH₂CHFCH₂— | Me | Me | Me | Me | —CH₂CHFCH₂— | Me | Me | Et |
| Me | —CH₂CF₂— | Me | Me | Me | Me | —CH₂CF₂— | Me | Me | Et |
| Me | —CH₂CHF— | Me | Me | Me | Me | —CH₂CHF— | Me | Me | Et |
| Me | —CH(CN)— | Me | Me | Me | Me | —CH(CN)— | Me | Me | Et |
| Me | $V^a$ | Me | Me | Me | Me | $V^a$ | Me | Me | Et |
| Me | $V^b$ | Me | Me | Me | Me | $V^b$ | Me | Me | Et |
| Me | $V^c$ | Me | Me | Me | Me | $V^c$ | Me | Me | Et |
| Me | $V^d$ | Me | Me | Me | Me | $V^d$ | Me | Me | Et |
| Me | $V^e$ | Me | Me | Me | Me | $V^e$ | Me | Me | Et |
| Me | $V^f$ | Me | Me | Me | Me | $V^f$ | Me | Me | Et |
| Me | $V^g$ | Me | Me | Me | Me | $V^g$ | Me | Me | Et |
| Me | $V^h$ | Me | Me | Me | Me | $V^h$ | Me | Me | Et |
| Me | —CH₂OC(═O)CH₂— | Me | Me | Me | Me | —CH₂OC(═O)CH₂— | Me | Me | Et |
| Me | —CH₂C(═O)CH₂— | Me | Me | Me | Me | —CH₂C(═O)CH₂— | Me | Me | Et |
| Me | —CH₂C(═O)— | Me | Me | Me | Me | —CH₂C(═O)— | Me | Me | Et |
| Me | —CH₂— | Me | Et | Et | Me | —CH₂— | Et | Et | Et |
| Me | —CH₂CH₂— | Me | Et | Et | Me | —CH₂CH₂— | Et | Et | Et |
| Me | —CH₂CH₂CH₂— | Me | Et | Et | Me | —CH₂CH₂CH₂— | Et | Et | Et |
| Me | —CH₂CH₂CH₂CH₂— | Me | Et | Et | Me | —CH₂CH₂CH₂CH₂— | Et | Et | Et |
| Me | —CH₂OCH₂CH₂— | Me | Et | Et | Me | —CH₂OCH₂CH₂— | Et | Et | Et |
| Me | —CH₂CH₂OCH₂— | Me | Et | Et | Me | —CH₂CH₂OCH₂— | Et | Et | Et |
| Me | —CH₂C(═O)CH₂CH₂— | Me | Et | Et | Me | —CH₂C(═O)CH₂CH₂— | Et | Et | Et |
| Me | —CH₂CH₂C(═O)CH₂— | Me | Et | Et | Me | —CH₂CH₂C(═O)CH₂— | Et | Et | Et |
| Me | —CH₂C(═S)CH₂CH₂— | Me | Et | Et | Me | —CH₂C(═S)CH₂CH₂— | Et | Et | Et |
| Me | —CH₂CH₂C(═S)CH₂— | Me | Et | Et | Me | —CH₂CH₂C(═S)CH₂— | Et | Et | Et |
| Me | —CH₂C(═O)CH₂— | Me | Et | Et | Me | —CH₂C(═O)CH₂— | Et | Et | Et |
| Me | —CH₂C(═S)CH₂— | Me | Et | Et | Me | —CH₂C(═S)CH₂— | Et | Et | Et |
| Me | —CH(Me)— | Me | Et | Et | Me | —CH(Me)— | Et | Et | Et |
| Me | —CH(OMe)— | Me | Et | Et | Me | —CH(OMe)— | Et | Et | Et |
| Me | —CH(Me)CH₂— | Me | Et | Et | Me | —CH(Me)CH₂— | Et | Et | Et |
| Me | —CH₂CH(Me)— | Me | Et | Et | Me | —CH₂CH(Me)— | Et | Et | Et |
| Me | —CH₂CH(OMe)— | Me | Et | Et | Me | —CH₂CH(OMe)— | Et | Et | Et |
| Me | —CH(Me)CH₂CH₂— | Me | Et | Et | Me | —CH(Me)CH₂CH₂— | Et | Et | Et |
| Me | —CH₂CH(Me)CH₂— | Me | Et | Et | Me | —CH₂CH(Me)CH₂— | Et | Et | Et |
| Me | —CH₂CH₂CH(Me)— | Me | Et | Et | Me | —CH₂CH₂CH(Me)— | Et | Et | Et |
| Me | —CH(Et)— | Me | Et | Et | Me | —CH(Et)— | Et | Et | Et |
| Me | —CH(Et)CH₂— | Me | Et | Et | Me | —CH(Et)CH₂— | Et | Et | Et |
| Me | —CH₂CH(Et)— | Me | Et | Et | Me | —CH₂CH(Et)— | Et | Et | Et |
| Me | —CH(Et)CH₂CH₂— | Me | Et | Et | Me | —CH(Et)CH₂CH₂— | Et | Et | Et |
| Me | —CH₂CH(Et)CH₂— | Me | Et | Et | Me | —CH₂CH(Et)CH₂— | Et | Et | Et |
| Me | —CH₂CH₂CH(Et)— | Me | Et | Et | Me | —CH₂CH₂CH(Et)— | Et | Et | Et |
| Me | —CH(OCF₃)— | Me | Et | Et | Me | —CH(OCF₃)— | Et | Et | Et |
| Me | —CH(CF₃)— | Me | Et | Et | Me | —CH(CF₃)— | Et | Et | Et |
| Me | —CH₂CF₂CH₂— | Me | Et | Et | Me | —CH₂CF₂CH₂— | Et | Et | Et |
| Me | —CH₂CHFCH₂— | Me | Et | Et | Me | —CH₂CHFCH₂— | Et | Et | Et |
| Me | —CH₂CF₂— | Me | Et | Et | Me | —CH₂CF₂— | Et | Et | Et |
| Me | —CH₂CHF— | Me | Et | Et | Me | —CH₂CHF— | Et | Et | Et |
| Me | —CH(CN)— | Me | Et | Et | Me | —CH(CN)— | Et | Et | Et |
| Me | $V^a$ | Me | Et | Et | Me | $V^a$ | Et | Et | Et |
| Me | $V^b$ | Me | Et | Et | Me | $V^b$ | Et | Et | Et |
| Me | $V^c$ | Me | Et | Et | Me | $V^c$ | Et | Et | Et |
| Me | $V^d$ | Me | Et | Et | Me | $V^d$ | Et | Et | Et |
| Me | $V^e$ | Me | Et | Et | Me | $V^e$ | Et | Et | Et |
| Me | $V^f$ | Me | Et | Et | Me | $V^f$ | Et | Et | Et |
| Me | $V^g$ | Me | Et | Et | Me | $V^g$ | Et | Et | Et |
| Me | $V^h$ | Me | Et | Et | Me | $V^h$ | Et | Et | Et |
| Me | —CH₂OC(═O)CH₂— | Me | Et | Et | Me | —CH₂OC(═O)CH₂— | Et | Et | Et |
| Me | —CH₂C(═O)CH₂— | Me | Et | Et | Me | —CH₂C(═O)CH₂— | Et | Et | Et |
| Me | —CH₂C(═O)— | Me | Et | Et | Me | —CH₂C(═O)— | Et | Et | Et |

TABLE 2-continued

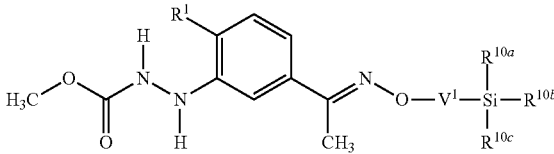

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | —CH₂— | Me | Me | i-Pr | Me | —CH₂— | Me | Et | i-Pr |
| Me | —CH₂CH₂— | Me | Me | i-Pr | Me | —CH₂CH₂— | Me | Et | i-Pr |
| Me | —CH₂CH₂CH₂— | Me | Me | i-Pr | Me | —CH₂CH₂CH₂— | Me | Et | i-Pr |
| Me | —CH₂CH₂CH₂CH₂— | Me | Me | i-Pr | Me | —CH₂CH₂CH₂CH₂— | Me | Et | i-Pr |
| Me | —CH₂OCH₂CH₂— | Me | Me | i-Pr | Me | —CH₂OCH₂CH₂— | Me | Et | i-Pr |
| Me | —CH₂CH₂OCH₂— | Me | Me | i-Pr | Me | —CH₂CH₂OCH₂— | Me | Et | i-Pr |
| Me | —CH₂C(=O)CH₂CH₂— | Me | Me | i-Pr | Me | —CH₂C(=O)CH₂CH₂— | Me | Et | i-Pr |
| Me | —CH₂CH₂C(=O)CH₂— | Me | Me | i-Pr | Me | —CH₂CH₂C(=O)CH₂— | Me | Et | i-Pr |
| Me | —CH₂C(=S)CH₂CH₂— | Me | Me | i-Pr | Me | —CH₂C(=S)CH₂CH₂— | Me | Et | i-Pr |
| Me | —CH₂CH₂C(=S)CH₂— | Me | Me | i-Pr | Me | —CH₂CH₂C(=S)CH₂— | Me | Et | i-Pr |
| Me | —CH₂C(=O)CH₂— | Me | Me | i-Pr | Me | —CH₂C(=O)CH₂— | Me | Et | i-Pr |
| Me | —CH₂C(=S)CH₂— | Me | Me | i-Pr | Me | —CH₂C(=S)CH₂— | Me | Et | i-Pr |
| Me | —CH(Me)— | Me | Me | i-Pr | Me | —CH(Me)— | Me | Et | i-Pr |
| Me | —CH(OMe)— | Me | Me | i-Pr | Me | —CH(OMe)— | Me | Et | i-Pr |
| Me | —CH(Me)CH₂— | Me | Me | i-Pr | Me | —CH(Me)CH₂— | Me | Et | i-Pr |
| Me | —CH₂CH(Me)— | Me | Me | i-Pr | Me | —CH₂CH(Me)— | Me | Et | i-Pr |
| Me | —CH₂CH(OMe)— | Me | Me | i-Pr | Me | —CH₂CH(OMe)— | Me | Et | i-Pr |
| Me | —CH(Me)CH₂CH₂— | Me | Me | i-Pr | Me | —CH(Me)CH₂CH₂— | Me | Et | i-Pr |
| Me | —CH₂CH(Me)CH₂— | Me | Me | i-Pr | Me | —CH₂CH(Me)CH₂— | Me | Et | i-Pr |
| Me | —CH₂CH₂CH(Me)— | Me | Me | i-Pr | Me | —CH₂CH₂CH(Me)— | Me | Et | i-Pr |
| Me | —CH(Et)— | Me | Me | i-Pr | Me | —CH(Et)— | Me | Et | i-Pr |
| Me | —CH(Et)CH₂— | Me | Me | i-Pr | Me | —CH(Et)CH₂— | Me | Et | i-Pr |
| Me | —CH₂CH(Et)— | Me | Me | i-Pr | Me | —CH₂CH(Et)— | Me | Et | i-Pr |
| Me | —CH(Et)CH₂CH₂— | Me | Me | i-Pr | Me | —CH(Et)CH₂CH₂— | Me | Et | i-Pr |
| Me | —CH₂CH(Et)CH₂— | Me | Me | i-Pr | Me | —CH₂CH(Et)CH₂— | Me | Et | i-Pr |
| Me | —CH₂CH₂CH(Et)— | Me | Me | i-Pr | Me | —CH₂CH₂CH(Et)— | Me | Et | i-Pr |
| Me | —CH(OCF₃)— | Me | Me | i-Pr | Me | —CH(OCF₃)— | Me | Et | i-Pr |
| Me | —CH(CF₃)— | Me | Me | i-Pr | Me | —CH(CF₃)— | Me | Et | i-Pr |
| Me | —CH₂CF₂CH₂— | Me | Me | i-Pr | Me | —CH₂CF₂CH₂— | Me | Et | i-Pr |
| Me | —CH₂CHFCH₂— | Me | Me | i-Pr | Me | —CH₂CHFCH₂— | Me | Et | i-Pr |
| Me | —CH₂CF₂— | Me | Me | i-Pr | Me | —CH₂CF₂— | Me | Et | i-Pr |
| Me | —CH₂CHF— | Me | Me | i-Pr | Me | —CH₂CHF— | Me | Et | i-Pr |
| Me | —CH(CN)— | Me | Me | i-Pr | Me | —CH(CN)— | Me | Et | i-Pr |
| Me | Vᵃ | Me | Me | i-Pr | Me | Vᵃ | Me | Et | i-Pr |
| Me | Vᵇ | Me | Me | i-Pr | Me | Vᵇ | Me | Et | i-Pr |
| Me | Vᶜ | Me | Me | i-Pr | Me | Vᶜ | Me | Et | i-Pr |
| Me | Vᵈ | Me | Me | i-Pr | Me | Vᵈ | Me | Et | i-Pr |
| Me | Vᵉ | Me | Me | i-Pr | Me | Vᵉ | Me | Et | i-Pr |
| Me | Vᶠ | Me | Me | i-Pr | Me | Vᶠ | Me | Et | i-Pr |
| Me | Vᵍ | Me | Me | i-Pr | Me | Vᵍ | Me | Et | i-Pr |
| Me | Vʰ | Me | Me | i-Pr | Me | Vʰ | Me | Et | i-Pr |
| Me | —CH₂OC(=O)CH₂— | Me | Me | i-Pr | Me | —CH₂OC(=O)CH₂— | Me | Et | i-Pr |
| Me | —CH₂C(=O)CH₂— | Me | Me | i-Pr | Me | —CH₂C(=O)CH₂— | Me | Et | i-Pr |
| Me | —CH₂C(=O)— | Me | Me | i-Pr | Me | —CH₂C(=O)— | Me | Et | i-Pr |
| Me | —CH₂— | Me | Me | Ph | Me | —CH₂— | Me | Me | 4-Cl—Ph |
| Me | —CH₂CH₂— | Me | Me | Ph | Me | —CH₂CH₂— | Me | Me | 4-Cl—Ph |
| Me | —CH₂CH₂CH₂— | Me | Me | Ph | Me | —CH₂CH₂CH₂— | Me | Me | 4-Cl—Ph |
| Me | —CH₂CH₂CH₂CH₂— | Me | Me | Ph | Me | —CH₂CH₂CH₂CH₂— | Me | Me | 4-Cl—Ph |
| Me | —CH₂OCH₂CH₂— | Me | Me | Ph | Me | —CH₂OCH₂CH₂— | Me | Me | 4-Cl—Ph |
| Me | —CH₂CH₂OCH₂— | Me | Me | Ph | Me | —CH₂CH₂OCH₂— | Me | Me | 4-Cl—Ph |
| Me | —CH₂C(=O)CH₂CH₂— | Me | Me | Ph | Me | —CH₂C(=O)CH₂CH₂— | Me | Me | 4-Cl—Ph |
| Me | —CH₂CH₂C(=O)CH₂— | Me | Me | Ph | Me | —CH₂CH₂C(=O)CH₂— | Me | Me | 4-Cl—Ph |
| Me | —CH₂C(=S)CH₂CH₂— | Me | Me | Ph | Me | —CH₂C(=S)CH₂CH₂— | Me | Me | 4-Cl—Ph |
| Me | —CH₂CH₂C(=S)CH₂— | Me | Me | Ph | Me | —CH₂CH₂C(=S)CH₂— | Me | Me | 4-Cl—Ph |
| Me | —CH₂C(=O)CH₂— | Me | Me | Ph | Me | —CH₂C(=O)CH₂— | Me | Me | 4-Cl—Ph |
| Me | —CH₂C(=S)CH₂— | Me | Me | Ph | Me | —CH₂C(=S)CH₂— | Me | Me | 4-Cl—Ph |
| Me | —CH(Me)— | Me | Me | Ph | Me | —CH(Me)— | Me | Me | 4-Cl—Ph |
| Me | —CH(OMe)— | Me | Me | Ph | Me | —CH(OMe)— | Me | Me | 4-Cl—Ph |
| Me | —CH(Me)CH₂— | Me | Me | Ph | Me | —CH(Me)CH₂— | Me | Me | 4-Cl—Ph |
| Me | —CH₂CH(Me)— | Me | Me | Ph | Me | —CH₂CH(Me)— | Me | Me | 4-Cl—Ph |
| Me | —CH₂CH(OMe)— | Me | Me | Ph | Me | —CH₂CH(OMe)— | Me | Me | 4-Cl—Ph |
| Me | —CH(Me)CH₂CH₂— | Me | Me | Ph | Me | —CH(Me)CH₂CH₂— | Me | Me | 4-Cl—Ph |
| Me | —CH₂CH(Me)CH₂— | Me | Me | Ph | Me | —CH₂CH(Me)CH₂— | Me | Me | 4-Cl—Ph |
| Me | —CH₂CH₂CH(Me)— | Me | Me | Ph | Me | —CH₂CH₂CH(Me)— | Me | Me | 4-Cl—Ph |
| Me | —CH(Et)— | Me | Me | Ph | Me | —CH(Et)— | Me | Me | 4-Cl—Ph |
| Me | —CH(Et)CH₂— | Me | Me | Ph | Me | —CH(Et)CH₂— | Me | Me | 4-Cl—Ph |
| Me | —CH₂CH(Et)— | Me | Me | Ph | Me | —CH₂CH(Et)— | Me | Me | 4-Cl—Ph |
| Me | —CH(Et)CH₂CH₂— | Me | Me | Ph | Me | —CH(Et)CH₂CH₂— | Me | Me | 4-Cl—Ph |
| Me | —CH₂CH(Et)CH₂— | Me | Me | Ph | Me | —CH₂CH(Et)CH₂— | Me | Me | 4-Cl—Ph |

TABLE 2-continued

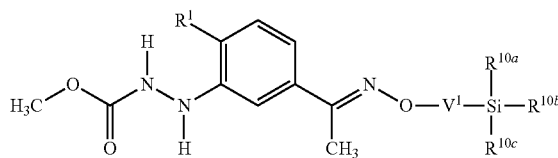

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | —CH₂CH₂CH(Et)— | Me | Me | Ph | Me | —CH₂CH₂CH(Et)— | Me | Me | 4-Cl—Ph |
| Me | —CH(OCF₃)— | Me | Me | Ph | Me | —CH(OCF₃)— | Me | Me | 4-Cl—Ph |
| Me | —CH(CF₃)— | Me | Me | Ph | Me | —CH(CF₃)— | Me | Me | 4-Cl—Ph |
| Me | —CH₂CF₂CH₂— | Me | Me | Ph | Me | —CH₂CF₂CH₂— | Me | Me | 4-Cl—Ph |
| Me | —CH₂CHFCH₂— | Me | Me | Ph | Me | —CH₂CHFCH₂— | Me | Me | 4-Cl—Ph |
| Me | —CH₂CF₂— | Me | Me | Ph | Me | —CH₂CF₂— | Me | Me | 4-Cl—Ph |
| Me | —CH₂CHF— | Me | Me | Ph | Me | —CH₂CHF— | Me | Me | 4-Cl—Ph |
| Me | —CH(CN)— | Me | Me | Ph | Me | —CH(CN)— | Me | Me | 4-Cl—Ph |
| Me | Vᵃ | Me | Me | Ph | Me | Vᵃ | Me | Me | 4-Cl—Ph |
| Me | Vᵇ | Me | Me | Ph | Me | Vᵇ | Me | Me | 4-Cl—Ph |
| Me | Vᶜ | Me | Me | Ph | Me | Vᶜ | Me | Me | 4-Cl—Ph |
| Me | Vᵈ | Me | Me | Ph | Me | Vᵈ | Me | Me | 4-Cl—Ph |
| Me | Vᵉ | Me | Me | Ph | Me | Vᵉ | Me | Me | 4-Cl—Ph |
| Me | Vᶠ | Me | Me | Ph | Me | Vᶠ | Me | Me | 4-Cl—Ph |
| Me | Vᵍ | Me | Me | Ph | Me | Vᵍ | Me | Me | 4-Cl—Ph |
| Me | Vʰ | Me | Me | Ph | Me | Vʰ | Me | Me | 4-Cl—Ph |
| Me | —CH₂OC(=O)CH₂— | Me | Me | Ph | Me | —CH₂OC(=O)CH₂— | Me | Me | 4-Cl—Ph |
| Me | —CH₂C(=O)CH₂— | Me | Me | Ph | Me | —CH₂C(=O)CH₂— | Me | Me | 4-Cl—Ph |
| Me | —CH₂C(=O)— | Me | Me | Ph | Me | —CH₂C(=O)— | Me | Me | 4-Cl—Ph |
| Me | —CH₂— | Me | Me | 3-Cl—Ph | Me | —CH₂— | Me | Me | 2-Cl—Ph |
| Me | —CH₂CH₂— | Me | Me | 3-Cl—Ph | Me | —CH₂CH₂— | Me | Me | 2-Cl—Ph |
| Me | —CH₂CH₂CH₂— | Me | Me | 3-Cl—Ph | Me | —CH₂CH₂CH₂— | Me | Me | 2-Cl—Ph |
| Me | —CH₂CH₂CH₂CH₂— | Me | Me | 3-Cl—Ph | Me | —CH₂CH₂CH₂CH₂— | Me | Me | 2-Cl—Ph |
| Me | —CH₂OCH₂CH₂— | Me | Me | 3-Cl—Ph | Me | —CH₂OCH₂CH₂— | Me | Me | 2-Cl—Ph |
| Me | —CH₂CH₂OCH₂— | Me | Me | 3-Cl—Ph | Me | —CH₂CH₂OCH₂— | Me | Me | 2-Cl—Ph |
| Me | —CH₂C(=O)CH₂CH₂— | Me | Me | 3-Cl—Ph | Me | —CH₂C(=O)CH₂CH₂— | Me | Me | 2-Cl—Ph |
| Me | —CH₂CH₂C(=O)CH₂— | Me | Me | 3-Cl—Ph | Me | —CH₂CH₂C(=O)CH₂— | Me | Me | 2-Cl—Ph |
| Me | —CH₂C(=S)CH₂CH₂— | Me | Me | 3-Cl—Ph | Me | —CH₂C(=S)CH₂CH₂— | Me | Me | 2-Cl—Ph |
| Me | —CH₂CH₂C(=S)CH₂— | Me | Me | 3-Cl—Ph | Me | —CH₂CH₂C(=S)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=S)CH₂— | Me | Me | 3-Cl—Ph | Me | —CH₂C(=S)CH₂— | Me | Me | 2-Cl—Ph |
| Me | —CH(Me)— | Me | Me | 3-Cl—Ph | Me | —CH(Me)— | Me | Me | 2-Cl—Ph |
| Me | —CH(OMe)— | Me | Me | 3-Cl—Ph | Me | —CH(OMe)— | Me | Me | 2-Cl—Ph |
| Me | —CH(Me)CH₂— | Me | Me | 3-Cl—Ph | Me | —CH(Me)CH₂— | Me | Me | 2-Cl—Ph |
| Me | —CH₂CH(Me)— | Me | Me | 3-Cl—Ph | Me | —CH₂CH(Me)— | Me | Me | 2-Cl—Ph |
| Me | —CH₂CH(OMe)— | Me | Me | 3-Cl—Ph | Me | —CH₂CH(OMe)— | Me | Me | 2-Cl—Ph |
| Me | —CH(Me)CH₂CH₂— | Me | Me | 3-Cl—Ph | Me | —CH(Me)CH₂CH₂— | Me | Me | 2-Cl—Ph |
| Me | —CH₂CH(Me)CH₂— | Me | Me | 3-Cl—Ph | Me | —CH₂CH(Me)CH₂— | Me | Me | 2-Cl—Ph |
| Me | —CH₂CH₂CH(Me)— | Me | Me | 3-Cl—Ph | Me | —CH₂CH₂CH(Me)— | Me | Me | 2-Cl—Ph |
| Me | —CH(Et)— | Me | Me | 3-Cl—Ph | Me | —CH(Et)— | Me | Me | 2-Cl—Ph |
| Me | —CH(Et)CH₂— | Me | Me | 3-Cl—Ph | Me | —CH(Et)CH₂— | Me | Me | 2-Cl—Ph |
| Me | —CH₂CH(Et)— | Me | Me | 3-Cl—Ph | Me | —CH₂CH(Et)— | Me | Me | 2-Cl—Ph |
| Me | —CH(Et)CH₂CH₂— | Me | Me | 3-Cl—Ph | Me | —CH(Et)CH₂CH₂— | Me | Me | 2-Cl—Ph |
| Me | —CH₂CH(Et)CH₂— | Me | Me | 3-Cl—Ph | Me | —CH₂CH(Et)CH₂— | Me | Me | 2-Cl—Ph |
| Me | —CH₂CH₂CH(Et)— | Me | Me | 3-Cl—Ph | Me | —CH₂CH₂CH(Et)— | Me | Me | 2-Cl—Ph |
| Me | —CH(OCF₃)— | Me | Me | 3-Cl—Ph | Me | —CH(OCF₃)— | Me | Me | 2-Cl—Ph |
| Me | —CH(CF₃)— | Me | Me | 3-Cl—Ph | Me | —CH(CF₃)— | Me | Me | 2-Cl—Ph |
| Me | —CH₂CF₂CH₂— | Me | Me | 3-Cl—Ph | Me | —CH₂CF₂CH₂— | Me | Me | 2-Cl—Ph |
| Me | —CH₂CHFCH₂— | Me | Me | 3-Cl—Ph | Me | —CH₂CHFCH₂— | Me | Me | 2-Cl—Ph |
| Me | —CH₂CF₂— | Me | Me | 3-Cl—Ph | Me | —CH₂CF₂— | Me | Me | 2-Cl—Ph |
| Me | —CH₂CHF— | Me | Me | 3-Cl—Ph | Me | —CH₂CHF— | Me | Me | 2-Cl—Ph |
| Me | —CH(CN)— | Me | Me | 3-Cl—Ph | Me | —CH(CN)— | Me | Me | 2-Cl—Ph |
| Me | Vᵃ | Me | Me | 3-Cl—Ph | Me | Vᵃ | Me | Me | 2-Cl—Ph |
| Me | Vᵇ | Me | Me | 3-Cl—Ph | Me | Vᵇ | Me | Me | 2-Cl—Ph |
| Me | Vᶜ | Me | Me | 3-Cl—Ph | Me | Vᶜ | Me | Me | 2-Cl—Ph |
| Me | Vᵈ | Me | Me | 3-Cl—Ph | Me | Vᵈ | Me | Me | 2-Cl—Ph |
| Me | Vᵉ | Me | Me | 3-Cl—Ph | Me | Vᵉ | Me | Me | 2-Cl—Ph |
| Me | Vᶠ | Me | Me | 3-Cl—Ph | Me | Vᶠ | Me | Me | 2-Cl—Ph |
| Me | Vᵍ | Me | Me | 3-Cl—Ph | Me | Vᵍ | Me | Me | 2-Cl—Ph |
| Me | Vʰ | Me | Me | 3-Cl—Ph | Me | Vʰ | Me | Me | 2-Cl—Ph |
| Me | —CH₂OC(=O)CH₂— | Me | Me | 3-Cl—Ph | Me | —CH₂OC(=O)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=O)— | Me | Me | 3-Cl—Ph | Me | —CH₂C(=O)— | Me | Me | 2-Cl—Ph |
| Me | —CH₂— | Me | Me | c-Pr | Me | —CH₂CH(Et)— | Me | Me | c-Pr |
| Me | —CH₂CH₂— | Me | Me | c-Pr | Me | —CH(Et)CH₂CH₂— | Me | Me | c-Pr |
| Me | —CH₂CH₂CH₂— | Me | Me | c-Pr | Me | —CH₂CH(Et)CH₂— | Me | Me | c-Pr |
| Me | —CH₂CH₂CH₂CH₂— | Me | Me | c-Pr | Me | —CH₂CH₂CH(Et)— | Me | Me | c-Pr |
| Me | —CH₂OCH₂CH₂— | Me | Me | c-Pr | Me | —CH(OCF₃)— | Me | Me | c-Pr |
| Me | —CH₂CH₂OCH₂— | Me | Me | c-Pr | Me | —CH(CF₃)— | Me | Me | c-Pr |

TABLE 2-continued

Structure: methyl carbazate group attached to benzene ring with R¹ substituent and oxime ether with silyl group (R¹⁰ₐ, R¹⁰ᵦ, R¹⁰ᵧ)

| R¹ | V¹ | R¹⁰ₐ | R¹⁰ᵦ | R¹⁰ᵧ | R¹ | V¹ | R¹⁰ₐ | R¹⁰ᵦ | R¹⁰ᵧ |
|---|---|---|---|---|---|---|---|---|---|
| Me | —CH₂C(=O)CH₂CH₂— | Me | Me | c-Pr | Me | —CH₂CF₂CH₂— | Me | Me | c-Pr |
| Me | —CH₂CH₂C(=O)CH₂— | Me | Me | c-Pr | Me | —CH₂CHFCH₂— | Me | Me | c-Pr |
| Me | —CH₂C(=S)CH₂CH₂— | Me | Me | c-Pr | Me | —CH₂CF₂— | Me | Me | c-Pr |
| Me | —CH₂CH₂C(=S)CH₂— | Me | Me | c-Pr | Me | —CH₂CHF— | Me | Me | c-Pr |
| Me | —CH₂C(=O)CH₂— | Me | Me | c-Pr | Me | —CH(CN)— | Me | Me | c-Pr |
| Me | —CH₂C(=S)CH₂— | Me | Me | c-Pr | Me | Vᵃ | Me | Me | c-Pr |
| Me | —CH(Me)— | Me | Me | c-Pr | Me | Vᵇ | Me | Me | c-Pr |
| Me | —CH(OMe)— | Me | Me | c-Pr | Me | Vᶜ | Me | Me | c-Pr |
| Me | —CH(Me)CH₂— | Me | Me | c-Pr | Me | Vᵈ | Me | Me | c-Pr |
| Me | —CH₂CH(Me)— | Me | Me | c-Pr | Me | Vᵉ | Me | Me | c-Pr |
| Me | —CH₂CH(OMe)— | Me | Me | c-Pr | Me | Vᶠ | Me | Me | c-Pr |
| Me | —CH(Me)CH₂CH₂— | Me | Me | c-Pr | Me | Vᵍ | Me | Me | c-Pr |
| Me | —CH₂CH(Me)CH₂— | Me | Me | c-Pr | Me | Vʰ | Me | Me | c-Pr |
| Me | —CH₂CH₂CH(Me)— | Me | Me | c-Pr | Me | —CH₂OC(=O)CH₂— | Me | Me | c-Pr |
| Me | —CH(Et)— | Me | Me | c-Pr | Me | —CH₂C(=O)CH₂— | Me | Me | c-Pr |
| Me | —CH(Et)CH₂— | Me | Me | c-Pr | Me | —CH₂C(=O)— | Me | Me | c-Pr |

TABLE 3

Structure: methyl carbamate with N—O linker attached to benzene ring with R¹ substituent and oxime ether with silyl group (R¹⁰ₐ, R¹⁰ᵦ, R¹⁰ᵧ)

| R¹ | V¹ | R¹⁰ₐ | R¹⁰ᵦ | R¹⁰ᵧ | R¹ | V¹ | R¹⁰ₐ | R¹⁰ᵦ | R¹⁰ᵧ |
|---|---|---|---|---|---|---|---|---|---|
| Cl | —CH₂— | Me | Me | Me | F | —CH₂— | Me | Me | Me |
| Cl | —CH₂CH₂— | Me | Me | Me | F | —CH₂CH₂— | Me | Me | Me |
| Cl | —CH₂CH₂CH₂— | Me | Me | Me | F | —CH₂CH₂CH₂— | Me | Me | Me |
| Cl | —CH₂CH₂CH₂CH₂— | Me | Me | Me | F | —CH₂CH₂CH₂CH₂— | Me | Me | Me |
| Cl | —CH₂OCH₂CH₂— | Me | Me | Me | F | —CH₂OCH₂CH₂— | Me | Me | Me |
| Cl | —CH₂CH₂OCH₂— | Me | Me | Me | F | —CH₂CH₂OCH₂— | Me | Me | Me |
| Cl | —CH₂C(=O)CH₂CH₂— | Me | Me | Me | F | —CH₂C(=O)CH₂CH₂— | Me | Me | Me |
| Cl | —CH₂CH₂C(=O)CH₂— | Me | Me | Me | F | —CH₂CH₂C(=O)CH₂— | Me | Me | Me |
| Cl | —CH₂C(=S)CH₂CH₂— | Me | Me | Me | F | —CH₂C(=S)CH₂CH₂— | Me | Me | Me |
| Cl | —CH₂CH₂C(=S)CH₂— | Me | Me | Me | F | —CH₂CH₂C(=S)CH₂— | Me | Me | Me |
| Cl | —CH₂C(=O)CH₂— | Me | Me | Me | F | —CH₂C(=O)CH₂— | Me | Me | Me |
| Cl | —CH₂C(=S)CH₂— | Me | Me | Me | F | —CH₂C(=S)CH₂— | Me | Me | Me |
| Cl | —CH(Me)— | Me | Me | Me | F | —CH(Me)— | Me | Me | Me |
| Cl | —CH(OMe)— | Me | Me | Me | F | —CH(OMe)— | Me | Me | Me |
| Cl | —CH(Me)CH₂— | Me | Me | Me | F | —CH(Me)CH₂— | Me | Me | Me |
| Cl | —CH₂CH(Me)— | Me | Me | Me | F | —CH₂CH(Me)— | Me | Me | Me |
| Cl | —CH₂CH(OMe)— | Me | Me | Me | F | —CH₂CH(OMe)— | Me | Me | Me |
| Cl | —CH(Me)CH₂CH₂— | Me | Me | Me | F | —CH(Me)CH₂CH₂— | Me | Me | Me |
| Cl | —CH₂CH(Me)CH₂— | Me | Me | Me | F | —CH₂CH(Me)CH₂— | Me | Me | Me |
| Cl | —CH₂CH₂CH(Me)— | Me | Me | Me | F | —CH₂CH₂CH(Me)— | Me | Me | Me |
| Cl | —CH(Et)— | Me | Me | Me | F | —CH(Et)— | Me | Me | Me |
| Cl | —CH(Et)CH₂— | Me | Me | Me | F | —CH(Et)CH₂— | Me | Me | Me |
| Cl | —CH₂CH(Et)— | Me | Me | Me | F | —CH₂CH(Et)— | Me | Me | Me |
| Cl | —CH(Et)CH₂CH₂— | Me | Me | Me | F | —CH(Et)CH₂CH₂— | Me | Me | Me |
| Cl | —CH₂CH(Et)CH₂— | Me | Me | Me | F | —CH₂CH(Et)CH₂— | Me | Me | Me |
| Cl | —CH₂CH₂CH(Et)— | Me | Me | Me | F | —CH₂CH₂CH(Et)— | Me | Me | Me |
| Cl | —CH(OCF₃)— | Me | Me | Me | F | —CH(OCF₃)— | Me | Me | Me |
| Cl | —CH(CF₃)— | Me | Me | Me | F | —CH(CF₃)— | Me | Me | Me |
| Cl | —CH₂CF₂CH₂— | Me | Me | Me | F | —CH₂CF₂CH₂— | Me | Me | Me |
| Cl | —CH₂CHFCH₂— | Me | Me | Me | F | —CH₂CHFCH₂— | Me | Me | Me |
| Cl | —CH₂CF₂— | Me | Me | Me | F | —CH₂CF₂— | Me | Me | Me |
| Cl | —CH₂CHF— | Me | Me | Me | F | —CH₂CHF— | Me | Me | Me |
| Cl | —CH(CN)— | Me | Me | Me | F | —CH(CN)— | Me | Me | Me |
| Cl | Vᵃ | Me | Me | Me | F | Vᵃ | Me | Me | Me |
| Cl | Vᵇ | Me | Me | Me | F | Vᵇ | Me | Me | Me |
| Cl | Vᶜ | Me | Me | Me | F | Vᶜ | Me | Me | Me |
| Cl | Vᵈ | Me | Me | Me | F | Vᵈ | Me | Me | Me |
| Cl | Vᵉ | Me | Me | Me | F | Vᵉ | Me | Me | Me |

TABLE 3-continued

Structure: H₃C—O—C(=O)—N(H)—O—[phenyl with R¹]—C(CH₃)=N—O—V¹—Si(R¹⁰ᵃ)(R¹⁰ᵇ)(R¹⁰ᶜ)

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | V$^f$ | Me | Me | Me | F | V$^f$ | Me | Me | Me |
| Cl | V$^g$ | Me | Me | Me | F | V$^g$ | Me | Me | Me |
| Cl | V$^h$ | Me | Me | Me | F | V$^h$ | Me | Me | Me |
| Cl | —CH₂OC(=O)CH₂— | Me | Me | Me | F | —CH₂OC(=O)CH₂— | Me | Me | Me |
| Cl | —CH₂C(=O)CH₂— | Me | Me | Me | F | —CH₂C(=O)CH₂— | Me | Me | Me |
| Cl | —CH₂C(=O)— | Me | Me | Me | F | —CH₂C(=O)— | Me | Me | Me |
| Cl | —CH₂— | Me | Me | Et | F | —CH₂— | Me | Me | Et |
| Cl | —CH₂CH₂— | Me | Me | Et | F | —CH₂CH₂— | Me | Me | Et |
| Cl | —CH₂CH₂CH₂— | Me | Me | Et | F | —CH₂CH₂CH₂— | Me | Me | Et |
| Cl | —CH₂CH₂CH₂CH₂— | Me | Me | Et | F | —CH₂CH₂CH₂CH₂— | Me | Me | Et |
| Cl | —CH₂OCH₂CH₂— | Me | Me | Et | F | —CH₂OCH₂CH₂— | Me | Me | Et |
| Cl | —CH₂CH₂OCH₂— | Me | Me | Et | F | —CH₂CH₂OCH₂— | Me | Me | Et |
| Cl | —CH₂C(=O)CH₂CH₂— | Me | Me | Et | F | —CH₂C(=O)CH₂CH₂— | Me | Me | Et |
| Cl | —CH₂CH₂C(=O)CH₂— | Me | Me | Et | F | —CH₂CH₂C(=O)CH₂— | Me | Me | Et |
| Cl | —CH₂C(=S)CH₂CH₂— | Me | Me | Et | F | —CH₂C(=S)CH₂CH₂— | Me | Me | Et |
| Cl | —CH₂CH₂C(=S)CH₂— | Me | Me | Et | F | —CH₂CH₂C(=S)CH₂— | Me | Me | Et |
| Cl | —CH₂C(=O)CH₂— | Me | Me | Et | F | —CH₂C(=O)CH₂— | Me | Me | Et |
| Cl | —CH₂C(=S)CH₂— | Me | Me | Et | F | —CH₂C(=S)CH₂— | Me | Me | Et |
| Cl | —CH(Me)— | Me | Me | Et | F | —CH(Me)— | Me | Me | Et |
| Cl | —CH(OMe)— | Me | Me | Et | F | —CH(OMe)— | Me | Me | Et |
| Cl | —CH(Me)CH₂— | Me | Me | Et | F | —CH(Me)CH₂— | Me | Me | Et |
| Cl | —CH₂CH(Me)— | Me | Me | Et | F | —CH₂CH(Me)— | Me | Me | Et |
| Cl | —CH₂CH(OMe)— | Me | Me | Et | F | —CH₂CH(OMe)— | Me | Me | Et |
| Cl | —CH(Me)CH₂CH₂— | Me | Me | Et | F | —CH(Me)CH₂CH₂— | Me | Me | Et |
| Cl | —CH₂CH(Me)CH₂— | Me | Me | Et | F | —CH₂CH(Me)CH₂— | Me | Me | Et |
| Cl | —CH₂CH₂CH(Me)— | Me | Me | Et | F | —CH₂CH₂CH(Me)— | Me | Me | Et |
| Cl | —CH(Et)— | Me | Me | Et | F | —CH(Et)— | Me | Me | Et |
| Cl | —CH(Et)CH₂— | Me | Me | Et | F | —CH(Et)CH₂— | Me | Me | Et |
| Cl | —CH₂CH(Et)— | Me | Me | Et | F | —CH₂CH(Et)— | Me | Me | Et |
| Cl | —CH(Et)CH₂CH₂— | Me | Me | Et | F | —CH(Et)CH₂CH₂— | Me | Me | Et |
| Cl | —CH₂CH(Et)CH₂— | Me | Me | Et | F | —CH₂CH(Et)CH₂— | Me | Me | Et |
| Cl | —CH₂CH₂CH(Et)— | Me | Me | Et | F | —CH₂CH₂CH(Et)— | Me | Me | Et |
| Cl | —CH(OCF₃)— | Me | Me | Et | F | —CH(OCF₃)— | Me | Me | Et |
| Cl | —CH(CF₃)— | Me | Me | Et | F | —CH(CF₃)— | Me | Me | Et |
| Cl | —CH₂CF₂CH₂— | Me | Me | Et | F | —CH₂CF₂CH₂— | Me | Me | Et |
| Cl | —CH₂CHFCH₂— | Me | Me | Et | F | —CH₂CHFCH₂— | Me | Me | Et |
| Cl | —CH₂CF₂— | Me | Me | Et | F | —CH₂CF₂— | Me | Me | Et |
| Cl | —CH₂CHF— | Me | Me | Et | F | —CH₂CHF— | Me | Me | Et |
| Cl | —CH(CN)— | Me | Me | Et | F | —CH(CN)— | Me | Me | Et |
| Cl | V$^a$ | Me | Me | Et | F | V$^a$ | Me | Me | Et |
| Cl | V$^b$ | Me | Me | Et | F | V$^b$ | Me | Me | Et |
| Cl | V$^c$ | Me | Me | Et | F | V$^c$ | Me | Me | Et |
| Cl | V$^d$ | Me | Me | Et | F | V$^d$ | Me | Me | Et |
| Cl | V$^e$ | Me | Me | Et | F | V$^e$ | Me | Me | Et |
| Cl | V$^f$ | Me | Me | Et | F | V$^f$ | Me | Me | Et |
| Cl | V$^g$ | Me | Me | Et | F | V$^g$ | Me | Me | Et |
| Cl | V$^h$ | Me | Me | Et | F | V$^h$ | Me | Me | Et |
| Cl | —CH₂OC(=O)CH₂— | Me | Me | Et | F | —CH₂OC(=O)CH₂— | Me | Me | Et |
| Cl | —CH₂C(=O)CH₂— | Me | Me | Et | F | —CH₂C(=O)CH₂— | Me | Me | Et |
| Cl | —CH₂C(=O)— | Me | Me | Et | F | —CH₂C(=O)— | Me | Me | Et |
| Cl | —CH₂— | Me | Et | Et | F | —CH₂— | Me | Et | Et |
| Cl | —CH₂CH₂— | Me | Et | Et | F | —CH₂CH₂— | Me | Et | Et |
| Cl | —CH₂CH₂CH₂— | Me | Et | Et | F | —CH₂CH₂CH₂— | Me | Et | Et |
| Cl | —CH₂CH₂CH₂CH₂— | Me | Et | Et | F | —CH₂CH₂CH₂CH₂— | Me | Et | Et |
| Cl | —CH₂OCH₂CH₂— | Me | Et | Et | F | —CH₂OCH₂CH₂— | Me | Et | Et |
| Cl | —CH₂CH₂OCH₂— | Me | Et | Et | F | —CH₂CH₂OCH₂— | Me | Et | Et |
| Cl | —CH₂C(=O)CH₂CH₂— | Me | Et | Et | F | —CH₂C(=O)CH₂CH₂— | Me | Et | Et |
| Cl | —CH₂CH₂C(=O)CH₂— | Me | Et | Et | F | —CH₂CH₂C(=O)CH₂— | Me | Et | Et |
| Cl | —CH₂C(=S)CH₂CH₂— | Me | Et | Et | F | —CH₂C(=S)CH₂CH₂— | Me | Et | Et |
| Cl | —CH₂CH₂C(=S)CH₂— | Me | Et | Et | F | —CH₂CH₂C(=S)CH₂— | Me | Et | Et |
| Cl | —CH₂C(=O)CH₂— | Me | Et | Et | F | —CH₂C(=O)CH₂— | Me | Et | Et |
| Cl | —CH₂C(=S)CH₂— | Me | Et | Et | F | —CH₂C(=S)CH₂— | Me | Et | Et |
| Cl | —CH(Me)— | Me | Et | Et | F | —CH(Me)— | Me | Et | Et |
| Cl | —CH(OMe)— | Me | Et | Et | F | —CH(OMe)— | Me | Et | Et |
| Cl | —CH(Me)CH₂— | Me | Et | Et | F | —CH(Me)CH₂— | Me | Et | Et |
| Cl | —CH₂CH(Me)— | Me | Et | Et | F | —CH₂CH(Me)— | Me | Et | Et |
| Cl | —CH₂CH(OMe)— | Me | Et | Et | F | —CH₂CH(OMe)— | Me | Et | Et |
| Cl | —CH(Me)CH₂CH₂— | Me | Et | Et | F | —CH(Me)CH₂CH₂— | Me | Et | Et |
| Cl | —CH₂CH(Me)CH₂— | Me | Et | Et | F | —CH₂CH(Me)CH₂— | Me | Et | Et |

TABLE 3-continued

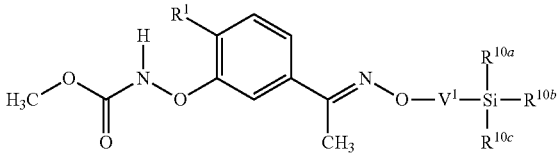

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂CH₂CH(Me)— | Me | Et | Et | F | —CH₂CH₂CH(Me)— | Me | Et | Et |
| Cl | —CH(Et)— | Me | Et | Et | F | —CH(Et)— | Me | Et | Et |
| Cl | —CH(Et)CH₂— | Me | Et | Et | F | —CH(Et)CH₂— | Me | Et | Et |
| Cl | —CH₂CH(Et)— | Me | Et | Et | F | —CH₂CH(Et)— | Me | Et | Et |
| Cl | —CH(Et)CH₂CH₂— | Me | Et | Et | F | —CH(Et)CH₂CH₂— | Me | Et | Et |
| Cl | —CH₂CH(Et)CH₂— | Me | Et | Et | F | —CH₂CH(Et)CH₂— | Me | Et | Et |
| Cl | —CH₂CH₂CH(Et)— | Me | Et | Et | F | —CH₂CH₂CH(Et)— | Me | Et | Et |
| Cl | —CH(OCF₃)— | Me | Et | Et | F | —CH(OCF₃)— | Me | Et | Et |
| Cl | —CH(CF₃)— | Me | Et | Et | F | —CH(CF₃)— | Me | Et | Et |
| Cl | —CH₂CF₂CH₂— | Me | Et | Et | F | —CH₂CF₂CH₂— | Me | Et | Et |
| Cl | —CH₂CHFCH₂— | Me | Et | Et | F | —CH₂CHFCH₂— | Me | Et | Et |
| Cl | —CH₂CF₂— | Me | Et | Et | F | —CH₂CF₂— | Me | Et | Et |
| Cl | —CH₂CHF— | Me | Et | Et | F | —CH₂CHF— | Me | Et | Et |
| Cl | —CH(CN)— | Me | Et | Et | F | —CH(CN)— | Me | Et | Et |
| Cl | Vᵃ | Me | Et | Et | F | Vᵃ | Me | Et | Et |
| Cl | Vᵇ | Me | Et | Et | F | Vᵇ | Me | Et | Et |
| Cl | Vᶜ | Me | Et | Et | F | Vᶜ | Me | Et | Et |
| Cl | Vᵈ | Me | Et | Et | F | Vᵈ | Me | Et | Et |
| Cl | Vᵉ | Me | Et | Et | F | Vᵉ | Me | Et | Et |
| Cl | Vᶠ | Me | Et | Et | F | Vᶠ | Me | Et | Et |
| Cl | Vᵍ | Me | Et | Et | F | Vᵍ | Me | Et | Et |
| Cl | Vʰ | Me | Et | Et | F | Vʰ | Me | Et | Et |
| Cl | —CH₂OC(=O)CH₂— | Me | Et | Et | F | —CH₂OC(=O)CH₂— | Me | Et | Et |
| Cl | —CH₂C(=O)CH₂— | Me | Et | Et | F | —CH₂C(=O)CH₂— | Me | Et | Et |
| Cl | —CH₂C(=O)— | Me | Et | Et | F | —CH₂C(=O)— | Me | Et | Et |
| Cl | —CH₂— | Et | Et | Et | F | —CH₂— | Et | Et | Et |
| Cl | —CH₂CH₂— | Et | Et | Et | F | —CH₂CH₂— | Et | Et | Et |
| Cl | —CH₂CH₂CH₂— | Et | Et | Et | F | —CH₂CH₂CH₂— | Et | Et | Et |
| Cl | —CH₂CH₂CH₂CH₂— | Et | Et | Et | F | —CH₂CH₂CH₂CH₂— | Et | Et | Et |
| Cl | —CH₂OCH₂CH₂— | Et | Et | Et | F | —CH₂OCH₂CH₂— | Et | Et | Et |
| Cl | —CH₂CH₂OCH₂— | Et | Et | Et | F | —CH₂CH₂OCH₂— | Et | Et | Et |
| Cl | —CH₂C(=O)CH₂CH₂— | Et | Et | Et | F | —CH₂C(=O)CH₂CH₂— | Et | Et | Et |
| Cl | —CH₂CH₂C(=O)CH₂— | Et | Et | Et | F | —CH₂CH₂C(=O)CH₂— | Et | Et | Et |
| Cl | —CH₂C(=S)CH₂CH₂— | Et | Et | Et | F | —CH₂C(=S)CH₂CH₂— | Et | Et | Et |
| Cl | —CH₂CH₂C(=S)CH₂— | Et | Et | Et | F | —CH₂CH₂C(=S)CH₂— | Et | Et | Et |
| Cl | —CH₂C(=O)CH₂— | Et | Et | Et | F | —CH₂C(=O)CH₂— | Et | Et | Et |
| Cl | —CH₂C(=S)CH₂— | Et | Et | Et | F | —CH₂C(=S)CH₂— | Et | Et | Et |
| Cl | —CH(Me)— | Et | Et | Et | F | —CH(Me)— | Et | Et | Et |
| Cl | —CH(OMe)— | Et | Et | Et | F | —CH(OMe)— | Et | Et | Et |
| Cl | —CH(Me)CH₂— | Et | Et | Et | F | —CH(Me)CH₂— | Et | Et | Et |
| Cl | —CH₂CH(Me)— | Et | Et | Et | F | —CH₂CH(Me)— | Et | Et | Et |
| Cl | —CH₂CH(OMe)— | Et | Et | Et | F | —CH₂CH(OMe)— | Et | Et | Et |
| Cl | —CH(Me)CH₂CH₂— | Et | Et | Et | F | —CH(Me)CH₂CH₂— | Et | Et | Et |
| Cl | —CH₂CH(Me)CH₂— | Et | Et | Et | F | —CH₂CH(Me)CH₂— | Et | Et | Et |
| Cl | —CH₂CH₂CH(Me)— | Et | Et | Et | F | —CH₂CH₂CH(Me)— | Et | Et | Et |
| Cl | —CH(Et)— | Et | Et | Et | F | —CH(Et)— | Et | Et | Et |
| Cl | —CH(Et)CH₂— | Et | Et | Et | F | —CH(Et)CH₂— | Et | Et | Et |
| Cl | —CH₂CH(Et)— | Et | Et | Et | F | —CH₂CH(Et)— | Et | Et | Et |
| Cl | —CH(Et)CH₂CH₂— | Et | Et | Et | F | —CH(Et)CH₂CH₂— | Et | Et | Et |
| Cl | —CH₂CH(Et)CH₂— | Et | Et | Et | F | —CH₂CH(Et)CH₂— | Et | Et | Et |
| Cl | —CH₂CH₂CH(Et)— | Et | Et | Et | F | —CH₂CH₂CH(Et)— | Et | Et | Et |
| Cl | —CH(OCF₃)— | Et | Et | Et | F | —CH(OCF₃)— | Et | Et | Et |
| Cl | —CH(CF₃)— | Et | Et | Et | F | —CH(CF₃)— | Et | Et | Et |
| Cl | —CH₂CF₂CH₂— | Et | Et | Et | F | —CH₂CF₂CH₂— | Et | Et | Et |
| Cl | —CH₂CHFCH₂— | Et | Et | Et | F | —CH₂CHFCH₂— | Et | Et | Et |
| Cl | —CH₂CF₂— | Et | Et | Et | F | —CH₂CF₂— | Et | Et | Et |
| Cl | —CH₂CHF— | Et | Et | Et | F | —CH₂CHF— | Et | Et | Et |
| Cl | —CH(CN)— | Et | Et | Et | F | —CH(CN)— | Et | Et | Et |
| Cl | Vᵃ | Et | Et | Et | F | Vᵃ | Et | Et | Et |
| Cl | Vᵇ | Et | Et | Et | F | Vᵇ | Et | Et | Et |
| Cl | Vᶜ | Et | Et | Et | F | Vᶜ | Et | Et | Et |
| Cl | Vᵈ | Et | Et | Et | F | Vᵈ | Et | Et | Et |
| Cl | Vᵉ | Et | Et | Et | F | Vᵉ | Et | Et | Et |
| Cl | Vᶠ | Et | Et | Et | F | Vᶠ | Et | Et | Et |
| Cl | Vᵍ | Et | Et | Et | F | Vᵍ | Et | Et | Et |
| Cl | Vʰ | Et | Et | Et | F | Vʰ | Et | Et | Et |
| Cl | —CH₂OC(=O)CH₂— | Et | Et | Et | F | —CH₂OC(=O)CH₂— | Et | Et | Et |
| Cl | —CH₂C(=O)CH₂— | Et | Et | Et | F | —CH₂C(=O)CH₂— | Et | Et | Et |
| Cl | —CH₂C(=O)— | Et | Et | Et | F | —CH₂C(=O)— | Et | Et | Et |

TABLE 3-continued

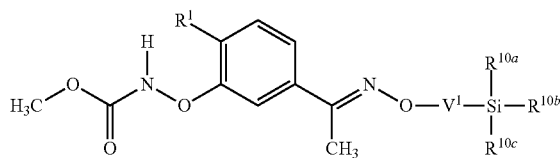

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂— | Me | Me | i-Pr | F | —CH₂— | Me | Me | i-Pr |
| Cl | —CH₂CH₂— | Me | Me | i-Pr | F | —CH₂CH₂— | Me | Me | i-Pr |
| Cl | —CH₂CH₂CH₂— | Me | Me | i-Pr | F | —CH₂CH₂CH₂— | Me | Me | i-Pr |
| Cl | —CH₂CH₂CH₂CH₂— | Me | Me | i-Pr | F | —CH₂CH₂CH₂CH₂— | Me | Me | i-Pr |
| Cl | —CH₂OCH₂CH₂— | Me | Me | i-Pr | F | —CH₂OCH₂CH₂— | Me | Me | i-Pr |
| Cl | —CH₂CH₂OCH₂— | Me | Me | i-Pr | F | —CH₂CH₂OCH₂— | Me | Me | i-Pr |
| Cl | —CH₂C(=O)CH₂CH₂— | Me | Me | i-Pr | F | —CH₂C(=O)CH₂CH₂— | Me | Me | i-Pr |
| Cl | —CH₂CH₂C(=O)CH₂— | Me | Me | i-Pr | F | —CH₂CH₂C(=O)CH₂— | Me | Me | i-Pr |
| Cl | —CH₂C(=S)CH₂CH₂— | Me | Me | i-Pr | F | —CH₂C(=S)CH₂CH₂— | Me | Me | i-Pr |
| Cl | —CH₂CH₂C(=S)CH₂— | Me | Me | i-Pr | F | —CH₂CH₂C(=S)CH₂— | Me | Me | i-Pr |
| Cl | —CH₂C(=O)CH₂— | Me | Me | i-Pr | F | —CH₂C(=O)CH₂— | Me | Me | i-Pr |
| Cl | —CH₂C(=S)CH₂— | Me | Me | i-Pr | F | —CH₂C(=S)CH₂— | Me | Me | i-Pr |
| Cl | —CH(Me)— | Me | Me | i-Pr | F | —CH(Me)— | Me | Me | i-Pr |
| Cl | —CH(OMe)— | Me | Me | i-Pr | F | —CH(OMe)— | Me | Me | i-Pr |
| Cl | —CH(Me)CH₂— | Me | Me | i-Pr | F | —CH(Me)CH₂— | Me | Me | i-Pr |
| Cl | —CH₂CH(Me)— | Me | Me | i-Pr | F | —CH₂CH(Me)— | Me | Me | i-Pr |
| Cl | —CH₂CH(OMe)— | Me | Me | i-Pr | F | —CH₂CH(OMe)— | Me | Me | i-Pr |
| Cl | —CH(Me)CH₂CH₂— | Me | Me | i-Pr | F | —CH(Me)CH₂CH₂— | Me | Me | i-Pr |
| Cl | —CH₂CH(Me)CH₂— | Me | Me | i-Pr | F | —CH₂CH(Me)CH₂— | Me | Me | i-Pr |
| Cl | —CH₂CH₂CH(Me)— | Me | Me | i-Pr | F | —CH₂CH₂CH(Me)— | Me | Me | i-Pr |
| Cl | —CH(Et)— | Me | Me | i-Pr | F | —CH(Et)— | Me | Me | i-Pr |
| Cl | —CH(Et)CH₂— | Me | Me | i-Pr | F | —CH(Et)CH₂— | Me | Me | i-Pr |
| Cl | —CH₂CH(Et)— | Me | Me | i-Pr | F | —CH₂CH(Et)— | Me | Me | i-Pr |
| Cl | —CH(Et)CH₂CH₂— | Me | Me | i-Pr | F | —CH(Et)CH₂CH₂— | Me | Me | i-Pr |
| Cl | —CH₂CH(Et)CH₂— | Me | Me | i-Pr | F | —CH₂CH(Et)CH₂— | Me | Me | i-Pr |
| Cl | —CH₂CH₂CH(Et)— | Me | Me | i-Pr | F | —CH₂CH₂CH(Et)— | Me | Me | i-Pr |
| Cl | —CH(OCF₃)— | Me | Me | i-Pr | F | —CH(OCF₃)— | Me | Me | i-Pr |
| Cl | —CH(CF₃)— | Me | Me | i-Pr | F | —CH(CF₃)— | Me | Me | i-Pr |
| Cl | —CH₂CF₂CH₂— | Me | Me | i-Pr | F | —CH₂CF₂CH₂— | Me | Me | i-Pr |
| Cl | —CH₂CHFCH₂— | Me | Me | i-Pr | F | —CH₂CHFCH₂— | Me | Me | i-Pr |
| Cl | —CH₂CF₂— | Me | Me | i-Pr | F | —CH₂CF₂— | Me | Me | i-Pr |
| Cl | —CH₂CHF— | Me | Me | i-Pr | F | —CH₂CHF— | Me | Me | i-Pr |
| Cl | —CH(CN)— | Me | Me | i-Pr | F | —CH(CN)— | Me | Me | i-Pr |
| Cl | Vᵃ | Me | Me | i-Pr | F | Vᵃ | Me | Me | i-Pr |
| Cl | Vᵇ | Me | Me | i-Pr | F | Vᵇ | Me | Me | i-Pr |
| Cl | Vᶜ | Me | Me | i-Pr | F | Vᶜ | Me | Me | i-Pr |
| Cl | Vᵈ | Me | Me | i-Pr | F | Vᵈ | Me | Me | i-Pr |
| Cl | Vᵉ | Me | Me | i-Pr | F | Vᵉ | Me | Me | i-Pr |
| Cl | Vᶠ | Me | Me | i-Pr | F | Vᶠ | Me | Me | i-Pr |
| Cl | Vᵍ | Me | Me | i-Pr | F | Vᵍ | Me | Me | i-Pr |
| Cl | Vʰ | Me | Me | i-Pr | F | Vʰ | Me | Me | i-Pr |
| Cl | —CH₂OC(=O)CH₂— | Me | Me | i-Pr | F | —CH₂OC(=O)CH₂— | Me | Me | i-Pr |
| Cl | —CH₂C(=O)CH₂— | Me | Me | i-Pr | F | —CH₂C(=O)CH₂— | Me | Me | i-Pr |
| Cl | —CH₂C(=O)— | Me | Me | i-Pr | F | —CH₂C(=O)— | Me | Me | i-Pr |
| Cl | —CH₂— | Me | Et | i-Pr | F | —CH₂— | Me | Et | i-Pr |
| Cl | —CH₂CH₂— | Me | Et | i-Pr | F | —CH₂CH₂— | Me | Et | i-Pr |
| Cl | —CH₂CH₂CH₂— | Me | Et | i-Pr | F | —CH₂CH₂CH₂— | Me | Et | i-Pr |
| Cl | —CH₂CH₂CH₂CH₂— | Me | Et | i-Pr | F | —CH₂CH₂CH₂CH₂— | Me | Et | i-Pr |
| Cl | —CH₂OCH₂CH₂— | Me | Et | i-Pr | F | —CH₂OCH₂CH₂— | Me | Et | i-Pr |
| Cl | —CH₂CH₂OCH₂— | Me | Et | i-Pr | F | —CH₂CH₂OCH₂— | Me | Et | i-Pr |
| Cl | —CH₂C(=O)CH₂CH₂— | Me | Et | i-Pr | F | —CH₂C(=O)CH₂CH₂— | Me | Et | i-Pr |
| Cl | —CH₂CH₂C(=O)CH₂— | Me | Et | i-Pr | F | —CH₂CH₂C(=O)CH₂— | Me | Et | i-Pr |
| Cl | —CH₂C(=S)CH₂CH₂— | Me | Et | i-Pr | F | —CH₂C(=S)CH₂CH₂— | Me | Et | i-Pr |
| Cl | —CH₂CH₂C(=S)CH₂— | Me | Et | i-Pr | F | —CH₂CH₂C(=S)CH₂— | Me | Et | i-Pr |
| Cl | —CH₂C(=O)CH₂— | Me | Et | i-Pr | F | —CH₂C(=O)CH₂— | Me | Et | i-Pr |
| Cl | —CH₂C(=S)CH₂— | Me | Et | i-Pr | F | —CH₂C(=S)CH₂— | Me | Et | i-Pr |
| Cl | —CH(Me)— | Me | Et | i-Pr | F | —CH(Me)— | Me | Et | i-Pr |
| Cl | —CH(OMe)— | Me | Et | i-Pr | F | —CH(OMe)— | Me | Et | i-Pr |
| Cl | —CH(Me)CH₂— | Me | Et | i-Pr | F | —CH(Me)CH₂— | Me | Et | i-Pr |
| Cl | —CH₂CH(Me)— | Me | Et | i-Pr | F | —CH₂CH(Me)— | Me | Et | i-Pr |
| Cl | —CH₂CH(OMe)— | Me | Et | i-Pr | F | —CH₂CH(OMe)— | Me | Et | i-Pr |
| Cl | —CH(Me)CH₂CH₂— | Me | Et | i-Pr | F | —CH(Me)CH₂CH₂— | Me | Et | i-Pr |
| Cl | —CH₂CH(Me)CH₂— | Me | Et | i-Pr | F | —CH₂CH(Me)CH₂— | Me | Et | i-Pr |
| Cl | —CH₂CH₂CH(Me)— | Me | Et | i-Pr | F | —CH₂CH₂CH(Me)— | Me | Et | i-Pr |
| Cl | —CH(Et)— | Me | Et | i-Pr | F | —CH(Et)— | Me | Et | i-Pr |
| Cl | —CH(Et)CH₂— | Me | Et | i-Pr | F | —CH(Et)CH₂— | Me | Et | i-Pr |
| Cl | —CH₂CH(Et)— | Me | Et | i-Pr | F | —CH₂CH(Et)— | Me | Et | i-Pr |
| Cl | —CH(Et)CH₂CH₂— | Me | Et | i-Pr | F | —CH(Et)CH₂CH₂— | Me | Et | i-Pr |
| Cl | —CH₂CH(Et)CH₂— | Me | Et | i-Pr | F | —CH₂CH(Et)CH₂— | Me | Et | i-Pr |

TABLE 3-continued

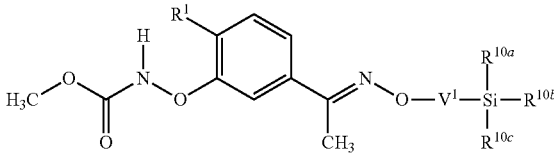

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂CH₂CH(Et)— | Me | Et | i-Pr | F | —CH₂CH₂CH(Et)— | Me | Et | i-Pr |
| Cl | —CH(OCF₃)— | Me | Et | i-Pr | F | —CH(OCF₃)— | Me | Et | i-Pr |
| Cl | —CH(CF₃)— | Me | Et | i-Pr | F | —CH(CF₃)— | Me | Et | i-Pr |
| Cl | —CH₂CF₂CH₂— | Me | Et | i-Pr | F | —CH₂CF₂CH₂— | Me | Et | i-Pr |
| Cl | —CH₂CHFCH₂— | Me | Et | i-Pr | F | —CH₂CHFCH₂— | Me | Et | i-Pr |
| Cl | —CH₂CF₂— | Me | Et | i-Pr | F | —CH₂CF₂— | Me | Et | i-Pr |
| Cl | —CH₂CHF— | Me | Et | i-Pr | F | —CH₂CHF— | Me | Et | i-Pr |
| Cl | —CH(CN)— | Me | Et | i-Pr | F | —CH(CN)— | Me | Et | i-Pr |
| Cl | Vᵃ | Me | Et | i-Pr | F | Vᵃ | Me | Et | i-Pr |
| Cl | Vᵇ | Me | Et | i-Pr | F | Vᵇ | Me | Et | i-Pr |
| Cl | Vᶜ | Me | Et | i-Pr | F | Vᶜ | Me | Et | i-Pr |
| Cl | Vᵈ | Me | Et | i-Pr | F | Vᵈ | Me | Et | i-Pr |
| Cl | Vᵉ | Me | Et | i-Pr | F | Vᵉ | Me | Et | i-Pr |
| Cl | Vᶠ | Me | Et | i-Pr | F | Vᶠ | Me | Et | i-Pr |
| Cl | Vᵍ | Me | Et | i-Pr | F | Vᵍ | Me | Et | i-Pr |
| Cl | Vʰ | Me | Et | i-Pr | F | Vʰ | Me | Et | i-Pr |
| Cl | —CH₂OC(=O)CH₂— | Me | Et | i-Pr | F | —CH₂OC(=O)CH₂— | Me | Et | i-Pr |
| Cl | —CH₂C(=O)CH₂— | Me | Et | i-Pr | F | —CH₂C(=O)CH₂— | Me | Et | i-Pr |
| Cl | —CH₂C(=O)— | Me | Et | i-Pr | F | —CH₂C(=O)— | Me | Et | i-Pr |
| Cl | —CH₂— | Me | Me | Ph | F | —CH₂— | Me | Me | Ph |
| Cl | —CH₂CH₂— | Me | Me | Ph | F | —CH₂CH₂— | Me | Me | Ph |
| Cl | —CH₂CH₂CH₂— | Me | Me | Ph | F | —CH₂CH₂CH₂— | Me | Me | Ph |
| Cl | —CH₂CH₂CH₂CH₂— | Me | Me | Ph | F | —CH₂CH₂CH₂CH₂— | Me | Me | Ph |
| Cl | —CH₂OCH₂CH₂— | Me | Me | Ph | F | —CH₂OCH₂CH₂— | Me | Me | Ph |
| Cl | —CH₂CH₂OCH₂— | Me | Me | Ph | F | —CH₂CH₂OCH₂— | Me | Me | Ph |
| Cl | —CH₂C(=O)CH₂CH₂— | Me | Me | Ph | F | —CH₂C(=O)CH₂CH₂— | Me | Me | Ph |
| Cl | —CH₂CH₂C(=O)CH₂— | Me | Me | Ph | F | —CH₂CH₂C(=O)CH₂— | Me | Me | Ph |
| Cl | —CH₂C(=S)CH₂CH₂— | Me | Me | Ph | F | —CH₂C(=S)CH₂CH₂— | Me | Me | Ph |
| Cl | —CH₂CH₂C(=S)CH₂— | Me | Me | Ph | F | —CH₂CH₂C(=S)CH₂— | Me | Me | Ph |
| Cl | —CH₂C(=O)CH₂— | Me | Me | Ph | F | —CH₂C(=O)CH₂— | Me | Me | Ph |
| Cl | —CH₂C(=S)CH₂— | Me | Me | Ph | F | —CH₂C(=S)CH₂— | Me | Me | Ph |
| Cl | —CH(Me)— | Me | Me | Ph | F | —CH(Me)— | Me | Me | Ph |
| Cl | —CH(OMe)— | Me | Me | Ph | F | —CH(OMe)— | Me | Me | Ph |
| Cl | —CH(Me)CH₂— | Me | Me | Ph | F | —CH(Me)CH₂— | Me | Me | Ph |
| Cl | —CH₂CH(Me)— | Me | Me | Ph | F | —CH₂CH(Me)— | Me | Me | Ph |
| Cl | —CH₂CH(OMe)— | Me | Me | Ph | F | —CH₂CH(OMe)— | Me | Me | Ph |
| Cl | —CH(Me)CH₂CH₂— | Me | Me | Ph | F | —CH(Me)CH₂CH₂— | Me | Me | Ph |
| Cl | —CH₂CH(Me)CH₂— | Me | Me | Ph | F | —CH₂CH(Me)CH₂— | Me | Me | Ph |
| Cl | —CH₂CH₂CH(Me)— | Me | Me | Ph | F | —CH₂CH₂CH(Me)— | Me | Me | Ph |
| Cl | —CH(Et)— | Me | Me | Ph | F | —CH(Et)— | Me | Me | Ph |
| Cl | —CH(Et)CH₂— | Me | Me | Ph | F | —CH(Et)CH₂— | Me | Me | Ph |
| Cl | —CH₂CH(Et)— | Me | Me | Ph | F | —CH₂CH(Et)— | Me | Me | Ph |
| Cl | —CH(Et)CH₂CH₂— | Me | Me | Ph | F | —CH(Et)CH₂CH₂— | Me | Me | Ph |
| Cl | —CH₂CH(Et)CH₂— | Me | Me | Ph | F | —CH₂CH(Et)CH₂— | Me | Me | Ph |
| Cl | —CH₂CH₂CH(Et)— | Me | Me | Ph | F | —CH₂CH₂CH(Et)— | Me | Me | Ph |
| Cl | —CH(OCF₃)— | Me | Me | Ph | F | —CH(OCF₃)— | Me | Me | Ph |
| Cl | —CH(CF₃)— | Me | Me | Ph | F | —CH(CF₃)— | Me | Me | Ph |
| Cl | —CH₂CF₂CH₂— | Me | Me | Ph | F | —CH₂CF₂CH₂— | Me | Me | Ph |
| Cl | —CH₂CHFCH₂— | Me | Me | Ph | F | —CH₂CHFCH₂— | Me | Me | Ph |
| Cl | —CH₂CF₂— | Me | Me | Ph | F | —CH₂CF₂— | Me | Me | Ph |
| Cl | —CH₂CHF— | Me | Me | Ph | F | —CH₂CHF— | Me | Me | Ph |
| Cl | —CH(CN)— | Me | Me | Ph | F | —CH(CN)— | Me | Me | Ph |
| Cl | Vᵃ | Me | Me | Ph | F | Vᵃ | Me | Me | Ph |
| Cl | Vᵇ | Me | Me | Ph | F | Vᵇ | Me | Me | Ph |
| Cl | Vᶜ | Me | Me | Ph | F | Vᶜ | Me | Me | Ph |
| Cl | Vᵈ | Me | Me | Ph | F | Vᵈ | Me | Me | Ph |
| Cl | Vᵉ | Me | Me | Ph | F | Vᵉ | Me | Me | Ph |
| Cl | Vᶠ | Me | Me | Ph | F | Vᶠ | Me | Me | Ph |
| Cl | Vᵍ | Me | Me | Ph | F | Vᵍ | Me | Me | Ph |
| Cl | Vʰ | Me | Me | Ph | F | Vʰ | Me | Me | Ph |
| Cl | —CH₂OC(=O)CH₂— | Me | Me | Ph | F | —CH₂OC(=O)CH₂— | Me | Me | Ph |
| Cl | —CH₂C(=O)CH₂— | Me | Me | Ph | F | —CH₂C(=O)CH₂— | Me | Me | Ph |
| Cl | —CH₂C(=O)— | Me | Me | Ph | F | —CH₂C(=O)— | Me | Me | Ph |
| Cl | —CH₂— | Me | Me | 4-Cl—Ph | F | —CH₂— | Me | Me | 4-Cl—Ph |
| Cl | —CH₂CH₂— | Me | Me | 4-Cl—Ph | F | —CH₂CH₂— | Me | Me | 4-Cl—Ph |
| Cl | —CH₂CH₂CH₂— | Me | Me | 4-Cl—Ph | F | —CH₂CH₂CH₂— | Me | Me | 4-Cl—Ph |
| Cl | —CH₂CH₂CH₂CH₂— | Me | Me | 4-Cl—Ph | F | —CH₂CH₂CH₂CH₂— | Me | Me | 4-Cl—Ph |
| Cl | —CH₂OCH₂CH₂— | Me | Me | 4-Cl—Ph | F | —CH₂OCH₂CH₂— | Me | Me | 4-Cl—Ph |
| Cl | —CH₂CH₂OCH₂— | Me | Me | 4-Cl—Ph | F | —CH₂CH₂OCH₂— | Me | Me | 4-Cl—Ph |

TABLE 3-continued

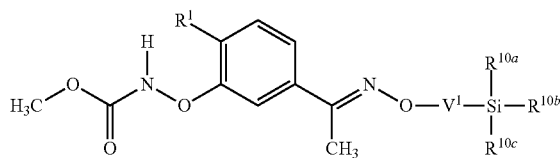

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH₂C(=O)CH₂CH₂— | Me | Me | 4-Cl—Ph | F | —CH₂C(=O)CH₂CH₂— | Me | Me | 4-Cl—Ph |
| Cl | —CH₂CH₂C(=O)CH₂— | Me | Me | 4-Cl—Ph | F | —CH₂CH₂C(=O)CH₂— | Me | Me | 4-Cl—Ph |
| Cl | —CH₂C(=S)CH₂CH₂— | Me | Me | 4-Cl—Ph | F | —CH₂C(=S)CH₂CH₂— | Me | Me | 4-Cl—Ph |
| Cl | —CH₂CH₂C(=S)CH₂— | Me | Me | 4-Cl—Ph | F | —CH₂CH₂C(=S)CH₂— | Me | Me | 4-Cl—Ph |
| Cl | —CH₂C(=O)CH₂— | Me | Me | 4-Cl—Ph | F | —CH₂C(=O)CH₂— | Me | Me | 4-Cl—Ph |
| Cl | —CH₂C(=S)CH₂— | Me | Me | 4-Cl—Ph | F | —CH₂C(=S)CH₂— | Me | Me | 4-Cl—Ph |
| Cl | —CH(Me)— | Me | Me | 4-Cl—Ph | F | —CH(Me)— | Me | Me | 4-Cl—Ph |
| Cl | —CH(OMe)— | Me | Me | 4-Cl—Ph | F | —CH(OMe)— | Me | Me | 4-Cl—Ph |
| Cl | —CH(Me)CH₂— | Me | Me | 4-Cl—Ph | F | —CH(Me)CH₂— | Me | Me | 4-Cl—Ph |
| Cl | —CH₂CH(Me)— | Me | Me | 4-Cl—Ph | F | —CH₂CH(Me)— | Me | Me | 4-Cl—Ph |
| Cl | —CH₂CH(OMe)— | Me | Me | 4-Cl—Ph | F | —CH₂CH(OMe)— | Me | Me | 4-Cl—Ph |
| Cl | —CH(Me)CH₂CH₂— | Me | Me | 4-Cl—Ph | F | —CH(Me)CH₂CH₂— | Me | Me | 4-Cl—Ph |
| Cl | —CH₂CH(Me)CH₂— | Me | Me | 4-Cl—Ph | F | —CH₂CH(Me)CH₂— | Me | Me | 4-Cl—Ph |
| Cl | —CH₂CH₂CH(Me)— | Me | Me | 4-Cl—Ph | F | —CH₂CH₂CH(Me)— | Me | Me | 4-Cl—Ph |
| Cl | —CH(Et)— | Me | Me | 4-Cl—Ph | F | —CH(Et)— | Me | Me | 4-Cl—Ph |
| Cl | —CH(Et)CH₂— | Me | Me | 4-Cl—Ph | F | —CH(Et)CH₂— | Me | Me | 4-Cl—Ph |
| Cl | —CH₂CH(Et)— | Me | Me | 4-Cl—Ph | F | —CH₂CH(Et)— | Me | Me | 4-Cl—Ph |
| Cl | —CH(Et)CH₂CH₂— | Me | Me | 4-Cl—Ph | F | —CH(Et)CH₂CH₂— | Me | Me | 4-Cl—Ph |
| Cl | —CH₂CH(Et)CH₂— | Me | Me | 4-Cl—Ph | F | —CH₂CH(Et)CH₂— | Me | Me | 4-Cl—Ph |
| Cl | —CH₂CH₂CH(Et)— | Me | Me | 4-Cl—Ph | F | —CH₂CH₂CH(Et)— | Me | Me | 4-Cl—Ph |
| Cl | —CH(OCF₃)— | Me | Me | 4-Cl—Ph | F | —CH(OCF₃)— | Me | Me | 4-Cl—Ph |
| Cl | —CH(CF₃)— | Me | Me | 4-Cl—Ph | F | —CH(CF₃)— | Me | Me | 4-Cl—Ph |
| Cl | —CH₂CF₂CH₂— | Me | Me | 4-Cl—Ph | F | —CH₂CF₂CH₂— | Me | Me | 4-Cl—Ph |
| Cl | —CH₂CHFCH₂— | Me | Me | 4-Cl—Ph | F | —CH₂CHFCH₂— | Me | Me | 4-Cl—Ph |
| Cl | —CH₂CF₂— | Me | Me | 4-Cl—Ph | F | —CH₂CF₂— | Me | Me | 4-Cl—Ph |
| Cl | —CH₂CHF— | Me | Me | 4-Cl—Ph | F | —CH₂CHF— | Me | Me | 4-Cl—Ph |
| Cl | —CH(CN)— | Me | Me | 4-Cl—Ph | F | —CH(CN)— | Me | Me | 4-Cl—Ph |
| Cl | Vᵃ | Me | Me | 4-Cl—Ph | F | Vᵃ | Me | Me | 4-Cl—Ph |
| Cl | Vᵇ | Me | Me | 4-Cl—Ph | F | Vᵇ | Me | Me | 4-Cl—Ph |
| Cl | Vᶜ | Me | Me | 4-Cl—Ph | F | Vᶜ | Me | Me | 4-Cl—Ph |
| Cl | Vᵈ | Me | Me | 4-Cl—Ph | F | Vᵈ | Me | Me | 4-Cl—Ph |
| Cl | Vᵉ | Me | Me | 4-Cl—Ph | F | Vᵉ | Me | Me | 4-Cl—Ph |
| Cl | Vᶠ | Me | Me | 4-Cl—Ph | F | Vᶠ | Me | Me | 4-Cl—Ph |
| Cl | Vᵍ | Me | Me | 4-Cl—Ph | F | Vᵍ | Me | Me | 4-Cl—Ph |
| Cl | Vʰ | Me | Me | 4-Cl—Ph | F | Vʰ | Me | Me | 4-Cl—Ph |
| Cl | —CH₂OC(=O)CH₂— | Me | Me | 4-Cl—Ph | F | —CH₂OC(=O)CH₂— | Me | Me | 4-Cl—Ph |
| Cl | —CH₂C(=O)CH₂— | Me | Me | 4-Cl—Ph | F | —CH₂C(=O)CH₂— | Me | Me | 4-Cl—Ph |
| Cl | —CH₂C(=O)— | Me | Me | 4-Cl—Ph | F | —CH₂C(=O)— | Me | Me | 4-Cl—Ph |
| Cl | —CH₂— | Me | Me | 3-Cl—Ph | F | —CH₂— | Me | Me | 3-Cl—Ph |
| Cl | —CH₂CH₂— | Me | Me | 3-Cl—Ph | F | —CH₂CH₂— | Me | Me | 3-Cl—Ph |
| Cl | —CH₂CH₂CH₂— | Me | Me | 3-Cl—Ph | F | —CH₂CH₂CH₂— | Me | Me | 3-Cl—Ph |
| Cl | —CH₂CH₂CH₂CH₂— | Me | Me | 3-Cl—Ph | F | —CH₂CH₂CH₂CH₂— | Me | Me | 3-Cl—Ph |
| Cl | —CH₂OCH₂CH₂— | Me | Me | 3-Cl—Ph | F | —CH₂OCH₂CH₂— | Me | Me | 3-Cl—Ph |
| Cl | —CH₂CH₂OCH₂— | Me | Me | 3-Cl—Ph | F | —CH₂CH₂OCH₂— | Me | Me | 3-Cl—Ph |
| Cl | —CH₂C(=O)CH₂CH₂— | Me | Me | 3-Cl—Ph | F | —CH₂C(=O)CH₂CH₂— | Me | Me | 3-Cl—Ph |
| Cl | —CH₂CH₂C(=O)CH₂— | Me | Me | 3-Cl—Ph | F | —CH₂CH₂C(=O)CH₂— | Me | Me | 3-Cl—Ph |
| Cl | —CH₂C(=S)CH₂CH₂— | Me | Me | 3-Cl—Ph | F | —CH₂C(=S)CH₂CH₂— | Me | Me | 3-Cl—Ph |
| Cl | —CH₂CH₂C(=S)CH₂— | Me | Me | 3-Cl—Ph | F | —CH₂CH₂C(=S)CH₂— | Me | Me | 3-Cl—Ph |
| Cl | —CH₂C(=O)CH₂— | Me | Me | 3-Cl—Ph | F | —CH₂C(=O)CH₂— | Me | Me | 3-Cl—Ph |
| Cl | —CH₂C(=S)CH₂— | Me | Me | 3-Cl—Ph | F | —CH₂C(=S)CH₂— | Me | Me | 3-Cl—Ph |
| Cl | —CH(Me)— | Me | Me | 3-Cl—Ph | F | —CH(Me)— | Me | Me | 3-Cl—Ph |
| Cl | —CH(OMe)— | Me | Me | 3-Cl—Ph | F | —CH(OMe)— | Me | Me | 3-Cl—Ph |
| Cl | —CH(Me)CH₂— | Me | Me | 3-Cl—Ph | F | —CH(Me)CH₂— | Me | Me | 3-Cl—Ph |
| Cl | —CH₂CH(Me)— | Me | Me | 3-Cl—Ph | F | —CH₂CH(Me)— | Me | Me | 3-Cl—Ph |
| Cl | —CH₂CH(OMe)— | Me | Me | 3-Cl—Ph | F | —CH₂CH(OMe)— | Me | Me | 3-Cl—Ph |
| Cl | —CH(Me)CH₂CH₂— | Me | Me | 3-Cl—Ph | F | —CH(Me)CH₂CH₂— | Me | Me | 3-Cl—Ph |
| Cl | —CH₂CH(Me)CH₂— | Me | Me | 3-Cl—Ph | F | —CH₂CH(Me)CH₂— | Me | Me | 3-Cl—Ph |
| Cl | —CH₂CH₂CH(Me)— | Me | Me | 3-Cl—Ph | F | —CH₂CH₂CH(Me)— | Me | Me | 3-Cl—Ph |
| Cl | —CH(Et)— | Me | Me | 3-Cl—Ph | F | —CH(Et)— | Me | Me | 3-Cl—Ph |
| Cl | —CH(Et)CH₂— | Me | Me | 3-Cl—Ph | F | —CH(Et)CH₂— | Me | Me | 3-Cl—Ph |
| Cl | —CH₂CH(Et)— | Me | Me | 3-Cl—Ph | F | —CH₂CH(Et)— | Me | Me | 3-Cl—Ph |
| Cl | —CH(Et)CH₂CH₂— | Me | Me | 3-Cl—Ph | F | —CH(Et)CH₂CH₂— | Me | Me | 3-Cl—Ph |
| Cl | —CH₂CH(Et)CH₂— | Me | Me | 3-Cl—Ph | F | —CH₂CH(Et)CH₂— | Me | Me | 3-Cl—Ph |
| Cl | —CH₂CH₂CH(Et)— | Me | Me | 3-Cl—Ph | F | —CH₂CH₂CH(Et)— | Me | Me | 3-Cl—Ph |
| Cl | —CH(OCF₃)— | Me | Me | 3-Cl—Ph | F | —CH(OCF₃)— | Me | Me | 3-Cl—Ph |
| Cl | —CH(CF₃)— | Me | Me | 3-Cl—Ph | F | —CH(CF₃)— | Me | Me | 3-Cl—Ph |
| Cl | —CH₂CF₂CH₂— | Me | Me | 3-Cl—Ph | F | —CH₂CF₂CH₂— | Me | Me | 3-Cl—Ph |
| Cl | —CH₂CHFCH₂— | Me | Me | 3-Cl—Ph | F | —CH₂CHFCH₂— | Me | Me | 3-Cl—Ph |
| Cl | —CH₂CF₂— | Me | Me | 3-Cl—Ph | F | —CH₂CF₂— | Me | Me | 3-Cl—Ph |

TABLE 3-continued

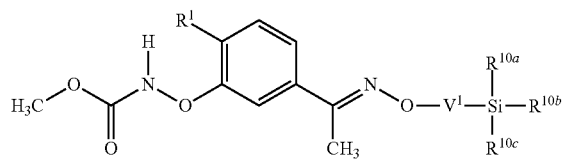

| $R^1$ | $V^1$ | $R^{10a}$ | $R^{10b}$ | $R^{10c}$ | $R^1$ | $V^1$ | $R^{10a}$ | $R^{10b}$ | $R^{10c}$ |
|---|---|---|---|---|---|---|---|---|---|
| Cl | —CH$_2$CHF— | Me | Me | 3-Cl—Ph | F | —CH$_2$CHF— | Me | Me | 3-Cl—Ph |
| Cl | —CH(CN)— | Me | Me | 3-Cl—Ph | F | —CH(CN)— | Me | Me | 3-Cl—Ph |
| Cl | $V^a$ | Me | Me | 3-Cl—Ph | F | $V^a$ | Me | Me | 3-Cl—Ph |
| Cl | $V^b$ | Me | Me | 3-Cl—Ph | F | $V^b$ | Me | Me | 3-Cl—Ph |
| Cl | $V^c$ | Me | Me | 3-Cl—Ph | F | $V^c$ | Me | Me | 3-Cl—Ph |
| Cl | $V^d$ | Me | Me | 3-Cl—Ph | F | $V^d$ | Me | Me | 3-Cl—Ph |
| Cl | $V^e$ | Me | Me | 3-Cl—Ph | F | $V^e$ | Me | Me | 3-Cl—Ph |
| Cl | $V^f$ | Me | Me | 3-Cl—Ph | F | $V^f$ | Me | Me | 3-Cl—Ph |
| Cl | $V^g$ | Me | Me | 3-Cl—Ph | F | $V^g$ | Me | Me | 3-Cl—Ph |
| Cl | $V^h$ | Me | Me | 3-Cl—Ph | F | $V^h$ | Me | Me | 3-Cl—Ph |
| Cl | —CH$_2$OC(=O)CH$_2$— | Me | Me | 3-Cl—Ph | F | —CH$_2$OC(=O)CH$_2$— | Me | Me | 3-Cl—Ph |
| Cl | —CH$_2$C(=O)CH$_2$— | Me | Me | 3-Cl—Ph | F | —CH$_2$C(=O)CH$_2$— | Me | Me | 3-Cl—Ph |
| Cl | —CH$_2$C(=O)— | Me | Me | 3-Cl—Ph | F | —CH$_2$C(=O)— | Me | Me | 3-Cl—Ph |
| Cl | —CH$_2$— | Me | Me | 2-Cl—Ph | F | —CH$_2$— | Me | Me | 2-Cl—Ph |
| Cl | —CH$_2$CH$_2$— | Me | Me | 2-Cl—Ph | F | —CH$_2$CH$_2$— | Me | Me | 2-Cl—Ph |
| Cl | —CH$_2$CH$_2$CH$_2$— | Me | Me | 2-Cl—Ph | F | —CH$_2$CH$_2$CH$_2$— | Me | Me | 2-Cl—Ph |
| Cl | —CH$_2$CH$_2$CH$_2$CH$_2$— | Me | Me | 2-Cl—Ph | F | —CH$_2$CH$_2$CH$_2$CH$_2$— | Me | Me | 2-Cl—Ph |
| Cl | —CH$_2$OCH$_2$CH$_2$— | Me | Me | 2-Cl—Ph | F | —CH$_2$OCH$_2$CH$_2$— | Me | Me | 2-Cl—Ph |
| Cl | —CH$_2$CH$_2$OCH$_2$— | Me | Me | 2-Cl—Ph | F | —CH$_2$CH$_2$OCH$_2$— | Me | Me | 2-Cl—Ph |
| Cl | —CH$_2$C(=O)CH$_2$CH$_2$— | Me | Me | 2-Cl—Ph | F | —CH$_2$C(=O)CH$_2$CH$_2$— | Me | Me | 2-Cl—Ph |
| Cl | —CH$_2$CH$_2$C(=O)CH$_2$— | Me | Me | 2-Cl—Ph | F | —CH$_2$CH$_2$C(=O)CH$_2$— | Me | Me | 2-Cl—Ph |
| Cl | —CH$_2$C(=S)CH$_2$CH$_2$— | Me | Me | 2-Cl—Ph | F | —CH$_2$C(=S)CH$_2$CH$_2$— | Me | Me | 2-Cl—Ph |
| Cl | —CH$_2$CH$_2$C(=S)CH$_2$— | Me | Me | 2-Cl—Ph | F | —CH$_2$CH$_2$C(=S)CH$_2$— | Me | Me | 2-Cl—Ph |
| Cl | —CH$_2$C(=O)CH$_2$— | Me | Me | 2-Cl—Ph | F | —CH$_2$C(=O)CH$_2$— | Me | Me | 2-Cl—Ph |
| Cl | —CH$_2$C(=S)CH$_2$— | Me | Me | 2-Cl—Ph | F | —CH$_2$C(=S)CH$_2$— | Me | Me | 2-Cl—Ph |
| Cl | —CH(Me)— | Me | Me | 2-Cl—Ph | F | —CH(Me)— | Me | Me | 2-Cl—Ph |
| Cl | —CH(OMe)— | Me | Me | 2-Cl—Ph | F | —CH(OMe)— | Me | Me | 2-Cl—Ph |
| Cl | —CH(Me)CH$_2$— | Me | Me | 2-Cl—Ph | F | —CH(Me)CH$_2$— | Me | Me | 2-Cl—Ph |
| Cl | —CH$_2$CH(Me)— | Me | Me | 2-Cl—Ph | F | —CH$_2$CH(Me)— | Me | Me | 2-Cl—Ph |
| Cl | —CH$_2$CH(OMe)— | Me | Me | 2-Cl—Ph | F | —CH$_2$CH(OMe)— | Me | Me | 2-Cl—Ph |
| Cl | —CH(Me)CH$_2$CH$_2$— | Me | Me | 2-Cl—Ph | F | —CH(Me)CH$_2$CH$_2$— | Me | Me | 2-Cl—Ph |
| Cl | —CH$_2$CH(Me)CH$_2$— | Me | Me | 2-Cl—Ph | F | —CH$_2$CH(Me)CH$_2$— | Me | Me | 2-Cl—Ph |
| Cl | —CH$_2$CH$_2$CH(Me)— | Me | Me | 2-Cl—Ph | F | —CH$_2$CH$_2$CH(Me)— | Me | Me | 2-Cl—Ph |
| Cl | —CH(Et)— | Me | Me | 2-Cl—Ph | F | —CH(Et)— | Me | Me | 2-Cl—Ph |
| Cl | —CH(Et)CH$_2$— | Me | Me | 2-Cl—Ph | F | —CH(Et)CH$_2$— | Me | Me | 2-Cl—Ph |
| Cl | —CH$_2$CH(Et)— | Me | Me | 2-Cl—Ph | F | —CH$_2$CH(Et)— | Me | Me | 2-Cl—Ph |
| Cl | —CH(Et)CH$_2$CH$_2$— | Me | Me | 2-Cl—Ph | F | —CH(Et)CH$_2$CH$_2$— | Me | Me | 2-Cl—Ph |
| Cl | —CH$_2$CH(Et)CH$_2$— | Me | Me | 2-Cl—Ph | F | —CH$_2$CH(Et)CH$_2$— | Me | Me | 2-Cl—Ph |
| Cl | —CH$_2$CH$_2$CH(Et)— | Me | Me | 2-Cl—Ph | F | —CH$_2$CH$_2$CH(Et)— | Me | Me | 2-Cl—Ph |
| Cl | —CH(OCF$_3$)— | Me | Me | 2-Cl—Ph | F | —CH(OCF$_3$)— | Me | Me | 2-Cl—Ph |
| Cl | —CH(CF$_3$)— | Me | Me | 2-Cl—Ph | F | —CH(CF$_3$)— | Me | Me | 2-Cl—Ph |
| Cl | —CH$_2$CF$_2$CH$_2$— | Me | Me | 2-Cl—Ph | F | —CH$_2$CF$_2$CH$_2$— | Me | Me | 2-Cl—Ph |
| Cl | —CH$_2$CHFCH$_2$— | Me | Me | 2-Cl—Ph | F | —CH$_2$CHFCH$_2$— | Me | Me | 2-Cl—Ph |
| Cl | —CH$_2$CF$_2$— | Me | Me | 2-Cl—Ph | F | —CH$_2$CF$_2$— | Me | Me | 2-Cl—Ph |
| Cl | —CH$_2$CHF— | Me | Me | 2-Cl—Ph | F | —CH$_2$CHF— | Me | Me | 2-Cl—Ph |
| Cl | —CH(CN)— | Me | Me | 2-Cl—Ph | F | —CH(CN)— | Me | Me | 2-Cl—Ph |
| Cl | $V^a$ | Me | Me | 2-Cl—Ph | F | $V^a$ | Me | Me | 2-Cl—Ph |
| Cl | $V^b$ | Me | Me | 2-Cl—Ph | F | $V^b$ | Me | Me | 2-Cl—Ph |
| Cl | $V^c$ | Me | Me | 2-Cl—Ph | F | $V^c$ | Me | Me | 2-Cl—Ph |
| Cl | $V^d$ | Me | Me | 2-Cl—Ph | F | $V^d$ | Me | Me | 2-Cl—Ph |
| Cl | $V^e$ | Me | Me | 2-Cl—Ph | F | $V^e$ | Me | Me | 2-Cl—Ph |
| Cl | $V^f$ | Me | Me | 2-Cl—Ph | F | $V^f$ | Me | Me | 2-Cl—Ph |
| Cl | $V^g$ | Me | Me | 2-Cl—Ph | F | $V^g$ | Me | Me | 2-Cl—Ph |
| Cl | $V^h$ | Me | Me | 2-Cl—Ph | F | $V^h$ | Me | Me | 2-Cl—Ph |
| Cl | —CH$_2$OC(=O)CH$_2$— | Me | Me | 2-Cl—Ph | F | —CH$_2$OC(=O)CH$_2$— | Me | Me | 2-Cl—Ph |
| Cl | —CH$_2$C(=O)CH$_2$— | Me | Me | 2-Cl—Ph | F | —CH$_2$C(=O)CH$_2$— | Me | Me | 2-Cl—Ph |
| Cl | —CH$_2$C(=O)— | Me | Me | 2-Cl—Ph | F | —CH$_2$C(=O)— | Me | Me | 2-Cl—Ph |
| Cl | —CH$_2$— | Me | Me | c-Pr | F | —CH$_2$— | Me | Me | c-Pr |
| Cl | —CH$_2$CH$_2$— | Me | Me | c-Pr | F | —CH$_2$CH$_2$— | Me | Me | c-Pr |
| Cl | —CH$_2$CH$_2$CH$_2$— | Me | Me | c-Pr | F | —CH$_2$CH$_2$CH$_2$— | Me | Me | c-Pr |
| Cl | —CH$_2$CH$_2$CH$_2$CH$_2$— | Me | Me | c-Pr | F | —CH$_2$CH$_2$CH$_2$CH$_2$— | Me | Me | c-Pr |
| Cl | —CH$_2$OCH$_2$CH$_2$— | Me | Me | c-Pr | F | —CH$_2$OCH$_2$CH$_2$— | Me | Me | c-Pr |
| Cl | —CH$_2$CH$_2$OCH$_2$— | Me | Me | c-Pr | F | —CH$_2$CH$_2$OCH$_2$— | Me | Me | c-Pr |
| Cl | —CH$_2$C(=O)CH$_2$CH$_2$— | Me | Me | c-Pr | F | —CH$_2$C(=O)CH$_2$CH$_2$— | Me | Me | c-Pr |
| Cl | —CH$_2$CH$_2$C(=O)CH$_2$— | Me | Me | c-Pr | F | —CH$_2$CH$_2$C(=O)CH$_2$— | Me | Me | c-Pr |
| Cl | —CH$_2$C(=S)CH$_2$CH$_2$— | Me | Me | c-Pr | F | —CH$_2$C(=S)CH$_2$CH$_2$— | Me | Me | c-Pr |
| Cl | —CH$_2$CH$_2$C(=S)CH$_2$— | Me | Me | c-Pr | F | —CH$_2$CH$_2$C(=S)CH$_2$— | Me | Me | c-Pr |
| Cl | —CH$_2$C(=O)CH$_2$— | Me | Me | c-Pr | F | —CH$_2$C(=O)CH$_2$— | Me | Me | c-Pr |
| Cl | —CH$_2$C(=S)CH$_2$— | Me | Me | c-Pr | F | —CH$_2$C(=S)CH$_2$— | Me | Me | c-Pr |

TABLE 3-continued

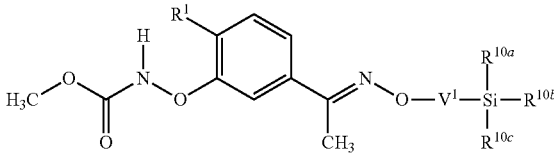

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Cl | —CH(Me)— | Me | Me | c-Pr | F | —CH(Me)— | Me | Me | c-Pr |
| Cl | —CH(OMe)— | Me | Me | c-Pr | F | —CH(OMe)— | Me | Me | c-Pr |
| Cl | —CH(Me)CH₂— | Me | Me | c-Pr | F | —CH(Me)CH₂— | Me | Me | c-Pr |
| Cl | —CH₂CH(Me)— | Me | Me | c-Pr | F | —CH₂CH(Me)— | Me | Me | c-Pr |
| Cl | —CH₂CH(OMe)— | Me | Me | c-Pr | F | —CH₂CH(OMe)— | Me | Me | c-Pr |
| Cl | —CH(Me)CH₂CH₂— | Me | Me | c-Pr | F | —CH(Me)CH₂CH₂— | Me | Me | c-Pr |
| Cl | —CH₂CH(Me)CH₂— | Me | Me | c-Pr | F | —CH₂CH(Me)CH₂— | Me | Me | c-Pr |
| Cl | —CH₂CH₂CH(Me)— | Me | Me | c-Pr | F | —CH₂CH₂CH(Me)— | Me | Me | c-Pr |
| Cl | —CH(Et)— | Me | Me | c-Pr | F | —CH(Et)— | Me | Me | c-Pr |
| Cl | —CH(Et)CH₂— | Me | Me | c-Pr | F | —CH(Et)CH₂— | Me | Me | c-Pr |
| Cl | —CH₂CH(Et)— | Me | Me | c-Pr | F | —CH₂CH(Et)— | Me | Me | c-Pr |
| Cl | —CH(Et)CH₂CH₂— | Me | Me | c-Pr | F | —CH(Et)CH₂CH₂— | Me | Me | c-Pr |
| Cl | —CH₂CH(Et)CH₂— | Me | Me | c-Pr | F | —CH₂CH(Et)CH₂— | Me | Me | c-Pr |
| Cl | —CH₂CH₂CH(Et)— | Me | Me | c-Pr | F | —CH₂CH₂CH(Et)— | Me | Me | c-Pr |
| Cl | —CH(OCF₃)— | Me | Me | c-Pr | F | —CH(OCF₃)— | Me | Me | c-Pr |
| Cl | —CH(CF₃)— | Me | Me | c-Pr | F | —CH(CF₃)— | Me | Me | c-Pr |
| Cl | —CH₂CF₂CH₂— | Me | Me | c-Pr | F | —CH₂CF₂CH₂— | Me | Me | c-Pr |
| Cl | —CH₂CHFCH₂— | Me | Me | c-Pr | F | —CH₂CHFCH₂— | Me | Me | c-Pr |
| Cl | —CH₂CF₂— | Me | Me | c-Pr | F | —CH₂CF₂— | Me | Me | c-Pr |
| Cl | —CH₂CHF— | Me | Me | c-Pr | F | —CH₂CHF— | Me | Me | c-Pr |
| Cl | —CH(CN)— | Me | Me | c-Pr | F | —CH(CN)— | Me | Me | c-Pr |
| Cl | Vᵃ | Me | Me | c-Pr | F | Vᵃ | Me | Me | c-Pr |
| Cl | Vᵇ | Me | Me | c-Pr | F | Vᵇ | Me | Me | c-Pr |
| Cl | Vᶜ | Me | Me | c-Pr | F | Vᶜ | Me | Me | c-Pr |
| Cl | Vᵈ | Me | Me | c-Pr | F | Vᵈ | Me | Me | c-Pr |
| Cl | Vᵉ | Me | Me | c-Pr | F | Vᵉ | Me | Me | c-Pr |
| Cl | Vᶠ | Me | Me | c-Pr | F | Vᶠ | Me | Me | c-Pr |
| Cl | Vᵍ | Me | Me | c-Pr | F | Vᵍ | Me | Me | c-Pr |
| Cl | Vʰ | Me | Me | c-Pr | F | Vʰ | Me | Me | c-Pr |
| Cl | —CH₂OC(=O)CH₂— | Me | Me | c-Pr | F | —CH₂OC(=O)CH₂— | Me | Me | c-Pr |
| Cl | —CH₂C(=O)CH₂— | Me | Me | c-Pr | F | —CH₂C(=O)CH₂— | Me | Me | c-Pr |
| Cl | —CH₂C(=O)— | Me | Me | c-Pr | F | —CH₂C(=O)— | Me | Me | c-Pr |
| Me | —CH₂— | Me | Me | Me | Me | —CH₂— | Me | Me | Et |
| Me | —CH₂CH₂— | Me | Me | Me | Me | —CH₂CH₂— | Me | Me | Et |
| Me | —CH₂CH₂CH₂— | Me | Me | Me | Me | —CH₂CH₂CH₂— | Me | Me | Et |
| Me | —CH₂CH₂CH₂CH₂— | Me | Me | Me | Me | —CH₂CH₂CH₂CH₂— | Me | Me | Et |
| Me | —CH₂OCH₂CH₂— | Me | Me | Me | Me | —CH₂OCH₂CH₂— | Me | Me | Et |
| Me | —CH₂CH₂OCH₂— | Me | Me | Me | Me | —CH₂CH₂OCH₂— | Me | Me | Et |
| Me | —CH₂C(=O)CH₂CH₂— | Me | Me | Me | Me | —CH₂C(=O)CH₂CH₂— | Me | Me | Et |
| Me | —CH₂CH₂C(=O)CH₂— | Me | Me | Me | Me | —CH₂CH₂C(=O)CH₂— | Me | Me | Et |
| Me | —CH₂C(=S)CH₂CH₂— | Me | Me | Me | Me | —CH₂C(=S)CH₂CH₂— | Me | Me | Et |
| Me | —CH₂CH₂C(=S)CH₂— | Me | Me | Me | Me | —CH₂CH₂C(=S)CH₂— | Me | Me | Et |
| Me | —CH₂C(=O)CH₂— | Me | Me | Me | Me | —CH₂C(=O)CH₂— | Me | Me | Et |
| Me | —CH₂C(=S)CH₂— | Me | Me | Me | Me | —CH₂C(=S)CH₂— | Me | Me | Et |
| Me | —CH(Me)— | Me | Me | Me | Me | —CH(Me)— | Me | Me | Et |
| Me | —CH(OMe)— | Me | Me | Me | Me | —CH(OMe)— | Me | Me | Et |
| Me | —CH(Me)CH₂— | Me | Me | Me | Me | —CH(Me)CH₂— | Me | Me | Et |
| Me | —CH₂CH(Me)— | Me | Me | Me | Me | —CH₂CH(Me)— | Me | Me | Et |
| Me | —CH₂CH(OMe)— | Me | Me | Me | Me | —CH₂CH(OMe)— | Me | Me | Et |
| Me | —CH(Me)CH₂CH₂— | Me | Me | Me | Me | —CH(Me)CH₂CH₂— | Me | Me | Et |
| Me | —CH₂CH(Me)CH₂— | Me | Me | Me | Me | —CH₂CH(Me)CH₂— | Me | Me | Et |
| Me | —CH₂CH₂CH(Me)— | Me | Me | Me | Me | —CH₂CH₂CH(Me)— | Me | Me | Et |
| Me | —CH(Et)— | Me | Me | Me | Me | —CH(Et)— | Me | Me | Et |
| Me | —CH(Et)CH₂— | Me | Me | Me | Me | —CH(Et)CH₂— | Me | Me | Et |
| Me | —CH₂CH(Et)— | Me | Me | Me | Me | —CH₂CH(Et)— | Me | Me | Et |
| Me | —CH(Et)CH₂CH₂— | Me | Me | Me | Me | —CH(Et)CH₂CH₂— | Me | Me | Et |
| Me | —CH₂CH(Et)CH₂— | Me | Me | Me | Me | —CH₂CH(Et)CH₂— | Me | Me | Et |
| Me | —CH₂CH₂CH(Et)— | Me | Me | Me | Me | —CH₂CH₂CH(Et)— | Me | Me | Et |
| Me | —CH(OCF₃)— | Me | Me | Me | Me | —CH(OCF₃)— | Me | Me | Et |
| Me | —CH(CF₃)— | Me | Me | Me | Me | —CH(CF₃)— | Me | Me | Et |
| Me | —CH₂CF₂CH₂— | Me | Me | Me | Me | —CH₂CF₂CH₂— | Me | Me | Et |
| Me | —CH₂CHFCH₂— | Me | Me | Me | Me | —CH₂CHFCH₂— | Me | Me | Et |
| Me | —CH₂CF₂— | Me | Me | Me | Me | —CH₂CF₂— | Me | Me | Et |
| Me | —CH₂CHF— | Me | Me | Me | Me | —CH₂CHF— | Me | Me | Et |
| Me | —CH(CN)— | Me | Me | Me | Me | —CH(CN)— | Me | Me | Et |
| Me | Vᵃ | Me | Me | Me | Me | Vᵃ | Me | Me | Et |
| Me | Vᵇ | Me | Me | Me | Me | Vᵇ | Me | Me | Et |
| Me | Vᶜ | Me | Me | Me | Me | Vᶜ | Me | Me | Et |
| Me | Vᵈ | Me | Me | Me | Me | Vᵈ | Me | Me | Et |

TABLE 3-continued

Structure: H3C-O-C(=O)-N(H)-O-[phenyl with R¹]-C(CH₃)=N-O-V¹-Si(R¹⁰ᵃ)(R¹⁰ᵇ)(R¹⁰ᶜ)

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | Vᵉ | Me | Me | Me | Me | Vᵉ | Me | Me | Et |
| Me | Vᶠ | Me | Me | Me | Me | Vᶠ | Me | Me | Et |
| Me | Vᵍ | Me | Me | Me | Me | Vᵍ | Me | Me | Et |
| Me | Vʰ | Me | Me | Me | Me | Vʰ | Me | Me | Et |
| Me | —CH₂OC(=O)CH₂— | Me | Me | Me | Me | —CH₂OC(=O)CH₂— | Me | Me | Et |
| Me | —CH₂C(=O)CH₂— | Me | Me | Me | Me | —CH₂C(=O)CH₂— | Me | Me | Et |
| Me | —CH₂C(=O)— | Me | Me | Me | Me | —CH₂C(=O)— | Me | Me | Et |
| Me | —CH₂— | Me | Et | Et | Me | —CH₂— | Et | Et | Et |
| Me | —CH₂CH₂— | Me | Et | Et | Me | —CH₂CH₂— | Et | Et | Et |
| Me | —CH₂CH₂CH₂— | Me | Et | Et | Me | —CH₂CH₂CH₂— | Et | Et | Et |
| Me | —CH₂CH₂CH₂CH₂— | Me | Et | Et | Me | —CH₂CH₂CH₂CH₂— | Et | Et | Et |
| Me | —CH₂OCH₂CH₂— | Me | Et | Et | Me | —CH₂OCH₂CH₂— | Et | Et | Et |
| Me | —CH₂CH₂OCH₂— | Me | Et | Et | Me | —CH₂CH₂OCH₂— | Et | Et | Et |
| Me | —CH₂C(=O)CH₂CH₂— | Me | Et | Et | Me | —CH₂C(=O)CH₂CH₂— | Et | Et | Et |
| Me | —CH₂CH₂C(=O)CH₂— | Me | Et | Et | Me | —CH₂CH₂C(=O)CH₂— | Et | Et | Et |
| Me | —CH₂C(=S)CH₂CH₂— | Me | Et | Et | Me | —CH₂C(=S)CH₂CH₂— | Et | Et | Et |
| Me | —CH₂CH₂C(=S)CH₂— | Me | Et | Et | Me | —CH₂CH₂C(=S)CH₂— | Et | Et | Et |
| Me | —CH₂C(=O)CH₂— | Me | Et | Et | Me | —CH₂C(=O)CH₂— | Et | Et | Et |
| Me | —CH₂C(=S)CH₂— | Me | Et | Et | Me | —CH₂C(=S)CH₂— | Et | Et | Et |
| Me | —CH(Me)— | Me | Et | Et | Me | —CH(Me)— | Et | Et | Et |
| Me | —CH(OMe)— | Me | Et | Et | Me | —CH(OMe)— | Et | Et | Et |
| Me | —CH(Me)CH₂— | Me | Et | Et | Me | —CH(Me)CH₂— | Et | Et | Et |
| Me | —CH₂CH(Me)— | Me | Et | Et | Me | —CH₂CH(Me)— | Et | Et | Et |
| Me | —CH₂CH(OMe)— | Me | Et | Et | Me | —CH₂CH(OMe)— | Et | Et | Et |
| Me | —CH(Me)CH₂CH₂— | Me | Et | Et | Me | —CH(Me)CH₂CH₂— | Et | Et | Et |
| Me | —CH₂CH(Me)CH₂— | Me | Et | Et | Me | —CH₂CH(Me)CH₂— | Et | Et | Et |
| Me | —CH₂CH₂CH(Me)— | Me | Et | Et | Me | —CH₂CH₂CH(Me)— | Et | Et | Et |
| Me | —CH(Et)— | Me | Et | Et | Me | —CH(Et)— | Et | Et | Et |
| Me | —CH(Et)CH₂— | Me | Et | Et | Me | —CH(Et)CH₂— | Et | Et | Et |
| Me | —CH₂CH(Et)— | Me | Et | Et | Me | —CH₂CH(Et)— | Et | Et | Et |
| Me | —CH(Et)CH₂CH₂— | Me | Et | Et | Me | —CH(Et)CH₂CH₂— | Et | Et | Et |
| Me | —CH₂CH(Et)CH₂— | Me | Et | Et | Me | —CH₂CH(Et)CH₂— | Et | Et | Et |
| Me | —CH₂CH₂CH(Et)— | Me | Et | Et | Me | —CH₂CH₂CH(Et)— | Et | Et | Et |
| Me | —CH(OCF₃)— | Me | Et | Et | Me | —CH(OCF₃)— | Et | Et | Et |
| Me | —CH(CF₃)— | Me | Et | Et | Me | —CH(CF₃)— | Et | Et | Et |
| Me | —CH₂CF₂CH₂— | Me | Et | Et | Me | —CH₂CF₂CH₂— | Et | Et | Et |
| Me | —CH₂CHFCH₂— | Me | Et | Et | Me | —CH₂CHFCH₂— | Et | Et | Et |
| Me | —CH₂CF₂— | Me | Et | Et | Me | —CH₂CF₂— | Et | Et | Et |
| Me | —CH₂CHF— | Me | Et | Et | Me | —CH₂CHF— | Et | Et | Et |
| Me | —CH(CN)— | Me | Et | Et | Me | —CH(CN)— | Et | Et | Et |
| Me | Vᵃ | Me | Et | Et | Me | Vᵃ | Et | Et | Et |
| Me | Vᵇ | Me | Et | Et | Me | Vᵇ | Et | Et | Et |
| Me | Vᶜ | Me | Et | Et | Me | Vᶜ | Et | Et | Et |
| Me | Vᵈ | Me | Et | Et | Me | Vᵈ | Et | Et | Et |
| Me | Vᵉ | Me | Et | Et | Me | Vᵉ | Et | Et | Et |
| Me | Vᶠ | Me | Et | Et | Me | Vᶠ | Et | Et | Et |
| Me | Vᵍ | Me | Et | Et | Me | Vᵍ | Et | Et | Et |
| Me | Vʰ | Me | Et | Et | Me | Vʰ | Et | Et | Et |
| Me | —CH₂OC(=O)CH₂— | Me | Et | Et | Me | —CH₂OC(=O)CH₂— | Et | Et | Et |
| Me | —CH₂C(=O)CH₂— | Me | Et | Et | Me | —CH₂C(=O)CH₂— | Et | Et | Et |
| Me | —CH₂C(=O)— | Me | Et | Et | Me | —CH₂C(=O)— | Et | Et | Et |
| Me | —CH₂— | Me | Me | i-Pr | Me | —CH₂— | Me | Et | i-Pr |
| Me | —CH₂CH₂— | Me | Me | i-Pr | Me | —CH₂CH₂— | Me | Et | i-Pr |
| Me | —CH₂CH₂CH₂— | Me | Me | i-Pr | Me | —CH₂CH₂CH₂— | Me | Et | i-Pr |
| Me | —CH₂CH₂CH₂CH₂— | Me | Me | i-Pr | Me | —CH₂CH₂CH₂CH₂— | Me | Et | i-Pr |
| Me | —CH₂OCH₂CH₂— | Me | Me | i-Pr | Me | —CH₂OCH₂CH₂— | Me | Et | i-Pr |
| Me | —CH₂CH₂OCH₂— | Me | Me | i-Pr | Me | —CH₂CH₂OCH₂— | Me | Et | i-Pr |
| Me | —CH₂C(=O)CH₂CH₂— | Me | Me | i-Pr | Me | —CH₂C(=O)CH₂CH₂— | Me | Et | i-Pr |
| Me | —CH₂CH₂C(=O)CH₂— | Me | Me | i-Pr | Me | —CH₂CH₂C(=O)CH₂— | Me | Et | i-Pr |
| Me | —CH₂C(=S)CH₂CH₂— | Me | Me | i-Pr | Me | —CH₂C(=S)CH₂CH₂— | Me | Et | i-Pr |
| Me | —CH₂CH₂C(=S)CH₂— | Me | Me | i-Pr | Me | —CH₂CH₂C(=S)CH₂— | Me | Et | i-Pr |
| Me | —CH₂C(=O)CH₂— | Me | Me | i-Pr | Me | —CH₂C(=O)CH₂— | Me | Et | i-Pr |
| Me | —CH₂C(=S)CH₂— | Me | Me | i-Pr | Me | —CH₂C(=S)CH₂— | Me | Et | i-Pr |
| Me | —CH(Me)— | Me | Me | i-Pr | Me | —CH(Me)— | Me | Et | i-Pr |
| Me | —CH(OMe)— | Me | Me | i-Pr | Me | —CH(OMe)— | Me | Et | i-Pr |
| Me | —CH(Me)CH₂— | Me | Me | i-Pr | Me | —CH(Me)CH₂— | Me | Et | i-Pr |
| Me | —CH₂CH(Me)— | Me | Me | i-Pr | Me | —CH₂CH(Me)— | Me | Et | i-Pr |
| Me | —CH₂CH(OMe)— | Me | Me | i-Pr | Me | —CH₂CH(OMe)— | Me | Et | i-Pr |
| Me | —CH(Me)CH₂CH₂— | Me | Me | i-Pr | Me | —CH(Me)CH₂CH₂— | Me | Et | i-Pr |

TABLE 3-continued

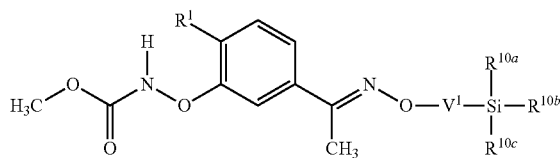

| R$^1$ | V$^1$ | R$^{10a}$ | R$^{10b}$ | R$^{10c}$ | R$^1$ | V$^1$ | R$^{10a}$ | R$^{10b}$ | R$^{10c}$ |
|---|---|---|---|---|---|---|---|---|---|
| Me | —CH$_2$CH(Me)CH$_2$— | Me | Me | i-Pr | Me | —CH$_2$CH(Me)CH$_2$— | Me | Et | i-Pr |
| Me | —CH$_2$CH$_2$CH(Me)— | Me | Me | i-Pr | Me | —CH$_2$CH$_2$CH(Me)— | Me | Et | i-Pr |
| Me | —CH(Et)— | Me | Me | i-Pr | Me | —CH(Et)— | Me | Et | i-Pr |
| Me | —CH(Et)CH$_2$— | Me | Me | i-Pr | Me | —CH(Et)CH$_2$— | Me | Et | i-Pr |
| Me | —CH$_2$CH(Et)— | Me | Me | i-Pr | Me | —CH$_2$CH(Et)— | Me | Et | i-Pr |
| Me | —CH(Et)CH$_2$CH$_2$— | Me | Me | i-Pr | Me | —CH(Et)CH$_2$CH$_2$— | Me | Et | i-Pr |
| Me | —CH$_2$CH(Et)CH$_2$— | Me | Me | i-Pr | Me | —CH$_2$CH(Et)CH$_2$— | Me | Et | i-Pr |
| Me | —CH$_2$CH$_2$CH(Et)— | Me | Me | i-Pr | Me | —CH$_2$CH$_2$CH(Et)— | Me | Et | i-Pr |
| Me | —CH(OCF$_3$)— | Me | Me | i-Pr | Me | —CH(OCF$_3$)— | Me | Et | i-Pr |
| Me | —CH(CF$_3$)— | Me | Me | i-Pr | Me | —CH(CF$_3$)— | Me | Et | i-Pr |
| Me | —CH$_2$CF$_2$CH$_2$— | Me | Me | i-Pr | Me | —CH$_2$CF$_2$CH$_2$— | Me | Et | i-Pr |
| Me | —CH$_2$CHFCH$_2$— | Me | Me | i-Pr | Me | —CH$_2$CHFCH$_2$— | Me | Et | i-Pr |
| Me | —CH$_2$CF$_2$— | Me | Me | i-Pr | Me | —CH$_2$CF$_2$— | Me | Et | i-Pr |
| Me | —CH$_2$CHF— | Me | Me | i-Pr | Me | —CH$_2$CHF— | Me | Et | i-Pr |
| Me | —CH(CN)— | Me | Me | i-Pr | Me | —CH(CN)— | Me | Et | i-Pr |
| Me | V$^a$ | Me | Me | i-Pr | Me | V$^a$ | Me | Et | i-Pr |
| Me | V$^b$ | Me | Me | i-Pr | Me | V$^b$ | Me | Et | i-Pr |
| Me | V$^c$ | Me | Me | i-Pr | Me | V$^c$ | Me | Et | i-Pr |
| Me | V$^d$ | Me | Me | i-Pr | Me | V$^d$ | Me | Et | i-Pr |
| Me | V$^e$ | Me | Me | i-Pr | Me | V$^e$ | Me | Et | i-Pr |
| Me | V$^f$ | Me | Me | i-Pr | Me | V$^f$ | Me | Et | i-Pr |
| Me | V$^g$ | Me | Me | i-Pr | Me | V$^g$ | Me | Et | i-Pr |
| Me | V$^h$ | Me | Me | i-Pr | Me | V$^h$ | Me | Et | i-Pr |
| Me | —CH$_2$OC(=O)CH$_2$— | Me | Me | i-Pr | Me | —CH$_2$OC(=O)CH$_2$— | Me | Et | i-Pr |
| Me | —CH$_2$C(=O)CH$_2$— | Me | Me | i-Pr | Me | —CH$_2$C(=O)CH$_2$— | Me | Et | i-Pr |
| Me | —CH$_2$C(=O)— | Me | Me | i-Pr | Me | —CH$_2$C(=O)— | Me | Et | i-Pr |
| Me | —CH$_2$— | Me | Me | Ph | Me | —CH$_2$— | Me | Me | 4-Cl—Ph |
| Me | —CH$_2$CH$_2$— | Me | Me | Ph | Me | —CH$_2$CH$_2$— | Me | Me | 4-Cl—Ph |
| Me | —CH$_2$CH$_2$CH$_2$— | Me | Me | Ph | Me | —CH$_2$CH$_2$CH$_2$— | Me | Me | 4-Cl—Ph |
| Me | —CH$_2$CH$_2$CH$_2$CH$_2$— | Me | Me | Ph | Me | —CH$_2$CH$_2$CH$_2$CH$_2$— | Me | Me | 4-Cl—Ph |
| Me | —CH$_2$OCH$_2$CH$_2$— | Me | Me | Ph | Me | —CH$_2$OCH$_2$CH$_2$— | Me | Me | 4-Cl—Ph |
| Me | —CH$_2$CH$_2$OCH$_2$— | Me | Me | Ph | Me | —CH$_2$CH$_2$OCH$_2$— | Me | Me | 4-Cl—Ph |
| Me | —CH$_2$C(=O)CH$_2$CH$_2$— | Me | Me | Ph | Me | —CH$_2$C(=O)CH$_2$CH$_2$— | Me | Me | 4-Cl—Ph |
| Me | —CH$_2$CH$_2$C(=O)CH$_2$— | Me | Me | Ph | Me | —CH$_2$CH$_2$C(=O)CH$_2$— | Me | Me | 4-Cl—Ph |
| Me | —CH$_2$C(=S)CH$_2$CH$_2$— | Me | Me | Ph | Me | —CH$_2$C(=S)CH$_2$CH$_2$— | Me | Me | 4-Cl—Ph |
| Me | —CH$_2$CH$_2$C(=S)CH$_2$— | Me | Me | Ph | Me | —CH$_2$CH$_2$C(=S)CH$_2$— | Me | Me | 4-Cl—Ph |
| Me | —CH$_2$C(=O)CH$_2$— | Me | Me | Ph | Me | —CH$_2$C(=O)CH$_2$— | Me | Me | 4-Cl—Ph |
| Me | —CH$_2$C(=S)CH$_2$— | Me | Me | Ph | Me | —CH$_2$C(=S)CH$_2$— | Me | Me | 4-Cl—Ph |
| Me | —CH(Me)— | Me | Me | Ph | Me | —CH(Me)— | Me | Me | 4-Cl—Ph |
| Me | —CH(OMe)— | Me | Me | Ph | Me | —CH(OMe)— | Me | Me | 4-Cl—Ph |
| Me | —CH(Me)CH$_2$— | Me | Me | Ph | Me | —CH(Me)CH$_2$— | Me | Me | 4-Cl—Ph |
| Me | —CH$_2$CH(Me)— | Me | Me | Ph | Me | —CH$_2$CH(Me)— | Me | Me | 4-Cl—Ph |
| Me | —CH$_2$CH(OMe)— | Me | Me | Ph | Me | —CH$_2$CH(OMe)— | Me | Me | 4-Cl—Ph |
| Me | —CH(Me)CH$_2$CH$_2$— | Me | Me | Ph | Me | —CH(Me)CH$_2$CH$_2$— | Me | Me | 4-Cl—Ph |
| Me | —CH$_2$CH(Me)CH$_2$— | Me | Me | Ph | Me | —CH$_2$CH(Me)CH$_2$— | Me | Me | 4-Cl—Ph |
| Me | —CH$_2$CH$_2$CH(Me)— | Me | Me | Ph | Me | —CH$_2$CH$_2$CH(Me)— | Me | Me | 4-Cl—Ph |
| Me | —CH(Et)— | Me | Me | Ph | Me | —CH(Et)— | Me | Me | 4-Cl—Ph |
| Me | —CH(Et)CH$_2$— | Me | Me | Ph | Me | —CH(Et)CH$_2$— | Me | Me | 4-Cl—Ph |
| Me | —CH$_2$CH(Et)— | Me | Me | Ph | Me | —CH$_2$CH(Et)— | Me | Me | 4-Cl—Ph |
| Me | —CH(Et)CH$_2$CH$_2$— | Me | Me | Ph | Me | —CH(Et)CH$_2$CH$_2$— | Me | Me | 4-Cl—Ph |
| Me | —CH$_2$CH(Et)CH$_2$— | Me | Me | Ph | Me | —CH$_2$CH(Et)CH$_2$— | Me | Me | 4-Cl—Ph |
| Me | —CH$_2$CH$_2$CH(Et)— | Me | Me | Ph | Me | —CH$_2$CH$_2$CH(Et)— | Me | Me | 4-Cl—Ph |
| Me | —CH(OCF$_3$)— | Me | Me | Ph | Me | —CH(OCF$_3$)— | Me | Me | 4-Cl—Ph |
| Me | —CH(CF$_3$)— | Me | Me | Ph | Me | —CH(CF$_3$)— | Me | Me | 4-Cl—Ph |
| Me | —CH$_2$CF$_2$CH$_2$— | Me | Me | Ph | Me | —CH$_2$CF$_2$CH$_2$— | Me | Me | 4-Cl—Ph |
| Me | —CH$_2$CHFCH$_2$— | Me | Me | Ph | Me | —CH$_2$CHFCH$_2$— | Me | Me | 4-Cl—Ph |
| Me | —CH$_2$CF$_2$— | Me | Me | Ph | Me | —CH$_2$CF$_2$— | Me | Me | 4-Cl—Ph |
| Me | —CH$_2$CHF— | Me | Me | Ph | Me | —CH$_2$CHF— | Me | Me | 4-Cl—Ph |
| Me | —CH(CN)— | Me | Me | Ph | Me | —CH(CN)— | Me | Me | 4-Cl—Ph |
| Me | V$^a$ | Me | Me | Ph | Me | V$^a$ | Me | Me | 4-Cl—Ph |
| Me | V$^b$ | Me | Me | Ph | Me | V$^b$ | Me | Me | 4-Cl—Ph |
| Me | V$^c$ | Me | Me | Ph | Me | V$^c$ | Me | Me | 4-Cl—Ph |
| Me | V$^d$ | Me | Me | Ph | Me | V$^d$ | Me | Me | 4-Cl—Ph |
| Me | V$^e$ | Me | Me | Ph | Me | V$^e$ | Me | Me | 4-Cl—Ph |
| Me | V$^f$ | Me | Me | Ph | Me | V$^f$ | Me | Me | 4-Cl—Ph |
| Me | V$^g$ | Me | Me | Ph | Me | V$^g$ | Me | Me | 4-Cl—Ph |
| Me | V$^h$ | Me | Me | Ph | Me | V$^h$ | Me | Me | 4-Cl—Ph |
| Me | —CH$_2$OC(=O)CH$_2$— | Me | Me | Ph | Me | —CH$_2$OC(=O)CH$_2$— | Me | Me | 4-Cl—Ph |
| Me | —CH$_2$C(=O)CH$_2$— | Me | Me | Ph | Me | —CH$_2$C(=O)CH$_2$— | Me | Me | 4-Cl—Ph |

TABLE 3-continued

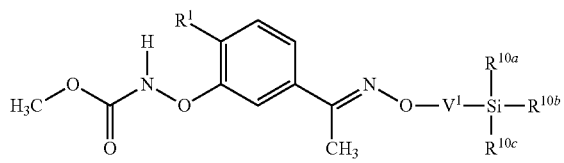

| R¹ | V¹ | R¹⁰ᵃ | R¹⁰ᵇ | R¹⁰ᶜ | R¹ | V¹ | R¹⁰ᵃ | R¹⁰ᵇ | R¹⁰ᶜ |
|---|---|---|---|---|---|---|---|---|---|
| Me | —CH₂C(=O)— | Me | Me | Ph | Me | —CH₂C(=O)— | Me | Me | 4-Cl—Ph |
| Me | —CH₂— | Me | Me | 3-Cl—Ph | Me | —CH₂— | Me | Me | 2-Cl—Ph |
| Me | —CH₂CH₂— | Me | Me | 3-Cl—Ph | Me | —CH₂CH₂— | Me | Me | 2-Cl—Ph |
| Me | —CH₂CH₂CH₂— | Me | Me | 3-Cl—Ph | Me | —CH₂CH₂CH₂— | Me | Me | 2-Cl—Ph |
| Me | —CH₂CH₂CH₂CH₂— | Me | Me | 3-Cl—Ph | Me | —CH₂CH₂CH₂CH₂— | Me | Me | 2-Cl—Ph |
| Me | —CH₂OCH₂CH₂— | Me | Me | 3-Cl—Ph | Me | —CH₂OCH₂CH₂— | Me | Me | 2-Cl—Ph |
| Me | —CH₂CH₂OCH₂— | Me | Me | 3-Cl—Ph | Me | —CH₂CH₂OCH₂— | Me | Me | 2-Cl—Ph |
| Me | —CH₂C(=O)CH₂CH₂— | Me | Me | 3-Cl—Ph | Me | —CH₂C(=O)CH₂CH₂— | Me | Me | 2-Cl—Ph |
| Me | —CH₂CH₂C(=O)CH₂— | Me | Me | 3-Cl—Ph | Me | —CH₂CH₂C(=O)CH₂— | Me | Me | 2-Cl—Ph |
| Me | —CH₂C(=S)CH₂CH₂— | Me | Me | 3-Cl—Ph | Me | —CH₂C(=S)CH₂CH₂— | Me | Me | 2-Cl—Ph |
| Me | —CH₂CH₂C(=S)CH₂— | Me | Me | 3-Cl—Ph | Me | —CH₂CH₂C(=S)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=S)CH₂— | Me | Me | 3-Cl—Ph | Me | —CH₂C(=S)CH₂— | Me | Me | 2-Cl—Ph |
| Me | —CH(Me)— | Me | Me | 3-Cl—Ph | Me | —CH(Me)— | Me | Me | 2-Cl—Ph |
| Me | —CH(OMe)— | Me | Me | 3-Cl—Ph | Me | —CH(OMe)— | Me | Me | 2-Cl—Ph |
| Me | —CH(Me)CH₂— | Me | Me | 3-Cl—Ph | Me | —CH(Me)CH₂— | Me | Me | 2-Cl—Ph |
| Me | —CH₂CH(Me)— | Me | Me | 3-Cl—Ph | Me | —CH₂CH(Me)— | Me | Me | 2-Cl—Ph |
| Me | —CH₂CH(OMe)— | Me | Me | 3-Cl—Ph | Me | —CH₂CH(OMe)— | Me | Me | 2-Cl—Ph |
| Me | —CH(Me)CH₂CH₂— | Me | Me | 3-Cl—Ph | Me | —CH(Me)CH₂CH₂— | Me | Me | 2-Cl—Ph |
| Me | —CH₂CH(Me)CH₂— | Me | Me | 3-Cl—Ph | Me | —CH₂CH(Me)CH₂— | Me | Me | 2-Cl—Ph |
| Me | —CH₂CH₂CH(Me)— | Me | Me | 3-Cl—Ph | Me | —CH₂CH₂CH(Me)— | Me | Me | 2-Cl—Ph |
| Me | —CH(Et)— | Me | Me | 3-Cl—Ph | Me | —CH(Et)— | Me | Me | 2-Cl—Ph |
| Me | —CH(Et)CH₂— | Me | Me | 3-Cl—Ph | Me | —CH(Et)CH₂— | Me | Me | 2-Cl—Ph |
| Me | —CH₂CH(Et)— | Me | Me | 3-Cl—Ph | Me | —CH₂CH(Et)— | Me | Me | 2-Cl—Ph |
| Me | —CH(Et)CH₂CH₂— | Me | Me | 3-Cl—Ph | Me | —CH(Et)CH₂CH₂— | Me | Me | 2-Cl—Ph |
| Me | —CH₂CH(Et)CH₂— | Me | Me | 3-Cl—Ph | Me | —CH₂CH(Et)CH₂— | Me | Me | 2-Cl—Ph |
| Me | —CH₂CH₂CH(Et)— | Me | Me | 3-Cl—Ph | Me | —CH₂CH₂CH(Et)— | Me | Me | 2-Cl—Ph |
| Me | —CH(OCF₃)— | Me | Me | 3-Cl—Ph | Me | —CH(OCF₃)— | Me | Me | 2-Cl—Ph |
| Me | —CH(CF₃)— | Me | Me | 3-Cl—Ph | Me | —CH(CF₃)— | Me | Me | 2-Cl—Ph |
| Me | —CH₂CF₂CH₂— | Me | Me | 3-Cl—Ph | Me | —CH₂CF₂CH₂— | Me | Me | 2-Cl—Ph |
| Me | —CH₂CHFCH₂— | Me | Me | 3-Cl—Ph | Me | —CH₂CHFCH₂— | Me | Me | 2-Cl—Ph |
| Me | —CH₂CF₂— | Me | Me | 3-Cl—Ph | Me | —CH₂CF₂— | Me | Me | 2-Cl—Ph |
| Me | —CH₂CHF— | Me | Me | 3-Cl—Ph | Me | —CH₂CHF— | Me | Me | 2-Cl—Ph |
| Me | —CH(CN)— | Me | Me | 3-Cl—Ph | Me | —CH(CN)— | Me | Me | 2-Cl—Ph |
| Me | Vᵃ | Me | Me | 3-Cl—Ph | Me | Vᵃ | Me | Me | 2-Cl—Ph |
| Me | Vᵇ | Me | Me | 3-Cl—Ph | Me | Vᵇ | Me | Me | 2-Cl—Ph |
| Me | Vᶜ | Me | Me | 3-Cl—Ph | Me | Vᶜ | Me | Me | 2-Cl—Ph |
| Me | Vᵈ | Me | Me | 3-Cl—Ph | Me | Vᵈ | Me | Me | 2-Cl—Ph |
| Me | Vᵉ | Me | Me | 3-Cl—Ph | Me | Vᵉ | Me | Me | 2-Cl—Ph |
| Me | Vᶠ | Me | Me | 3-Cl—Ph | Me | Vᶠ | Me | Me | 2-Cl—Ph |
| Me | Vᵍ | Me | Me | 3-Cl—Ph | Me | Vᵍ | Me | Me | 2-Cl—Ph |
| Me | Vʰ | Me | Me | 3-Cl—Ph | Me | Vʰ | Me | Me | 2-Cl—Ph |
| Me | —CH₂OC(=O)CH₂— | Me | Me | 3-Cl—Ph | Me | —CH₂OC(=O)CH₂— | Me | Me | 2-Cl—Ph |
| Me | —CH₂C(=O)CH₂— | Me | Me | 3-Cl—Ph | Me | —CH₂C(=O)CH₂— | Me | Me | 2-Cl—Ph |
| Me | —CH₂C(=O)— | Me | Me | 3-Cl—Ph | Me | —CH₂C(=O)— | Me | Me | 2-Cl—Ph |
| Me | —CH₂— | Me | Me | c-Pr | Me | —CH₂CH(Et)— | Me | Me | c-Pr |
| Me | —CH₂CH₂— | Me | Me | c-Pr | Me | —CH(Et)CH₂CH₂— | Me | Me | c-Pr |
| Me | —CH₂CH₂CH₂— | Me | Me | c-Pr | Me | —CH₂CH(Et)CH₂— | Me | Me | c-Pr |
| Me | —CH₂CH₂CH₂CH₂— | Me | Me | c-Pr | Me | —CH₂CH₂CH(Et)— | Me | Me | c-Pr |
| Me | —CH₂OCH₂CH₂— | Me | Me | c-Pr | Me | —CH(OCF₃)— | Me | Me | c-Pr |
| Me | —CH₂CH₂OCH₂— | Me | Me | c-Pr | Me | —CH(CF₃)— | Me | Me | c-Pr |
| Me | —CH₂C(=O)CH₂CH₂— | Me | Me | c-Pr | Me | —CH₂CF₂CH₂— | Me | Me | c-Pr |
| Me | —CH₂CH₂C(=O)CH₂— | Me | Me | c-Pr | Me | —CH₂CHFCH₂— | Me | Me | c-Pr |
| Me | —CH₂C(=S)CH₂CH₂— | Me | Me | c-Pr | Me | —CH₂CF₂— | Me | Me | c-Pr |
| Me | —CH₂CH₂C(=S)CH₂— | Me | Me | c-Pr | Me | —CH₂CHF— | Me | Me | c-Pr |
| Me | —CH₂C(=O)CH₂— | Me | Me | c-Pr | Me | —CH(CN)— | Me | Me | c-Pr |
| Me | —CH₂C(=S)CH₂— | Me | Me | c-Pr | Me | Vᵃ | Me | Me | c-Pr |
| Me | —CH(Me)— | Me | Me | c-Pr | Me | Vᵇ | Me | Me | c-Pr |
| Me | —CH(OMe)— | Me | Me | c-Pr | Me | Vᶜ | Me | Me | c-Pr |
| Me | —CH(Me)CH₂— | Me | Me | c-Pr | Me | Vᵈ | Me | Me | c-Pr |
| Me | —CH₂CH(Me)— | Me | Me | c-Pr | Me | Vᵉ | Me | Me | c-Pr |
| Me | —CH₂CH(OMe)— | Me | Me | c-Pr | Me | Vᶠ | Me | Me | c-Pr |
| Me | —CH(Me)CH₂CH₂— | Me | Me | c-Pr | Me | Vᵍ | Me | Me | c-Pr |
| Me | —CH₂CH(Me)CH₂— | Me | Me | c-Pr | Me | Vʰ | Me | Me | c-Pr |
| Me | —CH₂CH₂CH(Me)— | Me | Me | c-Pr | Me | —CH₂OC(=O)CH₂— | Me | Me | c-Pr |
| Me | —CH(Et)— | Me | Me | c-Pr | Me | —CH₂C(=O)CH₂— | Me | Me | c-Pr |
| Me | —CH(Et)CH₂— | Me | Me | c-Pr | Me | —CH₂C(=O)— | Me | Me | c-Pr |

TABLE 4

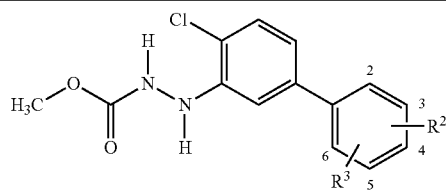

| R² | R³ | R² | R³ | R² | R³ | R² | R³ |
|---|---|---|---|---|---|---|---|
| 2-OCF₃ | H | 3-OCF₃ | 2-Me | 2-CH₂SiMe₃ | 3-F | 4-SiMe₃ | 5-CN |
| 3-OCF₃ | H | 3-OCF₃ | 4-Me | 2-CH₂SiMe₃ | 4-F | 4-SiMe₃ | 6-CN |
| 4-OCF₃ | H | 3-OCF₃ | 5-Me | 2-CH₂SiMe₃ | 5-F | 2-CH₂SiMe₃ | 3-CN |
| 2-OCF₂H | H | 3-OCF₃ | 6-Me | 2-CH₂SiMe₃ | 6-F | 2-CH₂SiMe₃ | 4-CN |
| 3-OCF₂H | H | 4-OCF₃ | 2-Me | 3-CH₂SiMe₃ | 2-F | 2-CH₂SiMe₃ | 5-CN |
| 4-OCF₂H | H | 4-OCF₃ | 3-Me | 3-CH₂SiMe₃ | 4-F | 2-CH₂SiMe₃ | 6-CN |
| 2-OCFH₂ | H | 4-OCF₃ | 5-Me | 3-CH₂SiMe₃ | 5-F | 3-CH₂SiMe₃ | 2-CN |
| 3-OCFH₂ | H | 4-OCF₃ | 6-Me | 3-CH₂SiMe₃ | 6-F | 3-CH₂SiMe₃ | 4-CN |
| 4-OCFH₂ | H | 2-OCF₂H | 3-Me | 4-CH₂SiMe₃ | 2-F | 3-CH₂SiMe₃ | 5-CN |
| 2-OCF₃ | 3-F | 2-OCF₂H | 4-Me | 4-CH₂SiMe₃ | 3-F | 3-CH₂SiMe₃ | 6-CN |
| 2-OCF₃ | 4-F | 2-OCF₂H | 5-Me | 4-CH₂SiMe₃ | 5-F | 4-CH₂SiMe₃ | 2-CN |
| 2-OCF₃ | 5-F | 2-OCF₂H | 6-Me | 4-CH₂SiMe₃ | 6-F | 4-CH₂SiMe₃ | 3-CN |
| 2-OCF₃ | 6-F | 3-OCF₂H | 2-Me | 2-SiMe₃ | 3-Cl | 4-CH₂SiMe₃ | 5-CN |
| 3-OCF₃ | 2-F | 3-OCF₂H | 4-Me | 2-SiMe₃ | 4-Cl | 4-CH₂SiMe₃ | 6-CN |
| 3-OCF₃ | 4-F | 3-OCF₂H | 5-Me | 2-SiMe₃ | 5-Cl | 2-SiMe₂Et | H |
| 3-OCF₃ | 5-F | 3-OCF₂H | 6-Me | 2-SiMe₃ | 6-Cl | 3-SiMe₂Et | H |
| 3-OCF₃ | 6-F | 4-OCFH₂ | 2-Me | 3-SiMe₃ | 2-Cl | 4-SiMe₂Et | H |
| 4-OCF₃ | 2-F | 4-OCFH₂ | 3-Me | 3-SiMe₃ | 4-Cl | 2-SiMe₂Et | 3-F |
| 4-OCF₃ | 3-F | 4-OCFH₂ | 5-Me | 3-SiMe₃ | 5-Cl | 2-SiMe₂Et | 4-F |
| 4-OCF₃ | 5-F | 4-OCFH₂ | 6-Me | 3-SiMe₃ | 6-Cl | 2-SiMe₂Et | 5-F |
| 4-OCF₃ | 6-F | 3-OCFH₂ | 2-Me | 4-SiMe₃ | 2-Cl | 2-SiMe₂Et | 6-F |
| 2-OCF₂H | 3-F | 3-OCFH₂ | 4-Me | 4-SiMe₃ | 3-Cl | 3-SiMe₂Et | 2-F |
| 2-OCF₂H | 4-F | 3-OCFH₂ | 5-Me | 4-SiMe₃ | 5-Cl | 3-SiMe₂Et | 4-F |
| 2-OCF₂H | 5-F | 3-OCFH₂ | 6-Me | 4-SiMe₃ | 6-Cl | 3-SiMe₂Et | 5-F |
| 2-OCF₂H | 6-F | 2-OCF₃ | 3-CN | 2-CH₂SiMe₃ | 3-Cl | 3-SiMe₂Et | 6-F |
| 3-OCF₂H | 2-F | 2-OCF₃ | 4-CN | 2-CH₂SiMe₃ | 4-Cl | 4-SiMe₂Et | 2-F |
| 3-OCF₂H | 4-F | 2-OCF₃ | 5-CN | 2-CH₂SiMe₃ | 5-Cl | 4-SiMe₂Et | 3-F |
| 3-OCF₂H | 5-F | 2-OCF₃ | 6-CN | 2-CH₂SiMe₃ | 6-Cl | 4-SiMe₂Et | 5-F |
| 3-OCF₂H | 6-F | 3-OCF₃ | 2-CN | 3-CH₂SiMe₃ | 2-Cl | 4-SiMe₂Et | 6-F |
| 4-OCFH₂ | 2-F | 3-OCF₃ | 4-CN | 3-CH₂SiMe₃ | 4-Cl | 2-SiMe₂Et | 3-Cl |
| 4-OCFH₂ | 3-F | 3-OCF₃ | 5-CN | 3-CH₂SiMe₃ | 5-Cl | 2-SiMe₂Et | 4-Cl |
| 4-OCFH₂ | 5-F | 3-OCF₃ | 6-CN | 3-CH₂SiMe₃ | 6-Cl | 2-SiMe₂Et | 5-Cl |
| 4-OCFH₂ | 6-F | 4-OCF₃ | 2-CN | 4-CH₂SiMe₃ | 2-Cl | 2-SiMe₂Et | 6-Cl |
| 3-OCFH₂ | 2-F | 4-OCF₃ | 3-CN | 4-CH₂SiMe₃ | 3-Cl | 3-SiMe₂Et | 2-Cl |
| 3-OCFH₂ | 4-F | 4-OCF₃ | 5-CN | 4-CH₂SiMe₃ | 5-Cl | 3-SiMe₂Et | 4-Cl |
| 3-OCFH₂ | 5-F | 4-OCF₃ | 6-CN | 4-CH₂SiMe₃ | 6-Cl | 3-SiMe₂Et | 5-Cl |
| 3-OCFH₂ | 6-F | 2-OCF₂H | 3-CN | 2-SiMe₃ | 3-Me | 3-SiMe₂Et | 6-Cl |
| 2-OCF₃ | 3-Cl | 2-OCF₂H | 4-CN | 2-SiMe₃ | 4-Me | 4-SiMe₂Et | 2-Cl |
| 2-OCF₃ | 4-Cl | 2-OCF₂H | 5-CN | 2-SiMe₃ | 5-Me | 4-SiMe₂Et | 3-Cl |
| 2-OCF₃ | 5-Cl | 2-OCF₂H | 6-CN | 2-SiMe₃ | 6-Me | 4-SiMe₂Et | 5-Cl |
| 2-OCF₃ | 6-Cl | 3-OCF₂H | 2-CN | 3-SiMe₃ | 2-Me | 4-SiMe₂Et | 6-Cl |
| 3-OCF₃ | 2-Cl | 3-OCF₂H | 4-CN | 3-SiMe₃ | 4-Me | 2-SiMe₂Et | 3-Me |
| 3-OCF₃ | 4-Cl | 3-OCF₂H | 5-CN | 3-SiMe₃ | 5-Me | 2-SiMe₂Et | 4-Me |
| 3-OCF₃ | 5-Cl | 3-OCF₂H | 6-CN | 3-SiMe₃ | 6-Me | 2-SiMe₂Et | 5-Me |
| 3-OCF₃ | 6-Cl | 4-OCFH₂ | 2-CN | 4-SiMe₃ | 2-Me | 2-SiMe₂Et | 6-Me |
| 4-OCF₃ | 2-Cl | 4-OCFH₂ | 3-CN | 4-SiMe₃ | 3-Me | 3-SiMe₂Et | 2-Me |
| 4-OCF₃ | 3-Cl | 4-OCFH₂ | 5-CN | 4-SiMe₃ | 5-Me | 3-SiMe₂Et | 4-Me |
| 4-OCF₃ | 5-Cl | 4-OCFH₂ | 6-CN | 4-SiMe₃ | 6-Me | 3-SiMe₂Et | 5-Me |
| 4-OCF₃ | 6-Cl | 3-OCFH₂ | 2-CN | 2-CH₂SiMe₃ | 3-Me | 3-SiMe₂Et | 6-Me |
| 2-OCF₂H | 3-Cl | 3-OCFH₂ | 4-CN | 2-CH₂SiMe₃ | 4-Me | 4-SiMe₂Et | 2-Me |
| 2-OCF₂H | 4-Cl | 3-OCFH₂ | 5-CN | 2-CH₂SiMe₃ | 5-Me | 4-SiMe₂Et | 3-Me |
| 2-OCF₂H | 5-Cl | 3-OCFH₂ | 6-CN | 2-CH₂SiMe₃ | 6-Me | 4-SiMe₂Et | 5-Me |
| 2-OCF₂H | 6-Cl | 2-SiMe₃ | H | 3-CH₂SiMe₃ | 2-Me | 4-SiMe₂Et | 6-Me |
| 3-OCF₂H | 2-Cl | 3-SiMe₃ | H | 3-CH₂SiMe₃ | 4-Me | 2-SiMe₂Et | 3-CN |
| 3-OCF₂H | 4-Cl | 4-SiMe₃ | H | 3-CH₂SiMe₃ | 5-Me | 2-SiMe₂Et | 4-CN |
| 3-OCF₂H | 5-Cl | 2-CH₂SiMe₃ | H | 3-CH₂SiMe₃ | 6-Me | 2-SiMe₂Et | 5-CN |
| 3-OCF₂H | 6-Cl | 3-CH₂SiMe₃ | H | 4-CH₂SiMe₃ | 2-Me | 2-SiMe₂Et | 6-CN |
| 4-OCFH₂ | 2-Cl | 4-CH₂SiMe₃ | H | 4-CH₂SiMe₃ | 3-Me | 3-SiMe₂Et | 2-CN |
| 4-OCFH₂ | 3-Cl | 2-SiMe₃ | 3-F | 4-CH₂SiMe₃ | 5-Me | 3-SiMe₂Et | 4-CN |
| 4-OCFH₂ | 5-Cl | 2-SiMe₃ | 4-F | 4-CH₂SiMe₃ | 6-Me | 3-SiMe₂Et | 5-CN |
| 4-OCFH₂ | 6-Cl | 2-SiMe₃ | 5-F | 2-SiMe₃ | 3-CN | 3-SiMe₂Et | 6-CN |
| 3-OCFH₂ | 2-Cl | 2-SiMe₃ | 6-F | 2-SiMe₃ | 4-CN | 4-SiMe₂Et | 2-CN |
| 3-OCFH₂ | 4-Cl | 3-SiMe₃ | 2-F | 2-SiMe₃ | 5-CN | 4-SiMe₂Et | 3-CN |
| 3-OCFH₂ | 5-Cl | 3-SiMe₃ | 4-F | 2-SiMe₃ | 6-CN | 4-SiMe₂Et | 5-CN |
| 3-OCFH₂ | 6-Cl | 3-SiMe₃ | 5-F | 3-SiMe₃ | 2-CN | 4-SiMe₂Et | 6-CN |
| 2-OCF₃ | 3-Me | 3-SiMe₃ | 6-F | 3-SiMe₃ | 4-CN | 4-SiMe₃ | 6-F |
| 2-OCF₃ | 4-Me | 4-SiMe₃ | 2-F | 3-SiMe₃ | 5-CN | 4-SiMe₃ | 3-CN |
| 2-OCF₃ | 5-Me | 4-SiMe₃ | 3-F | 3-SiMe₃ | 6-CN | | |

TABLE 4-continued

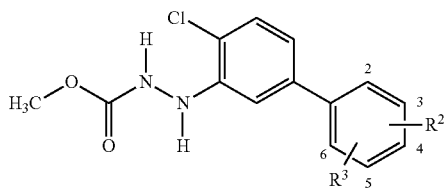

| R² | R³ | R² | R³ | R² | R³ | R² | R³ |
|---|---|---|---|---|---|---|---|
| 2-OCF₃ | 6-Me | 4-SiMe₃ | 5-F | 4-SiMe₃ | 2-CN | | |

TABLE 5

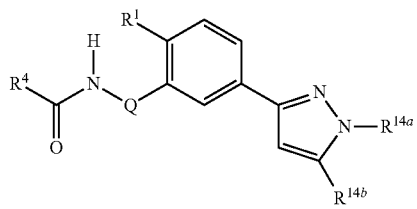

| R¹ | R⁴ | Q | R$^{14a}$ | R$^{14b}$ | R¹ | R⁴ | Q | R$^{14a}$ | R$^{14b}$ |
|---|---|---|---|---|---|---|---|---|---|
| Cl | MeO | —CH₂— | 4-Cl—Ph | H | Cl | MeO | —CH₂— | 4-F—Ph | H |
| Cl | MeO | —CH₂— | 3-Cl—Ph | H | Cl | MeO | —CH₂— | 3-F—Ph | H |
| Cl | MeO | —CH₂— | 2-Cl—Ph | H | Cl | MeO | —CH₂— | 2-F—Ph | H |
| Cl | MeO | —CH₂— | 4-Br—Ph | H | Cl | MeO | —CH₂— | 4-Me—Ph | H |
| Cl | MeO | —CH₂— | 3-Br—Ph | H | Cl | MeO | —CH₂— | 3-Me—Ph | H |
| Cl | MeO | —CH₂— | 2-Br—Ph | H | Cl | MeO | —CH₂— | 2-Me—Ph | H |
| Cl | MeO | —CH₂— | 4-Et—Ph | H | Cl | MeO | —CH₂— | 4-i-Pr—Ph | H |
| Cl | MeO | —CH₂— | 3-Et—Ph | H | Cl | MeO | —CH₂— | 3-i-Pr—Ph | H |
| Cl | MeO | —CH₂— | 2-Et—Ph | H | Cl | MeO | —CH₂— | 2-i-Pr—Ph | H |
| Cl | MeO | —CH₂— | 4-CN—Ph | H | Cl | MeO | —CH₂— | 4-c-Pr—Ph | H |
| Cl | MeO | —CH₂— | 3-CN—Ph | H | Cl | MeO | —CH₂— | 3-c-Pr—Ph | H |
| Cl | MeO | —CH₂— | 2-CN—Ph | H | Cl | MeO | —CH₂— | 2-c-Pr—Ph | H |
| Cl | MeO | —CH₂— | 4-CF₃—Ph | H | Cl | MeO | —CH₂— | 4-CF₃O—Ph | H |
| Cl | MeO | —CH₂— | 3-CF₃—Ph | H | Cl | MeO | —CH₂— | 3-CF₃O—Ph | H |
| Cl | MeO | —CH₂— | 2-CF₃—Ph | H | Cl | MeO | —CH₂— | 2-CF₃O—Ph | H |
| Cl | MeO | —CH₂— | 4-Ac—Ph | H | Cl | MeO | —CH₂— | 2-(CF₃C=O)—Ph | H |
| Cl | MeO | —CH₂— | 3-Ac—Ph | H | Cl | MeO | —CH₂— | 3-(CF₃C=O)—Ph | H |
| Cl | MeO | —CH₂— | 2-Ac—Ph | H | Cl | MeO | —CH₂— | 4-(CF₃C=O)—Ph | H |
| Cl | MeO | —CH₂— | 4-MeO—Ph | H | Cl | MeO | —CH₂— | 4-EtO—Ph | H |
| Cl | MeO | —CH₂— | 3-MeO—Ph | H | Cl | MeO | —CH₂— | 3-EtO—Ph | H |
| Cl | MeO | —CH₂— | 2-MeO—Ph | H | Cl | MeO | —CH₂— | 2-EtO—Ph | H |
| Cl | MeO | —CH₂— | 4-i-PrO—Ph | H | Cl | MeO | —CH₂— | 4-NO₂—Ph | H |
| Cl | MeO | —CH₂— | 3-i-PrO—Ph | H | Cl | MeO | —CH₂— | 3-NO₂—Ph | H |
| Cl | MeO | —CH₂— | 2-i-PrO—Ph | H | Cl | MeO | —CH₂— | 2-NO₂—Ph | H |
| Cl | MeO | —CH₂— | 4-I—Ph | H | Cl | MeO | —CH₂— | 4-(CO₂Me)—Ph | H |
| Cl | MeO | —CH₂— | 3-I—Ph | H | Cl | MeO | —CH₂— | 3-(CO₂Me)—Ph | H |
| Cl | MeO | —CH₂— | 2-I—Ph | H | Cl | MeO | —CH₂— | 2-(CO₂Me)—Ph | H |
| Cl | MeO | —CH₂— | 4-Me(C=NH)—Ph | H | Cl | MeO | —CH₂— | 4-Me(C=NMe)—Ph | H |
| Cl | MeO | —CH₂— | 3-Me(C=NH)—Ph | H | Cl | MeO | —CH₂— | 3-Me(C=NMe)—Ph | H |
| Cl | MeO | —CH₂— | 2-Me(C=NH)—Ph | H | Cl | MeO | —CH₂— | 2-Me(C=NMe)—Ph | H |
| Cl | MeO | —CH₂— | 4-Me(C=NOMe)—Ph | H | Cl | MeO | —CH₂— | 4-Me(C=NOEt)—Ph | H |
| Cl | MeO | —CH₂— | 3-Me(C=NOMe)—Ph | H | Cl | MeO | —CH₂— | 3-Me(C=NOEt)—Ph | H |
| Cl | MeO | —CH₂— | 2-Me(C=NOMe)—Ph | H | Cl | MeO | —CH₂— | 2-Me(C=NOEt)—Ph | H |
| Cl | MeO | —CH₂— | 4-MeNH(C=O)—Ph | H | Cl | MeO | —CH₂— | 4-SiMe₃—Ph | H |
| Cl | MeO | —CH₂— | 3-MeNH(C=O)—Ph | H | Cl | MeO | —CH₂— | 3-SiMe₃—Ph | H |
| Cl | MeO | —CH₂— | 2-MeNH(C=O)—Ph | H | Cl | MeO | —CH₂— | 2-SiMe₃—Ph | H |
| Cl | MeO | —CH₂— | 2,6-di-Cl—Ph | H | Cl | MeO | —CH₂— | 2,6-di-F—Ph | H |
| Cl | MeO | —CH₂— | 2,5-di-Cl—Ph | H | Cl | MeO | —CH₂— | 2,5-di-F—Ph | H |
| Cl | MeO | —CH₂— | 2,4-di-Cl—Ph | H | Cl | MeO | —CH₂— | 2,4-di-F—Ph | H |
| Cl | MeO | —CH₂— | 3,3-di-Cl—Ph | H | Cl | MeO | —CH₂— | 3,3-di-F—Ph | H |
| Cl | MeO | —CH₂— | 3,4-di-Cl—Ph | H | Cl | MeO | —CH₂— | 3,4-di-F—Ph | H |
| Cl | MeO | —CH₂— | 2,6-di-Me—Ph | H | Cl | MeO | —CH₂— | 2,6-di-CF₃—Ph | H |
| Cl | MeO | —CH₂— | 2,5-di-Me—Ph | H | Cl | MeO | —CH₂— | 2,5-di-CF₃—Ph | H |
| Cl | MeO | —CH₂— | 2,4-di-Me—Ph | H | Cl | MeO | —CH₂— | 2,4-di-CF₃—Ph | H |
| Cl | MeO | —CH₂— | 3,3-di-Me—Ph | H | Cl | MeO | —CH₂— | 3,3-di-CF₃—Ph | H |
| Cl | MeO | —CH₂— | 3,4-di-Me—Ph | H | Cl | MeO | —CH₂— | 3,4-di-CF₃—Ph | H |
| Cl | MeO | —CH₂— | 2,6-di-CF₃O—Ph | H | Cl | MeO | —CH₂— | 2,6-di-MeO—Ph | H |
| Cl | MeO | —CH₂— | 2,5-di-CF₃O—Ph | H | Cl | MeO | —CH₂— | 2,5-di-MeO—Ph | H |
| Cl | MeO | —CH₂— | 2,4-di-CF₃O—Ph | H | Cl | MeO | —CH₂— | 2,4-di-MeO—Ph | H |

TABLE 5-continued

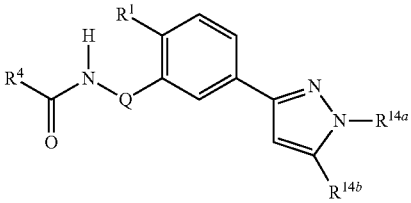

| R$^1$ | R$^4$ | Q | R$^{14a}$ | R$^{14b}$ | R$^1$ | R$^4$ | Q | R$^{14a}$ | R$^{14b}$ |
|---|---|---|---|---|---|---|---|---|---|
| Cl | MeO | —CH$_2$— | 3,3-di-CF$_3$O—Ph | H | Cl | MeO | —CH$_2$— | 3,3-di-MeO—Ph | H |
| Cl | MeO | —CH$_2$— | 3,4-di-CF$_3$O—Ph | H | Cl | MeO | —CH$_2$— | 3,4-di-MeO—Ph | H |
| Cl | MeO | —CH$_2$— | 4-CF$_2$—Ph | H | Cl | MeO | —CH$_2$— | 4-CF$_2$O—Ph | H |
| Cl | MeO | —CH$_2$— | 3-CF$_2$—Ph | H | Cl | MeO | —CH$_2$— | 3-CF$_2$O—Ph | H |
| Cl | MeO | —CH$_2$— | 2-CF$_2$—Ph | H | Cl | MeO | —CH$_2$— | 2-CF$_2$O—Ph | H |
| Cl | MeO | —CH$_2$— | 2-F-3-Cl—Ph | H | Cl | MeO | —CH$_2$— | 2-F-3-CF$_3$—Ph | H |
| Cl | MeO | —CH$_2$— | 2-F-4-Cl—Ph | H | Cl | MeO | —CH$_2$— | 2-F-4-CF$_3$—Ph | H |
| Cl | MeO | —CH$_2$— | 2-F-5-Cl—Ph | H | Cl | MeO | —CH$_2$— | 2-F-5-CF$_3$—Ph | H |
| Cl | MeO | —CH$_2$— | 2-F-6-Cl—Ph | H | Cl | MeO | —CH$_2$— | 2-F-6-CF$_3$—Ph | H |
| Cl | MeO | —CH$_2$— | 3-F-2-Cl—Ph | H | Cl | MeO | —CH$_2$— | 3-F-2-CF$_3$—Ph | H |
| Cl | MeO | —CH$_2$— | 3-F-4-Cl—Ph | H | Cl | MeO | —CH$_2$— | 3-F-4-CF$_3$—Ph | H |
| Cl | MeO | —CH$_2$— | 3-F-5-Cl—Ph | H | Cl | MeO | —CH$_2$— | 3-F-5-CF$_3$—Ph | H |
| Cl | MeO | —CH$_2$— | 3-F-6-Cl—Ph | H | Cl | MeO | —CH$_2$— | 3-F-6-CF$_3$—Ph | H |
| Cl | MeO | —CH$_2$— | 4-F-3-Cl—Ph | H | Cl | MeO | —CH$_2$— | 4-F-3-CF$_3$—Ph | H |
| Cl | MeO | —CH$_2$— | 4-F-2-Cl—Ph | H | Cl | MeO | —CH$_2$— | 4-F-2-CF$_3$—Ph | H |
| Cl | MeO | —CH$_2$— | pyrid-2-yl | H | Cl | MeO | —CH$_2$— | pyrid-3-yl | H |
| Cl | MeO | —CH$_2$— | pyrid-4-yl | H | Cl | MeO | —CH$_2$— | 2,4,6-triazin-1-yl | H |
| Cl | MeO | —CH$_2$— | 3-CF$_3$-pyrid-2-yl | H | Cl | MeO | —CH$_2$— | 2-CF$_3$-pyrid-3-yl | H |
| Cl | MeO | —CH$_2$— | 4-CF$_3$-pyrid-2-yl | H | Cl | MeO | —CH$_2$— | 4-CF$_3$-pyrid-3-yl | H |
| Cl | MeO | —CH$_2$— | 5-CF$_3$-pyrid-2-yl | H | Cl | MeO | —CH$_2$— | 5-CF$_3$-pyrid-3-yl | H |
| Cl | MeO | —CH$_2$— | 6-CF$_3$-pyrid-2-yl | H | Cl | MeO | —CH$_2$— | 6-CF$_3$-pyrid-3-yl | H |
| Cl | MeO | —CH$_2$— | 2-CF$_3$-pyrid-4-yl | H | Cl | MeO | —CH$_2$— | 2-Me-pyrid-4-yl | H |
| Cl | MeO | —CH$_2$— | 3-CF$_3$-pyrid-4-yl | H | Cl | MeO | —CH$_2$— | 3-Me-pyrid-4-yl | H |
| Cl | MeO | —CH$_2$— | 3-Me-pyrid-2-yl | H | Cl | MeO | —CH$_2$— | 2-Me-pyrid-3-yl | H |
| Cl | MeO | —CH$_2$— | 4-Me-pyrid-2-yl | H | Cl | MeO | —CH$_2$— | 4-Me-pyrid-3-yl | H |
| Cl | MeO | —CH$_2$— | 5-Me-pyrid-2-yl | H | Cl | MeO | —CH$_2$— | 5-Me-pyrid-3-yl | H |
| Cl | MeO | —CH$_2$— | 6-Me-pyrid-2-yl | H | Cl | MeO | —CH$_2$— | 6-Me-pyrid-3-yl | H |
| Cl | MeO | —CH$_2$— | 5-Cl-thien-2-yl | H | Cl | MeO | —CH$_2$— | 5-F-thien-2-yl | H |
| Cl | MeO | —CH$_2$— | 4-Cl-thien-2-yl | H | Cl | MeO | —CH$_2$— | 4-F-thien-2-yl | H |
| Cl | MeO | —CH$_2$— | 3-Cl-thien-2-yl | H | Cl | MeO | —CH$_2$— | 3-F-thien-2-yl | H |
| Cl | MeO | —CH$_2$— | 5-CF$_3$-thien-2-yl | H | Cl | MeO | —CH$_2$— | 5-OCF$_3$-thien-2-yl | H |
| Cl | MeO | —CH$_2$— | 4-CF$_3$-thien-2-yl | H | Cl | MeO | —CH$_2$— | 4-OCF$_3$-thien-2-yl | H |
| Cl | MeO | —CH$_2$— | 3-CF$_3$-thien-2-yl | H | Cl | MeO | —CH$_2$— | 3-OCF$_3$-thien-2-yl | H |
| Cl | MeO | —CH$_2$— | 5-Cl-thien-3-yl | H | Cl | MeO | —CH$_2$— | 5-F-thien-3-yl | H |
| Cl | MeO | —CH$_2$— | 4-Cl-thien-3-yl | H | Cl | MeO | —CH$_2$— | 4-F-thien-3-yl | H |
| Cl | MeO | —CH$_2$— | 2-Cl-thien-3-yl | H | Cl | MeO | —CH$_2$— | 2-F-thien-3-yl | H |
| Cl | MeO | —CH$_2$— | 5-CF$_3$-thien-3-yl | H | Cl | MeO | —CH$_2$— | 5-OCF$_3$-thien-3-yl | H |
| Cl | MeO | —CH$_2$— | 4-CF$_3$-thien-3-yl | H | Cl | MeO | —CH$_2$— | 4-OCF$_3$-thien-3-yl | H |
| Cl | MeO | —CH$_2$— | 2-CF$_3$-thien-3-yl | H | Cl | MeO | —CH$_2$— | 2-OCF$_3$-thien-3-yl | H |
| Cl | MeO | —CH$_2$— | thien-2-yl | H | Cl | MeO | —CH$_2$— | thien-3-yl | H |
| Cl | MeO | —CH$_2$— | 4-Cl-benzyl | H | Cl | MeO | —CH$_2$— | 4-F-benzyl | H |
| Cl | MeO | —CH$_2$— | 3-Cl-benzyl | H | Cl | MeO | —CH$_2$— | 3-F-benzyl | H |
| Cl | MeO | —CH$_2$— | 2-Cl-benzyl | H | Cl | MeO | —CH$_2$— | 2-F-benzyl | H |
| Cl | MeO | —CH$_2$— | 4-Br-benzyl | H | Cl | MeO | —CH$_2$— | 4-Me-benzyl | H |
| Cl | MeO | —CH$_2$— | 3-Br-benzyl | H | Cl | MeO | —CH$_2$— | 3-Me-benzyl | H |
| Cl | MeO | —CH$_2$— | 2-Br-benzyl | H | Cl | MeO | —CH$_2$— | 2-Me-benzyl | H |
| Cl | MeO | —CH$_2$— | 4-Et-benzyl | H | Cl | MeO | —CH$_2$— | 4-i-Pr-benzyl | H |
| Cl | MeO | —CH$_2$— | 3-Et-benzyl | H | Cl | MeO | —CH$_2$— | 3-i-Pr-benzyl | H |
| Cl | MeO | —CH$_2$— | 2-Et-benzyl | H | Cl | MeO | —CH$_2$— | 2-i-Pr-benzyl | H |
| Cl | MeO | —CH$_2$— | 4-CN-benzyl | H | Cl | MeO | —CH$_2$— | 4-c-Pr-benzyl | H |
| Cl | MeO | —CH$_2$— | 3-CN-benzyl | H | Cl | MeO | —CH$_2$— | 3-c-Pr-benzyl | H |
| Cl | MeO | —CH$_2$— | 2-CN-benzyl | H | Cl | MeO | —CH$_2$— | 2-c-Pr-benzyl | H |
| Cl | MeO | —CH$_2$— | 4-CF$_3$-benzyl | H | Cl | MeO | —CH$_2$— | 4-CF$_3$O-benzyl | H |
| Cl | MeO | —CH$_2$— | 3-CF$_3$-benzyl | H | Cl | MeO | —CH$_2$— | 3-CF$_3$O-benzyl | H |
| Cl | MeO | —CH$_2$— | 2-CF$_3$-benzyl | H | Cl | MeO | —CH$_2$— | 2-CF$_3$O-benzyl | H |
| Cl | MeO | —CH$_2$— | 4-CHF$_2$-benzyl | H | Cl | MeO | —CH$_2$— | 4-CHF$_2$O-benzyl | H |
| Cl | MeO | —CH$_2$— | 3-CHF$_2$-benzyl | H | Cl | MeO | —CH$_2$— | 3-CHF$_2$O-benzyl | H |
| Cl | MeO | —CH$_2$— | 2-CHF$_2$-benzyl | H | Cl | MeO | —CH$_2$— | 2-CHF$_2$O-benzyl | H |
| Cl | MeO | —CH$_2$— | 4-Ac-benzyl | H | Cl | MeO | —CH$_2$— | 2-(CF$_3$C=O)-benzyl | H |
| Cl | MeO | —CH$_2$— | 3-Ac-benzyl | H | Cl | MeO | —CH$_2$— | 3-(CF$_3$C=O)-benzyl | H |
| Cl | MeO | —CH$_2$— | 2-Ac-benzyl | H | Cl | MeO | —CH$_2$— | 5-(CF$_3$C=O)-benzyl | H |
| Cl | MeO | —CH$_2$— | 4-MeO-benzyl | H | Cl | MeO | —CH$_2$— | 4-EtO-benzyl | H |
| Cl | MeO | —CH$_2$— | 3-MeO-benzyl | H | Cl | MeO | —CH$_2$— | 3-EtO-benzyl | H |
| Cl | MeO | —CH$_2$— | 2-MeO-benzyl | H | Cl | MeO | —CH$_2$— | 2-EtO-benzyl | H |
| Cl | MeO | —CH$_2$— | 4-i-PrO-benzyl | H | Cl | MeO | —CH$_2$— | 4-NO$_2$-benzyl | H |
| Cl | MeO | —CH$_2$— | 3-i-PrO-benzyl | H | Cl | MeO | —CH$_2$— | 3-NO$_2$-benzyl | H |
| Cl | MeO | —CH$_2$— | 2-i-PrO-benzyl | H | Cl | MeO | —CH$_2$— | 2-NO$_2$-benzyl | H |

TABLE 5-continued

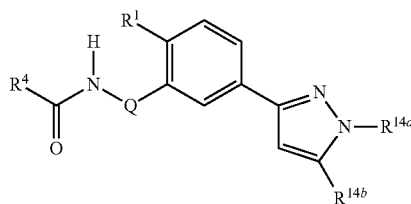

| R¹ | R⁴ | Q | R¹⁴ᵃ | R¹⁴ᵇ | R¹ | R⁴ | Q | R¹⁴ᵃ | R¹⁴ᵇ |
|---|---|---|---|---|---|---|---|---|---|
| Cl | MeO | —CH₂— | benzyl | H | Cl | MeO | —CH₂— | phenethyl | H |
| Cl | MeO | —CH₂— | methyl | H | Cl | MeO | —CH₂— | ethyl | H |
| Cl | MeO | —CH₂— | n-propyl | H | Cl | MeO | —CH₂— | n-butyl | H |
| Cl | MeO | —CH₂— | i-propyl | H | Cl | MeO | —CH₂— | i-butyl | H |
| Cl | MeO | —CH₂— | c-propyl | H | Cl | MeO | —CH₂— | c-butyl | H |
| Cl | MeO | —CH₂— | n-pentyl | H | Cl | MeO | —CH₂— | s-butyl | H |
| Cl | MeO | —CH₂— | c-pentyl | H | Cl | MeO | —CH₂— | n-hexyl | H |
| Cl | MeO | —CH₂— | n-heptyl | H | Cl | MeO | —CH₂— | c-hexyl | H |
| Cl | MeO | —CH₂— | 1-naphthyl | H | Cl | MeO | —CH₂— | 2-naphthyl | H |
| Cl | MeO | N | 4-Cl—Ph | H | Cl | MeO | N | 4-F—Ph | H |
| Cl | MeO | N | 3-Cl—Ph | H | Cl | MeO | N | 3-F—Ph | H |
| Cl | MeO | N | 2-Cl—Ph | H | Cl | MeO | N | 2-F—Ph | H |
| Cl | MeO | N | 4-Br—Ph | H | Cl | MeO | N | 4-Me—Ph | H |
| Cl | MeO | N | 3-Br—Ph | H | Cl | MeO | N | 3-Me—Ph | H |
| Cl | MeO | N | 2-Br—Ph | H | Cl | MeO | N | 2-Me—Ph | H |
| Cl | MeO | N | 4-Et—Ph | H | Cl | MeO | N | 4-i-Pr—Ph | H |
| Cl | MeO | N | 3-Et—Ph | H | Cl | MeO | N | 3-i-Pr—Ph | H |
| Cl | MeO | N | 2-Et—Ph | H | Cl | MeO | N | 2-i-Pr—Ph | H |
| Cl | MeO | N | 4-CN—Ph | H | Cl | MeO | N | 4-c-Pr—Ph | H |
| Cl | MeO | N | 3-CN—Ph | H | Cl | MeO | N | 3-c-Pr—Ph | H |
| Cl | MeO | N | 2-CN—Ph | H | Cl | MeO | N | 2-c-Pr—Ph | H |
| Cl | MeO | N | 4-CF₃—Ph | H | Cl | MeO | N | 4-CF₃O—Ph | H |
| Cl | MeO | N | 3-CF₃—Ph | H | Cl | MeO | N | 3-CF₃O—Ph | H |
| Cl | MeO | N | 2-CF₃—Ph | H | Cl | MeO | N | 2-CF₃O—Ph | H |
| Cl | MeO | N | 4-Ac—Ph | H | Cl | MeO | N | 2-(CF₃C=O)—Ph | H |
| Cl | MeO | N | 3-Ac—Ph | H | Cl | MeO | N | 3-(CF₃C=O)—Ph | H |
| Cl | MeO | N | 2-Ac—Ph | H | Cl | MeO | N | 5-(CF₃C=O)—Ph | H |
| Cl | MeO | N | 4-MeO—Ph | H | Cl | MeO | N | 4-EtO—Ph | H |
| Cl | MeO | N | 3-MeO—Ph | H | Cl | MeO | N | 3-EtO—Ph | H |
| Cl | MeO | N | 2-MeO—Ph | H | Cl | MeO | N | 2-EtO—Ph | H |
| Cl | MeO | N | 4-i-PrO—Ph | H | Cl | MeO | N | 4-NO₂—Ph | H |
| Cl | MeO | N | 3-i-PrO—Ph | H | Cl | MeO | N | 3-NO₂—Ph | H |
| Cl | MeO | N | 2-i-PrO—Ph | H | Cl | MeO | N | 2-NO₂—Ph | H |
| Cl | MeO | N | 4-Cl-benzyl | H | Cl | MeO | N | 4-F-benzyl | H |
| Cl | MeO | N | 3-Cl-benzyl | H | Cl | MeO | N | 3-F-benzyl | H |
| Cl | MeO | N | 2-Cl-benzyl | H | Cl | MeO | N | 2-F-benzyl | H |
| Cl | MeO | N | 4-Br-benzyl | H | Cl | MeO | N | 4-Me-benzyl | H |
| Cl | MeO | N | 3-Br-benzyl | H | Cl | MeO | N | 3-Me-benzyl | H |
| Cl | MeO | N | 2-Br-benzyl | H | Cl | MeO | N | 2-Me-benzyl | H |
| Cl | MeO | N | 4-Et-benzyl | H | Cl | MeO | N | 4-i-Pr-benzyl | H |
| Cl | MeO | N | 3-Et-benzyl | H | Cl | MeO | N | 3-i-Pr-benzyl | H |
| Cl | MeO | N | 2-Et-benzyl | H | Cl | MeO | N | 2-i-Pr-benzyl | H |
| Cl | MeO | N | 4-CN-benzyl | H | Cl | MeO | N | 4-c-Pr-benzyl | H |
| Cl | MeO | N | 3-CN-benzyl | H | Cl | MeO | N | 3-c-Pr-benzyl | H |
| Cl | MeO | N | 2-CN-benzyl | H | Cl | MeO | N | 2-c-Pr-benzyl | H |
| Cl | MeO | N | 4-CF₃-benzyl | H | Cl | MeO | N | 4-CF₃O-benzyl | H |
| Cl | MeO | N | 3-CF₃-benzyl | H | Cl | MeO | N | 3-CF₃O-benzyl | H |
| Cl | MeO | N | 2-CF₃-benzyl | H | Cl | MeO | N | 2-CF₃O-benzyl | H |
| Cl | MeO | N | 4-CHF₂-benzyl | H | Cl | MeO | N | 4-CHF₂O-benzyl | H |
| Cl | MeO | N | 3-CHF₂-benzyl | H | Cl | MeO | N | 3-CHF₂O-benzyl | H |
| Cl | MeO | N | 2-CHF₂-benzyl | H | Cl | MeO | N | 2-CHF₂O-benzyl | H |
| Cl | MeO | N | 4-Ac-benzyl | H | Cl | MeO | N | 2-(CF₃C=O)-benzyl | H |
| Cl | MeO | N | 3-Ac-benzyl | H | Cl | MeO | N | 3-(CF₃C=O)-benzyl | H |
| Cl | MeO | N | 2-Ac-benzyl | H | Cl | MeO | N | 5-(CF₃C=O)-benzyl | H |
| Cl | MeO | N | 4-MeO-benzyl | H | Cl | MeO | N | 4-EtO-benzyl | H |
| Cl | MeO | N | 3-MeO-benzyl | H | Cl | MeO | N | 3-EtO-benzyl | H |
| Cl | MeO | N | 2-MeO-benzyl | H | Cl | MeO | N | 2-EtO-benzyl | H |
| Cl | MeO | N | 4-i-PrO-benzyl | H | Cl | MeO | N | 4-NO₂-benzyl | H |
| Cl | MeO | N | 3-i-PrO-benzyl | H | Cl | MeO | N | 3-NO₂-benzyl | H |
| Cl | MeO | N | 2-i-PrO-benzyl | H | Cl | MeO | N | 2-NO₂-benzyl | H |
| Cl | MeO | O | 4-Cl—Ph | H | Cl | MeO | O | 4-F—Ph | H |
| Cl | MeO | O | 3-Cl—Ph | H | Cl | MeO | O | 3-F—Ph | H |
| Cl | MeO | O | 2-Cl—Ph | H | Cl | MeO | O | 2-F—Ph | H |
| Cl | MeO | O | 4-Br—Ph | H | Cl | MeO | O | 4-Me—Ph | H |
| Cl | MeO | O | 3-Br—Ph | H | Cl | MeO | O | 3-Me—Ph | H |
| Cl | MeO | O | 2-Br—Ph | H | Cl | MeO | O | 2-Me—Ph | H |
| Cl | MeO | O | 4-Et—Ph | H | Cl | MeO | O | 4-i-Pr—Ph | H |

TABLE 5-continued

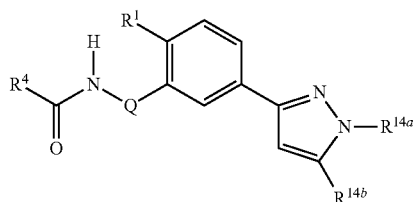

| R¹ | R⁴ | Q | R¹⁴ᵃ | R¹⁴ᵇ | R¹ | R⁴ | Q | R¹⁴ᵃ | R¹⁴ᵇ |
|---|---|---|---|---|---|---|---|---|---|
| Cl | MeO | O | 3-Et—Ph | H | Cl | MeO | O | 3-i-Pr—Ph | H |
| Cl | MeO | O | 2-Et—Ph | H | Cl | MeO | O | 2-i-Pr—Ph | H |
| Cl | MeO | O | 4-CN—Ph | H | Cl | MeO | O | 4-c-Pr—Ph | H |
| Cl | MeO | O | 3-CN—Ph | H | Cl | MeO | O | 3-c-Pr—Ph | H |
| Cl | MeO | O | 2-CN—Ph | H | Cl | MeO | O | 2-c-Pr—Ph | H |
| Cl | MeO | O | 4-CF₃—Ph | H | Cl | MeO | O | 4-CF₃O—Ph | H |
| Cl | MeO | O | 3-CF₃—Ph | H | Cl | MeO | O | 3-CF₃O—Ph | H |
| Cl | MeO | O | 2-CF₃—Ph | H | Cl | MeO | O | 2-CF₃O—Ph | H |
| Cl | MeO | O | 4-Ac—Ph | H | Cl | MeO | O | 2-(CF₃C=O)—Ph | H |
| Cl | MeO | O | 3-Ac—Ph | H | Cl | MeO | O | 3-(CF₃C=O)—Ph | H |
| Cl | MeO | O | 2-Ac—Ph | H | Cl | MeO | O | 5-(CF₃C=O)—Ph | H |
| Cl | MeO | O | 4-MeO—Ph | H | Cl | MeO | O | 4-EtO—Ph | H |
| Cl | MeO | O | 3-MeO—Ph | H | Cl | MeO | O | 3-EtO—Ph | H |
| Cl | MeO | O | 2-MeO—Ph | H | Cl | MeO | O | 2-EtO—Ph | H |
| Cl | MeO | O | 4-Cl-benzyl | H | Cl | MeO | O | 4-F-benzyl | H |
| Cl | MeO | O | 3-Cl-benzyl | H | Cl | MeO | O | 3-F-benzyl | H |
| Cl | MeO | O | 2-Cl-benzyl | H | Cl | MeO | O | 2-F-benzyl | H |
| Cl | MeO | O | 4-Br-benzyl | H | Cl | MeO | O | 4-Me benzyl | H |
| Cl | MeO | O | 3-Br-benzyl | H | Cl | MeO | O | 3-Me benzyl | H |
| Cl | MeO | O | 2-Br-benzyl | H | Cl | MeO | O | 2-Me-benzyl | H |
| Cl | MeO | O | 4-Et-benzyl | H | Cl | MeO | O | 4-i-Pr-benzyl | H |
| Cl | MeO | O | 3-Et-benzyl | H | Cl | MeO | O | 3-i-Pr-benzyl | H |
| Cl | MeO | O | 2-Et-benzyl | H | Cl | MeO | O | 2-i-Pr-benzyl | H |
| Cl | MeO | O | 4-CN-benzyl | H | Cl | MeO | O | 4-c-Pr-benzyl | H |
| Cl | MeO | O | 3-CN-benzyl | H | Cl | MeO | O | 3-c-Pr-benzyl | H |
| Cl | MeO | O | 2-CN-benzyl | H | Cl | MeO | O | 2-c-Pr-benzyl | H |
| Cl | MeO | O | 4-CF₃-benzyl | H | Cl | MeO | O | 4-CF₃O-benzyl | H |
| Cl | MeO | O | 3-CF₃-benzyl | H | Cl | MeO | O | 3-CF₃O-benzyl | H |
| Cl | MeO | O | 2-CF₃-benzyl | H | Cl | MeO | O | 2-CF₃O-benzyl | H |
| Cl | MeO | O | 4-CHF₂-benzyl | H | Cl | MeO | O | 4-CHF₂O-benzyl | H |
| Cl | MeO | O | 3-CHF₂-benzyl | H | Cl | MeO | O | 3-CHF₂O-benzyl | H |
| Cl | MeO | O | 2-CHF₂-benzyl | H | Cl | MeO | O | 2-CHF₂O-benzyl | H |
| Cl | MeO | O | 4-Ac-benzyl | H | Cl | MeO | O | 2-(CF₃C=O)-benzyl | H |
| Cl | MeO | O | 3-Ac-benzyl | H | Cl | MeO | O | 3-(CF₃C=O)-benzyl | H |
| Cl | MeO | O | 2-Ac-benzyl | H | Cl | MeO | O | 5-(CF₃C=O)-benzyl | H |
| Cl | MeO | O | 4-MeO-benzyl | H | Cl | MeO | O | 4-EtO-benzyl | H |
| Cl | MeO | O | 3-MeO-benzyl | H | Cl | MeO | O | 3-EtO-benzyl | H |
| Cl | MeO | O | 2-MeO-benzyl | H | Cl | MeO | O | 2-EtO-benzyl | H |
| Cl | MeO | O | 4-i-PrO-benzyl | H | Cl | MeO | O | 4-I-benzyl | H |
| Cl | MeO | O | 3-i-PrO-benzyl | H | Cl | MeO | O | 3-I-benzyl | H |
| Cl | MeO | O | 2-i-PrO-benzyl | H | Cl | MeO | O | 2-I-benzyl | H |
| Me | MeO | —CH₂— | 4-Cl—Ph | H | Me | MeO | —CH₂— | 4-F—Ph | H |
| Me | MeO | —CH₂— | 3-Cl—Ph | H | Me | MeO | —CH₂— | 3-F—Ph | H |
| Me | MeO | —CH₂— | 2-Cl—Ph | H | Me | MeO | —CH₂— | 2-F—Ph | H |
| Me | MeO | —CH₂— | 4-Br—Ph | H | Me | MeO | —CH₂— | 4-Me—Ph | H |
| Me | MeO | —CH₂— | 3-Br—Ph | H | Me | MeO | —CH₂— | 3-Me—Ph | H |
| Me | MeO | —CH₂— | 2-Br—Ph | H | Me | MeO | —CH₂— | 2-Me—Ph | H |
| Me | MeO | —CH₂— | 4-Et—Ph | H | Me | MeO | —CH₂— | 4-i-Pr—Ph | H |
| Me | MeO | —CH₂— | 3-Et—Ph | H | Me | MeO | —CH₂— | 3-i-Pr—Ph | H |
| Me | MeO | —CH₂— | 2-Et—Ph | H | Me | MeO | —CH₂— | 2-i-Pr—Ph | H |
| Me | MeO | —CH₂— | 4-CN—Ph | H | Me | MeO | —CH₂— | 4-c-Pr—Ph | H |
| Me | MeO | —CH₂— | 3-CN—Ph | H | Me | MeO | —CH₂— | 3-c-Pr—Ph | H |
| Me | MeO | —CH₂— | 2-CN—Ph | H | Me | MeO | —CH₂— | 2-c-Pr—Ph | H |
| Me | MeO | —CH₂— | 4-CF₃—Ph | H | Me | MeO | —CH₂— | 4-CF₃O—Ph | H |
| Me | MeO | —CH₂— | 3-CF₃—Ph | H | Me | MeO | —CH₂— | 3-CF₃O—Ph | H |
| Me | MeO | —CH₂— | 2-CF₃—Ph | H | Me | MeO | —CH₂— | 2-CF₃O—Ph | H |
| Me | MeO | —CH₂— | 4-Ac—Ph | H | Me | MeO | —CH₂— | 2-(CF₃C=O)—Ph | H |
| Me | MeO | —CH₂— | 3-Ac—Ph | H | Me | MeO | —CH₂— | 3-(CF₃C=O)—Ph | H |
| Me | MeO | —CH₂— | 2-Ac—Ph | H | Me | MeO | —CH₂— | 5-(CF₃C=O)—Ph | H |
| Me | MeO | —CH₂— | 4-MeO—Ph | H | Me | MeO | —CH₂— | 4-EtO—Ph | H |
| Me | MeO | —CH₂— | 3-MeO—Ph | H | Me | MeO | —CH₂— | 3-EtO—Ph | H |
| Me | MeO | —CH₂— | 2-MeO—Ph | H | Me | MeO | —CH₂— | 2-EtO—Ph | H |
| Me | MeO | —CH₂— | 4-i-PrO—Ph | H | Me | MeO | —CH₂— | 4-NO₂—Ph | H |
| Me | MeO | —CH₂— | 3-i-PrO—Ph | H | Me | MeO | —CH₂— | 3-NO₂—Ph | H |
| Me | MeO | —CH₂— | 2-i-PrO—Ph | H | Me | MeO | —CH₂— | 2-NO₂—Ph | H |
| Me | MeO | —CH₂— | 4-Cl-benzyl | H | Me | MeO | —CH₂— | 4-F-benzyl | H |
| Me | MeO | —CH₂— | 3-Cl-benzyl | H | Me | MeO | —CH₂— | 3-F-benzyl | H |

TABLE 5-continued

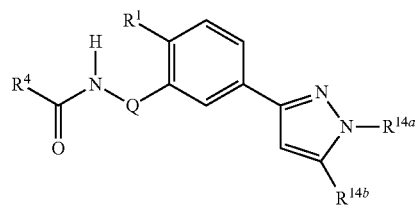

| R$^1$ | R$^4$ | Q | R$^{14a}$ | R$^{14b}$ | R$^1$ | R$^4$ | Q | R$^{14a}$ | R$^{14b}$ |
|---|---|---|---|---|---|---|---|---|---|
| Me | MeO | —CH$_2$— | 2-Cl-benzyl | H | Me | MeO | —CH$_2$— | 2-F-benzyl | H |
| Me | MeO | —CH$_2$— | 4-Br-benzyl | H | Me | MeO | —CH$_2$— | 4-Me-benzyl | H |
| Me | MeO | —CH$_2$— | 3-Br-benzyl | H | Me | MeO | —CH$_2$— | 3-Me-benzyl | H |
| Me | MeO | —CH$_2$— | 2-Br-benzyl | H | Me | MeO | —CH$_2$— | 2-Me-benzyl | H |
| Me | MeO | —CH$_2$— | 4-Et-benzyl | H | Me | MeO | —CH$_2$— | 4-i-Pr-benzyl | H |
| Me | MeO | —CH$_2$— | 3-Et-benzyl | H | Me | MeO | —CH$_2$— | 3-i-Pr-benzyl | H |
| Me | MeO | —CH$_2$— | 2-Et-benzyl | H | Me | MeO | —CH$_2$— | 2-i-Pr-benzyl | H |
| Me | MeO | —CH$_2$— | 4-CN-benzyl | H | Me | MeO | —CH$_2$— | 4-c-Pr-benzyl | H |
| Me | MeO | —CH$_2$— | 3-CN-benzyl | H | Me | MeO | —CH$_2$— | 3-c-Pr-benzyl | H |
| Me | MeO | —CH$_2$— | 2-CN-benzyl | H | Me | MeO | —CH$_2$— | 2-c-Pr-benzyl | H |
| Me | MeO | —CH$_2$— | 4-CF$_3$-benzyl | H | Me | MeO | —CH$_2$— | 4-CF$_3$O-benzyl | H |
| Me | MeO | —CH$_2$— | 3-CF$_3$-benzyl | H | Me | MeO | —CH$_2$— | 3-CF$_3$O-benzyl | H |
| Me | MeO | —CH$_2$— | 2-CF$_3$-benzyl | H | Me | MeO | —CH$_2$— | 2-CF$_3$O-benzyl | H |
| Me | MeO | —CH$_2$— | 4-CHF$_2$-benzyl | H | Me | MeO | —CH$_2$— | 4-CHF$_2$O-benzyl | H |
| Me | MeO | —CH$_2$— | 3-CHF$_2$-benzyl | H | Me | MeO | —CH$_2$— | 3-CHF$_2$O-benzyl | H |
| Me | MeO | —CH$_2$— | 2-CHF$_2$-benzyl | H | Me | MeO | —CH$_2$— | 2-CHF$_2$O-benzyl | H |
| Me | MeO | —CH$_2$— | 4-Ac-benzyl | H | Me | MeO | —CH$_2$— | 2-(CF$_3$C=O)-benzyl | H |
| Me | MeO | —CH$_2$— | 3-Ac-benzyl | H | Me | MeO | —CH$_2$— | 3-(CF$_3$C=O)-benzyl | H |
| Me | MeO | —CH$_2$— | 2-Ac-benzyl | H | Me | MeO | —CH$_2$— | 5-(CF$_3$C=O)-benzyl | H |
| Me | MeO | —CH$_2$— | 4-MeO-benzyl | H | Me | MeO | —CH$_2$— | 4-EtO-benzyl | H |
| Me | MeO | —CH$_2$— | 3-MeO-benzyl | H | Me | MeO | —CH$_2$— | 3-EtO-benzyl | H |
| Me | MeO | —CH$_2$— | 2-MeO-benzyl | H | Me | MeO | —CH$_2$— | 2-EtO-benzyl | H |
| Me | MeO | —CH$_2$— | 4-i-PrO-benzyl | H | Me | MeO | —CH$_2$— | 4-NO$_2$-benzyl | H |
| Me | MeO | —CH$_2$— | 3-i-PrO-benzyl | H | Me | MeO | —CH$_2$— | 3-NO$_2$-benzyl | H |
| Me | MeO | —CH$_2$— | 2-i-PrO-benzyl | H | Me | MeO | —CH$_2$— | 2-NO$_2$-benzyl | H |
| Cl | MeO | —CH$_2$— | 4-Cl—Ph | Me | Cl | MeO | —CH$_2$— | 4-F—Ph | Me |
| Cl | MeO | —CH$_2$— | 3-Cl—Ph | Me | Cl | MeO | —CH$_2$— | 3-F—Ph | Me |
| Cl | MeO | —CH$_2$— | 2-Cl—Ph | Me | Cl | MeO | —CH$_2$— | 2-F—Ph | Me |
| Cl | MeO | —CH$_2$— | 4-Br—Ph | Me | Cl | MeO | —CH$_2$— | 4-Me—Ph | Me |
| Cl | MeO | —CH$_2$— | 3-Br—Ph | Me | Cl | MeO | —CH$_2$— | 3-Me—Ph | Me |
| Cl | MeO | —CH$_2$— | 2-Br—Ph | Me | Cl | MeO | —CH$_2$— | 2-Me—Ph | Me |
| Cl | MeO | —CH$_2$— | 4-Et—Ph | Me | Cl | MeO | —CH$_2$— | 4-i-Pr—Ph | Me |
| Cl | MeO | —CH$_2$— | 3-Et—Ph | Me | Cl | MeO | —CH$_2$— | 3-i-Pr—Ph | Me |
| Cl | MeO | —CH$_2$— | 2-Et—Ph | Me | Cl | MeO | —CH$_2$— | 2-i-Pr—Ph | Me |
| Cl | MeO | —CH$_2$— | 4-CN—Ph | Me | Cl | MeO | —CH$_2$— | 4-c-Pr—Ph | Me |
| Cl | MeO | —CH$_2$— | 3-CN—Ph | Me | Cl | MeO | —CH$_2$— | 3-c-Pr—Ph | Me |
| Cl | MeO | —CH$_2$— | 2-CN—Ph | Me | Cl | MeO | —CH$_2$— | 2-c-Pr—Ph | Me |
| Cl | MeO | —CH$_2$— | 4-CF$_3$—Ph | Me | Cl | MeO | —CH$_2$— | 4-CF$_3$O—Ph | Me |
| Cl | MeO | —CH$_2$— | 3-CF$_3$—Ph | Me | Cl | MeO | —CH$_2$— | 3-CF$_3$O—Ph | Me |
| Cl | MeO | —CH$_2$— | 2-CF$_3$—Ph | Me | Cl | MeO | —CH$_2$— | 2-CF$_3$O—Ph | Me |
| Cl | MeO | —CH$_2$— | 4-Ac—Ph | Me | Cl | MeO | —CH$_2$— | 2-(CF$_3$C=O)—Ph | Me |
| Cl | MeO | —CH$_2$— | 3-Ac—Ph | Me | Cl | MeO | —CH$_2$— | 3-(CF$_3$C=O)—Ph | Me |
| Cl | MeO | —CH$_2$— | 2-Ac—Ph | Me | Cl | MeO | —CH$_2$— | 5-(CF$_3$C=O)—Ph | Me |
| Cl | MeO | —CH$_2$— | 4-MeO—Ph | Me | Cl | MeO | —CH$_2$— | 4-EtO—Ph | Me |
| Cl | MeO | —CH$_2$— | 3-MeO—Ph | Me | Cl | MeO | —CH$_2$— | 3-EtO—Ph | Me |
| Cl | MeO | —CH$_2$— | 2-MeO—Ph | Me | Cl | MeO | —CH$_2$— | 2-EtO—Ph | Me |
| Cl | MeO | —CH$_2$— | 4-i-PrO—Ph | Me | Cl | MeO | —CH$_2$— | 4-NO$_2$—Ph | Me |
| Cl | MeO | —CH$_2$— | 3-i-PrO—Ph | Me | Cl | MeO | —CH$_2$— | 3-NO$_2$—Ph | Me |
| Cl | MeO | —CH$_2$— | 2-i-PrO—Ph | Me | Cl | MeO | —CH$_2$— | 2-NO$_2$—Ph | Me |
| Cl | MeO | —CH$_2$— | 4-Cl-benzyl | H | Cl | MeO | —CH$_2$— | 4-F benzyl | H |
| Cl | MeO | —CH$_2$— | 3-Cl-benzyl | H | Cl | MeO | —CH$_2$— | 3-F-benzyl | H |
| Cl | MeO | —CH$_2$— | 2-Cl-benzyl | H | Cl | MeO | —CH$_2$— | 2-F-benzyl | H |
| Cl | MeO | —CH$_2$— | 4-Br-benzyl | H | Cl | MeO | —CH$_2$— | 4-Me-benzyl | H |
| Cl | MeO | —CH$_2$— | 3-Br-benzyl | H | Cl | MeO | —CH$_2$— | 3-Me-benzyl | H |
| Cl | MeO | —CH$_2$— | 2-Br-benzyl | H | Cl | MeO | —CH$_2$— | 2-Me-benzyl | H |
| Cl | MeO | —CH$_2$— | 4-Et-benzyl | H | Cl | MeO | —CH$_2$— | 4-i-Pr-benzyl | H |
| Cl | MeO | —CH$_2$— | 3-Et-benzyl | H | Cl | MeO | —CH$_2$— | 3-i-Pr-benzyl | H |
| Cl | MeO | —CH$_2$— | 2-Et-benzyl | H | Cl | MeO | —CH$_2$— | 2-i-Pr-benzyl | H |
| Cl | MeO | —CH$_2$— | 4-CN-benzyl | H | Cl | MeO | —CH$_2$— | 4-c-Pr-benzyl | H |
| Cl | MeO | —CH$_2$— | 3-CN-benzyl | H | Cl | MeO | —CH$_2$— | 3-c-Pr-benzyl | H |
| Cl | MeO | —CH$_2$— | 2-CN-benzyl | H | Cl | MeO | —CH$_2$— | 2-c-Pr-benzyl | H |
| Cl | MeO | —CH$_2$— | 4-CF$_3$-benzyl | H | Cl | MeO | —CH$_2$— | 4-CF$_3$O-benzyl | H |
| Cl | MeO | —CH$_2$— | 3-CF$_3$-benzyl | H | Cl | MeO | —CH$_2$— | 3-CF$_3$O-benzyl | H |
| Cl | MeO | —CH$_2$— | 2-CF$_3$-benzyl | H | Cl | MeO | —CH$_2$— | 2-CF$_3$O-benzyl | H |
| Cl | MeO | —CH$_2$— | 4-CHF$_2$-benzyl | H | Cl | MeO | —CH$_2$— | 4-CHF$_2$O-benzyl | H |
| Cl | MeO | —CH$_2$— | 3-CHF$_2$-benzyl | H | Cl | MeO | —CH$_2$— | 3-CHF$_2$O-benzyl | H |
| Cl | MeO | —CH$_2$— | 2-CHF$_2$-benzyl | H | Cl | MeO | —CH$_2$— | 2-CHF$_2$O-benzyl | H |

TABLE 5-continued

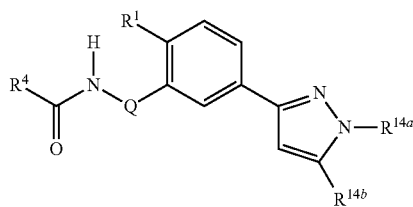

| R¹ | R⁴ | Q | R¹⁴ᵃ | R¹⁴ᵇ | R¹ | R⁴ | Q | R¹⁴ᵃ | R¹⁴ᵇ |
|---|---|---|---|---|---|---|---|---|---|
| Cl | MeO | —CH₂— | 4-Ac-benzyl | H | Cl | MeO | —CH₂— | 2-(CF₃C=O)-benzyl | H |
| Cl | MeO | —CH₂— | 3-Ac-benzyl | H | Cl | MeO | —CH₂— | 3-(CF₃C=O)-benzyl | H |
| Cl | MeO | —CH₂— | 2-Ac-benzyl | H | Cl | MeO | —CH₂— | 5-(CF₃C=O)-benzyl | H |
| Cl | MeO | —CH₂— | 4-MeO-benzyl | H | Cl | MeO | —CH₂— | 4-EtO-benzyl | H |
| Cl | MeO | —CH₂— | 3-MeO-benzyl | H | Cl | MeO | —CH₂— | 3-EtO-benzyl | H |
| Cl | MeO | —CH₂— | 2-MeO-benzyl | H | Cl | MeO | —CH₂— | 2-EtO-benzyl | H |
| Cl | MeNH | —CH₂— | 4-i-PrO-benzyl | H | Cl | MeNH | —CH₂— | 4-NO₂-benzyl | H |
| Cl | MeNH | —CH₂— | 3-i-PrO-benzyl | H | Cl | MeNH | —CH₂— | 3-NO₂-benzyl | H |
| Cl | MeNH | —CH₂— | 2-i-PrO-benzyl | H | Cl | MeNH | —CH₂— | 2-NO₂-benzyl | H |
| Cl | MeNH | —CH₂— | 4-Cl—Ph | H | Cl | MeNH | —CH₂— | 4-F—Ph | H |
| Cl | MeNH | —CH₂— | 3-Cl—Ph | H | Cl | MeNH | —CH₂— | 3-F—Ph | H |
| Cl | MeNH | —CH₂— | 2-Cl—Ph | H | Cl | MeNH | —CH₂— | 2-F—Ph | H |
| Cl | MeNH | —CH₂— | 4-Br—Ph | H | Cl | MeNH | —CH₂— | 4-Me—Ph | H |
| Cl | MeNH | —CH₂— | 3-Br—Ph | H | Cl | MeNH | —CH₂— | 3-Me—Ph | H |
| Cl | MeNH | —CH₂— | 2-Br—Ph | H | Cl | MeNH | —CH₂— | 2-Me—Ph | H |
| Cl | MeNH | —CH₂— | 4-Et—Ph | H | Cl | MeNH | —CH₂— | 4-i-Pr—Ph | H |
| Cl | MeNH | —CH₂— | 3-Et—Ph | H | Cl | MeNH | —CH₂— | 3-i-Pr—Ph | H |
| Cl | MeNH | —CH₂— | 2-Et—Ph | H | Cl | MeNH | —CH₂— | 2-i-Pr—Ph | H |
| Cl | MeNH | —CH₂— | 4-CN—Ph | H | Cl | MeNH | —CH₂— | 4-c-Pr—Ph | H |
| Cl | MeNH | —CH₂— | 3-CN—Ph | H | Cl | MeNH | —CH₂— | 3-c-Pr—Ph | H |
| Cl | MeNH | —CH₂— | 2-CN—Ph | H | Cl | MeNH | —CH₂— | 2-c-Pr—Ph | H |
| Cl | MeNH | —CH₂— | 4-CF₃—Ph | H | Cl | MeNH | —CH₂— | 4-CF₃O—Ph | H |
| Cl | MeNH | —CH₂— | 3-CF₃—Ph | H | Cl | MeNH | —CH₂— | 3-CF₃O—Ph | H |
| Cl | MeNH | —CH₂— | 2-CF₃—Ph | H | Cl | MeNH | —CH₂— | 2-CF₃O—Ph | H |
| Cl | MeNH | —CH₂— | 4-Ac—Ph | H | Cl | MeNH | —CH₂— | 2-(CF₃C=O)—Ph | H |
| Cl | MeNH | —CH₂— | 3-Ac—Ph | H | Cl | MeNH | —CH₂— | 3-(CF₃C=O)—Ph | H |
| Cl | MeNH | —CH₂— | 2-Ac—Ph | H | Cl | MeNH | —CH₂— | 5-(CF₃C=O)—Ph | H |
| Cl | MeNH | —CH₂— | 4-MeO—Ph | H | Cl | MeNH | —CH₂— | 4-EtO—Ph | H |
| Cl | MeNH | —CH₂— | 3-MeO—Ph | H | Cl | MeNH | —CH₂— | 3-EtO—Ph | H |
| Cl | MeNH | —CH₂— | 2-MeO—Ph | H | Cl | MeNH | —CH₂— | 2-EtO—Ph | H |
| Cl | MeNH | —CH₂— | 4-i-PrO—Ph | H | Cl | MeNH | —CH₂— | 4-NO₂—Ph | H |
| Cl | MeNH | —CH₂— | 3-i-PrO—Ph | H | Cl | MeNH | —CH₂— | 3-NO₂—Ph | H |
| Cl | MeNH | —CH₂— | 2-i-PrO—Ph | H | Cl | MeNH | —CH₂— | 2-NO₂—Ph | H |
| Cl | MeNH | —CH₂— | 4-Cl-benzyl | H | Cl | MeNH | —CH₂— | 4-F benzyl | H |
| Cl | MeNH | —CH₂— | 3-Cl-benzyl | H | Cl | MeNH | —CH₂— | 3-F-benzyl | H |
| Cl | MeNH | —CH₂— | 2-Cl-benzyl | H | Cl | MeNH | —CH₂— | 2-F-benzyl | H |
| Cl | MeNH | —CH₂— | 4-Br-benzyl | H | Cl | MeNH | —CH₂— | 4-Me-benzyl | H |
| Cl | MeNH | —CH₂— | 3-Br-benzyl | H | Cl | MeNH | —CH₂— | 3-Me-benzyl | H |
| Cl | MeNH | —CH₂— | 2-Br-benzyl | H | Cl | MeNH | —CH₂— | 2-Me-benzyl | H |
| Cl | MeNH | —CH₂— | 4-Et-benzyl | H | Cl | MeNH | —CH₂— | 4-i-Pr-benzyl | H |
| Cl | MeNH | —CH₂— | 3-Et-benzyl | H | Cl | MeNH | —CH₂— | 3-i-Pr-benzyl | H |
| Cl | MeNH | —CH₂— | 2-Et-benzyl | H | Cl | MeNH | —CH₂— | 2-i-Pr-benzyl | H |
| Cl | MeNH | —CH₂— | 4-CN-benzyl | H | Cl | MeNH | —CH₂— | 4-c-Pr-benzyl | H |
| Cl | MeNH | —CH₂— | 3-CN-benzyl | H | Cl | MeNH | —CH₂— | 3-c-Pr-benzyl | H |
| Cl | MeNH | —CH₂— | 2-CN-benzyl | H | Cl | MeNH | —CH₂— | 2-c-Pr-benzyl | H |
| Cl | MeNH | —CH₂— | 4-CF₃-benzyl | H | Cl | MeNH | —CH₂— | 4-CF₃O-benzyl | H |
| Cl | MeNH | —CH₂— | 3-CF₃-benzyl | H | Cl | MeNH | —CH₂— | 3-CF₃O-benzyl | H |
| Cl | MeNH | —CH₂— | 2-CF₃-benzyl | H | Cl | MeNH | —CH₂— | 2-CF₃O-benzyl | H |
| Cl | MeNH | —CH₂— | 4-CHF₂-benzyl | H | Cl | MeNH | —CH₂— | 4-CHF₂O benzyl | H |
| Cl | MeNH | —CH₂— | 3-CHF₂-benzyl | H | Cl | MeNH | —CH₂— | 3-CHF₂O-benzyl | H |
| Cl | MeNH | —CH₂— | 2-CHF₂-benzyl | H | Cl | MeNH | —CH₂— | 2-CHF₂O-benzyl | H |
| Cl | MeNH | —CH₂— | 4-Ac-benzyl | H | Cl | MeNH | —CH₂— | 2-(CF₃C=O)-benzyl | H |
| Cl | MeNH | —CH₂— | 3-Ac-benzyl | H | Cl | MeNH | —CH₂— | 3-(CF₃C=O)-benzyl | H |
| Cl | MeNH | —CH₂— | 2-Ac-benzyl | H | Cl | MeNH | —CH₂— | 5-(CF₃C=O)-benzyl | H |
| Cl | MeNH | —CH₂— | 4-MeO-benzyl | H | Cl | MeNH | —CH₂— | 4-EtO-benzyl | H |
| Cl | MeNH | —CH₂— | 3-MeO-benzyl | H | Cl | MeNH | —CH₂— | 3-EtO-benzyl | H |
| Cl | MeNH | —CH₂— | 2-MeO-benzyl | H | Cl | MeNH | —CH₂— | 2-EtO-benzyl | H |
| Cl | MeNH | —CH₂— | 4-i-PrO-benzyl | H | Cl | MeNH | —CH₂— | 4-NO₂-benzyl | H |
| Cl | MeNH | —CH₂— | 3-i-PrO-benzyl | H | Cl | MeNH | —CH₂— | 3-NO₂-benzyl | H |
| Cl | MeNH | —CH₂— | 2-i-PrO-benzyl | H | Cl | MeNH | —CH₂— | 2-NO₂-benzyl | H |

TABLE 6

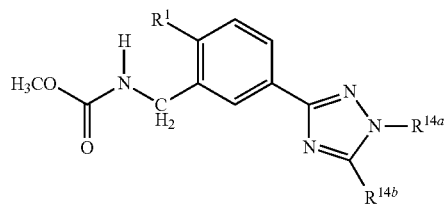
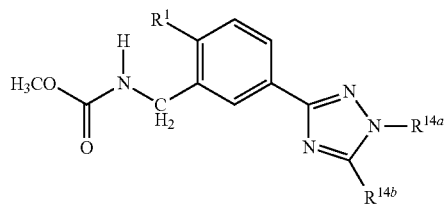

| $R^1$ | $R^{14a}$ | $R^{14b}$ | $R^1$ | $R^{14a}$ | $R^{14b}$ | $R^1$ | $R^{14a}$ | $R^{14b}$ | $R^1$ | $R^{14a}$ | $R^{14b}$ |
|---|---|---|---|---|---|---|---|---|---|---|---|
| Cl | 4-Cl—Ph | H | Cl | 4-F—Ph | H | Cl | 4-$CF_3$-pyrid-2-yl | H | Cl | 4-$CF_3$-pyrid-3-yl | H |
| Cl | 3-Cl—Ph | H | Cl | 3-F—Ph | H | Cl | 5-$CF_3$-pyrid-2-yl | H | Cl | 5-$CF_3$-pyrid-3-yl | H |
| Cl | 2-Cl—Ph | H | Cl | 2-F—Ph | H | Cl | 6-$CF_3$-pyrid-2-yl | H | Cl | 6-$CF_3$-pyrid-3-yl | H |
| Cl | 4-Br—Ph | H | Cl | 4-Me—Ph | H | Cl | 2-$CF_3$-pyrid-4-yl | H | Cl | 2-Me-pyrid-4-yl | H |
| Cl | 3-Br—Ph | H | Cl | 3-Me—Ph | H | Cl | 3-$CF_3$-pyrid-4-yl | H | Cl | 3-Me-pyrid-4-yl | H |
| Cl | 2-Br—Ph | H | Cl | 2-Me—Ph | H | Cl | 3-Me-pyrid-2-yl | H | Cl | 2-Me-pyrid-3-yl | H |
| Cl | 4-Et—Ph | H | Cl | 4-i-Pr—Ph | H | Cl | 4-Me-pyrid-2-yl | H | Cl | 4-Me-pyrid-3-yl | H |
| Cl | 3-Et—Ph | H | Cl | 3-i-Pr—Ph | H | Cl | 5-Me-pyrid-2-yl | H | Cl | 5-Me-pyrid-3-yl | H |
| Cl | 2-Et—Ph | H | Cl | 2-i-Pr—Ph | H | Cl | 6-Me-pyrid-2-yl | H | Cl | 6-Me-pyrid-3-yl | H |
| Cl | 4-CN—Ph | H | Cl | 4-c-Pr—Ph | H | Cl | 5-Cl-thien-2-yl | H | Cl | 5-F-thien-2-yl | H |
| Cl | 3-CN—Ph | H | Cl | 3-c-Pr—Ph | H | Cl | 4-Cl-thien-2-yl | H | Cl | 4-F-thien-2-yl | H |
| Cl | 2-CN—Ph | H | Cl | 2-c-Pr—Ph | H | Cl | 3-Cl-thien-2-yl | H | Cl | 3-F-thien-2-yl | H |
| Cl | 4-$CF_3$—Ph | H | Cl | 4-$CF_3$O—Ph | H | Cl | 5-$CF_3$-thien-2-yl | H | Cl | 5-$OCF_3$-thien-2-yl | H |
| Cl | 3-$CF_3$—Ph | H | Cl | 3-$CF_3$O—Ph | H | Cl | 4-$CF_3$-thien-2-yl | H | Cl | 4-$OCF_3$-thien-2-yl | H |
| Cl | 2-$CF_3$—Ph | H | Cl | 2-$CF_3$O—Ph | H | Cl | 3-$CF_3$-thien-2-yl | H | Cl | 3-$OCF_3$-thien-2-yl | H |
| Cl | 4-Ac—Ph | H | Cl | 2-($CF_3$C=O)—Ph | H | Cl | 5-Cl-thien-3-yl | H | Cl | 5-F-thien-3-yl | H |
| Cl | 3-Ac—Ph | H | Cl | 3-($CF_3$C=O)—Ph | H | Cl | 4-Cl-thien-3-yl | H | Cl | 4-F-thien-3-yl | H |
| Cl | 2-Ac—Ph | H | Cl | 4-($CF_3$C=O)—Ph | H | Cl | 2-Cl-thien-3-yl | H | Cl | 2-F-thien-3-yl | H |
| Cl | 4-MeO—Ph | H | Cl | 4-EtO—Ph | H | Cl | 5-$CF_3$-thien-3-yl | H | Cl | 5-$OCF_3$-thien-3-yl | H |
| Cl | 3-MeO—Ph | H | Cl | 3-EtO—Ph | H | Cl | 4-$CF_3$-thien-3-yl | H | Cl | 4-$OCF_3$-thien-3-yl | H |
| Cl | 2-MeO—Ph | H | Cl | 2-EtO—Ph | H | Cl | 2-$CF_3$-thien-3-yl | H | Cl | 2-$OCF_3$-thien-3-yl | H |
| Cl | 4-i-PrO—Ph | H | Cl | 4-$NO_2$—Ph | H | Cl | thien-2-yl | H | Cl | thien-3-yl | H |
| Cl | 3-i-PrO—Ph | H | Cl | 3-$NO_2$—Ph | H | Cl | 4-Cl-benzyl | H | Cl | 4-F-benzyl | H |
| Cl | 2-i-PrO—Ph | H | Cl | 2-$NO_2$—Ph | H | Cl | 3-Cl-benzyl | H | Cl | 3-F-benzyl | H |
| Cl | 4-I—Ph | H | Cl | 4-($CO_2$Me)—Ph | H | Cl | 2-Cl-benzyl | H | Cl | 2-F-benzyl | H |
| Cl | 3-I—Ph | H | Cl | 3-($CO_2$Me)—Ph | H | Cl | 4-Br-benzyl | H | Cl | 4-Me-benzyl | H |
| Cl | 2-I—Ph | H | Cl | 2-($CO_2$Me)—Ph | H | Cl | 3-Br-benzyl | H | Cl | 3-Me-benzyl | H |
| Cl | 4-Me(C=NH)—Ph | H | Cl | 4-Me(C=NMe)—Ph | H | Cl | 2-Br-benzyl | H | Cl | 2-Me-benzyl | H |
| Cl | 3-Me(C=NH)—Ph | H | Cl | 3-Me(C=NMe)—Ph | H | Cl | 4-Et-benzyl | H | Cl | 4-i-Pr-benzyl | H |
| Cl | 2-Me(C=NH)—Ph | H | Cl | 2-Me(C=NMe)—Ph | H | Cl | 3-Et-benzyl | H | Cl | 3-i-Pr-benzyl | H |
| Cl | 4-Me(C=NOMe)—Ph | H | Cl | 4-Me(C=NOEt)—Ph | H | Cl | 2-Et-benzyl | H | Cl | 2-i-Pr-benzyl | H |
| Cl | 3-Me(C=NOMe)—Ph | H | Cl | 3-Me(C=NOEt)—Ph | H | Cl | 4-CN-benzyl | H | Cl | 4-c-Pr-benzyl | H |
| Cl | 2-Me(C=NOMe)—Ph | H | Cl | 2-Me(C=NOEt)—Ph | H | Cl | 3-CN-benzyl | H | Cl | 3-c-Pr-benzyl | H |
| Cl | 4-MeNH(C=O)—Ph | H | Cl | 4-$SiMe_3$—Ph | H | Cl | 2-CN-benzyl | H | Cl | 2-c-Pr-benzyl | H |
| Cl | 3-MeNH(C=O)—Ph | H | Cl | 3-$SiMe_3$—Ph | H | Cl | 4-$CF_3$-benzyl | H | Cl | 4-$CF_3$O-benzyl | H |
| Cl | 2-MeNH(C=O)—Ph | H | Cl | 2-$SiMe_3$—Ph | H | Cl | 3-$CF_3$-benzyl | H | Cl | 3-$CF_3$O-benzyl | H |
| Cl | 2,6-di-Cl—Ph | H | Cl | 2,6-di-F—Ph | H | Cl | 2-$CF_3$-benzyl | H | Cl | 2-$CF_3$O-benzyl | H |
| Cl | 2,5-di-Cl—Ph | H | Cl | 2,5-di-F—Ph | H | Cl | 4-$CHF_2$-benzyl | H | Cl | 4-$CHF_2$O-benzyl | H |
| Cl | 2,4-di-Cl—Ph | H | Cl | 2,4-di-F—Ph | H | Cl | 3-$CHF_2$-benzyl | H | Cl | 3-$CHF_2$O-benzyl | H |
| Cl | 3,3-di-Cl—Ph | H | Cl | 3,3-di-F—Ph | H | Cl | 2-$CHF_2$-benzyl | H | Cl | 2-$CHF_2$O-benzyl | H |
| Cl | 3,4-di-Cl—Ph | H | Cl | 3,4-di-F—Ph | H | Cl | 4-Ac-benzyl | H | Cl | 2-($CF_3$C=O)-benzyl | H |
| Cl | 2,6-di-Me—Ph | H | Cl | 2,6-di-$CF_3$—Ph | H | Cl | 3-Ac-benzyl | H | Cl | 3-($CF_3$C=O)-benzyl | H |
| Cl | 2,5-di-Me—Ph | H | Cl | 2,5-di-$CF_3$—Ph | H | Cl | 2-Ac-benzyl | H | Cl | 5-($CF_3$C=O)-benzyl | H |
| Cl | 2,4-di-Me—Ph | H | Cl | 2,4-di-$CF_3$—Ph | H | Cl | 4-MeO-benzyl | H | Cl | 4-EtO-benzyl | H |
| Cl | 3,3-di-Me—Ph | H | Cl | 3,3-di-$CF_3$—Ph | H | Cl | 3-MeO-benzyl | H | Cl | 3-EtO-benzyl | H |
| Cl | 3,4-di-Me—Ph | H | Cl | 3,4-di-$CF_3$—Ph | H | Cl | 2-MeO-benzyl | H | Cl | 2-EtO-benzyl | H |
| Cl | 2,6-di-$CF_3$O—Ph | H | Cl | 2,6-di-MeO—Ph | H | Cl | 4-i-PrO-benzyl | H | Cl | 4-$NO_2$-benzyl | H |
| Cl | 2,5-di-$CF_3$O—Ph | H | Cl | 2,5-di-MeO—Ph | H | Cl | 3-i-PrO-benzyl | H | Cl | 3-$NO_2$-benzyl | H |
| Cl | 2,4-di-$CF_3$O—Ph | H | Cl | 2,4-di-MeO—Ph | H | Cl | 2-i-PrO-benzyl | H | Cl | 2-$NO_2$-benzyl | H |
| Cl | 3,3-di-$CF_3$O—Ph | H | Cl | 3,3-di-MeO—Ph | H | Cl | benzyl | H | Cl | phenethyl | H |
| Cl | 3,4-di-$CF_3$O—Ph | H | Cl | 3,4-di-MeO—Ph | H | Cl | methyl | H | Cl | ethyl | H |
| Cl | 4-$CHF_2$—Ph | H | Cl | 4-$CHF_2$O—Ph | H | Cl | n-propyl | H | Cl | n-butyl | H |
| Cl | 3-$CHF_2$—Ph | H | Cl | 3-$CHF_2$O—Ph | H | Cl | i-propyl | H | Cl | i-butyl | H |
| Cl | 2-$CHF_2$—Ph | H | Cl | 2-$CHF_2$O—Ph | H | Cl | c-propyl | H | Cl | c-butyl | H |
| Cl | 2-F-3-Cl—Ph | H | Cl | 2-F-3-$CF_3$—Ph | H | Cl | n-pentyl | H | Cl | s-butyl | H |
| Cl | 2-F-4-Cl—Ph | H | Cl | 2-F-4-$CF_3$—Ph | H | Cl | c-pentyl | H | Cl | n-hexyl | H |
| Cl | 2-F-5-Cl—Ph | H | Cl | 2-F-5-$CF_3$—Ph | H | Cl | n-heptyl | H | Cl | c-hexyl | H |
| Cl | 2-F-6-Cl—Ph | H | Cl | 2-F-6-$CF_3$—Ph | H | Cl | 1-naphthyl | H | Cl | 2-naphthyl | H |
| Cl | 3-F-2-Cl—Ph | H | Cl | 3-F-2-$CF_3$—Ph | H | Me | 4-Cl—Ph | H | Me | 4-F—Ph | H |
| Cl | 3-F-4-Cl—Ph | H | Cl | 3-F-4-$CF_3$—Ph | H | Me | 3-Cl—Ph | H | Me | 3-F—Ph | H |
| Cl | 3-F-5-Cl—Ph | H | Cl | 3-F-5-$CF_3$—Ph | H | Me | 2-Cl—Ph | H | Me | 2-F—Ph | H |
| Cl | 3-F-6-Cl—Ph | H | Cl | 3-F-6-$CF_3$—Ph | H | Me | 4-Br—Ph | H | Me | 4-Me—Ph | H |
| Cl | 4-F-3-Cl—Ph | H | Cl | 4-F-3-$CF_3$—Ph | H | Me | 3-Br—Ph | H | Me | 3-Me—Ph | H |
| Cl | 4-F-2-Cl—Ph | H | Cl | 4-F-2-$CF_3$—Ph | H | Me | 2-Br—Ph | H | Me | 2-Me—Ph | H |
| Cl | pyrid-2-yl | H | Cl | pyrid-3-yl | H | Me | 4-Et—Ph | H | Me | 4-i-Pr—Ph | H |
| Cl | pyrid-4-yl | H | Cl | triazin-1-yl | H | Me | 3-Et—Ph | H | Me | 3-i-Pr—Ph | H |
| Cl | 3-$CF_3$-pyrid-2-yl | H | Cl | 2-$CF_3$-pyrid-3-yl | H | Me | 2-Et—Ph | H | Me | 2-i-Pr—Ph | H |

TABLE 6-continued

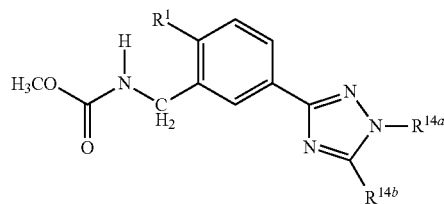

| R¹ | R¹⁴ᵃ | R¹⁴ᵇ | R¹ | R¹⁴ᵃ | R¹⁴ᵇ |
|---|---|---|---|---|---|
| Me | 4-CN—Ph | H | Me | 4-c-Pr—Ph | H |
| Me | 3-CN—Ph | H | Me | 3-c-Pr—Ph | H |
| Me | 2-CN—Ph | H | Me | 2-c-Pr—Ph | H |
| Me | 4-CF₃—Ph | H | Me | 4-CF₃O—Ph | H |
| Me | 3-CF₃—Ph | H | Me | 3-CF₃O—Ph | H |
| Me | 2-CF₃—Ph | H | Me | 2-CF₃O—Ph | H |
| Me | 4-Ac—Ph | H | Me | 2-(CF₃C=O)—Ph | H |
| Me | 3-Ac—Ph | H | Me | 3-(CF₃C=O)—Ph | H |
| Me | 2-Ac—Ph | H | Me | 4-(CF₃C=O)—Ph | H |
| Me | 4-MeO—Ph | H | Me | 4-EtO—Ph | H |
| Me | 3-MeO—Ph | H | Me | 3-EtO—Ph | H |
| Me | 2-MeO—Ph | H | Me | 2-EtO—Ph | H |
| Me | 4-i-PrO—Ph | H | Me | 4-NO₂—Ph | H |
| Me | 3-i-PrO—Ph | H | Me | 3-NO₂—Ph | H |
| Me | 2-i-PrO—Ph | H | Me | 2-NO₂—Ph | H |
| Me | 4-Cl-benzyl | H | Me | 4-F-benzyl | H |
| Me | 3-Cl-benzyl | H | Me | 3-F-benzyl | H |
| Me | 2-Cl-benzyl | H | Me | 2-F-benzyl | H |
| Me | 4-Br-benzyl | H | Me | 4-Me-benzyl | H |
| Me | 3-Br-benzyl | H | Me | 3-Me-benzyl | H |
| Me | 2-Br-benzyl | H | Me | 2-Me-benzyl | H |
| Me | 4-Et-benzyl | H | Me | 4-i-Pr-benzyl | H |
| Me | 3-Et-benzyl | H | Me | 3-i-Pr-benzyl | H |
| Me | 2-Et-benzyl | H | Me | 2-i-Pr-benzyl | H |
| Me | 4-CN-benzyl | H | Me | 4-c-Pr-benzyl | H |
| Me | 3-CN-benzyl | H | Me | 3-c-Pr-benzyl | H |
| Me | 2-CN-benzyl | H | Me | 2-c-Pr-benzyl | H |
| Me | 4-CF₃-benzyl | H | Me | 4-CF₃O-benzyl | H |
| Me | 3-CF₃-benzyl | H | Me | 3-CF₃O-benzyl | H |
| Me | 2-CF₃-benzyl | H | Me | 2-CF₃O-benzyl | H |
| Me | 4-CHF₂-benzyl | H | Me | 4-CHF₂O-benzyl | H |
| Me | 3-CHF₂-benzyl | H | Me | 3-CHF₂O-benzyl | H |
| Me | 2-CHF₂-benzyl | H | Me | 2-CHF₂O-benzyl | H |
| Me | 4-Ac-benzyl | H | Me | 2-(CF₃C=O)-benzyl | H |
| Me | 3-Ac-benzyl | H | Me | 3-(CF₃C=O)-benzyl | H |
| Me | 2-Ac-benzyl | H | Me | 5-(CF₃C=O)-benzyl | H |
| Me | 4-MeO-benzyl | H | Me | 4-EtO-benzyl | H |
| Me | 3-MeO-benzyl | H | Me | 3-EtO-benzyl | H |
| Me | 2-MeO-benzyl | H | Me | 2-EtO-benzyl | H |
| Me | 4-i-PrO-benzyl | H | Me | 4-NO₂-benzyl | H |
| Me | 3-i-PrO-benzyl | H | Me | 3-NO₂-benzyl | H |
| Me | 2-i-PrO-benzyl | H | Me | 2-NO₂-benzyl | H |
| Me | 4-Cl—Ph | Me | Me | 4-F—Ph | Me |
| Me | 3-Cl—Ph | Me | Me | 3-F—Ph | Me |
| Me | 2-Cl—Ph | Me | Me | 2-F—Ph | Me |
| Me | 4-Br—Ph | Me | Me | 4-Me—Ph | Me |
| Me | 3-Br—Ph | Me | Me | 3-Me—Ph | Me |
| Me | 2-Br—Ph | Me | Me | 2-Me—Ph | Me |
| Me | 4-Et—Ph | Me | Me | 4-i-Pr—Ph | Me |
| Me | 3-Et—Ph | Me | Me | 3-i-Pr—Ph | Me |
| Me | 2-Et—Ph | Me | Me | 2-i-Pr—Ph | Me |
| Me | 4-CN—Ph | Me | Me | 4-c-Pr—Ph | Me |
| Me | 3-CN—Ph | Me | Me | 3-c-Pr—Ph | Me |
| Me | 2-CN—Ph | Me | Me | 2-c-Pr—Ph | Me |
| Me | 4-CF₃—Ph | Me | Me | 4-CF₃O—Ph | Me |
| Me | 3-CF₃—Ph | Me | Me | 3-CF₃O—Ph | Me |
| Me | 2-CF₃—Ph | Me | Me | 2-CF₃O—Ph | Me |
| Me | 4-Ac—Ph | Me | Me | 2-(CF₃C=O)—Ph | Me |
| Me | 3-Ac—Ph | Me | Me | 3-(CF₃C=O)—Ph | Me |
| Me | 2-Ac—Ph | Me | Me | 4-(CF₃C=O)—Ph | Me |
| Me | 4-MeO—Ph | Me | Me | 4-EtO—Ph | Me |
| Me | 3-MeO—Ph | Me | Me | 3-EtO—Ph | Me |
| Me | 2-MeO—Ph | Me | Me | 2-EtO—Ph | Me |
| Me | 4-i-PrO—Ph | Me | Me | 4-NO₂—Ph | Me |
| Me | 3-i-PrO—Ph | Me | Me | 3-NO₂—Ph | Me |
| Me | 2-i-PrO—Ph | Me | Me | 2-NO₂—Ph | Me |
| Me | 4-Cl-benzyl | Me | Me | 4-F-benzyl | Me |

TABLE 6-continued

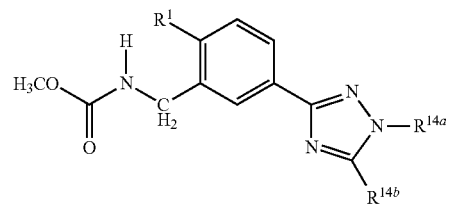

| R¹ | R¹⁴ᵃ | R¹⁴ᵇ | R¹ | R¹⁴ᵃ | R¹⁴ᵇ |
|---|---|---|---|---|---|
| Me | 3-Cl-benzyl | Me | Me | 3-F-benzyl | Me |
| Me | 2-Cl-benzyl | Me | Me | 2-F-benzyl | Me |
| Me | 4-Br-benzyl | Me | Me | 4-Me-benzyl | Me |
| Me | 3-Br-benzyl | Me | Me | 3-Me-benzyl | Me |
| Me | 2-Br-benzyl | Me | Me | 2-Me-benzyl | Me |
| Me | 4-Et-benzyl | Me | Me | 4-i-Pr-benzyl | Me |
| Me | 3-Et-benzyl | Me | Me | 3-i-Pr-benzyl | Me |
| Me | 2-Et-benzyl | Me | Me | 2-i-Pr-benzyl | Me |
| Me | 4-CN-benzyl | Me | Me | 4-c-Pr-benzyl | Me |
| Me | 3-CN-benzyl | Me | Me | 3-c-Pr-benzyl | Me |
| Me | 2-CN-benzyl | Me | Me | 2-c-Pr-benzyl | Me |
| Me | 4-CF₃-benzyl | Me | Me | 4-CF₃O-benzyl | Me |
| Me | 3-CF₃-benzyl | Me | Me | 3-CF₃O-benzyl | Me |
| Me | 2-CF₃-benzyl | Me | Me | 2-CF₃O-benzyl | Me |
| Me | 4-CHF₂-benzyl | Me | Me | 4-CHF₂O-benzyl | Me |
| Me | 3-CHF₂-benzyl | Me | Me | 3-CHF₂O-benzyl | Me |
| Me | 2-CHF₂-benzyl | Me | Me | 2-CHF₂O-benzyl | Me |
| Me | 4-Ac-benzyl | Me | Me | 2-(CF₃C=O)-benzyl | Me |
| Me | 3-Ac-benzyl | Me | Me | 3-(CF₃C=O)-benzyl | Me |
| Me | 2-Ac-benzyl | Me | Me | 5-(CF₃C=O)-benzyl | Me |
| Me | 4-MeO-benzyl | Me | Me | 4-EtO-benzyl | Me |
| Me | 3-MeO-benzyl | Me | Me | 3-EtO-benzyl | Me |
| Me | 2-MeO-benzyl | Me | Me | 2-EtO-benzyl | Me |
| Me | 4-i-PrO-benzyl | Me | Me | 4-NO₂-benzyl | Me |
| Me | 3-i-PrO-benzyl | Me | Me | 3-NO₂-benzyl | Me |
| Me | 2-i-PrO-benzyl | Me | Me | 2-NO₂-benzyl | Me |

TABLE 7

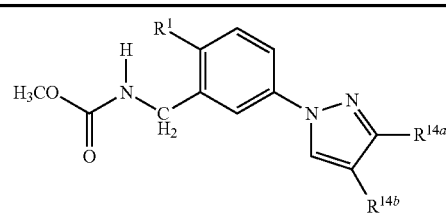

| R¹ | R¹⁴ᵃ | R¹⁴ᵇ | R¹ | R¹⁴ᵃ | R¹⁴ᵇ |
|---|---|---|---|---|---|
| Cl | 4-Cl—Ph | H | Cl | 4-F—Ph | H |
| Cl | 3-Cl—Ph | H | Cl | 3-F—Ph | H |
| Cl | 2-Cl—Ph | H | Cl | 2-F—Ph | H |
| Cl | 4-Br—Ph | H | Cl | 4-Me—Ph | H |
| Cl | 3-Br—Ph | H | Cl | 3-Me—Ph | H |
| Cl | 2-Br—Ph | H | Cl | 2-Me—Ph | H |
| Cl | 4-Et—Ph | H | Cl | 4-i-Pr—Ph | H |
| Cl | 3-Et—Ph | H | Cl | 3-i-Pr—Ph | H |
| Cl | 2-Et—Ph | H | Cl | 2-i-Pr—Ph | H |
| Cl | 4-CN—Ph | H | Cl | 4-c-Pr—Ph | H |
| Cl | 3-CN—Ph | H | Cl | 3-c-Pr—Ph | H |
| Cl | 2-CN—Ph | H | Cl | 2-c-Pr—Ph | H |
| Cl | 4-CF₃—Ph | H | Cl | 4-CF₃O—Ph | H |
| Cl | 3-CF₃—Ph | H | Cl | 3-CF₃O—Ph | H |
| Cl | 2-CF₃—Ph | H | Cl | 2-CF₃O—Ph | H |
| Cl | 4-Ac—Ph | H | Cl | 2-(CF₃C=O)—Ph | H |
| Cl | 3-Ac—Ph | H | Cl | 3-(CF₃C=O)—Ph | H |
| Cl | 2-Ac—Ph | H | Cl | 4-(CF₃C=O)—Ph | H |
| Cl | 4-MeO—Ph | H | Cl | 4-EtO—Ph | H |
| Cl | 3-MeO—Ph | H | Cl | 3-EtO—Ph | H |
| Cl | 2-MeO—Ph | H | Cl | 2-EtO—Ph | H |
| Cl | 4-i-PrO—Ph | H | Cl | 4-NO₂—Ph | H |
| Cl | 3-i-PrO—Ph | H | Cl | 3-NO₂—Ph | H |

TABLE 7-continued

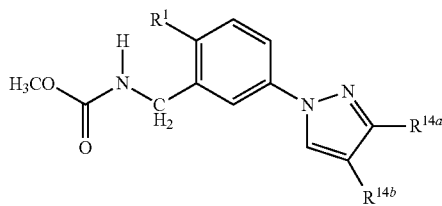

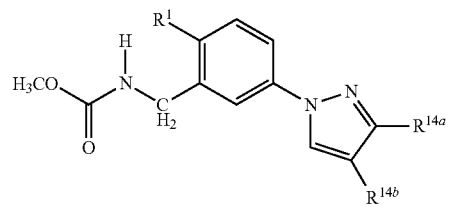

| R¹ | R¹⁴ᵃ | R¹⁴ᵇ | R¹ | R¹⁴ᵃ | R¹⁴ᵇ | R¹ | R¹⁴ᵃ | R¹⁴ᵇ | R¹ | R¹⁴ᵃ | R¹⁴ᵇ |
|---|---|---|---|---|---|---|---|---|---|---|---|
| Cl | 2-i-PrO—Ph | H | Cl | 2-NO₂—Ph | H | Cl | 3-Cl-benzyl | H | Cl | 3-F-benzyl | H |
| Cl | 4-I—Ph | H | Cl | 4-(CO₂Me)—Ph | H | Cl | 2-Cl-benzyl | H | Cl | 2-F-benzyl | H |
| Cl | 3-I—Ph | H | Cl | 3-(CO₂Me)—Ph | H | Cl | 4-Br-benzyl | H | Cl | 4-Me-benzyl | H |
| Cl | 2-I—Ph | H | Cl | 2-(CO₂Me)—Ph | H | Cl | 3-Br-benzyl | H | Cl | 3-Me-benzyl | H |
| Cl | 4-Me(C=NH)—Ph | H | Cl | 4-Me(C=NMe)—Ph | H | Cl | 2-Br-benzyl | H | Cl | 2-Me-benzyl | H |
| Cl | 3-Me(C=NH)—Ph | H | Cl | 3-Me(C=NMe)—Ph | H | Cl | 4-Et-benzyl | H | Cl | 4-i-Pr-benzyl | H |
| Cl | 2-Me(C=NH)—Ph | H | Cl | 2-Me(C=NMe)—Ph | H | Cl | 3-Et-benzyl | H | Cl | 3-i-Pr-benzyl | H |
| Cl | 4-Me(C=NOMe)—Ph | H | Cl | 4-Me(C=NOEt)—Ph | H | Cl | 2-Et-benzyl | H | Cl | 2-i-Pr-benzyl | H |
| Cl | 3-Me(C=NOMe)—Ph | H | Cl | 3-Me(C=NOEt)—Ph | H | Cl | 4-CN-benzyl | H | Cl | 4-c-Pr-benzyl | H |
| Cl | 2-Me(C=NOMe)—Ph | H | Cl | 2-Me(C=NOEt)—Ph | H | Cl | 3-CN-benzyl | H | Cl | 3-c-Pr-benzyl | H |
| Cl | 4-MeNH(C=O)—Ph | H | Cl | 4-SiMe₃—Ph | H | Cl | 2-CN-benzyl | H | Cl | 2-c-Pr-benzyl | H |
| Cl | 3- MeNH(C=O)—Ph | H | Cl | 3-SiMe₃—Ph | H | Cl | 4-CF₃-benzyl | H | Cl | 4-CF₃O-benzyl | H |
| Cl | 2- MeNH(C=O)—Ph | H | Cl | 2-SiMe₃—Ph | H | Cl | 3-CF₃-benzyl | H | Cl | 3-CF₃O-benzyl | H |
| Cl | 2,6-di-Cl—Ph | H | Cl | 2,6-di-F—Ph | H | Cl | 2-CF₃-benzyl | H | Cl | 2-CF₃O-benzyl | H |
| Cl | 2,5-di-Cl—Ph | H | Cl | 2,5-di-F—Ph | H | Cl | 4-CHF₂-benzyl | H | Cl | 4-CHF₂O-benzyl | H |
| Cl | 2,4-di-Cl—Ph | H | Cl | 2,4-di-F—Ph | H | Cl | 3-CHF₂-benzyl | H | Cl | 3-CHF₂O-benzyl | H |
| Cl | 3,3-di-Cl—Ph | H | Cl | 3,3-di-F—Ph | H | Cl | 2-CHF₂-benzyl | H | Cl | 2-CHF₂O-benzyl | H |
| Cl | 3,4-di-Cl—Ph | H | Cl | 3,4-di-F—Ph | H | Cl | 4-Ac-benzyl | H | Cl | 2-(CF₃C=O)-benzyl | H |
| Cl | 2,6-di-Me—Ph | H | Cl | 2,6-di-CF₃—Ph | H | Cl | 3-Ac-benzyl | H | Cl | 3-(CF₃C=O)-benzyl | H |
| Cl | 2,5-di-Me—Ph | H | Cl | 2,5-di-CF₃—Ph | H | Cl | 2-Ac-benzyl | H | Cl | 5-(CF₃C=O)-benzyl | H |
| Cl | 2,4-di-Me—Ph | H | Cl | 2,4-di-CF₃—Ph | H | Cl | 4-MeO-benzyl | H | Cl | 4-EtO-benzyl | H |
| Cl | 3,3-di-Me—Ph | H | Cl | 3,3-di-CF₃—Ph | H | Cl | 3-MeO-benzyl | H | Cl | 3-EtO-benzyl | H |
| Cl | 3,4-di-Me—Ph | H | Cl | 3,4-di-CF₃—Ph | H | Cl | 2-MeO-benzyl | H | Cl | 2-EtO-benzyl | H |
| Cl | 2,6-di-CF₃O—Ph | H | Cl | 2,6-di-MeO—Ph | H | Cl | 4-i-PrO-benzyl | H | Cl | 4-NO₂-benzyl | H |
| Cl | 2,5-di-CF₃O—Ph | H | Cl | 2,5-di-MeO—Ph | H | Cl | 3-i-PrO-benzyl | H | Cl | 3-NO₂-benzyl | H |
| Cl | 2,4-di-CF₃O—Ph | H | Cl | 2,4-di-MeO—Ph | H | Cl | 2-i-PrO-benzyl | H | Cl | 2-NO₂-benzyl | H |
| Cl | 3,3-di-CF₃O—Ph | H | Cl | 3,3-di-MeO—Ph | H | Cl | benzyl | H | Cl | phenethyl | H |
| Cl | 3,4-di-CF₃O—Ph | H | Cl | 3,4-di-MeO—Ph | H | Cl | methyl | H | Cl | ethyl | H |
| Cl | 4-CHF₂—Ph | H | Cl | 4-CHF₂O—Ph | H | Cl | n-propyl | H | Cl | n-butyl | H |
| Cl | 3-CHF₂—Ph | H | Cl | 3-CHF₂O—Ph | H | Cl | i-propyl | H | Cl | i-butyl | H |
| Cl | 2-CHF₂—Ph | H | Cl | 2-CHF₂O—Ph | H | Cl | c-propyl | H | Cl | c-butyl | H |
| Cl | 2-F-3-Cl—Ph | H | Cl | 2-F-3-CF₃—Ph | H | Cl | n-pentyl | H | Cl | s-butyl | H |
| Cl | 2-F-4-Cl—Ph | H | Cl | 2-F-4-CF₃—Ph | H | Cl | c-pentyl | H | Cl | n-hexyl | H |
| Cl | 2-F-5-Cl—Ph | H | Cl | 2-F-5-CF₃—Ph | H | Cl | n-heptyl | H | Cl | c-hexyl | H |
| Cl | 2-F-6-Cl—Ph | H | Cl | 2-F-6-CF₃—Ph | H | Cl | 1-naphthyl | H | Cl | 2-naphthyl | H |
| Cl | 3-F-2-Cl—Ph | H | Cl | 3-F-2-CF₃—Ph | H | Me | 4-Cl—Ph | H | Me | 4-F—Ph | H |
| Cl | 3-F-4-Cl—Ph | H | Cl | 3-F-4-CF₃—Ph | H | Me | 3-Cl—Ph | H | Me | 3-F—Ph | H |
| Cl | 3-F-5-Cl—Ph | H | Cl | 3-F-5-CF₃—Ph | H | Me | 2-Cl—Ph | H | Me | 2-F—Ph | H |
| Cl | 3-F-6-Cl—Ph | H | Cl | 3-F-6-CF₃—Ph | H | Me | 4-Br—Ph | H | Me | 4-Me—Ph | H |
| Cl | 4-F-3-Cl—Ph | H | Cl | 4-F-3-CF₃—Ph | H | Me | 3-Br—Ph | H | Me | 3-Me—Ph | H |
| Cl | 4-F-2-Cl—Ph | H | Cl | 4-F-2-CF₃—Ph | H | Me | 2-Br—Ph | H | Me | 2-Me—Ph | H |
| Cl | pyrid-2-yl | H | Cl | pyrid-3-yl | H | Me | 4-Et—Ph | H | Me | 4-i-Pr—Ph | H |
| Cl | pyrid-4-yl | H | Cl | triazin-1-yl | H | Me | 3-Et—Ph | H | Me | 3-i-Pr—Ph | H |
| Cl | 3-CF₃-pyrid-2-yl | H | Cl | 2-CF₃-pyrid-3-yl | H | Me | 2-Et—Ph | H | Me | 2-i-Pr—Ph | H |
| Cl | 4-CF₃-pyrid-2-yl | H | Cl | 4-CF₃-pyrid-3-yl | H | Me | 4-CN—Ph | H | Me | 4-c-Pr—Ph | H |
| Cl | 5-CF₃-pyrid-2-yl | H | Cl | 5-CF₃-pyrid-3-yl | H | Me | 3-CN—Ph | H | Me | 3-c-Pr—Ph | H |
| Cl | 6-CF₃-pyrid-2-yl | H | Cl | 6-CF₃-pyrid-3-yl | H | Me | 2-CN—Ph | H | Me | 2-c-Pr—Ph | H |
| Cl | 2-CF₃-pyrid-4-yl | H | Cl | 2-Me-pyrid-4-yl | H | Me | 4-CF₃—Ph | H | Me | 4-CF₃O—Ph | H |
| Cl | 3-CF₃-pyrid-4-yl | H | Cl | 3-Me-pyrid-4-yl | H | Me | 3-CF₃—Ph | H | Me | 3-CF₃O—Ph | H |
| Cl | 3-Me-pyrid-2-yl | H | Cl | 2-Me-pyrid-3-yl | H | Me | 2-CF₃—Ph | H | Me | 2-CF₃O—Ph | H |
| Cl | 4-Me-pyrid-2-yl | H | Cl | 4-Me-pyrid-3-yl | H | Me | 4-Ac—Ph | H | Me | 2-(CF₃C=O)—Ph | H |
| Cl | 5-Me-pyrid-2-yl | H | Cl | 5-Me-pyrid-3-yl | H | Me | 3-Ac—Ph | H | Me | 3-(CF₃C=O)—Ph | H |
| Cl | 6-Me-pyrid-2-yl | H | Cl | 6-Me-pyrid-3-yl | H | Me | 2-Ac—Ph | H | Me | 4-(CF₃C=O)—Ph | H |
| Cl | 5-Cl-thien-2-yl | H | Cl | 5-F-thien-2-yl | H | Me | 4-MeO—Ph | H | Me | 4-EtO—Ph | H |
| Cl | 4-Cl-thien-2-yl | H | Cl | 4-F-thien-2-yl | H | Me | 3-MeO—Ph | H | Me | 3-EtO—Ph | H |
| Cl | 3-Cl-thien-2-yl | H | Cl | 3-F-thien-2-yl | H | Me | 2-MeO—Ph | H | Me | 2-EtO—Ph | H |
| Cl | 5-CF₃-thien-2-yl | H | Cl | 5-OCF₃-thien-2-yl | H | Me | 4-i-PrO—Ph | H | Me | 4-NO₂—Ph | H |
| Cl | 4-CF₃-thien-2-yl | H | Cl | 4-OCF₃-thien-2-yl | H | Me | 3-i-PrO—Ph | H | Me | 3-NO₂—Ph | H |
| Cl | 3-CF₃-thien-2-yl | H | Cl | 3-OCF₃-thien-2-yl | H | Me | 2-i-PrO—Ph | H | Me | 2-NO₂—Ph | H |
| Cl | 5-Cl-thien-3-yl | H | Cl | 5-F-thien-3-yl | H | Me | 4-Cl-benzyl | H | Me | 4-F-benzyl | H |
| Cl | 4-Cl-thien-3-yl | H | Cl | 4-F-thien-3-yl | H | Me | 3-Cl-benzyl | H | Me | 3-F-benzyl | H |
| Cl | 2-Cl-thien-3-yl | H | Cl | 2-F-thien-3-yl | H | Me | 2-Cl-benzyl | H | Me | 2-F-benzyl | H |
| Cl | 5-CF₃-thien-3-yl | H | Cl | 5-OCF₃-thien-3-yl | H | Me | 4-Br-benzyl | H | Me | 4-Me-benzyl | H |
| Cl | 4-CF₃-thien-3-yl | H | Cl | 4-OCF₃-thien-3-yl | H | Me | 3-Br-benzyl | H | Me | 3-Me-benzyl | H |
| Cl | 2-CF₃-thien-3-yl | H | Cl | 2-OCF₃-thien-3-yl | H | Me | 2-Br-benzyl | H | Me | 2-Me-benzyl | H |
| Cl | thien-2-yl | H | Cl | thien-3-yl | H | Me | 4-Et-benzyl | H | Me | 4-i-Pr-benzyl | H |
| Cl | 4-Cl-benzyl | H | Cl | 4-F-benzyl | H | Me | 3-Et-benzyl | H | Me | 3-i-Pr-benzyl | H |

TABLE 7-continued

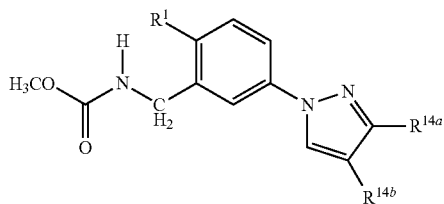

| R¹ | R¹⁴ᵃ | R¹⁴ᵇ | R¹ | R¹⁴ᵃ | R¹⁴ᵇ |
|---|---|---|---|---|---|
| Me | 2-Et-benzyl | H | Me | 2-i-Pr-benzyl | H |
| Me | 4-CN-benzyl | H | Me | 4-c-Pr-benzyl | H |
| Me | 3-CN-benzyl | H | Me | 3-c-Pr-benzyl | H |
| Me | 2-CN-benzyl | H | Me | 2-c-Pr-benzyl | H |
| Me | 4-CF₃-benzyl | H | Me | 4-CF₃O-benzyl | H |
| Me | 3-CF₃-benzyl | H | Me | 3-CF₃O-benzyl | H |
| Me | 2-CF₃-benzyl | H | Me | 2-CF₃O-benzyl | H |
| Me | 4-CHF₂-benzyl | H | Me | 4-CHF₂O-benzyl | H |
| Me | 3-CHF₂-benzyl | H | Me | 3-CHF₂O-benzyl | H |
| Me | 2-CHF₂-benzyl | H | Me | 2-CHF₂O-benzyl | H |
| Me | 4-Ac-benzyl | H | Me | 2-(CF₃C=O)-benzyl | H |
| Me | 3-Ac-benzyl | H | Me | 3-(CF₃C=O)-benzyl | H |
| Me | 2-Ac-benzyl | H | Me | 5-(CF₃C=O)-benzyl | H |
| Me | 4-MeO-benzyl | H | Me | 4-EtO-benzyl | H |
| Me | 3-MeO-benzyl | H | Me | 3-EtO-benzyl | H |
| Me | 2-MeO-benzyl | H | Me | 2-EtO-benzyl | H |
| Me | 4-i-PrO-benzyl | H | Me | 4-NO₂-benzyl | H |
| Me | 3-i-PrO-benzyl | H | Me | 3-NO₂-benzyl | H |
| Me | 2-i-PrO-benzyl | H | Me | 2-NO₂-benzyl | H |
| Me | 4-Cl—Ph | Me | Me | 4-F—Ph | Me |
| Me | 3-Cl—Ph | Me | Me | 3-F—Ph | Me |
| Me | 2-Cl—Ph | Me | Me | 2-F—Ph | Me |
| Me | 4-Br—Ph | Me | Me | 4-Me—Ph | Me |
| Me | 3-Br—Ph | Me | Me | 3-Me—Ph | Me |
| Me | 2-Br—Ph | Me | Me | 2-Me—Ph | Me |
| Me | 4-Et—Ph | Me | Me | 4-i-Pr—Ph | Me |
| Me | 3-Et—Ph | Me | Me | 3-i-Pr—Ph | Me |
| Me | 2-Et—Ph | Me | Me | 2-i-Pr—Ph | Me |
| Me | 4-CN—Ph | Me | Me | 4-c-Pr—Ph | Me |
| Me | 3-CN—Ph | Me | Me | 3-c-Pr—Ph | Me |
| Me | 2-CN—Ph | Me | Me | 2-c-Pr—Ph | Me |
| Me | 4-CF₃—Ph | Me | Me | 4-CF₃O—Ph | Me |
| Me | 3-CF₃—Ph | Me | Me | 3-CF₃O—Ph | Me |
| Me | 2-CF₃—Ph | Me | Me | 2-CF₃O—Ph | Me |
| Me | 4-Ac—Ph | Me | Me | 2-(CF₃C=O)—Ph | Me |
| Me | 3-Ac—Ph | Me | Me | 3-(CF₃C=O)—Ph | Me |
| Me | 2-Ac—Ph | Me | Me | 4-(CF₃C=O)—Ph | Me |
| Me | 4-MeO—Ph | Me | Me | 4-EtO—Ph | Me |
| Me | 3-MeO—Ph | Me | Me | 3-EtO—Ph | Me |
| Me | 2-MeO—Ph | Me | Me | 2-EtO—Ph | Me |
| Me | 4-i-PrO—Ph | Me | Me | 4-NO₂—Ph | Me |
| Me | 3-i-PrO—Ph | Me | Me | 3-NO₂—Ph | Me |
| Me | 2-i-PrO—Ph | Me | Me | 2-NO₂—Ph | Me |
| Me | 4-Cl-benzyl | Me | Me | 4-F-benzyl | Me |
| Me | 3-Cl-benzyl | Me | Me | 3-F-benzyl | Me |
| Me | 2-Cl-benzyl | Me | Me | 2-F-benzyl | Me |
| Me | 4-Br-benzyl | Me | Me | 4-Me-benzyl | Me |
| Me | 3-Br-benzyl | Me | Me | 3-Me-benzyl | Me |
| Me | 2-Br-benzyl | Me | Me | 2-Me-benzyl | Me |
| Me | 4-Et-benzyl | Me | Me | 4-i-Pr-benzyl | Me |
| Me | 3-Et-benzyl | Me | Me | 3-i-Pr-benzyl | Me |
| Me | 2-Et-benzyl | Me | Me | 2-i-Pr-benzyl | Me |
| Me | 4-CN-benzyl | Me | Me | 4-c-Pr-benzyl | Me |
| Me | 3-CN-benzyl | Me | Me | 3-c-Pr-benzyl | Me |
| Me | 2-CN-benzyl | Me | Me | 2-c-Pr-benzyl | Me |
| Me | 4-CF₃-benzyl | Me | Me | 4-CF₃O-benzyl | Me |
| Me | 3-CF₃-benzyl | Me | Me | 3-CF₃O-benzyl | Me |
| Me | 2-CF₃-benzyl | Me | Me | 2-CF₃O-benzyl | Me |
| Me | 4-CHF₂-benzyl | Me | Me | 4-CHF₂O-benzyl | Me |
| Me | 3-CHF₂-benzyl | Me | Me | 3-CHF₂O-benzyl | Me |
| Me | 2-CHF₂-benzyl | Me | Me | 2-CHF₂O-benzyl | Me |
| Me | 4-Ac-benzyl | Me | Me | 2-(CF₃C=O)-benzyl | Me |
| Me | 3-Ac-benzyl | Me | Me | 3-(CF₃C=O)-benzyl | Me |
| Me | 2-Ac-benzyl | Me | Me | 5-(CF₃C=O)-benzyl | Me |
| Me | 4-MeO-benzyl | Me | Me | 4-EtO-benzyl | Me |
| Me | 3-MeO-benzyl | Me | Me | 3-EtO-benzyl | Me |
| Me | 2-MeO-benzyl | Me | Me | 2-EtO-benzyl | Me |

TABLE 7-continued

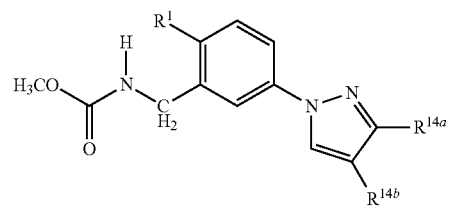

| R¹ | R¹⁴ᵃ | R¹⁴ᵇ | R¹ | R¹⁴ᵃ | R¹⁴ᵇ |
|---|---|---|---|---|---|
| Me | 4-i-PrO-benzyl | Me | Me | 4-NO₂-benzyl | Me |
| Me | 3-i-PrO-benzyl | Me | Me | 3-NO₂-benzyl | Me |
| Me | 2-i-PrO-benzyl | Me | Me | 2-NO₂-benzyl | Me |

TABLE 8

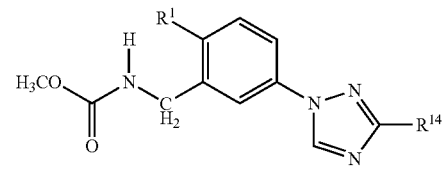

| R¹ | R¹⁴ | R¹ | R¹⁴ |
|---|---|---|---|
| Cl | 4-Cl—Ph | Cl | 4-F—Ph |
| Cl | 3-Cl—Ph | Cl | 3-F—Ph |
| Cl | 2-Cl—Ph | Cl | 2-F—Ph |
| Cl | 4-Br—Ph | Cl | 4-Me—Ph |
| Cl | 3-Br—Ph | Cl | 3-Me—Ph |
| Cl | 2-Br—Ph | Cl | 2-Me—Ph |
| Cl | 4-Et—Ph | Cl | 4-i-Pr—Ph |
| Cl | 3-Et—Ph | Cl | 3-i-Pr—Ph |
| Cl | 2-Et—Ph | Cl | 2-i-Pr—Ph |
| Cl | 4-CN—Ph | Cl | 4-c-Pr—Ph |
| Cl | 3-CN—Ph | Cl | 3-c-Pr—Ph |
| Cl | 2-CN—Ph | Cl | 2-c-Pr—Ph |
| Cl | 4-CF₃—Ph | Cl | 4-CF₃O—Ph |
| Cl | 3-CF₃—Ph | Cl | 3-CF₃O—Ph |
| Cl | 2-CF₃—Ph | Cl | 2-CF₃O—Ph |
| Cl | 4-Ac—Ph | Cl | 2-(CF₃C=O)—Ph |
| Cl | 3-Ac—Ph | Cl | 3-(CF₃C=O)—Ph |
| Cl | 2-Ac—Ph | Cl | 4-(CF₃C=O)—Ph |
| Cl | 4-MeO—Ph | Cl | 4-EtO—Ph |
| Cl | 3-MeO—Ph | Cl | 3-EtO—Ph |
| Cl | 2-MeO—Ph | Cl | 2-EtO—Ph |
| Cl | 4-i-PrO—Ph | Cl | 4-NO₂—Ph |
| Cl | 3-i-PrO—Ph | Cl | 3-NO₂—Ph |
| Cl | 2-i-PrO—Ph | Cl | 2-NO₂—Ph |
| Cl | 4-I—Ph | Cl | 4-(CO₂Me)—Ph |
| Cl | 3-I—Ph | Cl | 3-(CO₂Me)—Ph |
| Cl | 2-I—Ph | Cl | 2-(CO₂Me)—Ph |
| Cl | 4-Me(C=NH)—Ph | Cl | 4-Me(C=NMe)—Ph |
| Cl | 3-Me(C=NH)—Ph | Cl | 3-Me(C=NMe)—Ph |
| Cl | 2-Me(C=NH)—Ph | Cl | 2-Me(C=NMe)—Ph |
| Cl | 4-Me(C=NOMe)—Ph | Cl | 4-Me(C=NOEt)—Ph |
| Cl | 3-Me(C=NOMe)—Ph | Cl | 3-Me(C=NOEt)—Ph |
| Cl | 2-Me(C=NOMe)—Ph | Cl | 2-Me(C=NOEt)—Ph |
| Cl | 4-MeNH(C=O)—Ph | Cl | 4-SiMe₃—Ph |
| Cl | 3-MeNH(C=O)—Ph | Cl | 3-SiMe₃—Ph |
| Cl | 2-MeNH(C=O)—Ph | Cl | 2-SiMe₃—Ph |
| Cl | 2,6-di-Cl—Ph | Cl | 2,6-di-F—Ph |
| Cl | 2,5-di-Cl—Ph | Cl | 2,5-di-F—Ph |
| Cl | 2,4-di-Cl—Ph | Cl | 2,4-di-F—Ph |
| Cl | 3,3-di-Cl—Ph | Cl | 3,3-di-F—Ph |
| Cl | 3,4-di-Cl—Ph | Cl | 3,4-di-F—Ph |
| Cl | 2,6-di-Me—Ph | Cl | 2,6-di-CF₃—Ph |
| Cl | 2,5-di-Me—Ph | Cl | 2,5-di-CF₃—Ph |
| Cl | 2,4-di-Me—Ph | Cl | 2,4-di-CF₃—Ph |
| Cl | 3,3-di-Me—Ph | Cl | 3,3-di-CF₃—Ph |
| Cl | 3,4-di-Me—Ph | Cl | 3,4-di-CF₃—Ph |
| Cl | 2,6-di-CF₃O—Ph | Cl | 2,6-di-MeO—Ph |
| Cl | 2,5-di-CF₃O—Ph | Cl | 2,5-di-MeO—Ph |

TABLE 8-continued

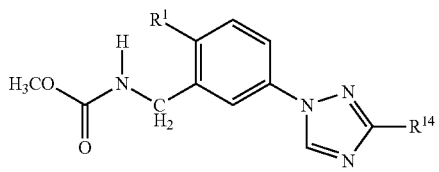

| $R^1$ | $R^{14}$ | $R^1$ | $R^{14}$ |
|---|---|---|---|
| Cl | 2,4-di-CF₃O—Ph | Cl | 2,4-di-MeO—Ph |
| Cl | 3,3-di-CF₃O—Ph | Cl | 3,3-di-MeO—Ph |
| Cl | 3,4-di-CF₃O—Ph | Cl | 3,4-di-MeO—Ph |
| Cl | 4-CHF₂—Ph | Cl | 4-CHF₂O—Ph |
| Cl | 3-CHF₂—Ph | Cl | 3-CHF₂O—Ph |
| Cl | 2-CHF₂—Ph | Cl | 2-CHF₂O—Ph |
| Cl | 2-F-3-Cl—Ph | Cl | 2-F-3-CF₃—Ph |
| Cl | 2-F-4-Cl—Ph | Cl | 2-F-4-CF₃—Ph |
| Cl | 2-F-5-Cl—Ph | Cl | 2-F-5-CF₃—Ph |
| Cl | 2-F-6-Cl—Ph | Cl | 2-F-6-CF₃—Ph |
| Cl | 3-F-2-Cl—Ph | Cl | 3-F-2-CF₃—Ph |
| Cl | 3-F-4-Cl—Ph | Cl | 3-F-4-CF₃—Ph |
| Cl | 3-F-5-Cl—Ph | Cl | 3-F-5-CF₃—Ph |
| Cl | 3-F-6-Cl—Ph | Cl | 3-F-6-CF₃—Ph |
| Cl | 4-F-3-Cl—Ph | Cl | 4-F-3-CF₃—Ph |
| Cl | 4-F-2-Cl—Ph | Cl | 4-F-2-CF₃—Ph |
| Cl | pyrid-2-yl | Cl | pyrid-3-yl |
| Cl | pyrid-4-yl | Cl | 2,4,6-triazin-1-yl |
| Cl | 3-CF₃-pyrid-2-yl | Cl | 2-CF₃-pyrid-3-yl |
| Cl | 4-CF₃-pyrid-2-yl | Cl | 4-CF₃-pyrid-3-yl |
| Cl | 5-CF₃-pyrid-2-yl | Cl | 5-CF₃-pyrid-3-yl |
| Cl | 6-CF₃-pyrid-2-yl | Cl | 6-CF₃-pyrid-3-yl |
| Cl | 2-CF₃-pyrid-4-yl | Cl | 2-Me-pyrid-4-yl |
| Cl | 3-CF₃-pyrid-4-yl | Cl | 3-Me-pyrid-4-yl |
| Cl | 3-Me-pyrid-2-yl | Cl | 2-Me-pyrid-3-yl |
| Cl | 4-Me-pyrid-2-yl | Cl | 4-Me-pyrid-3-yl |
| Cl | 5-Me-pyrid-2-yl | Cl | 5-Me-pyrid-3-yl |
| Cl | 6-Me-pyrid-2-yl | Cl | 6-Me-pyrid-3-yl |
| Cl | 5-Cl-thien-2-yl | Cl | 5-F-thien-2-yl |
| Cl | 4-Cl-thien-2-yl | Cl | 4-F-thien-2-yl |
| Cl | 3-Cl-thien-2-yl | Cl | 3-F-thien-2-yl |
| Cl | 5-CF₃-thien-2-yl | Cl | 5-OCF₃-thien-2-yl |
| Cl | 4-CF₃-thien-2-yl | Cl | 4-OCF₃-thien-2-yl |
| Cl | 3-CF₃-thien-2-yl | Cl | 3-OCF₃-thien-2-yl |
| Cl | 5-Cl-thien-3-yl | Cl | 5-F-thien-3-yl |
| Cl | 4-Cl-thien-3-yl | Cl | 4-F-thien-3-yl |
| Cl | 2-Cl-thien-3-yl | Cl | 2-F-thien-3-yl |
| Cl | 5-CF₃-thien-3-yl | Cl | 5-OCF₃-thien-3-yl |
| Cl | 4-CF₃-thien-3-yl | Cl | 4-OCF₃-thien-3-yl |
| Cl | 2-CF₃-thien-3-yl | Cl | 2-OCF₃-thien-3-yl |
| Cl | thien-2-yl | Cl | thien-3-yl |
| Cl | 4-Cl-benzyl | Cl | 4-F-benzyl |
| Cl | 3-Cl-benzyl | Cl | 3-F-benzyl |
| Cl | 2-Cl-benzyl | Cl | 2-F-benzyl |
| Cl | 4-Br-benzyl | Cl | 4-Me-benzyl |
| Cl | 3-Br-benzyl | Cl | 3-Me-benzyl |
| Cl | 2-Br-benzyl | Cl | 2-Me-benzyl |
| Cl | 4-Et-benzyl | Cl | 4-i-Pr-benzyl |
| Cl | 3-Et-benzyl | Cl | 3-i-Pr-benzyl |
| Cl | 2-Et-benzyl | Cl | 2-i-Pr-benzyl |
| Cl | 4-CN-benzyl | Cl | 4-c-Pr-benzyl |
| Cl | 3-CN-benzyl | Cl | 3-c-Pr-benzyl |
| Cl | 2-CN-benzyl | Cl | 2-c-Pr-benzyl |
| Cl | 4-CF₃-benzyl | Cl | 4-CF₃O-benzyl |
| Cl | 3-CF₃-benzyl | Cl | 3-CF₃O-benzyl |
| Cl | 2-CF₃-benzyl | Cl | 2-CF₃O-benzyl |
| Cl | 4-CHF₂-benzyl | Cl | 4-CHF₂O-benzyl |
| Cl | 3-CHF₂-benzyl | Cl | 3-CHF₂O-benzyl |
| Cl | 2-CHF₂-benzyl | Cl | 2-CHF₂O-benzyl |
| Cl | 4-Ac-benzyl | Cl | 2-(CF₃C═O)-benzyl |
| Cl | 3-Ac-benzyl | Cl | 3-(CF₃C═O)-benzyl |
| Cl | 2-Ac-benzyl | Cl | 5-(CF₃C═O)-benzyl |
| Cl | 4-MeO-benzyl | Cl | 4-EtO-benzyl |
| Cl | 3-MeO-benzyl | Cl | 3-EtO-benzyl |
| Cl | 2-MeO-benzyl | Cl | 2-EtO-benzyl |
| Cl | 4-i-PrO-benzyl | Cl | 4-NO₂-benzyl |
| Cl | 3-i-PrO-benzyl | Cl | 3-NO₂-benzyl |
| Cl | 2-i-PrO-benzyl | Cl | 2-NO₂-benzyl |
| Cl | benzyl | Cl | phenethyl |

TABLE 8-continued

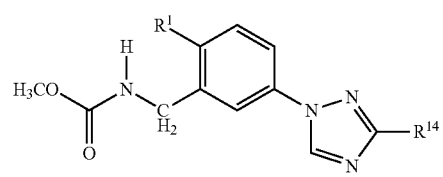

| $R^1$ | $R^{14}$ | $R^1$ | $R^{14}$ |
|---|---|---|---|
| Cl | methyl | Cl | ethyl |
| Cl | n-propyl | Cl | n-butyl |
| Cl | i-propyl | Cl | i-butyl |
| Cl | c-propyl | Cl | c-butyl |
| Cl | n-pentyl | Cl | s-butyl |
| Cl | c-pentyl | Cl | n-hexyl |
| Cl | n-heptyl | Cl | c-hexyl |
| Cl | 1-naphthyl | Cl | 2-naphthyl |
| Me | 4-Cl—Ph | Me | 4-F—Ph |
| Me | 3-Cl—Ph | Me | 3-F—Ph |
| Me | 2-Cl—Ph | Me | 2-F—Ph |
| Me | 4-Br—Ph | Me | 4-Me—Ph |
| Me | 3-Br—Ph | Me | 3-Me—Ph |
| Me | 2-Br—Ph | Me | 2-Me—Ph |
| Me | 4-Et—Ph | Me | 4-i-Pr—Ph |
| Me | 3-Et—Ph | Me | 3-i-Pr—Ph |
| Me | 2-Et—Ph | Me | 2-i-Pr—Ph |
| Me | 4-CN—Ph | Me | 4-c-Pr—Ph |
| Me | 3-CN—Ph | Me | 3-c-Pr—Ph |
| Me | 2-CN—Ph | Me | 2-c-Pr—Ph |
| Me | 4-CF₃—Ph | Me | 4-CF₃O—Ph |
| Me | 3-CF₃—Ph | Me | 3-CF₃O—Ph |
| Me | 2-CF₃—Ph | Me | 2-CF₃O—Ph |
| Me | 4-Ac—Ph | Me | 2-(CF₃C═O)—Ph |
| Me | 3-Ac—Ph | Me | 3-(CF₃C═O)—Ph |
| Me | 2-Ac—Ph | Me | 4-(CF₃C═O)—Ph |
| Me | 4-MeO—Ph | Me | 4-EtO—Ph |
| Me | 3-MeO—Ph | Me | 3-EtO—Ph |
| Me | 2-MeO—Ph | Me | 2-EtO—Ph |
| Me | 4-i-PrO—Ph | Me | 4-NO₂—Ph |
| Me | 3-i-PrO—Ph | Me | 3-NO₂—Ph |
| Me | 2-i-PrO—Ph | Me | 2-NO₂—Ph |
| Me | 4-Cl-benzyl | Me | 4-F-benzyl |
| Me | 3-Cl-benzyl | Me | 3-F-benzyl |
| Me | 2-Cl-benzyl | Me | 2-F-benzyl |
| Me | 4-Br-benzyl | Me | 4-Me-benzyl |
| Me | 3-Br-benzyl | Me | 3-Me-benzyl |
| Me | 2-Br-benzyl | Me | 2-Me-benzyl |
| Me | 4-Et-benzyl | Me | 4-i-Pr-benzyl |
| Me | 3-Et-benzyl | Me | 3-i-Pr-benzyl |
| Me | 2-Et-benzyl | Me | 2-i-Pr-benzyl |
| Me | 4-CN-benzyl | Me | 4-c-Pr-benzyl |
| Me | 3-CN-benzyl | Me | 3-c-Pr-benzyl |
| Me | 2-CN-benzyl | Me | 2-c-Pr-benzyl |
| Me | 4-CF₃-benzyl | Me | 4-CF₃O-benzyl |
| Me | 3-CF₃-benzyl | Me | 3-CF₃O-benzyl |
| Me | 2-CF₃-benzyl | Me | 2-CF₃O-benzyl |
| Me | 4-CHF₂-benzyl | Me | 4-CHF₂O-benzyl |
| Me | 3-CHF₂-benzyl | Me | 3-CHF₂O-benzyl |
| Me | 2-CHF₂-benzyl | Me | 2-CHF₂O-benzyl |
| Me | 4-Ac-benzyl | Me | 2-(CF₃C═O)-benzyl |
| Me | 3-Ac-benzyl | Me | 3-(CF₃C═O)-benzyl |
| Me | 2-Ac-benzyl | Me | 5-(CF₃C═O)-benzyl |
| Me | 4-MeO-benzyl | Me | 4-EtO-benzyl |
| Me | 3-MeO-benzyl | Me | 3-EtO-benzyl |
| Me | 2-MeO-benzyl | Me | 2-EtO-benzyl |
| Me | 4-i-PrO-benzyl | Me | 4-NO₂-benzyl |
| Me | 3-i-PrO-benzyl | Me | 3-NO₂-benzyl |
| Me | 2-i-PrO-benzyl | Me | 2-NO₂-benzyl |

TABLE 9

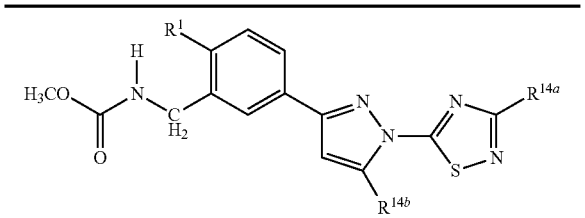

| R$^1$ | R$^{14a}$ | R$^{14b}$ | R$^1$ | R$^{14a}$ | R$^{14b}$ |
|---|---|---|---|---|---|
| Cl | Me | H | Cl | Et | H |
| Cl | n-propyl | H | Cl | c-propyl | H |
| Cl | n-butyl | H | Cl | c-butyl | H |
| Cl | n-pentyl | H | Cl | c-pentyl | H |
| Cl | n-hexyl | H | Cl | c-hexyl | H |
| Cl | Ph | H | Cl | benzyl | H |
| Cl | i-propyl | H | Cl | i-butyl | H |
| Cl | s-butyl | H | Cl | t-butyl | H |
| Cl | CF$_3$ | H | Cl | CHF$_2$ | H |
| Cl | CF$_3$CH$_2$ | H | Cl | CF$_2$CH$_2$ | H |
| Me | Me | H | Me | Et | H |
| Me | n-propyl | H | Me | c-propyl | H |
| Me | n-butyl | H | Me | c-butyl | H |
| Me | n-pentyl | H | Me | c-pentyl | H |
| Me | n-hexyl | H | Me | c-hexyl | H |
| Me | Ph | H | Me | benzyl | H |
| Me | i-propyl | H | Me | i-butyl | H |
| Me | s-butyl | H | Me | t-butyl | H |
| Me | CF$_3$ | H | Me | CHF$_2$ | H |
| Me | CF$_3$CH$_2$ | H | Me | CF$_2$CH$_2$ | H |
| Cl | Me | Me | Cl | Et | Me |
| Cl | n-propyl | Me | Cl | c-propyl | Me |
| Cl | n-butyl | Me | Cl | c-butyl | Me |
| Cl | n-pentyl | Me | Cl | c-pentyl | Me |
| Cl | n-hexyl | Me | Cl | c-hexyl | Me |
| Cl | Ph | Me | Cl | benzyl | Me |
| Cl | i-propyl | Me | Cl | i-butyl | Me |
| Cl | s-butyl | Me | Cl | t-butyl | Me |
| Cl | CF$_3$ | Me | Cl | CHF$_2$ | Me |
| Cl | CF$_3$CH$_2$ | Me | Cl | CF$_2$CH$_2$ | Me |
| Cl | Me | CF$_3$ | Cl | Et | CF$_3$ |
| Cl | n-propyl | CF$_3$ | Cl | c-propyl | CF$_3$ |
| Cl | n-butyl | CF$_3$ | Cl | c-butyl | CF$_3$ |
| Cl | n-pentyl | CF$_3$ | Cl | c-pentyl | CF$_3$ |
| Cl | n-hexyl | CF$_3$ | Cl | c-hexyl | CF$_3$ |
| Cl | Ph | CF$_3$ | Cl | benzyl | CF$_3$ |
| Cl | i-propyl | CF$_3$ | Cl | i-butyl | CF$_3$ |
| Cl | s-butyl | CF$_3$ | Cl | t-butyl | CF$_3$ |
| Cl | CF$_3$ | CF$_3$ | Cl | CHF$_2$ | CF$_3$ |
| Cl | CF$_3$CH$_2$ | CF$_3$ | Cl | CF$_2$CH$_2$ | CF$_3$ |

TABLE 10

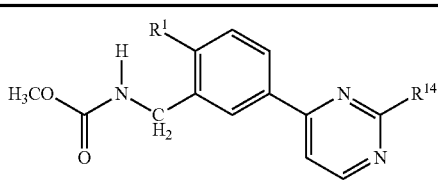

| R$^1$ | R$^{14}$ | R$^1$ | R$^{14}$ |
|---|---|---|---|
| Cl | 4-Cl—Ph | Cl | 4-F—Ph |
| Cl | 3-Cl—Ph | Cl | 3-F—Ph |
| Cl | 2-Cl—Ph | Cl | 2-F—Ph |
| Cl | 4-Br—Ph | Cl | 4-Me—Ph |
| Cl | 3-Br—Ph | Cl | 3-Me—Ph |
| Cl | 2-Br—Ph | Cl | 2-Me—Ph |
| Cl | 4-Et—Ph | Cl | 4-i-Pr—Ph |
| Cl | 3-Et—Ph | Cl | 3-i-Pr—Ph |
| Cl | 2-Et—Ph | Cl | 2-i-Pr—Ph |
| Cl | 4-CN—Ph | Cl | 4-c-Pr—Ph |
| Cl | 3-CN—Ph | Cl | 3-c-Pr—Ph |

TABLE 10-continued

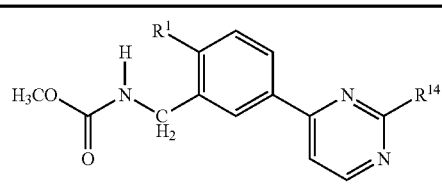

| R$^1$ | R$^{14}$ | R$^1$ | R$^{14}$ |
|---|---|---|---|
| Cl | 2-CN—Ph | Cl | 2-c-Pr—Ph |
| Cl | 4-CF$_3$—Ph | Cl | 4-CF$_3$O—Ph |
| Cl | 3-CF$_3$—Ph | Cl | 3-CF$_3$O—Ph |
| Cl | 2-CF$_3$—Ph | Cl | 2-CF$_3$O—Ph |
| Cl | 4-Ac—Ph | Cl | 2-(CF$_3$C=O)—Ph |
| Cl | 3-Ac—Ph | Cl | 3-(CF$_3$C=O)—Ph |
| Cl | 2-Ac—Ph | Cl | 4-(CF$_3$C=O)—Ph |
| Cl | 4-MeO—Ph | Cl | 4-EtO—Ph |
| Cl | 3-MeO—Ph | Cl | 3-EtO—Ph |
| Cl | 2-MeO—Ph | Cl | 2-EtO—Ph |
| Cl | 4-i-PrO—Ph | Cl | 4-NO$_2$—Ph |
| Cl | 3-i-PrO—Ph | Cl | 3-NO$_2$—Ph |
| Cl | 2-i-PrO—Ph | Cl | 2-NO$_2$—Ph |
| Cl | 4-I—Ph | Cl | 4-(CO$_2$Me)—Ph |
| Cl | 3-I—Ph | Cl | 3-(CO$_2$Me)—Ph |
| Cl | 2-I—Ph | Cl | 2-(CO$_2$Me)—Ph |
| Cl | 4-Me(C=NH)—Ph | Cl | 4-Me(C=NMe)—Ph |
| Cl | 3-Me(C=NH)—Ph | Cl | 3-Me(C=NMe)—Ph |
| Cl | 2-Me(C=NH)—Ph | Cl | 2-Me(C=NMe)—Ph |
| Cl | 4-Me(C=NOMe)—Ph | Cl | 4-Me(C=NOEt)—Ph |
| Cl | 3-Me(C=NOMe)—Ph | Cl | 3-Me(C=NOEt)—Ph |
| Cl | 2-Me(C=NOMe)—Ph | Cl | 2-Me(C=NOEt)—Ph |
| Cl | 4-MeNH(C=O)—Ph | Cl | 4-SiMe$_3$—Ph |
| Cl | 3-MeNH(C=O)—Ph | Cl | 3-SiMe$_3$—Ph |
| Cl | 2-MeNH(C=O)—Ph | Cl | 2-SiMe$_3$—Ph |
| Cl | pyrid-2-yl | Cl | pyrid-3-yl |
| Cl | pyrid-4-yl | Cl | 2,4,6-triazin-1-yl |
| Cl | 3-CF$_3$-pyrid-2-yl | Cl | 2-CF$_3$-pyrid-3-yl |
| Cl | 4-CF$_3$-pyrid-2-yl | Cl | 4-CF$_3$-pyrid-3-yl |
| Cl | 5-CF$_3$-pyrid-2-yl | Cl | 5-CF$_3$-pyrid-3-yl |
| Cl | 6-CF$_3$-pyrid-2-yl | Cl | 6-CF$_3$-pyrid-3-yl |
| Cl | 2-CF$_3$-pyrid-2-yl | Cl | 2-Me-pyrid-4-yl |
| Cl | 3-CF$_3$-pyrid-4-yl | Cl | 3-Me-pyrid-4-yl |
| Cl | 3-Me-pyrid-2-yl | Cl | 2-Me-pyrid-3-yl |
| Cl | 4-Me-pyrid-2-yl | Cl | 4-Me-pyrid-3-yl |
| Cl | 5-Me-pyrid-2-yl | Cl | 5-Me-pyrid-3-yl |
| Cl | 6-Me-pyrid-2-yl | Cl | 6-Me-pyrid-3-yl |
| Cl | 4-Cl-benzyl | Cl | 4-F-benzyl |
| Cl | 3-Cl-benzyl | Cl | 3-F-benzyl |
| Cl | 2-Cl-benzyl | Cl | 2-F-benzyl |
| Cl | 4-Br-benzyl | Cl | 4-Me-benzyl |
| Cl | 3-Br-benzyl | Cl | 3-Me-benzyl |
| Cl | 2-Br-benzyl | Cl | 2-Me-benzyl |
| Cl | 4-Et-benzyl | Cl | 4-i-Pr-benzyl |
| Cl | 3-Et-benzyl | Cl | 3-i-Pr-benzyl |
| Cl | 2-Et-benzyl | Cl | 2-i-Pr-benzyl |
| Cl | 4-CN-benzyl | Cl | 4-c-Pr-benzyl |
| Cl | 3-CN-benzyl | Cl | 3-c-Pr-benzyl |
| Cl | 2-CN-benzyl | Cl | 2-c-Pr-benzyl |
| Cl | 4-CF$_3$-benzyl | Cl | 4-CF$_3$O-benzyl |
| Cl | 3-CF$_3$-benzyl | Cl | 3-CF$_3$O-benzyl |
| Cl | 2-CF$_3$-benzyl | Cl | 2-CF$_3$O-benzyl |
| Cl | 4-CHF$_3$-benzyl | Cl | 4-CHF$_2$O-benzyl |
| Cl | 3-CHF$_3$-benzyl | Cl | 3-CHF$_2$O-benzyl |
| Cl | 2-CHF$_3$-benzyl | Cl | 2-CHF$_2$O-benzyl |
| Cl | 4-Ac-benzyl | Cl | 2-(CF$_3$C=O)-benzyl |
| Cl | 3-Ac-benzyl | Cl | 3-(CF$_3$C=O)-benzyl |
| Cl | 2-Ac-benzyl | Cl | 5-(CF$_3$C=O)-benzyl |
| Cl | 4-MeO-benzyl | Cl | 4-EtO-benzyl |
| Cl | 3-Meo-benzyl | Cl | 3-EtO-benzyl |
| Cl | 2-MeO-benzyl | Cl | 2-EtO-benzyl |
| Cl | 4-i-PrO-benzyl | Cl | 4-NO$_2$-benzyl |
| Cl | 3-i-PrO-benzyl | Cl | 3-NO$_2$-benzyl |
| Cl | 2-i-PrO-benzyl | Cl | 2-NO$_2$-benzyl |
| Cl | benzyl | Cl | phenethyl |
| Cl | methyl | Cl | ethyl |
| Cl | n-propyl | Cl | n-butyl |
| Cl | i-propyl | Cl | i-butyl |
| Cl | c-propyl | Cl | c-butyl |

TABLE 10-continued

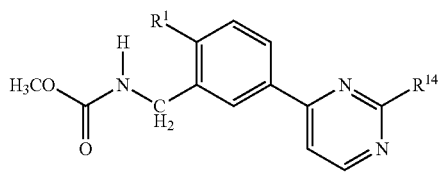

| R¹ | R¹⁴ | R¹ | R¹⁴ |
|---|---|---|---|
| Cl | n-pentyl | Cl | s-butyl |
| Cl | c-pentyl | Cl | n-hexyl |
| Cl | n-heptyl | Cl | c-hexyl |
| Me | 4-Cl—Ph | Me | 4-F—Ph |
| Me | 3-Cl—Ph | Me | 3-F—Ph |
| Me | 2-Cl—Ph | Me | 2-F—Ph |
| Me | 4-Br—Ph | Me | 4-Me—Ph |
| Me | 3-Br—Ph | Me | 3-Me—Ph |
| Me | 2-Br—Ph | Me | 2-Me—Ph |
| Me | 4-Et—Ph | Me | 4-i-Pr—Ph |
| Me | 3-Et—Ph | Me | 3-i-Pr—Ph |
| Me | 2-Et—Ph | Me | 2-i-Pr—Ph |
| Me | 4-CN—Ph | Me | 4-c-Pr—Ph |
| Me | 3-CN—Ph | Me | 3-c-Pr—Ph |
| Me | 2-CN—Ph | Me | 2-c-Pr—Ph |
| Me | 4-CF₃—Ph | Me | 4-CF₃O—Ph |
| Me | 3-CF₃—Ph | Me | 3-CF₃O—Ph |
| Me | 2-CF₃—Ph | Me | 2-CF₃O—Ph |
| Me | 4-Ac—Ph | Me | 2-(CF₃C=O)—Ph |
| Me | 3-Ac—Ph | Me | 3-(CF₃C=O)—Ph |
| Me | 2-Ac—Ph | Me | 4-(CF₃C=O)—Ph |
| Me | 4-MeO—Ph | Me | 4-EtO—Ph |
| Me | 3-MeO—Ph | Me | 3-EtO—Ph |
| Me | 2-MeO—Ph | Me | 2-EtO—Ph |
| Me | 4-i-PrO—Ph | Me | 4-NO₂—Ph |
| Me | 3-i-PrO—Ph | Me | 3-NO₂—Ph |
| Me | 2-i-PrO—Ph | Me | 2-NO₂—Ph |
| Me | 4-Cl-benzyl | Me | 4-F-benzyl |
| Me | 3-Cl-benzyl | Me | 3-F-benzyl |
| Me | 2-Cl-benzyl | Me | 2-F-benzyl |
| Me | 4-Br-benzyl | Me | 4-Me-benzyl |
| Me | 3-Br-benzyl | Me | 3-Me-benzyl |
| Me | 2-Br-benzyl | Me | 2-Me-benzyl |
| Me | 4-Et-benzyl | Me | 4-i-Pr-benzyl |
| Me | 3-Et-benzyl | Me | 3-i-Pr-benzyl |
| Me | 2-Et-benzyl | Me | 2-i-Pr-benzyl |
| Me | 4-CN-benzyl | Me | 4-c-Pr-benzyl |
| Me | 3-CN-benzyl | Me | 3-c-Pr-benzyl |
| Me | 2-CN-benzyl | Me | 2-c-Pr-benzyl |
| Me | 4-CF₃-benzyl | Me | 4-CF₃O-benzyl |
| Me | 3-CF₃-benzyl | Me | 3-CF₃O-benzyl |
| Me | 2-CF₃-benzyl | Me | 2-CF₃O-benzyl |
| Me | 4-CHF₂-benzyl | Me | 4-CHF₂O-benzyl |
| Me | 3-CHF₂-benzyl | Me | 3-CHF₂O-benzyl |
| Me | 2-CHF₂-benzyl | Me | 2-CHF₂O-benzyl |
| Me | 4-Ac-benzyl | Me | 2-(CF₃C=O)-benzyl |
| Me | 3-Ac-benzyl | Me | 3-(CF₃C=O)-benzyl |
| Me | 2-Ac-benzyl | Me | 5-(CF₃C=O)-benzyl |
| Me | 4-MeO-benzyl | Me | 4-EtO-benzyl |
| Me | 3-MeO-benzyl | Me | 3-EtO-benzyl |
| Me | 2-MeO-benzyl | Me | 2-EtO-benzyl |
| Me | 4-i-PrO-benzyl | Me | 4-NO₂-benzyl |
| Me | 3-i-PrO-benzyl | Me | 3-NO₂-benzyl |
| Me | 2-i-PrO-benzyl | Me | 2-NO₂-benzyl |

Formulation/Utility

A compound of this invention will generally be used as a fungicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional*

*Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 3 | 10.0% |
| attapulgite granules (low volatile matter, 0.71/0.30 mm; U.S.S. No. 25-50 sieves) | 90.0% |

Example D

| Extruded Pellet | |
|---|---|
| Compound 4 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 8 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 10 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 14 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuligena* and *Podosphaera leucotricha, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite, Puccinia striiformis, Puccinia hordei, Puccinia graminis* and *Puccinia arachidis*), *Hemileia vastatrix* and *Phakopsora pachyrhizi*; other pathogens including *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, acetamiprid, amidoflumet (S-1955), avermectin, azadirachtin, azinphos-methyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, enestroburin (SYP-Z071), esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, rynaxypyr, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, captafol, captan, carbendazim, carboxin, carpropamid, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, guazatine, hexaconazole, hymexazol, imazalil, imibenconazole, iminoctadine albesilate, iminoctadine triacetate, iodocarb, ipconazole, iprobenfos, iprodione, iprovalicarb, isoprothiolane, isotianil, kasugamycin, kresoximmethyl, mancozeb, mandipropamid, maneb, mepanipyrim, mepronil, meptyldinocap, metalaxyl, metalaxyl-M, metconazole, methasulfocarb, metiram, metominostrobin, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, pefurazoate, penconazole, pencycuron, penthiopyrad, phosphorous acid and salts, phthalide, picobenzamid, picoxystrobin, piperalin, polyoxin, probenazole, prochloraz, procymidone, propamocarb, propamocarb-hydrochloride, propiconazole, propineb, proquinazid, prothiocarb, prothioconazole, pryazophos, pyraclostrobin, pyribencarb, pyributicarb, pyrifenox, pyrimethanil, pyrrolnitrin, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolyfluanid, triadimefon, triadimenol, triazoxide, tricyclazole, tridemorph, trifloxystrobin, triflumizole, triforine, triticonazole, uniconazole, validamycin, valiphenal, vinclozolin, zineb, ziram, zoxamide, N-[2-(1,3-dimethylbutyl)phenyl]-5-fluoro-1,3-dimethyl-1H-pyrazol-4-carboxamide, N-[2-(1S, 2R)-[1,1'-bicyclopropyl]-2-ylphenyl]-3-(difluoromethyl)-1-methyl-1H-pyrazole-4-carboxamide, α-[methoxyimino]-N-methyl-2-[[[1-[3-(trifluoromethyl)-phenyl]-ethoxy]imino]methyl]benzeneacetamide, 2-[[[3-(2,6-dichlorophenyl)-1-methyl-2-propen-1-ylidene]amino]oxy]methyl]-α-(methoxyimino)-N-methylbenzeneacetamide, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]-methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3 difluorophenyl]methylene]benzene acetamide, N-[4-[4-chloro-3-(trifluoromethyl)phenoxy]-2,5-dimethylphenyl]-N-ethyl-N-methylmethanimidamide, and 1-[(2-propenylthio)carbonyl]-2-(1-methylethyl)-4-(2-methylphenyl)-5-amino-1H-pyrazol-3-one: nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e., insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by the compound of Formula 1 alone.

In one mixture embodiment, granules of a solid composition comprising a compound of Formula 1 is mixed with granules of a solid composition comprising another agricultural protectant. These granule mixtures can be in accordance with the general granule mixture disclosure of PCT Patent Publication WO 94/24861 or more preferably the homogenous granule mixture teaching of U.S. Pat. No. 6,022,552.

Of note are combinations (e.g., in the form of compositions) of (a) a compound of Formula 1 with (b) at least one other fungicide. Of particular note are such combinations where the other fungicide has different site of action from the compound of Formula 1. In certain instances, combinations with other fungicides having a similar spectrum of control but a different site of action will be particularly advantageous for resistance management. Of particular note are compositions which in addition to a compound of Formula 1 include at least one compound selected from the group consisting of (b1) methyl benzimidazole carbamate (MBC) fungicides;
(b2) dicarboximide fungicides;
(b3) demethylation inhibitor (DMI) fungicides;
(b4) phenylamide fungicides;
(b5) amine/morpholine fungicides;
(b6) phospholipid biosynthesis inhibitor fungicides;
(b7) carboxamide fungicides;
(b8) hydroxy(2-amino-)pyrimidine fungicides;
(b9) anilinopyrimidine fungicides;
(b10) N-phenyl carbamate fungicides;
(b11) quinone outside inhibitor (QoI) fungicides;
(b12) phenylpyrrole fungicides;
(b13) quinoline fungicides;
(b14) lipid peroxidation inhibitor fungicides;
(b15) melanin biosynthesis inhibitors-reductase (MBI-R) fungicides;
(b16) melanin biosynthesis inhibitors-dehydratase (MBI-D) fungicides;
(b17) hydroxyanilide fungicides;
(b18) squalene-epoxidase inhibitor fungicides;

(b19) polyoxin fungicides;
(b20) phenylurea fungicides;
(b21) quinone inside inhibitor (QiI) fungicides;
(b22) benzamide fungicides;
(b23) enopyranuronic acid antibiotic fungicides;
(b24) hexopyranosyl antibiotic fungicides;
(b25) glucopyranosyl antibiotic: protein synthesis fungicides;
(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide (CAA) fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicides other than fungicides of component (a) and components (b1) through (b45); and
salts of compounds of (b1) through (b46).

"Methyl benzimidazole carbamate (MBC) fungicides (b1)" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

"Dicarboximide fungicides (b2)" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

"Demethylation inhibitor (DMI) fungicides (b3)" (Fungicide Resistance Action Committee (FRAC) code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

"Phenylamide fungicides (b4)" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

"Amine/morpholine fungicides (b5)" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

"Phospholipid biosynthesis inhibitor fungicides (b6)" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

"Carboxamide fungicides (b7)" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The Benzamides include benodanil, flutolanil and mepronil. The furan carboxamides include fenfuram. The oxathiin carboxamide include carboxin and oxycarboxin. The thiazole carboxamides include thifluzamide. The pyrazole carboxamides include furametpyr, penthiopyrad, bixafen, N-[2-(1S, 2R)-[1,1'-bicyclopropyl]-2-ylphenyl]-3-(difluoromethyl)-1-methyl-1H-pyrazole-4-carboxamide and N-[2-(1,3-dimethylbutyl)phenyl]-5-fluoro-1,3-dimethyl-1H-pyrazole-4-carboxamide. The pyridine carboxamide include boscalid.

"Hydroxy(2-amino-)pyrimidine fungicides (b8)" (Fungicide Resistance Action Committee (FRAC) code 8) inhibit nucleic acid synthesis by interfering with adenosine deaminase. Examples include bupirimate, dimethirimol and ethirimol.

"Anilinopyrimidine fungicides (b9)" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

"N-Phenyl carbamate fungicides (b10)" (Fungicide Resistance Action Committee (FRAC) code 10) inhibit mitosis by binding to β-tubulin and disrupting microtubule assembly Inhibition of microtubule assembly can disrupt cell division, transport within the cell and cell structure. Examples include diethofencarb.

"Quinone outside inhibitor (QoI) fungicides (b11)" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_O$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]-ethoxy]imino]methyl]benzeneacetamide and 2-[[[3-(2,6-dichlorophenyl)-1-methyl-2-propen-1-ylidene]amino]oxy]methyl]-α-(methoxyimino)-N-methylbenzene acetamide. The oxazolidinediones include famoxadone. The dihydrodioxazines include fluoxastrobin. The imidazolinones include fenamidone. The benzylcarbamates include pyribencarb.

"Phenylpyrrole fungicides (b12)" (Fungicide Resistance Action Committee (FRAC) code 12) inhibit a MAP protein kinase associated with osmotic signal transduction in fungi. Fenpiclonil and fludioxonil are examples of this fungicide class.

"Quinoline fungicides (b13)" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

"Lipid peroxidation inhibitor fungicides (b14)" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbons include biphenyl, chloroneb, dicloran, quintozene, tecnazene and tolclofos-methyl. The 1,2,4-thiadiazoles include etridiazole.

"Melanin biosynthesis inhibitors-reductase (MBI-R) fungicides (b15)" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

"Melanin biosynthesis inhibitors-dehydratase (MBI-D) fungicides (b16)" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

"Hydroxyanilide fungicides (b17)" (Fungicide Resistance Action Committee (FRAC) code 17) inhibit C4-demethylase which plays a role in sterol production. Examples include fenhexamid.

"Squalene-epoxidase inhibitor fungicides (b18)" (Fungicide Resistance Action Committee (FRAC) code 18) inhibit squalene-epoxidase in ergosterol biosynthesis pathway. Sterols such as ergosterol are needed for membrane structure and function making them essential for the development of functional cell walls. Therefore exposure to these fungicides result in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

"Polyoxin fungicides (b19)" (Fungicide Resistance Action Committee (FRAC) code 19) inhibit chitin synthase. Examples include polyoxin.

"Phenylurea fungicides (b20)" (Fungicide Resistance Action Committee (FRAC) code 20) are proposed to affect cell division. Examples include pencycuron.

"Quinone inside inhibitor (QiI) fungicides (b21)" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

"Benzamide fungicides (b22)" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

"Enopyranuronic acid antibiotic fungicides (b23)" (Fungicide Resistance Action Committee (FRAC) code 23) inhibit growth of fungi by affecting protein biosynthesis. Examples include blasticidin-S.

"Hexopyranosyl antibiotic fungicides (b24)" (Fungicide Resistance Action Committee (FRAC) code 24) inhibit growth of fungi by affecting protein biosynthesis. Examples include kasugamycin.

"Glucopyranosyl antibiotic: protein synthesis fungicides (b25)" (Fungicide Resistance Action Committee (FRAC) code 25) inhibit growth of fungi by affecting protein biosynthesis. Examples include streptomycin.

"Glucopyranosyl antibiotic: trehalase and inositol biosynthesis fungicides (b26)" (Fungicide Resistance Action Committee (FRAC) code 26) inhibit trehalase in inositol biosynthesis pathway. Examples include validamycin.

"Cyanoacetamideoxime fungicides (b27) (Fungicide Resistance Action Committee (FRAC) code 27) include cymoxanil.

"Carbamate fungicides (b28)" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

"Oxidative phosphorylation uncoupling fungicides (b29)" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

"Organo tin fungicides (b30)" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

"Carboxylic acid fungicides (b31)" (Fungicide Resistance Action Committee (FRAC) code 31) inhibit growth of fungi by affecting deoxyribonucleic acid (DNA) topoisomerase type II (gyrase). Examples include oxolinic acid.

"Heteroaromatic fungicides (b32)" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

"Phosphonate fungicides (b33)" (Fungicide Resistance Action Committee (FRAC) code 33) include phosphorous acid and its various salts, including fosetyl-aluminum.

"Phthalamic acid fungicides (b34)" (Fungicide Resistance Action Committee (FRAC) code 34) include teclofthalam.

"Benzotriazine fungicides (b35)" (Fungicide Resistance Action Committee (FRAC) code 35) include triazoxide.

"Benzene-sulfonamide fungicides (b36)" (Fungicide Resistance Action Committee (FRAC) code 36) include flusulfamide.

"Pyridazinone fungicides (b37)" (Fungicide Resistance Action Committee (FRAC) code 37) include diclomezine.

"Thiophene-carboxamide fungicides (b38)" (Fungicide Resistance Action Committee (FRAC) code 38) are proposed to affect ATP production. Examples include silthiofam.

"Pyrimidinamide fungicides (b39)" (Fungicide Resistance Action Committee (FRAC) code 39) inhibit growth of fungi by affecting phospholipid biosynthesis and include diflumetorim.

"Carboxylic acid amide (CAA) fungicides (b40)" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]-ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino] butanamide.

"Tetracycline antibiotic fungicides (b41)" (Fungicide Resistance Action Committee (FRAC) code 41) inhibit growth of fungi by affecting complex 1 nicotinamide adenine dinucleotide (NADH) oxidoreductase. Examples include oxytetracycline.

"Thiocarbamate fungicides (b42)" (Fungicide Resistance Action Committee (FRAC) code 42) include methasulfocarb.

"Benzamide fungicides (b43)" (Fungicide Resistance Action Committee (FRAC) code 43) inhibit growth of fungi by delocalization of spectrin-like proteins. Examples include acylpicolide fungicides such as fluopicolide and fluopyram.

"Host plant defense induction fungicides (b44)" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

"Multi-site contact fungicides (b45)" inhibit fungal growth through multiple sites of action and have contact/preventive activity. This class of fungicides includes: "copper fungicides (b45.1) (Fungicide Resistance Action Committee (FRAC) code M1)", "sulfur fungicides (b45.2) (Fungicide Resistance Action Committee (FRAC) code M2)", "dithiocarbamate fungicides (b45.3) (Fungicide Resistance Action Committee (FRAC) code M3)", "phthalimide fungicides (b45.4) (Fungicide Resistance Action Committee (FRAC) code M4)", "chloronitrile fungicides (b45.5) (Fungicide Resistance Action Committee (FRAC) code M5)", "sulfamide fungicides (b45.6) (Fungicide Resistance Action Committee (FRAC) code M6)", "guanidine fungicides (b45.7) (Fungicide Resistance Action Committee (FRAC) code M7)" "triazines fungicides (b45.8) (Fungicide Resistance Action Committee (FRAC) code M8)" and "quinone fungicides (b45.9) (Fungicide Resistance Action Committee (FRAC) code M9)". "Copper fungicides" are inorganic compounds containing copper, typically in the copper (II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazines fungicides" include anilazine. "Quinone fungicides" include dithianon.

"Fungicides other than fungicides of component (a) and components (b1) through (b45); (b46)" include certain fungicides considered to have an unknown mode of action. These include: "thiazole carboxamide fungicide (b46.1) (Fungicide Resistance Action Committee (FRAC) code U5)", "phenyl-acetamide fungicide (b46.2) (Fungicide Resistance Action Committee (FRAC) code U6)", "quinazolinone fungicide (b46.3) (Fungicide Resistance Action Committee (FRAC) code U7)" and "benzophenone fungicide (b46.4) (Fungicide Resistance Action Committee (FRAC) code U8)". The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid, 6-bromo-3-propyl-2-propyloxy-4(3H)-quinazolinone, 6,8-diiodo-3- propyl-2-propyloxy-4-(3H)-quinazolinone, 6-chloro-2-propoxy-3-propylthieno[2,3-d]pyrimidin-4(3H)-one, 2,3-dibutyl-6-chlorothieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, 3-(cyclopropylmethyl)-6-iodo-2-(propylthio)pyrido[2,3-d]pyrimidin-4(3H)-one, 2-butoxy-6-iodo-3-propyl-4H-1-benzopyran-4-one, 2-ethoxy-6-iodo-3-propyl-4H-1-benzopyran-4-one, 6-iodo-2-propoxy-3-propyl-4H-1-benzopyran-4-one, 2-(2-butynyloxy)-6-iodo-3-propyl-4H-1-benzopyran-4-one, 6-iodo-2-(1-methylbutoxy)-3-propyl-4H-1-benzopyran-4-one, 2-(3-butenyloxy)-6-iodo-3-propyl-4H-1-benzopyran-4-one, 3-butyl-6-iodo-2-(1-methylethoxy)-4H-1-benzopyran-4-one, and 6-iodo-3-propyl-2H-1,3-benzoxazine-2,4(3H)-dione 2-(O-methyloxime). The benzophenones include metrafenone. The (b46) group also includes bethoxazin, neo-asozin (ferric methanearsonate), pyrrolnitrin, quinomethionate, 5-chloro-6-(2,4,6-trifluorophenyl)-7-(4-methylpiperidin-1-yl)[1,2,4]triazolo[1,5-a]pyrimidine (BAS600), 3-[5-(4-chlorophenyl)-2,3-dimethyl-3-isoxazolidinyl]pyridine (SYP-Z048), 4-fluorophenyl N-[1-[[[1-(4-cyanophenyl)ethyl]sulfonyl]methyl]propyl]carbamate (XR-539), N-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (OK-5203) and N-(4-chloro-2-nitrophenyl)-N-ethyl-4-methylbenzenesulfonamide (TF-991).

Embodiments of the present invention include:

Embodiment D1

The composition described in the Summary of the Invention (including but not limited to composition of Embodiments 1 through 32 and A through C5) wherein component (b) includes at least one compound selected from (b1) methyl benzimidazole carbamate fungicides such as benomyl, carbendazim and thiophanate-methyl.

Embodiment D2

The composition described in the Summary of the Invention (including but not limited to composition of Embodiments 1 through 32 and A through C5) wherein component (b) includes at least one compound selected from (b2) dicarboximide fungicides such as procymidone, iprodione and vinclozolin.

Embodiment D3

The composition described in the Summary of the Invention (including but not limited to composition of Embodiments 1 through 32 and A through C5) wherein component (b) includes at least one compound selected from (b3) demethylation inhibitor fungicides such as epoxiconazole, fluquinconazole, triadimenol, simeconazole, ipconazole, triforine, cyproconazole, difenoconazole, flusilazole, flutriafol, metconazole, myclobutanil, prochloraz, propiconazole, prothioconazole, tebuconazole and tetraconazole.

Embodiment D4

The composition described in the Summary of the Invention (including but not limited to composition of Embodiments 1 through 32 and A through C5) wherein component (b) includes at least one compound selected from (b4) phenylamide fungicides such as metalaxyl, metalaxyl-M, benalaxyl, benalaxyl-M, furalaxyl, ofurace and oxadixyl.

Embodiment D5

The composition described in the Summary of the Invention (including but not limited to composition of Embodiments 1 through 32 and A through C5) wherein component (b) includes at least one compound selected from (b5) amine/morpholine fungicides such as aldimorph, dodemorph, fenpropimorph, tridemorph, trimorphamide. fenpropidin, piperalin and spiroxamine.

Embodiment D6

The composition described in the Summary of the Invention (including but not limited to composition of Embodiments 1 through 32 and A through C5) wherein component (b) includes at least one compound selected from (b6) phospholipid biosynthesis inhibitor fungicides such as edifenphos and isoprothiolane.

Embodiment D7

The composition described in the Summary of the Invention (including but not limited to composition of Embodiments 1 through 32 and A through C5) wherein component (b) includes at least one compound selected from (b7) carboxamide fungicides such as boscalid, penthiopyrad, bixafen, carboxin and oxycarboxin.

Embodiment D8

The composition described in the Summary of the Invention (including but not limited to composition of Embodiments 1 through 32 and A through C5) wherein component (b) includes at least one compound selected from (b8) hydroxy(2-amino-)pyrimidine fungicides such as ethirimol.

Embodiment D9

The composition described in the Summary of the Invention (including but not limited to composition of Embodiments 1 through 32 and A through C5) wherein component (b) includes at least one compound selected from (b9) anilinopyrimidine fungicides such as cyprodinil.

Embodiment D10

The composition described in the Summary of the Invention (including but not limited to composition of Embodiments 1 through 29 and A through D) wherein component (b) includes at least one compound selected from (b10) N-phenyl carbamate fungicides such as diethofencarb.

Embodiment D11

The composition described in the Summary of the Invention (including but not limited to composition of Embodiments 1 through 32 and A through C5) wherein component (b) includes at least one compound selected from (b11) quinone outside inhibitor fungicides such as azoxystrobin, pyraclostrobin, kresoxim-methyl, trifloxystrobin, picoxystrobin, pyribencarb, famoxadone, fenamidone, enestrobin, dimoxystrobin, metominostrobin, orysastrobin and fluoxastrobin.

Embodiment D12

The composition described in the Summary of the Invention (including but not limited to composition of Embodiments 1 through 31 and A through C5) wherein component (b) includes at least one compound selected from (b12) phenylpyrrole fungicides compound such as fenpiclonil and fludioxonil.

Embodiment D13

The composition described in the Summary of the Invention (including but not limited to composition of Embodiments 1 through 32 and A through C5) wherein component (b) includes at least one compound selected from (b13) quinoline fungicides such as quinoxyfen.

Embodiment D14

The composition described in the Summary of the Invention (including but not limited to composition of Embodiments 1 through 32 and A through C5) wherein component (b) includes at least one compound selected from (b14) lipid peroxidation inhibitor fungicides such as chloroneb.

Embodiment D15

The composition described in the Summary of the Invention (including but not limited to composition of Embodiments 1 through 32 and A through C5) wherein component (b) includes at least one compound selected from (b15) melanin biosynthesis inhibitors-reductase fungicides such as pyroquilon and tricyclazole.

Embodiment D16

The composition described in the Summary of the Invention (including but not limited to composition of Embodiments 1 through 32 and A through C5) wherein component (b) includes at least one compound selected from (b16) melanin biosynthesis inhibitors-dehydratase fungicides such as carpropamid.

Embodiment D17

The composition described in the Summary of the Invention (including but not limited to composition of Embodiments 1 through 32 and A through C5) wherein component (b) includes at least one compound selected from (b17) hydroxyanilide fungicides such as fenhexamid.

Embodiment D18

The composition described in the Summary of the Invention (including but not limited to composition of Embodiments 1 through 32 and A through C5) wherein component (b) includes at least one compound selected from (b18) squalene-epoxidase inhibitor fungicides such as pyributicarb.

Embodiment D19

The composition described in the Summary of the Invention (including but not limited to composition of Embodiments 1 through 32 and A through C5) wherein component (b) includes at least one compound selected from (b19) polyoxin fungicides such as polyoxin.

Embodiment D20

The composition described in the Summary of the Invention (including but not limited to composition of Embodiments 1 through 32 and A through C5) wherein component (b) includes at least one compound selected from (b20) phenylurea fungicides such as pencycuron.

Embodiment D21

The composition described in the Summary of the Invention (including but not limited to composition of Embodiments 1 through 32 and A through C5) wherein component (b) includes at least one compound selected from (b21) quinone inside inhibitor fungicides such as cyazofamid and amisulbrom.

Embodiment D22

The composition described in the Summary of the Invention (including but not limited to composition of Embodiments 1 through 32 and A through C5) wherein component (b) includes at least one compound selected from (b22) benzamide fungicides such as zoxamide.

Embodiment D23

The composition described in the Summary of the Invention (including but not limited to composition of Embodiments 1 through 32 and A through C5) wherein component (b) includes at least one compound selected from (b23) enopyranuronic acid antibiotic fungicides such as blasticidin-S.

Embodiment D24

The composition described in the Summary of the Invention (including but not limited to composition of Embodiments 1 through 32 and A through C5) wherein component (b) includes at least one compound selected from (b24) hexopyranosyl antibiotic fungicides such as kasugamycin.

Embodiment D25

The composition described in the Summary of the Invention (including but not limited to composition of Embodiments 1 through 32 and A through C5) wherein component (b) includes at least one compound selected from (b25) glucopyranosyl antibiotic: protein synthesis fungicides such as streptomycin.

Embodiment D26

The composition described in the Summary of the Invention (including but not limited to composition of Embodiments 1 through 32 and A through C5) wherein component (b) includes at least one compound selected from (b26) glucopyranosyl antibiotic: trehalase and inositol biosynthesis fungicides such as validamycin.

Embodiment D27

The composition described in the Summary of the Invention (including but not limited to composition of Embodiments 1 through 32 and A through C5) wherein component (b) includes at least one compound selected from (b27) cyanoacetylamideoxime fungicides such as cymoxanil.

Embodiment D28

The composition described in the Summary of the Invention (including but not limited to composition of Embodiments 1 through 32 and A through C5) wherein component (b) includes at least one compound selected from (b28) carbamate fungicides such as propamacarb, propamacarb-hydrochloride, prothiocarb and iodocarb.

Embodiment D29

The composition described in the Summary of the Invention (including but not limited to composition of Embodiments 1 through 32 and A through C5) wherein component (b) includes at least one compound selected from (b29) oxidative phosphorylation uncoupling fungicides such as fluazinam, binapacryl, ferimzone, meptyldinocap and dinocap.

Embodiment D30

The composition described in the Summary of the Invention (including but not limited to composition of Embodiments 1 through 32 and A through C5) wherein component (b) includes at least one compound selected from (b30) organo tin fungicides such as fentin acetate.

Embodiment D31

The composition described in the Summary of the Invention (including but not limited to composition of Embodiments 1 through 32 and A through C5) wherein component (b) includes at least one compound selected from (b31) carboxylic acid fungicides such as oxolinic acid.

Embodiment D32

The composition described in the Summary of the Invention (including but not limited to composition of Embodiments 1 through 32 and A through C5) wherein component (b) includes at least one compound selected from (b32) heteroaromatic fungicides such as hymexazole.

Embodiment D33

The composition described in the Summary of the Invention (including but not limited to composition of Embodiments 1 through 32 and A through C5) wherein component (b) includes at least one compound selected from (b33) phosphonate fungicides such as phosphorous acid and its various salts, including fosetyl-aluminum.

Embodiment D34

The composition described in the Summary of the Invention (including but not limited to composition of Embodiments 1 through 32 and A through C5) wherein component (b) includes at least one compound selected from (b34) phthalamic acid fungicides such as teclofthalam.

Embodiment D35

The composition described in the Summary of the Invention (including but not limited to composition of Embodiments 1 through 32 and A through C5) wherein component (b) includes at least one compound selected from (b35) benzotriazine fungicides such as triazoxide.

Embodiment D36

The composition described in the Summary of the Invention (including but not limited to composition of Embodiments 1 through 32 and A through C5) wherein component (b) includes at least one compound selected from (b36) benzene-sulfonamide fungicides such as flusulfamide.

Embodiment D37

The composition described in the Summary of the Invention (including but not limited to composition of Embodiments 1 through 32 and A through C5) wherein component (b) includes at least one compound selected from (b37) pyridazinone fungicides such as diclomezine.

Embodiment D38

The composition described in the Summary of the Invention (including but not limited to composition of Embodiments 1 through 32 and A through C5) wherein component (b) includes at least one compound selected from (b38) thiophene-carboxamide fungicides such as silthiofam.

Embodiment D39

The composition described in the Summary of the Invention (including but not limited to composition of Embodiments 1 through 32 and A through C5) wherein component (b) includes at least one compound selected from (b39) pyrimidinamide fungicides such as diflumetorim.

Embodiment D40

The composition described in the Summary of the Invention (including but not limited to composition of Embodiments 1 through 32 and A through C5) wherein component (b) includes at least one compound selected from (b40) carboxylic acid amide fungicides such as dimethomorph, benthiavalicarb, benthiavalicarb-isopropyl, iprovalicarb, valiphenal, mandipropamid and flumorph.

Embodiment D41

The composition described in the Summary of the Invention (including but not limited to composition of Embodiments 1 through 32 and A through C5) wherein component (b) includes at least one compound selected from (b41) tetracycline antibiotic fungicides such as oxytetracycline.

Embodiment D42

The composition described in the Summary of the Invention (including but not limited to composition of Embodiments 1 through 32 and A through C5) wherein component (b) includes at least one compound selected from (b42) thiocarbamate fungicides such as methasulfocarb.

Embodiment D43

The composition described in the Summary of the Invention (including but not limited to composition of Embodiments 1 through 32 and A through C5) wherein component (b) includes at least one compound selected from (b43) benzamide fungicides such as fluopicolide and fluopyram.

Embodiment D44

The composition described in the Summary of the Invention (including but not limited to composition of Embodiments 1 through 32 and A through C5) wherein component (b) includes at least one compound selected from (b44) host plant defense induction fungicides such as acibenzolar-S-methyl.

Embodiment D45

The composition described in the Summary of the Invention (including but not limited to composition of Embodiments 1 through 32 and A through C5) wherein component (b) includes at least one compound selected from (b45) multi-site contact fungicides such as copper oxychloride, copper sulfate, copper hydroxide, Bordeaux composition (tribasic copper sulfide), elemental sulfur, mancozeb, metiram, propineb, ferbam, maneb, thiram, zineb, ziram, folpet, captan, captafol and chlorothalonil.

Embodiment D46

The composition described in the Summary of the Invention (including but not limited to composition of Embodiments 1 through 32 and A through C5) wherein component (b) includes at least one compound selected from (b46) fungicides other than fungicides of component (a) and components (b1) through (b45) such as ethaboxam, cyflufenamid, proquinazid, metrafenone, 5-chloro-6-(2,4,6-trifluorophenyl)-7-(4-methylpiperidin-1-yl)[1,2,4]triazolo[1,5-a]pyrimidine, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]benzeneacetamide, N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile and N-(4-chloro-2-nitrophenyl)-N-ethyl-4-methylbenzenesulfonamide.

The following TESTS demonstrate the control efficacy of compounds of this invention on specific pathogens. The pathogen control protection afforded by the compounds is not limited, however, to these species. See Index Tables A-J for compound descriptions. See Index Table K for $^1$H NMR data. The following abbreviations are used in the Index Tables which follow: i means iso, c means cyclo, n means normal, t means tertiary, Ac is acetyl, Me is methyl, Et is ethyl, Ph is phenyl, Bn is benzyl, OMe is methoxy, OEt is ethoxy, SMe is methylthio and CN is cyano. Substituents on benzyl are attached to the phenyl ring of the benzyl, and locant numbers for the substituents are relative to the phenyl position bonded to the methylene component of benzyl. The abbreviation "Ex." stands for "Example" and is followed by a number indicating in which example the compound is prepared. The abbreviation MP stands for "melting point".

INDEX TABLE A

| Cmpd. | $R^1$ | $R^4$ | Q | $V^1$ | $R^{10a}$ | $R^{10b}$ | $R^{10c}$ | MP |
|---|---|---|---|---|---|---|---|---|
| 1 (Ex. 1) | Cl | OMe | $CH_2$ | $CH_2CH_2$ | Me | Me | Me | ** |
| 2 (Ex. 2) | Cl | OMe | $CH_2$ | $CH_2CH_2CH_2$ | Me | Me | Me | ** |
| 3 | Cl | OMe | $CH_2$ | $CH_2C(=CH_2)CH_2$ | Me | Me | Me | * |
| 4 | Cl | OMe | $CH_2$ | $CH_2$ | Me | Me | $CH=CH_2$ | * |
| 5 | Cl | OMe | $CH_2$ | $CH_2$ | Me | Me | 4-Cl—Ph | * |
| 6 | Cl | OMe | $CH_2$ | $CH_2$ | Me | Me | Me | * |
| 7 | Cl | OMe | $CH_2$ | $CH_2$ | Me | Me | Et | * |
| 15 | Cl | OMe | $CH_2$ | $CH_2$ | Me | Me | Ph | * |
| 16 | Cl | OMe | $CH_2$ | $CH_2$ | Me | Me | 4-F—Ph | * |
| 17 | Cl | OMe | $CH_2$ | $CH_2$ | Me | Me | Bn | * |

* See Index Table K for $^1$H NMR data.
** See synthesis example for $^1$H NMR data.

INDEX TABLE B

| Cmpd. | $R^1$ | $R^4$ | Q | $R^{14}$ | MP |
|---|---|---|---|---|---|
| 8 (Ex. 3) | Cl | OMe | NH | 3-$OCF_3$ | ** |
| 9 | Cl | OMe | NH | 4-$SiMe_3$ | * |
| 10 | Cl | OEt | NH | 4-$OCF_3$ | * |
| 11 | Cl | OMe | NH | 4-$OCF_3$ | * |
| 12 | Cl | OMe | NH | 4-CN | * |
| 13 | Cl | OMe | NH | 4-$SCH_3$ | * |
| 14 | Cl | OMe | $CH_2$ | 4-$SiMe_3$ | * |
| 18 | Cl | OMe | O | 3-$OCF_3$ | * |
| 19 | Cl | OMe | O | 3-Cl | * |

* See Index Table K for $^1$H NMR data.
** See synthesis example for $^1$H NMR data.

INDEX TABLE C

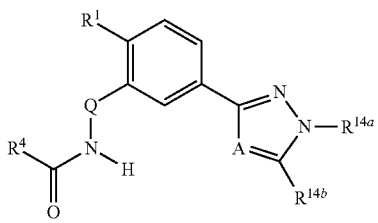

| Cmpd. | R¹ | R⁴ | Q | R¹⁴ᵃ | R¹⁴ᵇ | A | MP |
|---|---|---|---|---|---|---|---|
| 20 | Cl | OMe | $CH_2$ | (6-methyl-pyrid-2-yl)-$CH_2$— | H | CH | * |
| 21 | Cl | OMe | $CH_2$ | H | H | CH | * |
| 22 | Cl | OMe | $CH_2$ | 3-methyl-1-butyl | H | CH | * |
| 23 | Cl | OMe | $CH_2$ | 1-(3-trimethylsilyl-propyl)- | H | CH | * |
| 24 | Cl | OMe | $CH_2$ | 1-pent-4-ynyl | H | CH | * |
| 25 | Cl | OMe | $CH_2$ | (2-chloro-thiazolo-5-yl)-$CH_2$— | H | CH | * |
| 26 | Cl | OMe | $CH_2$ | —$CH_2CN$ | H | CH | * |
| 27 | Cl | OMe | $CH_2$ | (ethyl-dimethylsilyl)-$CH_2$— | H | CH | * |
| 28 | Cl | OMe | $CH_2$ | methyl | H | CH | * |
| 29 | Cl | OMe | $CH_2$ | 1-(1-trimethylsilyl-ethyl)- | H | CH | * |
| 30 | Cl | OMe | $CH_2$ | 1-(4-methyl-pent-3-enyl)- | H | CH | * |
| 31 | Cl | OMe | $CH_2$ | —$CH_2CH_2CN$ | H | CH | * |
| 32 | Cl | OMe | $CH_2$ | —$CH_2CH_2CH_2CN$ | H | CH | * |
| 34 | Cl | OMe | $CH_2$ | Ph | H | CH | * |
| 35 | Cl | OMe | $CH_2$ | $Me_2NSO_2$— | H | CH | * |
| 36 | Cl | OMe | $CH_2$ | 1-[4,4-bis-(4-fluorophenyl)-butyl] | H | CH | * |
| 37 | Cl | OMe | $CH_2$ | 2-Cl-benzyl | H | CH | * |
| 38 | Cl | OMe | $CH_2$ | 3-$CF_3$-benzyl | H | CH | * |
| 39 | Cl | OMe | $CH_2$ | 1-pent-4-ynyl | Me | CH | * |
| 40 | Cl | OMe | $CH_2$ | 1-(3-trimethylsilyl-propyl)- | Me | CH | * |
| 41 | Cl | OMe | $CH_2$ | 1-(4-methyl-pentyl)- | H | CH | * |
| 42 | Cl | OMe | $CH_2$ | 1-(3-phenyl-propyl)- | H | CH | * |
| 43 | Cl | OMe | $CH_2$ | 1-(3-fluoro-propyl)- | H | CH | * |
| 45 | Cl | OMe | $CH_2$ | 1-(3-trimethylsilyl-propyl)- | $CF_3$ | CH | * |
| 46 | Cl | OMe | $CH_2$ | butyl | H | CH | * |
| 47 | Cl | OMe | $CH_2$ | 1-(3-trimethylsilyl-propyl)- | H | CCl | * |
| 48 | Cl | OMe | $CH_2$ | 5-methyl-pyrid-2-yl | H | CH | * |
| 49 | Cl | OMe | $CH_2$ | 6-methyl-pyrid-2-yl | H | CH | * |
| 50 | Cl | OMe | $CH_2$ | 3-$CF_3$—Ph | H | CH | * |
| 51 | Cl | OMe | $CH_2$ | 2-$CF_3$—Ph | H | CH | * |
| 52 | Cl | OMe | $CH_2$ | 2-Cl—Ph | H | CH | * |
| 53 | Cl | OMe | $CH_2$ | 2-Cl-5-$CF_3$-benzyl | H | CH | * |
| 54 | Cl | OMe | $CH_2$ | 2-Ac—Ph | H | CH | * |
| 55 | Cl | OMe | $CH_2$ | 4-(2-CN—Ph)-benzyl | H | CH | * |
| 56 | Cl | OMe | $CH_2$ | 3-[1-(4-chloro-phenyl)-propane-1-one] | H | CH | * |
| 57 | Cl | OMe | $CH_2$ | benzyl | H | CH | * |
| 58 | Cl | OMe | $CH_2$ | phenethyl | H | CH | * |
| 59 | Cl | OMe | $CH_2$ | 1-(2-phenoxy-ethyl) | H | CH | * |
| 60 | Cl | OMe | $CH_2$ | 3-Cl-benzyl | H | CH | * |
| 61 | Cl | OMe | $CH_2$ | 1-(2-phenoxy-propyl) | H | CH | * |
| 62 | Cl | OMe | $CH_2$ | 2-$CF_3$-benzyl | H | CH | * |
| 63 | Cl | OMe | $CH_2$ | 3-$CF_3$-benzyl | H | CH | * |
| 64 | Cl | OMe | NH | 3-$CF_3$—Ph | H | CH | * |
| 65 | Cl | OMe | $CH_2$ | 3-$OCF_3$-benzyl | H | CH | * |
| 66 | Cl | OMe | $CH_2$ | 4-$OCF_3$-benzyl | H | CH | * |
| 67 | Cl | OMe | $CH_2$ | 4-Cl-benzyl | H | CH | 134-139 |
| 68 | Cl | OMe | $CH_2$ | 3-$OCF_3$—Ph | H | CH | 136-138 |
| 69 | Cl | OMe | $CH_2$ | 6-$CF_3$-pyrid-2-yl | H | CH | 171-173 |
| 70 | Cl | OMe | $CH_2$ | 2-Me-benzyl | H | CH | * |
| 71 | Cl | OMe | $CH_2$ | 3-Me-benzyl | H | CH | * |
| 72 | Cl | OMe | $CH_2$ | 4-Me-benzyl | H | CH | 126-129 |
| 73 | Cl | OMe | $CH_2$ | 3-$NO_2$-benzyl | H | CH | * |
| 74 | Cl | OMe | $CH_2$ | 4-Cl—Ph | H | CH | 151-153 |
| 75 | Cl | OMe | $CH_2$ | 3-CN-benzyl | H | CH | * |
| 76 | Cl | OMe | $CH_2$ | 2-$OCF_3$-benzyl | H | CH | * |
| 77 | Cl | OMe | $CH_2$ | 4-$OCF_3$—Ph | H | CH | 149-151 |
| 78 | Cl | OMe | $CH_2$ | 3,5-di-$CF_3$—Ph | H | CH | 164-166 |
| 79 | Cl | OMe | $CH_2$ | 4-$CF_3$—Ph | H | CH | 180 |
| 80 | Cl | OMe | $CH_2$ | 3-Cl—Ph | H | CH | 127-129 |
| 81 | Cl | OMe | $CH_2$ | 3-Me—Ph | H | CH | 115-118 |
| 82 | Cl | OMe | $CH_2$ | 4-Ph—Ph | H | CH | 172-174 |
| 86 | Cl | OMe | $CH_2$ | 4-$CF_3$-pyrid-2-yl | H | CH | 169-171 |

INDEX TABLE C-continued

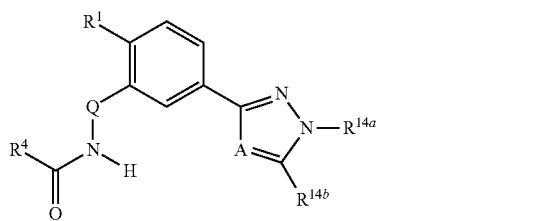

| Cmpd. | R¹ | R⁴ | Q | R¹⁴ᵃ | R¹⁴ᵇ | A | MP |
|---|---|---|---|---|---|---|---|
| 87 | Cl | OMe | $CH_2$ | 4-$CF_3$-pyrimid-2-yl | H | CH | 155-158 |
| 88 | Cl | OMe | $CH_2$ | 4-Cl-3-$CF_3$—Ph | H | CH | 165-180 |
| 89 | Cl | OMe | $CH_2$ | 3-$CF_3$—Ph | H | N | 160-163 |
| 90 | Cl | OMe | $CH_2$ | 3,5-di-MeO-triazin-1-yl | H | CH | * |
| 91 | Cl | OMe | $CH_2$ | 3-BnS-1,2,4-thiadiazol-5-yl | H | CH | * |
| 92 | Cl | OMe | $CH_2$ | 3-MeO-1,2,4-thiadiazol-5-yl | H | CH | * |
| 93 | Cl | OMe | $CH_2$ | 3-EtS-1,2,4-thiadiazol-5-yl | H | CH | * |
| 94 | Cl | OMe | $CH_2$ | 3-(4-$CF_3$—Ph)-1,2,4-thiadiazol-5-yl | H | CH | * |
| 95 | Cl | OMe | $CH_2$ | 3-c-Pr-1,2,4,-thiadiazol-5-yl | H | CH | * |
| 96 | Cl | OMe | $CH_2$ | 3-t-Bu-1,2,4-thiadiazol-5-yl | H | CH | * |
| 97 | Cl | OMe | $CH_2$ | 4-Br—Ph | H | N | 160-163 |
| 98 | Cl | OMe | $CH_2$ | Me | n-pentyl | CH | * |
| 99 | Cl | OMe | $CH_2$ | H | 4-t-bu-Ph | CH | * |
| 100 | Cl | OMe | $CH_2$ | H | $CF_3$ | CH | * |
| 101 | Cl | OMe | $CH_2$ | 1-(3,3-dimethylbutyl) | $CF_3$ | CH | * |
| 102 | Cl | OMe | $CH_2$ | n-butyl | $CF_3$ | CH | * |
| 103 | Cl | OMe | $CH_2$ | n-propyl | $CF_3$ | CH | * |
| 104 | Cl | OMe | $CH_2$ | 3-(2-propyl)-1,2,4-thiadiazol-5-yl | H | CH | * |
| 105 | Cl | OMe | $CH_2$ | 3-Me-1,2,4-thiadiazol-5-yl | H | CH | * |
| 106 | Cl | OMe | $CH_2$ | 4-MeO—Ph | H | CH | * |
| 107 | Cl | OMe | $CH_2$ | 3-MeO—Ph | H | CH | * |
| 108 | Cl | OMe | $CH_2$ | 4-($MeO_2C$)—Ph | H | CH | * |
| 109 | Cl | OMe | $CH_2$ | 4-Me—Ph | H | CH | * |
| 110 | Cl | OMe | $CH_2$ | 4-(i-propyl)-Ph | H | CH | * |
| 111 | Cl | OMe | $CH_2$ | 4-Br—Ph | H | CH | * |
| 112 | Cl | OMe | $CH_2$ | 3-Br—Ph | H | CH | * |
| 113 | Cl | OMe | $CH_2$ | 3-CN—Ph | H | CH | * |
| 114 | Cl | OMe | $CH_2$ | 4-CN—Ph | H | CH | * |
| 115 | Cl | OMe | $CH_2$ | 3-F—Ph | H | CH | * |
| 116 | Cl | OMe | $CH_2$ | 4-F—Ph | H | CH | * |
| 117 | Cl | OMe | $CH_2$ | 3,4-di-Cl—Ph | H | CH | * |
| 118 | Cl | OMe | $CH_2$ | 3,4-di-F—Ph | H | CH | * |
| 150 | Cl | OMe | $CH_2$ | 4-Ac—Ph | H | CH | * |

* See Index Table K for ¹H NMR data.

INDEX TABLE D

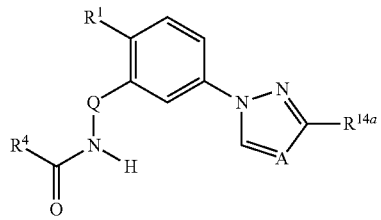

| Cmpd. | R¹ | R⁴ | Q | R¹⁴ᵃ | A | MP |
|---|---|---|---|---|---|---|
| 119 | Cl | OMe | $CH_2$ | 3-$CF_3$—Ph | CH | 125-130 |
| 120 | Cl | OMe | $CH_2$ | 3-$CF_3$—Ph | N | 155-157 |
| 121 | Cl | OMe | $CH_2$ | 3-Br—Ph | CH | 137-140 |
| 122 | Cl | OMe | $CH_2$ | 4-Cl—Ph | CH | 152-155 |
| 123 (Ex. 15) | Cl | OMe | $CH_2$ | 3-Cl—Ph | CH | 127-130 |
| 124 | Cl | OMe | $CH_2$ | 4-Br—Ph | CH | 168-170 |

INDEX TABLE E

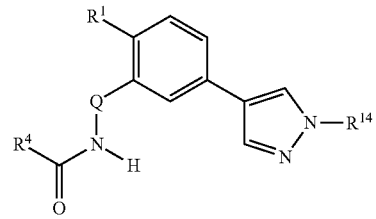

| Cmpd. | R¹ | R⁴ | Q | R¹⁴ | MP |
|---|---|---|---|---|---|
| 126 | Cl | OMe | $CH_2$ | 3-trimethylsilyl-1-propyl | * |
| 127 | Cl | OMe | $CH_2$ | H | * |
| 128 | Cl | OMe | $CH_2$ | benzyl | * |
| 129 | Cl | OMe | $CH_2$ | 2-Cl-benzyl | * |

INDEX TABLE F

| Cmpd. | R¹ | R⁴ | Q | R¹⁴ᵃ | R¹⁴ᵇ | A | Mp |
|---|---|---|---|---|---|---|---|
| 130 | Cl | OMe | CH₂ | Cl | H | CH | * |
| 131 | Cl | OMe | CH₂ | 2-Me-thiazol-4-yl | H | CH | * |
| 132 | Cl | OMe | CH₂ | 4-Me—Ph | H | CH | * |
| 133 | Cl | OMe | CH₂ | 3-Me—Ph | H | CH | * |
| 134 | Cl | OMe | CH₂ | Ph | H | CH | * |
| 137 | Cl | OMe | CH₂ | c-propyl | H | CH | * |
| 138 | Cl | OMe | CH₂ | CF₃ | H | CH | * |
| 139 | Cl | OMe | CH₂ | BnO | H | CH | * |

* See Index Table K for ¹H NMR data.

INDEX TABLE G

| Cmpd. | R¹ | R⁴ | Q | R¹⁴ᵃ | R¹⁴ᵇ | A | Mp |
|---|---|---|---|---|---|---|---|
| 140 | Cl | OMe | CH₂ | Ph | H | CH | * |
| 141 | Cl | OMe | CH₂ | Me | CF₃ | CH | * |
| 142 | Cl | OMe | CH₂ | 1-(3,3-dimethyl-butyl) | CF₃ | CH | * |
| 143 | Cl | OMe | CH₂ | i-butyl | CF₃ | CH | * |
| 144 | Cl | OMe | CH₂ | n-propyl | CF₃ | CH | * |

* See Index Table K for ¹H NMR data.

INDEX TABLE H

| Cmpd. | R¹ | R⁴ | Q | R¹⁴ | MP |
|---|---|---|---|---|---|
| 145 | Cl | OMe | CH₂ | H | * |
| 148 | Cl | OMe | CH₂ | 4-Cl—Ph | * |
| 149 | Cl | OMe | CH₂ | 4-Me-benzyl | * |

* See Index Table K for ¹H NMR data.

INDEX TABLE I

| Cmpd. | R¹ | R⁴ | Q | R¹⁴ | MP |
|---|---|---|---|---|---|
| 146 | Cl | OMe | CH₂ | 4-Me-benzyl | * |
| 147 | Cl | OMe | CH₂ | 4-Cl—Ph | * |

* See Index Table K for ¹H NMR data.

INDEX TABLE J

A dash ("—") indicates a direct bond.

| Cmpd. | R¹ | R⁴ | V | Q | R¹⁴ᵃ | R¹⁴ᵇ | MP |
|---|---|---|---|---|---|---|---|
| 83 | Me | OMe | — | C=O | 3-CF₃—Ph | H | * |
| 84 | Me | OMe | — | C=NOMe | 3-CF₃—Ph | H | * |
| 85 | Me | (MH)Me | — | C=NOMe | 3-CF₃—Ph | H | * |

* See Index Table K for ¹H NMR data.

INDEX TABLE K

| Compound No. | ¹H NMR Data (CDCl₃ solution unless indicated otherwise)ᵃ |
|---|---|
| 1 | δ 7.66 (br s, 1H), 7.51 (m, 1H), 7.34 (d, 1H), 5.21 (br s, 1H), 4.46 (d, 2H), 4.28 (m, 2H), 3.69 (s, 3H), 2.20 (s, 3H), 1.09 (m, 2H), 0.06 (s, 9H). |
| 2 | δ 7.66 (br s, 1H), 7.52 (m, 1H), 7.35 (m, 1H), 5.18 (m, 1H), 4.46 (d, 2H), 4.14 (m, 2H), 3.69 (s, 3H), 2.21 (s, 3H), 1.71 (m, 2H), 0.54 (m, 2H), 0.01 (m, 9H). |
| 3 | δ 7.66 (br s, 1H), 7.53 (m, 1H), 7.35 (d, 1H), 5.18 (br s, 1H), 4.92 (d, 1H), 4.74 (s, 1H), 4.58 (s, 2H), 4.46 (d, 2H), 3.70 (s, 3H), 2.25 (s, 3H), 1.60 (s, 2H), 0.06 (m, 9H). |
| 4 | δ 7.65 (m, 1H), 7.50 (m, 1H), 7.34 (d, 1H), 6.20 (m, 1H), 6.03 (m, 1H), 5.79 (m, 1H), 5.19 (s, 1H), 4.45 (d, 2H), 4.04 (s, 2H), 3.69 (s, 3H), 2.18 (s, 3H), 0.20 (s, 6H). |

INDEX TABLE K-continued

| Compound No. | $^1$H NMR Data (CDCl$_3$ solution unless indicated otherwise)$^a$ |
|---|---|
| 5 | δ 7.62 (s, 1H), 7.51 (m, 2H), 7.44 (m, 1H), 7.33 (m, 3H), 5.18 (s, 1H), 4.44 (d, 2H), 4.17 (s, 2H), 3.68 (s, 3H), 2.15 (s, 3H), 0.38 (m, 6 H). |
| 6 | δ 7.66 (s, 1H), 7.51 (m, 1H), 7.35 (d, 1H), 5.18 (s, 1H), 4.47 (d, 2H), 3.98 (s, 2H), 3.70 (s, 3H), 2.19 (s, 3H), 0.13 (m, 9H). |
| 7 | δ 7.65 (s, 1H), 7.49 (m, 1H), 7.33 (d, 1H), 5.25 (s, 1H), 4.45 (d, 2H), 4.00 (s, 2H), 3.68 (s, 3H), 2.17 (s, 3H), 1.00 (m, 3H), 0.62 (m, 2H), 0.09 (m, 6 H) |
| 8 | δ 7.45 (m, 2H), 7.35 (m, 2H), 7.20 (m, 1H), 7.11 (d, 1H), 7.02 (dd, 1H), 6.55 (br, 1H), 6.32 (br s, 1H), 3.78 (s, 3H). |
| 9 | δ 7.59 (d, 2H), 7.52 (d, 2H), 7.33 (d, 1H), 7.15 (d, 1H), 7.05 (dd, 1H), 6.53 (br s, 1H), 6.29 (br s, 1H), 3.78 (s, 3H), 0.30 (s, 9H). |
| 10 | δ 7.54 (d, 2H), 7.35 (d, 1H), 7.27 (d, 2H), 7.11 (d, 1H), 7.00 (dd, 1H), 6.49 (br s, 1H), 6.31 (br s, 1H), 4.22 (q, 2H), 1.28 (m, 3H). |
| 11 | δ 7.54 (d, 2H), 7.34 (d, 1H), 7.27 (d, 2H), 7.10 (d, 1H), 7.00 (dd, 1H), 6.49 (br s, 1H), 6.31 (br s, 1H), 3.78 (s, 3H). |
| 12 | δ 7.71 (d, 2H), 7.65 (d, 2H), 7.38 (d, 1H), 7.05 (d, 1H), 7.03 (dd, 1H), 6.54 (br s, 1H), 6.33 (br s, 1H), 3.78 (s, 3H). |
| 13 | δ 7.46 (d, 2H), 7.33 (d, 1H), 7.31 (d, 2H), 7.11 (d, 1H), 7.02 (dd, 1H), 6.51 (br, 1H), 6.29 (br, 1H), 3.77 (s, 3H), 2.52 (s, 3H). |
| 14 | δ 7.60 (m, 3H), 7.54 (m, 2H), 7.43 (m, 2H), 5.18 (br s, 1H), 4.51 (d, 2H), 3.69 (s, 3H), 0.30 (s, 9H). |
| 15 | δ 7.62 (br s, 1H), 7.59 (br m, 2H), 7.46 (br d, 1H), 7.38 (br m, 3H), 7.33 (br d, 1H), 4.45 (br d, 2H), 4.19 (s, 2H), 3.69 (s, 3H), 2.17 (s, 3H). 0.4 (s, 6H). |
| 16 | δ 7.63 (br s, 1H), 7.56 (m, 2H), 7.46 (d, 1H), 7.33 (d, 1H), 7.07 (t, 2H), 4.45 (d, 2H), 4.16 (s, 2H), 3.69 (s, 3H), 2.16 (s, 3H), 0.4 (s, 6H). |
| 17 | δ 7.66 (br s, 1H), 7.50 (d, 1H), 7.35 (d, 1H), 7.21 (t, 2H), 7.08 (t, 1H), 7.04 (d, 2H), 4.46 (m, 2H), 3.98 (s, 2H), 3.68 (s, 3H), 2.22 (s, 2H), 2.17 (s, 3H), 0.1(s, 6H). |
| 18 | δ 7.85 (s, 1H), 7.52 (d, 1H), 7.45 (m, 3H), 7.38 (s, 1H), 7.23 (m, 1H), 7.20 (d, 1H), 3.86 (s, 3H). |
| 19 | δ 7.84 (s, 1H), 7.52 (m, 1H), 7.51 (d, 1H), 7.41 (m, 2H), 7.37 (d, 1H), 7.34 (m, 1H), 7.19 (m, 1H), 3.86 (s, 3H). |
| 20 | δ 7.82 (s, 1H), 7.69 (d, 1H), 7.53 (m, 2H), 7.38 (d, 1H), 7.07 (d, 1H), 6.81 (d, 1H), 6.59 (d, 1H), 5.46 (s, 2H), 5.17 (br s, 1H), 4.50 (d, 2H), 3.69 (s, 3H), 2.57 (s, 3H). |
| 21 | δ 7.80 (s, 1H), 7.64 (m, 2H), 7.41 (d, 1H), 6.62 (d, 1H), 5.19 (br s, 1H), 4.50 (d, 2H), 3.70 (s, 3H). |
| 22 | δ 7.80 (s, 1H), 7.66 (d, 1H), 7.39 (d, 1H), 7.37 (d, 1H), 6.50 (d, 1H), 5.17 (br s, 1H), 4.49 (d, 2H), 4.15 (m, 2H), 3.69 (s, 3H), 1.80 (m, 2H), 1.63 (m, 1H), 0.97 (d, 6 H). |
| 23 | δ 7.80 (s, 1H), 7.67 (d, 1H), 7.40 (d, 1H), 7.37 (d, 1H), 6.51 (d, 1H), 5.15 (br s, 1H), 4.49 (br s, 2H), 4.11 (m, 2H), 3.69 (s, 3H), 1.88 (m, 2H), 0.50 (m, 2H), 0.00 (s, 9H). |
| 24 | δ 7.80 (s, 1H), 7.66 (d, 1H), 7.44 (d, 1H), 7.38 (d, 1H), 6.51 (d, 1H), 5.15 (br s, 1H), 4.49 (d, 2H), 4.29 (m, 2H), 3.69 (s, 3H), 2.21 (m, 2H), 2.15 (m, 1H), 2.12 (m, 2H), 2.03 (m, 1H). |
| 25 | δ 7.80 (s, 1H), 7.66 (d, 1H), 7.51 (s, 1H), 7.45 (d, 1H), 7.38 (d, 1H), 6.56 (d, 1H), 5.44 (s, 2H), 5.27 (br s, 1H), 4.49 (d, 2H), 3.70 (s, 3H). |
| 26 | δ 7.81 (s, 1H), 7.66 (d, 1H), 7.58 (d, 1H), 7.40 (d, 1H), 6.65 (d, 1H), 5.19 (br s, 1H), 5.11 (s, 2H), 4.50 (m, 2H), 3.70 (s, 3H). |
| 27 | δ 7.77 (d, 1H), 7.65 (d, 1H), 7.35 (d, 1H), 7.27 (d, 1H), 6.49 (d, 1H), 5.14 (br s, 1H), 4.49 (d, 2H), 3.77 (s, 2H), 3.70 (s, 3H), 0.96 (m, 3H), 0.63 (m, 2H), 0.11 (s, 6 H). |
| 28 | δ 7.80 (s, 1H), 7.66 (d, 1H), 7.38 (m, 2H), 6.52 (d, 1H), 5.15 (br s, 1H), 4.50 (d, 2H), 3.95 (s, 3H), 3.70 (s, 3H). |
| 29 | δ 7.78 (s, 1H), 7.66 (d, 1H), 7.35 (d, 1H), 7.32 (d, 1H), 6.49 (d, 1H), 5.14 (br s, 1H), 4.49 (d, 2H), 3.86 (m, 1H), 3.70 (s, 3H), 1.56 (d, 3H), 0.09 (s, 9H). |
| 30 | δ 7.80 (s, 1H), 7.66 (d, 1H), 7.38 (s, 1H), 7.36 (m, 1H), 6.49 (d, 1H), 5.16 (br s, 1H), 5.10 (m, 1H), 4.50 (d, 2H), 4.12 (m, 2H), 3.69 (s, 3H), 2.57 (m, 2H), 1.99 (m, 1H), 1.69 (s, 3H), 1.53 (s, 3H). |
| 31 | δ 7.81 (s, 1H), 7.64 (d, 1H), 7.52 (d, 1H), 7.39 (d, 1H), 6.56 (d, 1H), 5.19 (br s., 1H), 4.50 (d, 2H), 4.42 (m, 2H), 3.70 (s, 3H), 3.01 (m, 2H). |
| 32 | δ 7.80 (s, 1H), 7.65 (d, 1H), 7.45 (d, 1H), 7.38 (d, 1H), 6.54 (d, 1H), 5.19 (br s, 1H), 4.49 (d, 2H), 4.30 (m, 2H), 3.69 (s, 3H), 2.34 (m, 4H). |
| 34 | δ 7.95 (d, 1H), 7.92 (s, 1H), 7.76 (m, 3H), 7.47 (m, 2H), 7.41 (d, 1H), 7.30 (m, 1H), 6.76 (d, 1H), 5.21 (br s, 1H), 4.52 (d, 2H), 3.70 (s, 3H). |
| 35 | δ 8.19 (s, 1H), 7.97 (s, 1H), 7.53 (s, 1H), 7.38 (m, 2H), 5.27 (br s, 1H), 4.47 (d, 2H), 3.70 (s, 3H), 2.99 (m, 6H). |
| 36 | δ 7.79 (s, 1H), 7.64 (d, 1H), 7.37 (d, 1H), 7.34 (d, 1H), 7.11 (m, 4 H), 6.95 (m, 4 H), 6.51 (d, 1H), 5.17 (br s, 1H), 4.49 (d, 2H), 4.14 (m, 2H), 3.88 (m, 1H), 3.67 (s, 3H), 1.99 (m, 2H), 1.86 (m, 2H). |
| 37 | δ 7.69 (d, 1H), 7.56 (d, 1H), 7.36 (d, 1H), 7.28 (d, 1H), 7.23 (d, 1H), 7.12 (m, 2H), 6.88 (d, 1H), 6.47 (d, 1H), 5.56 (br s, 1H), 5.35 (s, 2H), 4.37 (d, 2H), 3.57 (s, 3H). |
| 38 | δ 7.82 (s, 1H), 7.68 (d, 1H), 7.57 (m, 1H), 7.52 (s, 1H), 7.48 (m, 1H), 7.40 (m, 3H), 6.59 (d, 1H), 5.41 (s, 2H), 5.17 (br s, 1H), 4.50 (d, 2H), 3.69 (s, 3H). |
| 39 | δ 7.76 (s, 1H), 7.62 (d, 1H), 7.35 (d, 1H), 6.28 (s, 1H), 5.19 (br s, 1H), 4.48 (d, 2H), 4.17 (m, 2H), 3.69 (s, 3H), 2.34 (s, 3H), 2.22 (m, 2H), 2.11 (m, 2H), 2.02 (t, 1H). |
| 40 | δ 7.77 (s, 1H), 7.62 (d, 1H), 7.36 (d, 1H), 6.29 (s, 1H), 5.14 (br s, 1H), 4.49 (d, 2H), 4.03 (m, 2H), 3.70 (s, 3H), 2.31 (s, 3H), 1.84 (m, 2H), 0.52 (m, 2H), 0.00 (m, 9H). |
| 41 | δ 7.80 (s, 1H), 7.66 (d, 1H), 7.38 (m, 2H), 6.51 (d, 1H), 5.15 (br s, 1H), 4.50 (d, 2H), 4.12 (m, 2H), 3.69 (s, 3H), 1.91 (m, 2H), 1.58 (m, 1H), 1.22 (m, 2H), 0.89 (d, 6H). |
| 42 | δ 7.80 (s, 1H), 7.66 (d, 1H), 7.37 (m, 2H), 7.29 (m, 2H), 7.20 (m, 3H), 6.51 (d, 1H), 5.19 (br s, 1H), 4.49 (d, 2H), 4.14 (m, 2H), 3.68 (s, 3H), 2.65 (m, 2H), 2.25 (m, 2H). |

INDEX TABLE K-continued

| Compound No. | $^1$H NMR Data (CDCl$_3$ solution unless indicated otherwise)$^a$ |
|---|---|
| 43 | δ 7.80 (s, 1H), 7.65 (d, 1H), 7.43 (d, 1H), 7.37 (d, 1H), 6.52 (d, 1H), 5.21 (br s, 1H), 4.50 (m, 3H), 4.39 (m, 1H), 4.30 (m, 2H), 3.69 (s, 3H), 2.30 (m, 2H). |
| 45 | δ 7.78 (s, 1H), 7.64 (d, 1H), 7.39 (d, 1H), 6.84 (s, 1H), 5.22 (br s, 1H), 4.49 (d, 2H), 4.19 (m, 2H), 3.69 (s, 3H), 1.91 (m, 2H), 0.52 (m, 2H), 0.00 (s, 9H). |
| 46 | δ 7.80 (s, 1H), 7.66 (d, 1H), 7.38 (d, 1H), 7.36 (s, 0 H), 6.50 (d, 1H), 5.16 (br s, 1H), 4.49 (d, 2H), 4.14 (m, 2H), 3.69 (s, 3H), 1.88 (m, 2H), 1.36 (m, 2H), 0.96 (m, 3H). |
| 47 | δ 7.92 (s, 1H), 7.77 (d, 1H), 7.43 (m, 2H), 5.15 (br s, 1H), 4.51 (d, 2H), 4.06 (m, 2H), 3.69 (s, 3H), 1.86 (m, 2H), 0.49 (m, 2H), 0.00 (s, 9H). |
| 48 | δ 8.55 (d, 1H), 8.23 (s, 1H), 7.98 (d, 1H), 7.94 (s, 1H), 7.78 (d, 1H), 7.64 (d, 1H), 7.42 (d, 1H), 6.75 (d, 1H), 5.20 (br s, 1H), 4.53 (d, 2H), 3.71 (s, 3H), 2.37 (s, 3H). |
| 49 | 8.62 (d, 1H), 7.94 (s, 1H), 7.87 (d, 1H), 7.79 (d, 1H), 7.71 (m, 1H), 7.42 (d, 1H), 7.04 (d, 1H), 6.75 (d, 1H), 5.20 (br s, 1H), 4.53 (d, 2H), 3.71 (s, 3H), 2.57 (s, 3H). |
| 50 | δ 8.05 (s, 1H), 8.01 (d, 1H), 7.93 (m, 2H), 7.79 (d, 1H), 7.58 (m, 2H), 7.43 (d, 1H), 6.80 (d, 1H), 5.22 (br s, 1H), 4.53 (d, 2H), 3.71 (s, 3H). |
| 51 | δ 7.88 (s, 1H), 7.82 (m, 1H), 7.72 (m, 3H), 7.64 (m, 2H), 7.41 (d, 1H), 6.76 (d, 1H), 5.15 (br s, 1H), 4.50 (br s, 2H), 3.70 (s, 3H). |
| 52 | δ 7.92 (d, 1H), 7.90 (s, 1H), 7.76 (d, 1H), 7.68 (d, 1H), 7.54 (d, 1H), 7.41 (m, 2H), 7.36 (m, 1H), 6.77 (d, 1H), 5.18 (br s, 1H), 4.51 (d, 2H), 3.70 (s, 3H). |
| 53 | δ 7.81 (s, 1H), 7.68 (d, 1H), 7.52 (m, 3H), 7.39 (d, 1H), 6.62 (d, 1H), 5.50 (s, 2H), 5.16 (br s, 1H), 4.50 (d, 2H), 3.69 (s, 3H). |
| 54 | δ 8.31 (s, 1H), 8.04 (m, 2H), 7.93 (s, 1H), 7.88 (d, 1H), 7.80 (d, 1H), 7.59 (m, 1H), 7.43 (d, 1H), 6.80 (d, 1H), 5.22 (br s, 1H), 4.53 (d, 2H), 3.71 (s, 3H), 2.69 (s, 3H). |
| 55 | δ 7.83 (s, 1H), 7.74 (d, 1H), 7.69 (d, 1H), 7.62 (m, 1H), 7.54 (d, 2H), 7.45 (m, 3H), 7.36 (m, 3H), 6.59 (d, 1H), 5.41 (s, 2H), 5.24 (br s, 1H), 4.49 (d, 2H), 3.68 (s, 3H). |
| 56 | δ 7.90 (m, 2H), 7.79 (s, 1H), 7.61 (d, 1H), 7.52 (d, 1H), 7.43 (d, 2H), 7.36 (d, 1H), 6.47 (d, 1H), 5.16 (br s, 1H), 4.61 (m, 2H), 4.48 (d, 2H), 3.69 (s, 3H), 3.61 (m, 2H). |
| 57 | δ 7.81 (s, 1H), 7.68 (d, 1H), 7.35 (m, 4 H), 7.26 (m, 3H), 6.55 (d, 1H), 5.35 (s, 2H), 5.17 (br s, 1H), 4.49 (d, 2H), 3.70 (s, 3H). |
| 58 | δ 7.81 (s, 1H), 7.68 (d, 1H), 7.38 (d, 1H), 7.27 (m, 3H), 7.16 (d, 1H), 7.11 (d, 2H), 6.44 (d, 1H), 5.18 (br s, 1H), 4.51 (d, 2H), 4.36 (m, 2H), 3.70 (s, 3H), 3.20 (t, 2H). |
| 59 | δ 7.79 (s, 1H), 7.64 (d, 1H), 7.55 (d, 1H), 7.36 (d, 1H), 7.26 (m, 2H), 6.95 (m, 1H), 6.87 (d, 2H), 6.51 (d, 1H), 5.22 (br s, 1H), 4.52 (m, 2H), 4.48 (d, 2H), 4.35 (m, 2H), 3.68 (s, 3H). |
| 60 | δ 7.81 (s, 1H), 7.68 (d, 1H), 7.39 (m, 2H), 7.28 (m, 2H), 7.22 (s, 1H), 7.12 (m, 1H), 6.58 (d, 1H), 5.32 (s, 2H), 5.18 (br s, 1H), 4.49 (d, 2H), 3.69 (s, 3H). |
| 61 | δ 7.79 (s, 1H), 7.64 (d, 1H), 7.38 (m, 2H), 7.28 (m, 2H), 6.96 (d, 1H), 6.89 (d, 2H), 6.48 (d, 1H), 5.17 (br s, 1H), 4.49 (d, 2H), 4.38 (m, 2H), 3.94 (m, 2H), 3.69 (s, 3H), 2.38 (m, 2H). |
| 62 | δ 7.83 (s, 1H), 7.69 (d, 2H), 7.43 (m, 4 H), 7.02 (d, 1H), 6.61 (d, 1H), 5.58 (s, 2H), 5.21 (br s, 1H), 4.49 (d, 2H), 3.69 (s, 3H) |
| 63 | δ 7.82 (s, 1H), 7.67 (d, 1H), 7.60 (d, 2H), 7.42 (d, 1H), 7.38 (d, 1H), 7.33 (d, 2H), 6.59 (d, 1H), 5.41 (s, 2H), 5.19 (br s, 1H), 4.49 (d, 2H), 3.69 (s, 3H). |
| 64 | δ 8.0 (s, 1H), 7.98 (s, 1H), 7.90 (d, 1H), 7.59 (t, 1H), 7.5 (d, 1H), 7.4 (s, 1H), 7.3 (d, 1H), 7.1 (d, 1H), 6.7 (s, 1H), 6.58 (br s, 1H), 5.7(br s, 1H), 3.7(s, 3H), 2.2(s, 3H). |
| 65 | δ 7.81 (s, 1H), 7.67 (m, 1H), 7.39 (m, 3H), 7.15 (t, 2H), 7.08 (s, 1H), 6.59 (d, 1H), 5.36 (s, 2H), 5.20 (br s, 1H), 4.49 (d, 2H), 3.69 (s, 3H). |
| 66 | δ 7.81 (s, 1H), 7.67 (d, 1H), 7.54 (m, 1H), 7.38 (m, 2H), 7.26 (m, 1H), 7.19 (m, 2H), 6.58 (d, 1H), 5.35 (s, 2H), 5.19 (br s, 1H), 4.49 (d, 2H), 3.69 (s, 3H). |
| 70 | δ 7.81 (s, 1H), 7.68 (d, 1H), 7.37 (d, 1H), 7.22 (m, 4 H), 7.05 (d, 1H), 6.53 (d, 1H), 5.34 (s, 2H), 5.21 (br s, 1H), 4.49 (d, 2H), 3.68 (s, 3H), 2.30 (s, 3H). |
| 71 | δ 7.81 (s, 1H), 7.68 (d, 1H), 7.36 (m, 2H), 7.25 (m, 1H), 7.12 (d, 1H), 7.05 (m, 2H), 6.54 (d, 1H), 5.30 (s, 2H), 5.20 (br s, 1H), 4.49 (d, 2H), 3.68 (s, 3H), 2.33 (s, 3H). |
| 73 | δ 8.17 (m, 1H), 8.12 (s, 1H), 7.81 (s, 1H), 7.67 (d, 1H), 7.55 (m, 2H), 7.47 (d, 1H), 7.38 (d, 1H), 6.62 (d, 1H), 5.45 (s, 2H), 5.21 (br s, 1H), 4.49 (d, 2H), 3.69 (s, 3H). |
| 75 | δ 7.81 (s, 1H), 7.67 (d, 1H), 7.60 (m, 1H), 7.49 (s, 1H), 7.45 (m, 3H), 7.38 (d, 1H), 6.61 (d, 1H), 5.38 (s, 2H), 5.22 (br s, 1H), 4.49 (d, 2H), 3.68 (s, 3H). |
| 76 | δ 7.80 (s, 1H), 7.67 (d, 1H), 7.43 (d, 1H), 7.29 (m, 4 H), 7.11 (d, 1H), 6.57 (d, 1H), 5.43 (s, 2H), 5.22 (br s, 1H), 4.48 (d, 2H), 3.68 (s, 3H). |
| 83 | δ 8.2 (s, 1H), 8.0-8.1 (m,3H), 7.9 (d, 1H), 7.5-7.6(m, 2H), 7.4 (d, 1H), 6.8 (d, 1H), 4.0 (s, 3H), 2.6 (s, 3H). |
| 84 | δ 8.0 (s, 1H), 7.99 (d, 1H), 7.9 (d, 1H), 7.8(d, 1H), 7.63 (s, 1H), 7.5-7.6 (m, 2H), 7.3 (d, 1H), 6.7 (d, 1H), 4.07 (s, 3H), 3.89 (s, 3H), 2.23 (s, 3H). |
| 85 | δ 8.0 (s, 1H), 7.99 (d, 1H), 7.9 (d, 1H), 7.8 (d, 1H), 7.63 (s, 1H), 7.5-7.6 (m, 2H), 7.3 (d, 1H), 6.7 (d, 1H), ), 3.89 (s, 3H), 2.9 (d, 3H), 2.2 (s, 3H). |
| 90 | δ 8.63 (d, 1H), 7.96 (s, 1H), 7.86 (d, 1H), 7.44 (d, 1H), 6.83 (d, 1H), 5.20 (br s, 1H), 4.52 (d, 2H), 4.16 (s, 6 H), 3.70 (s, 3H) |
| 91 | δ 8.29 (d, 1H), 7.87 (s, 1H), 7.75 (d, 1H), 7.46 (m, 3H), 7.31 (m, 3H), 6.82 (d, 1H), 5.25 (br, 1H), 4.51 (m, 4H), 3.71 (s, 3H). |
| 92 | δ 8.27 (d, 1H), 7.86 (s, 1H), 7.73 (d, 1H), 7.43 (d, 1H), 6.81 (d, 1H), 5.32 (br s, 1H), 4.51 (d, 2H), 4.11 (s, 3H), 3.71 (s, 3H). |
| 93 | δ 8.28 (d, 1H), 7.86 (s, 1H), 7.73 (d, 1H), 7.44 (d, 1H), 6.81 (d, 1H), 5.31 (br s, 1H), 4.51 (d, 2H), 3.71 (s, 3H), 3.26 (m, 2H), 1.47 (t, 3H). |
| 94 | δ 8.43 (d, 1H), 8.41 (d, 2H), 7.91 (s, 1H), 7.78 (d, 1H), 7.76 (d, 2H), 7.46 (d, 1H), 6.88 (d, 1H), 5.27 (br s, 1H), 4.53 (d, 2H), 3.72 (s, 3H). |
| 95 | δ 8.25 (d, 1H), 7.84 (s, 1H), 7.71 (d, 1H), 7.41 (d, 1H), 6.77 (d, 1H), 5.37 (br s, 1H), 4.49 (d, 2H), 3.70 (s, 3H), 2.27 (m, 1H), 1.15 (m, 2H), 1.06 (m, 2H). |

INDEX TABLE K-continued

| Compound No. | ¹H NMR Data (CDCl₃ solution unless indicated otherwise)[a] |
|---|---|
| 96 | δ 8.32 (d, 1H), 7.85 (s, 1H), 7.73 (d, 1H), 7.39 (m, 1H), 6.78 (d, 1H), 5.44 (br s, 1H), 4.49 (d, 2H), 3.70 (s, 3H), 1.45 (s, 9H). |
| 98 | δ 7.44 (d, 1H), 7.36 (d, 1H), 7.26 (m, 1H), 5.25 (br s, 1H), 4.48 (d, 2H), 3.81 (s, 3H), 3.69 (s, 3H), 2.6 (m, 2H), 1.67 (m, 2H), 1.37 (m, 4H), 0.92 (m, 3H). |
| 99 | δ 7.80 (s, 1H), 7.57 (m, 3H), 7.39 (m, 3H), 6.74 (s, 1H), 5.72 (br s, 1H), 5.34 (br s, 1H), 4.41 (d, 2H), 3.62 (s, 3H), 1.34 (s, 9H). |
| 100 | (DMSO-d₆) δ 7.82 (s, 1H), 7.74 (d, 1H), 7.65 (m, 1H), 7.57 (d, 1H), 7.19 (s, 1H), 4.31 (d, 2H), 3.59 (s, 3H). |
| 101 | δ 7.78 (s, 1H), 7.63 (d, 1H), 7.39 (d, 1H), 6.84 (s, 1H), 5.24 (br s, 1H), 4.47 (d, 2H), 4.24 (t, 2H), 3.70 (s, 3H), 1.83 (m, 2H), 1.01 (s, 9H). |
| 102 | δ 7.79 (s, 1H), 7.63 (d, 1H), 7.39 (d, 1H), 6.85 (s, 1H), 5.23 (br s, 1H), 4.49 (d, 2H), 4.23 (t, 2H), 3.70 (s, 3H), 1.93 (m, 2H), 1.40 (m, 2H), 0.97 (t, 3H). |
| 103 | δ 7.79 (s, 1H), 7.64 (d, 1H), 7.39 (d, 1H), 6.85 (s, 1H), 5.23 (br s, 1H), 4.49 (d, 2H), 4.19 (t, 2H), 3.70 (s, 3H), 1.97 (m, 2H), 0.97 (t, 3H). |
| 104 | δ 8.22 (d, 1H), 7.79 (s, 1H), 7.63 (d, 1H), 7.38 (d, 1H), 6.74 (d, 1H), 5.42 (br s, 1H), 4.42 (d, 2H), 3.67 (s, 3H), 3.18 (m, 1H), 1.37 (d, 6H). |
| 105 | δ 8.29 (d, 1H), 7.86 (s, 1H), 7.74 (d, 1H), 7.43 (d, 1H), 6.81 (d, 1H), 5.32 (br s, 1H), 4.51 (d, 2H), 3.71 (s, 3H), 2.62 (s, 3H). |
| 106 | δ 7.90 (d, 1H), 7.84 (d, 1H), 7.76 (d, 1H), 7.65 (d, 2H), 7.40 (d, 1H), 6.98 (d, 2H), 6.72 (d, 1H), 5.19 (br s, 1H), 4.51 (d, 2H), 3.85 (s, 3H), 3.70 (s, 3H). |
| 107 | δ 7.93 (m, 2H), 7.78 (d, 1H), 7.41 (d, 1H), 7.37 (m, 2H) 7.30 (m, 1H), 6.84 (d, 1H), 6.75 (d, 1H), 5.19 (br s, 1H), 4.52 (d, 2H), 3.89 (s, 3H), 3.70 (s, 3H). |
| 108 | δ 8.15 (d, 2H), 8.03 (d, 1H), 7.93 (s, 1H), 7.85 (d, 2H), 7.78 (d, 1H), 7.43 (d, 1H), 6.81 (d, 1H) 5.21 (br s, 1H), 4.52 (d, 2H), 3.95 (s, 3H), 3.71 (s, 3H). |
| 109 | δ 7.90 (m, 2H), 7.77 (d, 1H), 7.63 (m, 2H), 7.41 (d, 1H), 7.27 (m, 2H), 6.73 (d, 1H), 5.19 (br s, 1H), 4.51 (d, 2H), 3.70 (s, 3H), 2.39 (s, 3H). |
| 110 | δ 7.91 (d, 2H), 7.77 (d, 1H), 7.65 (d, 2H), 7.41 (d, 1H), 7.29 (m, 2H), 6.73 (d, 1H), 5.17 (br s, 1H), 4.51 (d, 2H), 3.70 (s, 3H), 2.96 (m, 1H), 1.28 (d, 6H). |
| 111 | δ 7.92 (m, 2H), 7.77 (d, 1H), 7.61 (m, 4H), 7.41 (m, 1H), 6.77 (d, 1H), 5.19 (br s, 1H), 4.51 (d, 2H), 3.70 (s, 3H). |
| 112 | δ 7.94 (m, 3H), 7.79 (d, 1H), 7.68 (d, 1H), 7.42 (d, 2H), 7.33 (m, 1H), 6.77 (d, 1H), 5.20 (br s, 1H), 4.52 (d, 2H), 3.71 (s, 3H). |
| 113 | δ 8.1 (d, 1H), 7.99 (m, 2H), 7.91 (d, 1H), 7.78 (d, 1H), 7.59 (m, 2H), 7.44 (d, 1H), 6.81 (d, 1H), 5.21 (br s, 1H), 4.52 (d, 2H), 3.71 (s, 3H). |
| 114 | δ 8.02 (d, 1H), 7.91 (m, 3H), 7.77 (m, 3H), 7.44 (d, 1H) 6.83 (d, 1H), 5.22 (br s, 1H), 4.52 (d, 2H), 3.70 (s, 3H). |
| 115 | δ 7.95 (d, 1H), 7.93 (d, 1H), 7.78 (d, 1H), 7.54 (m, 2H), 7.42 (m, 2H), 6.99 (m, 1H), 6.77 (d, 1H), 5.20 (br s, 1H), 4.52 (d, 2H), 3.70 (s, 3H). |
| 116 | δ 7.89 (m, 2H), 7.74 (m, 3H), 7.44 (d, 1H), 7.16 (m, 2H), 6.75 (d, 1H), 5.22 (br s, 1H), 4.51 (d, 2H), 3.70 (s, 3H). |
| 117 | δ 7.92 (m, 3H), 7.77 (d, 1H), 7.59 (d, 1H), 7.53 (d, 1H), 7.42 (d, 1H), 6.78 (d, 1H), 5.21 (br s, 1H), 4.52 (d, 2H), 3.70 (s, 3H). |
| 118 | δ 7.90 (m, 2H), 7.77 (d, 1H), 7.66 (m, 1H), 7.45 (m, 2H), 7.26 (m, 1H), 6.77 (d, 1H), 5.21 (br s, 1H), 4.51 (d, 2H), 3.70 (s, 3H). |
| 126 | δ 7.74 (s, 1H), 7.63 (s, 1H), 7.49 (s, 1H), 7.34 (d, 2H), 5.23 (br s, 1H), 4.46 (d, 2H), 4.10 (d, 2H), 3.69 (s, 3H), 1.88 (m, 2H), 0.49 (m, 2H), 0.00 (s, 9H). |
| 127 | δ 8.02 (s, 1H), 7.83 (s, 2H), 7.36 (s, 2H), 5.30 (br s, 1H), 4.47 (d, 2H), 3.70 (s, 3H). |
| 128 | δ 7.78 (s, 1H), 7.60 (m, 1H), 7.31 (m, 8 H), 5.32 (s, 2H), 5.28 (s, 1H), 4.43 (d, 2H), 3.67 (s, 3H). |
| 129 | δ 7.80 (s, 1H), 7.69 (s, 1H), 7.48 (s, 1H), 7.41 (d, 1H), 7.33 (s, 2H), 7.26 (m, 2H), 7.09 (d, 1H), 5.45 (s, 2H), 5.24 (br s, 1H), 4.44 (d, 2H), 3.68 (s, 3H). |
| 130 | δ 8.65 (d, 1H), 8.09 (s, 1H), 7.98 (d, 1H), 7.63 (d, 1H), 7.51 (d, 1H), 5.35 (br s, 1H), 4.52 (d, 2H), 3.70 (s, 3H). |
| 131 | δ 8.84 (d, 1H), 8.27 (s, 1H), 8.18 (s, 1H), 8.03 (m, 1H), 7.55 (d, 1H), 7.49 (d, 1H), 5.58 (m, 1H), 4.54 (d, 2H), 3.71 (s, 3H), 2.84 (s, 3H). |
| 132 | δ 8.81 (d, 1H), 8.44 (d, 2H), 8.21 (br s, 1H), 8.10 (d, 1H), 7.52 (m, 2H), 7.32 (d, 2H), 5.29 (br s, 1H), 4.55 (d, 2H), 3.72 (s, 3H), 2.44 (s, 3H). |
| 133 | δ 8.83 (d, 1H), 8.36 (d, 2H), 8.21 (s, 1H), 8.10 (d, 1H), 7.55 (d, 1H), 7.52 (d, 1H), 7.41 (m, 1H), 7.32 (d, 1H), 5.29 (br s, 1H), 4.56 (d, 2H), 3.72 (s, 3H), 2.48 (s, 3H). |
| 134 | δ 8.85 (d, 1H), 8.56 (m, 2H), 8.24 (s, 1H), 8.12 (d, 1H), 7.58 (d, 1H), 7.52 (m, 4 H), 5.29 (br s, 1H), 4.56 (d, 2H), 3.73 (s, 3H). |
| 137 | δ 8.58 (d, 1H), 8.08 (s, 1H), 7.94 (d, 1H), 7.46 (d, 1H), 7.40 (d, 1H), 5.39 (br s, 1H), 4.52 (d, 2H), 3.71 (s, 3H), 2.31 (m, 1H), 1.20 (m, 2H), 1.09 (m, 2H). |
| 138 | δ 8.92 (d, 1H), 8.16 (d, 1H), 8.08 (d, 1H), 7.87 (d, 1H), 7.54 (d, 1H), 5.31 (br s, 1H), 4.54 (d, 2H), 3.71 (s, 3H). |
| 139 | δ 8.56 (d, 1H), 8.10 (s, 1H), 7.95 (d, 1H), 7.52 (d, 2H), 7.47 (d, 1H), 7.37 (m, 2H), 7.30 (d, 1H), 7.32 (d, 1H), 5.52 (s, 2H), 5.31 (br s, 1H), 4.52 (d, 2H), 3.69 (s, 3H). |
| 140 | δ 7.71 (d, 1H), 7.34 (m, 3H), 7.27 (m, 4 H), 7.03 (d, 1H), 6.51 (d, 1H), 5.12 (br s, 1H), 4.37 (d, 2H), 3.66 (s, 3H). |
| 141 | δ 7.49 (m, 2H), 7.29 (m, 1H), 6.56 (s, 1H), 4.49 (d, 2H), 3.91 (s, 3H), 3.68 (s, 3H). |
| 142 | δ 7.49 (d, 1H), 7.44 (s, 1H), 7.26 (d, 1H), 6.51 (s, 1H), 5.23 (br s, 1H), 4.50 (d, 2H), 4.14 (m, 2H), 3.69 (s, 3H), 1.75 (m, 2H), 0.87 (s, 9H). |
| 143 | δ 7.48 (d, 1H), 7.43 (s, 1H), 7.25 (d, 1H), 6.51 (s, 1H), 5.23 (br s, 1H), 4.50 (d, 2H), 4.11 (t, 2H), 3.69 (s, 3H), 1.79 (m, 2H), 1.24 (m, 2H), 0.86 (t, 3H). |
| 144 | δ 7.48 (d, 1H), 7.43 (s, 1H), 7.25 (d, 1H), 6.51 (s, 1H), 5.24 (br s, 1H), 4.50 (d, 2H), 4.08 (t, 2H), 3.69 (s, 3H), 1.84 (m, 2H), 0.85 (t, 3H). |

INDEX TABLE K-continued

| Compound No. | ¹H NMR Data (CDCl₃ solution unless indicated otherwise)[a] |
|---|---|
| 145 | δ 7.94 (s, 1H), 7.83 (s, 1H), 7.70 (d, 1H), 7.42 (d, 1H), 5.28 (br s, 1H), 4.50 (d, 2H), 3.71 (s, 3H). |
| 146 | δ 7.82 (s, 1H), 7.79 (br s, 1H), 7.61 (d, 1H), 7.38 (d, 1H), 7.24 (d, 2H), 7.13 (d, 2H), 5.56 (s, 2H), 5.23 (br s, 1H), 4.48 (d, 2H), 3.69 (s, 3H), 2.32 (s, 3H). |
| 147 | δ 8.08 (d, 2H), 8.04 (s, 1H), 7.96 (br s, 1H), 7.75 (dd, 1H), 7.48-7.44 (m, 3H), 5.25 (br s, 1H), 4.51 (d, 2H), 3.71 (s, 3H). |
| 148 | δ 8.20 (s, 1H), 7.89 (s, 1H), 7.83 (d, 1H), 7.74 (d, 2H), 7.53 (d, 2H), 5.24 (br s, 1H), 4.52 (d, 2H), 3.70 (s, 3H). |
| 149 | δ 7.77 (s, 1H), 7.72 (d, 1H), 7.65 (s, 1H), 7.39 (d, 1H), 7.21 (apparent s, 4H), 5.52 (s, 2H), 5.21 (br s, 1H), 4.41 (d, 2H), 3.67 (2, 3H), 2.36 (s, 3H). |
| 150 | δ 8.10 (m, 3H), 7.92 (m, 3H), 7.80 (d, 1H), 6.83 (s, 1H), 5.23 (br s, 1H), 4.54 (d, 2H), 3.75 (s, 3H), 2.65 (s, 3H). |

[a]¹H NMR data are in ppm downfield from tetramethylsilane. Couplings are designated by (s)-singlet, (br s)-broad singlet, (d)-doublet, (t)-triplet, (q)-quartet, (m)-multiplet, (dd)-doublet of doublets.

Biological Examples of the Invention

General Protocol for Preparing Test Suspensions for Tests A-L

The test compounds were first dissolved in acetone in an amount equal to 3% of the final volume and then suspended at the desired concentration (in ppm) in acetone and purified water (50/50 mix) containing 250 ppm of the surfactant Trem® 014 (polyhydric alcohol esters). The resulting test suspensions were then used in Tests A-L. Spraying a 200 ppm test suspension to the point of run-off on the test plants was the equivalent of an application rate of 500 g/ha.

Test A

The test suspension was sprayed to the point of run-off on wheat seedlings. The following day the seedlings were inoculated with a spore dust of *Erysiphe graminis* f. sp. *tritici* (the causal agent of wheat powdery mildew) and incubated in a growth chamber at 20° C. for 8 days, after which time disease ratings were made.

Test B

The test suspension was sprayed to the point of run-off on wheat seedlings. The following day the seedlings were inoculated with a spore suspension of *Puccinia recondite* f. sp. *tritici* (the causal agent of wheat leaf rust) and incubated in a saturated atmosphere at 20° C. for 24 h, and then moved to a growth chamber at 20° C. for 7 days, after which time disease ratings were made.

Test C

The test suspension was sprayed to the point of run-off on wheat seedlings. The following day the seedlings were inoculated with a spore suspension of *Septoria nodorum* (the causal agent of wheat glume blotch) and incubated in a saturated atmosphere at 20° C. for 48 h, and then moved to a growth chamber at 20° C. for 7 days, after which time disease ratings were made.

Test D

The test suspension was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 19 days, after which time disease ratings were made.

Test E

The test suspension was sprayed to the point of run-off on wheat seedlings. The following day the seedlings were inoculated with a spore suspension of *Fusarium graminearum* (the causal agent of wheat head scab) and incubated in a saturated atmosphere at 24° C. for 72 H, and then moved to a growth chamber at 20° C. for 5 days, after which time disease ratings were made.

Test F

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time disease ratings were made.

Test G

The test suspension was sprayed to the point of run-off on cucumber seedlings. The following day the seedlings were inoculated with a spore suspension of *Colletotrichum orbiculare* (the causal agent of cucumber *Colletotrichum* anthracnose) and incubated in saturated atmosphere at 20° C. for 24 h, and moved to a growth chamber at 24° C. for 5 additional days, after which time disease ratings were made.

Test H

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time disease ratings were made.

Test I

The test suspension was sprayed to the point of run-off on creeping bent grass seedlings. The following day the seedlings were inoculated with a spore suspension of *Rhizocto-* nia oryzae (the causal agent of turf brown patch) and incubated in a saturated atmosphere at 27° C. for 48 h, and then moved to a growth chamber at 27° C. for 3 days, after which time disease ratings were made.

Test J

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 4 days, after which time disease ratings were made.

Test K

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings and then moved to a growth chamber at 20° C. for 6 days, after which the test units were placed back into a saturated atmosphere at 20° C. for 24 h. Upon removal, disease ratings were made.

Test L

The test suspension was sprayed to the point of run-off on bluegrass seedlings. The following day the seedlings were inoculated with a spore suspension of *Pythium aphanidermatum* (the causal agent of bluegrass *pythium* blight) and incubated in a covered saturated atmosphere at 27° C. for 48 h, and then the covers where removed and the plants left at 27° C. for 3 additional days, after which time disease ratings were made.

Results for Tests A-L are given in Table A. In the table, a rating of 100 indicates 100% disease control, and a rating of 0 indicates no disease control (relative to the controls). A dash (-) indicates no test results. All results are for 200 ppm except where followed by an "*", which indicates 40 ppm or "**", which indicates 50 ppm.

TABLE A

RESULTS OF BIOLOGICAL TESTS

Percentage Disease Control

| Cmpd No. | Test A | Test B | Test C | Test D | Test E | Test F | Test G | Test H | Test I | Test J | Test K | Test L |
|---|---|---|---|---|---|---|---|---|---|---|---|---|
| 1 | 100 | 100 | 100 | 100* | 100 | 0 | — | 0 | 0 | 0 | 66 | 0 |
| 2 | 100 | 100 | 99 | 91* | 100 | 0 | — | — | 0 | 0 | 70 | 0 |
| 3 | 98 | 100 | 99 | 16* | 87 | 0 | — | 0 | 0 | 0 | 26 | 0 |
| 4 | 98 | 99 | 99 | 59* | 97 | 37 | — | — | 0 | 0 | 74 | 0 |
| 5 | 99 | 100 | 99 | 100* | 0 | 0 | — | 77 | 0 | 0 | 23 | 0 |
| 6 | 99* | 100* | 96* | 100* | 68* | — | — | — | — | — | — | — |
| 7 | 100* | 100* | 99* | 100* | 0* | — | — | — | — | — | — | — |
| 8 | 100 | 100 | 99 | — | 92 | 0 | 100 | — | 0 | 100 | 99 | 33 |
| 9 | 95 | 99 | 100 | — | 0 | 29 | 99 | — | 0 | 0 | 0 | 0 |
| 10 | 98 | 79 | 82 | — | 0 | 0 | 25 | — | 0 | 0 | 0 | 0 |
| 11 | 100 | 100 | 96 | — | 86 | 0 | 99 | — | 0 | 93 | 79 | 87 |
| 12 | 98 | 95 | 98 | — | 98 | 45 | 91 | — | 0 | 0 | 0 | 63 |
| 13 | 46 | 89 | 99 | — | 0 | 0 | — | — | 0 | 0 | 0 | 0 |
| 14 | 96 | 98 | 93 | — | 0 | 0 | 0 | — | 0 | 0 | 0 | 80 |
| 15 | 100* | 100* | 100* | 100* | — | 0 | — | 33 | — | — | — | — |
| 16 | 99* | 100* | 100* | 100* | — | 67 | — | 95* | — | — | — | — |
| 17 | 67 | 99* | 100 | 100* | — | 0 | — | 38 | — | — | — | — |
| 18 | 100* | 99* | 99* | 98* | 100 | 0 | — | 70 | 0 | 89 | 81 | 98 |
| 19 | 99* | 99* | 97* | 98* | 99* | 0* | — | 63* | — | — | — | — |
| 20 | 99 | 100 | 96 | — | 72 | 0 | — | 0 | 0 | 0 | 0 | 0 |
| 21 | 0 | 79 | 0 | — | 0 | 0 | — | 0 | 0 | 0 | 0 | 0 |
| 22 | 99* | 95* | 99 | 85* | 99 | 0 | — | 0 | 0 | 50 | 99 | 94* |
| 23 | 99* | 100* | 100* | 98* | 99 | 0 | — | 0 | 0 | 91 | 99* | 93* |
| 24 | 96* | 99* | 99* | — | 96* | 0 | — | 0 | 0 | 0* | 83 | — |
| 25 | 91 | 96 | 78 | 96 | 77 | 37 | — | 76 | 0 | 0 | 63 | 0 |
| 26 | 0 | 73 | 0 | 26 | 0 | 0 | — | 0 | 0 | 60 | 6 | 0 |
| 27 | 96 | 99* | 94* | 96* | 93 | 0 | — | 0 | 0 | 0 | 76 | 0 |
| 28 | 54 | 88 | 0 | 86 | 0 | 0 | — | 28 | 0 | 0 | 25 | 0 |
| 29 | 78** | 98** | 82** | 96** | — | 0** | — | 67** | 0** | 0** | 27** | 0** |
| 30 | 83 | 98 | 73 | 90 | — | 0 | — | 0 | 0 | 0 | 74 | 0 |
| 31 | 0* | 0* | 0* | 69* | — | 0* | — | 0* | 0* | 0* | 20* | 0* |
| 32 | 41 | 80 | 0 | 88 | — | 0 | — | 0 | 0 | 0 | 34 | 0 |
| 34 | 97* | 100* | 97* | 100* | 98* | 0 | — | 90* | 0 | 0 | 78 | 0 |
| 35 | 76 | 76 | 0 | 100 | 0 | 0 | — | 0 | — | — | — | — |
| 36 | 93* | 99* | 99* | 97* | 26 | 0 | — | 78 | — | — | — | — |
| 37 | 99* | 100* | 100* | 100* | 99* | 0 | — | 0 | — | — | — | — |
| 38 | 98* | 99* | 100* | 100* | 96* | 0 | — | 82 | — | — | — | — |
| 39 | 99* | 100* | 99* | 100* | 91* | 0 | — | 0 | — | — | — | — |
| 40 | 99* | 100* | 99* | 100* | 13* | 0* | — | 50* | — | — | — | — |
| 41 | 99 | 100 | 100 | 98* | 99* | 0 | — | 0 | — | — | — | — |
| 42 | 98* | 100* | 100* | 100* | 100* | 0 | — | 0 | — | — | — | — |
| 43 | 91 | 99 | 95 | 93 | 94 | 0 | — | 0 | — | — | — | — |
| 45 | 99* | 100* | 100 | 99* | 26 | 0 | — | 0 | — | — | — | — |
| 46 | 94* | 99* | 99 | 91* | 94* | 0 | — | 0 | — | — | — | — |
| 47 | 98* | 100* | 100* | 99* | 94 | 0 | — | 66 | — | — | — | — |

TABLE A-continued

RESULTS OF BIOLOGICAL TESTS

Percentage Disease Control

| Cmpd No. | Test A | Test B | Test C | Test D | Test E | Test F | Test G | Test H | Test I | Test J | Test K | Test L |
|---|---|---|---|---|---|---|---|---|---|---|---|---|
| 48 | 65* | 100* | 99* | 99* | 94* | 0* | — | 99* | — | — | — | — |
| 49 | 79 | 100* | 99 | 100* | 99* | 0 | — | 99* | — | — | — | — |
| 50 | 100* | 99* | 100* | 100* | 97* | 0 | — | 55 | — | — | — | — |
| 51 | 97* | 99* | 98* | 100* | — | 0* | — | 60* | — | — | — | — |
| 52 | 100* | 100* | 100* | 100* | — | 99 | — | 92 | — | — | — | — |
| 53 | 98* | 99* | 94* | 99* | — | 0* | — | 92* | — | — | — | — |
| 54 | 99* | 100* | 99* | 99* | — | 0* | — | — | — | — | — | — |
| 55 | 88* | 88* | 92* | 95* | — | 0* | — | 16* | — | — | — | — |
| 56 | 89* | 97* | 97* | 90* | — | 0* | — | 92* | — | — | — | — |
| 57 | 97* | 100* | 87* | 100* | — | 0* | — | 96* | — | — | — | — |
| 58 | 98* | 100* | 100* | 99* | — | 0* | — | 89* | — | — | — | — |
| 59 | 98* | 100* | 99* | 97* | — | 0* | — | 87* | — | — | — | — |
| 60 | 98* | 99* | 99* | 99* | — | 0* | — | 24* | — | — | — | — |
| 61 | 84* | 100* | 99* | 99* | — | 0* | — | 0* | — | — | — | — |
| 62 | 99* | 99* | 100* | 100* | — | 0* | — | 0* | — | — | — | — |
| 63 | 97* | 100* | 99* | 100* | — | 0* | — | 98* | — | — | — | — |
| 64 | 99* | 100* | 99 | 93* | — | 16 | — | 62 | — | — | — | — |
| 65 | 99* | 99* | 99* | 100* | — | 0* | — | 8* | — | — | — | — |
| 66 | 99* | 100* | 100* | 100* | — | 0* | — | 96* | — | — | — | — |
| 67 | 96* | 99* | 99* | 100* | — | 0* | — | 96* | — | — | — | — |
| 68 | 97* | 100* | 99* | 100* | — | 0 | — | 86* | — | — | — | — |
| 69 | 97* | 92* | 98* | 98* | — | 0 | — | 32 | — | — | — | — |
| 70 | 99* | 99* | 100* | 100* | — | — | — | 96* | — | — | — | — |
| 71 | 99* | 100* | 100* | 100* | — | — | — | 84* | — | — | — | — |
| 72 | 99* | 99* | 100* | 100* | — | 97* | — | 94* | — | — | — | — |
| 73 | 74* | 98* | 96* | 98* | — | 95* | — | 14* | — | — | — | — |
| 74 | 100* | 100* | 100* | 100* | — | 51* | — | 99* | — | — | — | — |
| 75 | 72* | 93* | 40* | 91* | — | 20* | — | 61* | — | — | — | — |
| 76 | 99* | 100* | 99* | 100* | — | 0* | — | 0* | — | — | — | — |
| 77 | 99* | 100* | 100* | 100* | — | — | — | 96* | — | — | — | — |
| 78 | 100* | 85* | 0* | 90* | — | 33* | — | 0* | — | — | — | — |
| 79 | 99* | 99* | 100* | 99* | — | 0* | — | — | — | — | — | — |
| 80 | 98* | 98* | 100* | 100* | — | 60* | — | 29* | — | — | — | — |
| 81 | 85* | 99* | 100* | 99* | — | 81* | — | 97* | — | — | — | — |
| 82 | 60* | 0* | 86* | — | — | 0* | — | 7* | — | — | — | — |
| 83 | 19 | 0 | 0 | 89 | — | 0 | — | 0 | — | — | — | — |
| 84 | 98* | 80 | 92 | 99* | — | 67 | — | 54 | — | — | — | — |
| 85 | 100* | 97* | 99* | 99* | — | 0 | — | 86 | — | — | — | — |
| 86 | 99* | 100* | 100* | 98* | — | 0* | — | 9* | — | — | — | — |
| 87 | 82* | 100* | 97* | 99* | — | 0* | — | 9* | — | — | — | — |
| 88 | 95* | 97* | 100* | 100* | — | 0* | — | 0* | — | — | — | — |
| 89 | 100* | 100* | 100* | 100* | — | 0 | — | 89* | — | — | — | — |
| 90 | 0* | 90* | 0* | 80* | — | 0* | — | 0* | — | — | — | — |
| 91 | 0 | 85 | 64 | 97 | — | 0 | — | 33 | — | — | — | — |
| 92 | 82 | 97* | 92* | 72 | — | 0 | — | 15 | — | — | — | — |
| 93 | 93* | 98* | 100* | 96* | — | 0 | — | 15 | — | — | — | — |
| 94 | 0 | 17 | 0 | 40 | — | 0 | — | 0 | — | — | — | — |
| 95 | 100* | 100* | 100* | 100* | — | 90* | — | 25 | — | — | — | — |
| 96 | 100* | 100* | 100* | 100* | — | 0 | — | 59 | — | — | — | — |
| 97 | 98* | 100* | 100* | 100* | — | 0 | — | 85 | — | — | — | — |
| 98 | 91 | 98* | 90* | 98 | — | 0 | — | 0 | — | — | — | — |
| 99 | 82 | 74 | 0 | 92 | — | 98 | — | 0 | — | — | — | — |
| 100 | 0 | 0 | 0 | 40 | — | 0 | — | 0 | — | — | — | — |
| 101 | 98* | 99* | 100* | 95* | — | 0 | — | 0 | — | — | — | — |
| 102 | 98* | 98* | 96* | 98* | — | 0 | — | — | — | — | — | — |
| 103 | 99* | 98* | 87 | 99* | — | 0 | — | — | — | — | — | — |
| 104 | 100* | 100* | 100* | 100* | — | 0 | — | 40 | — | — | — | — |
| 105 | 51 | 100* | 100* | 99* | — | 0 | — | 90* | — | — | — | — |
| 106 | 98* | 100* | 100* | 100* | — | 0 | — | 92* | — | — | — | — |
| 107 | 100* | 100* | 100* | 99* | — | 89 | — | 99* | — | — | — | — |
| 108 | 0 | 86 | 95 | 98* | — | 0 | — | 28 | — | — | — | — |
| 109 | 98* | 100* | 100* | 99* | — | 92* | — | 100* | — | — | — | — |
| 110 | 100* | 100* | 100* | 97* | — | 96* | — | 85 | — | — | — | — |
| 111 | 99* | 100* | 100* | 100* | — | 95 | — | 90* | — | — | — | — |
| 112 | 88 | 99* | 100* | 100* | — | 0 | — | 93 | — | — | — | — |
| 113 | 92 | 99 | 100 | 100 | — | 24 | — | 0 | — | — | — | — |
| 114 | 93 | 99 | 100 | 100 | — | 0 | — | 0 | — | — | — | — |
| 115 | 98 | 99 | 100 | 100 | — | 32 | — | 96 | — | — | — | — |
| 116 | 99 | 100 | 100 | 96 | — | 0 | — | 99 | — | — | — | — |
| 117 | 98 | 99 | 100 | 100 | — | 94 | — | 95 | — | — | — | — |
| 118 | 100 | 100 | 100 | 100 | — | 40 | — | 99 | — | — | — | — |
| 119 | 100* | 100* | 100* | 100* | — | 51 | — | 57 | — | — | — | — |
| 120 | 98* | 79 | 0 | 94* | — | 0 | — | 0 | — | — | — | — |

TABLE A-continued

RESULTS OF BIOLOGICAL TESTS

Percentage Disease Control

| Cmpd No. | Test A | Test B | Test C | Test D | Test E | Test F | Test G | Test H | Test I | Test J | Test K | Test L |
|---|---|---|---|---|---|---|---|---|---|---|---|---|
| 121 | 98* | 98* | 100* | 99* | — | 0 | — | 90* | — | — | — | — |
| 122 | 100* | 100* | 100* | 100* | — | 63 | — | 97* | — | — | — | — |
| 123 | 98* | 99* | 100* | 99* | — | 63 | — | 87 | — | — | — | — |
| 124 | 100* | 100* | 100* | 100* | — | 0 | — | 99* | — | — | — | — |
| 126 | 95 | 98* | 99 | 97* | 0 | 0 | — | 0 | — | — | — | — |
| 127 | 0 | 9 | 0 | 53 | — | 0 | — | 0 | — | — | — | — |
| 128 | 29 | 98 | 82 | 96* | — | 0 | — | 0 | — | — | — | — |
| 129 | 94 | 98 | 90 | 92* | — | 0 | — | 0 | — | — | — | — |
| 130 | 80 | 67 | 92 | 96 | — | 0 | — | 0 | — | — | — | — |
| 131 | 0 | 0 | 0 | 13 | — | 0 | — | 0 | — | — | — | — |
| 132 | 80 | 95* | 98* | 100* | — | 0 | — | 0 | — | — | — | — |
| 133 | 94 | 93 | 93 | 92* | — | 0 | — | 0 | — | — | — | — |
| 134 | 0 | 84 | 96* | 87 | — | 0 | — | 0 | — | — | — | — |
| 137 | 95 | 99 | 90* | 97* | — | 0 | — | 15 | — | — | — | — |
| 138 | 56 | 48 | 92 | 77 | — | 0 | — | 0 | — | — | — | — |
| 139 | 87 | 100* | 99* | 92* | — | 0 | — | 26 | — | — | — | — |
| 140 | 0 | 32 | 0 | 96 | — | 0 | — | 0 | — | — | — | — |
| 141 | 96 | 89 | 82 | 98 | — | 0 | — | 0 | — | — | — | — |
| 142 | 85 | 55 | 0 | 92 | — | 0 | — | 16 | — | — | — | — |
| 143 | 93 | 19 | 0 | 93 | — | 0 | — | 0 | — | — | — | — |
| 144 | 97 | 19 | 0 | 95 | — | 0 | — | 0 | — | — | — | — |
| 145 | 0 | 0 | 0 | 30 | — | 0 | — | 15 | — | — | — | — |
| 146 | 52 | 93 | 99 | 93 | — | 0 | — | 22 | — | — | — | — |
| 147 | 100* | 99* | 99* | 100* | — | 61 | — | 15 | — | — | — | — |
| 148 | 85 | 90* | 90 | 98* | — | 46 | — | 0 | — | — | — | — |
| 149 | 0 | 99 | 100 | 99 | — | 0 | — | 0 | — | — | — | — |
| 150 | 71 | 98 | 100 | 99 | — | 0 | — | 92 | — | — | — | — |

What is claimed is:
1. A compound selected from Formula 1, N-oxides and salts thereof,

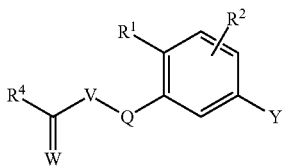

wherein
each $R^1$ and $R^2$ is independently H, halogen, CN, $C_1$-$C_3$ alkyl, $C_1$-$C_3$ alkoxy, $C_1$-$C_3$ haloalkyl, $C_1$-$C_3$ haloalkoxy, $C_3$-$C_6$ cycloalkyl, $C_3$-$C_{15}$ trialkylsilyl or $C_3$-$C_{15}$ halotrialkylsilyl;
V is a direct bond or $NR^3$;
$R^3$ is H, $C_1$-$C_3$ alkyl, $C_3$-$C_6$ cycloalkyl, $C_1$-$C_3$ haloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;
$R^4$ is H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_3$-$C_6$ cycloalkoxy, $C_1$-$C_6$ alkylamino, $C_1$-$C_6$ haloalkylamino, $C_2$-$C_8$ dialkylamino, $C_2$-$C_8$ halodialkylamino or $C_3$-$C_6$ cycloalkylamino;
W is O or S;
Q is $CR^{6a}R^{6b}$ or $NR^7$;
Y is $-C(R^5)=N-O-(CR^{8a}R^{8b})_p-X-(CR^{9a}R^{9b})_q-SiR^{10a}R^{10b}R^{10c}$;
$R^5$ is H, CN, $C_1$-$C_6$ alkyl, $C_3$-$C_6$ cycloalkyl, $C_1$-$C_6$ haloalkyl, $C_3$-$C_6$ halocycloalkyl, $C_3$-$C_{15}$ trialkylsilyl or $C_3$-$C_{15}$ halotrialkylsilyl;

$R^{6a}$ is H, OH, halogen, CN, $C_1$-$C_6$ alkyl, $C_1$-$C_6$ haloalkyl, $C_2$-$C_6$ alkoxyalkyl, $C_1$-$C_6$ alkoxy, $C_1$-$C_6$ haloalkoxy or $C_1$-$C_6$ alkylsulfonyl;
$R^{6b}$ is H, $C_1$-$C_6$ alkyl, $C_1$-$C_6$ haloalkyl, $C_2$-$C_6$ alkoxyalkyl, $C_1$-$C_6$ alkoxy or $C_1$-$C_6$ haloalkoxy; or
$R^{6a}$ and $R^{6b}$ are taken together with the carbon atom to which they are attached to form a $C_3$-$C_6$ cycloalkyl ring or $C_3$-$C_6$ halocycloalkyl ring;
$R^7$ is H, $C_1$-$C_3$ alkyl, $C_1$-$C_3$ haloalkyl, $C_2$-$C_3$ alkylcarbonyl or $C_2$-$C_3$ haloalkylcarbonyl;
each $R^{8a}$ and $R^{9a}$ is independently H, OH, CN, halogen, $C_1$-$C_5$ alkyl, $C_1$-$C_5$ haloalkyl or $C_1$-$C_5$ alkoxy;
each $R^{8b}$ and $R^{9b}$ is independently H, CN, halogen, $C_1$-$C_5$ alkyl, $C_1$-$C_5$ haloalkyl or $C_1$-$C_5$ alkoxy; or
each pair of $R^{8a}$ and $R^{8b}$ or $R^{9a}$ and $R^{9b}$ attached to the same carbon atom can be independently taken together with the carbon atom to which they are attached to form a $C_3$-$C_6$ cycloalkyl or $C_3$-$C_6$ halocycloalkyl ring; or
each $R^{8a}$, $R^{8b}$, $R^{9a}$ or $R^{9b}$ can be independently taken together with a $R^{8a}$, $R^{8b}$, $R^{9a}$ or $R^{9b}$ attached to an adjacent carbon atom and the carbon atoms to which they are attached to form a $C_3$-$C_6$ cycloalkyl or $C_3$-$C_6$ halocycloalkyl ring;
each $R^{10a}$, $R^{10b}$ and $R^{10c}$ is independently $C_1$-$C_6$ alkyl, $C_1$-$C_6$ haloalkyl, $C_1$-$C_6$ alkoxy, $C_1$-$C_6$ haloalkoxy, $C_2$-$C_8$ alkoxyalkyl, $C_2$-$C_8$ haloalkoxyalkyl, $C_2$-$C_6$ alkenyl, $C_2$-$C_6$ alkynyl, $C_3$-$C_6$ cycloalkyl, $C_3$-$C_6$ halocycloalkyl, $C_4$-$C_7$ alkylcycloalkyl, $C_5$-$C_{10}$ alkylcycloalkylalkyl, $C_2$-$C_6$ haloalkenyl, $C_1$-$C_6$ alkylthio, $C_2$-$C_6$ alkylcarbonyl, $C_2$-$C_6$ alkoxycarbonyl, $C_4$-$C_{12}$ trialkylsilylalkyl or J;
each J is independently a phenyl ring; a 5- or 6-membered heteroaromatic ring; or an 8-, 9- or 10-membered fused bicyclic ring system, or 3- to 6-membered nonaromatic carbocyclic or heterocyclic ring, said ring or ring system optionally including ring members selected from the group consisting of C(=O), C(=S), C(=NR$^{11}$), NR$^{11}$, SiR$^{12a}$R$^{12b}$ and S(=O)$_u$(=NR$^{11}$)$_z$, and each ring or ring system optionally substituted with up to 5 substituents independently selected from R$^{13}$; or two of R$^{10a}$, R$^{10b}$ or R$^{10c}$ are taken together with the silicon atom to which they are attached to form a saturated ring containing from 3 to 6 carbon atoms in addition to the silicon atom as ring members, the ring optionally substituted on carbon atoms with halogen;

X is a direct bond, O, NR$^{11}$, C(=O), C(=S) or C(=NR$^{11}$); or a phenyl ring, a 5- or 6-membered heteroaromatic ring or a 3- to 8-membered nonaromatic carbocyclic or heterocyclic ring, said ring optionally including ring members selected from the group consisting of C(=O), C(=S), C(=NR$^{11}$), NR$^{11}$, SiR$^{12a}$R$^{12b}$ and S(=O)$_u$(=NR$^{11}$)$_z$, and optionally substituted with up to 5 substituents independently selected from R$^{13}$;

each R$^{11}$ is independently H, CN, NH$_2$, OH, C$_1$-C$_6$ alkyl, C$_3$-C$_8$ cycloalkyl, C$_2$-C$_6$ alkylcarbonyl, C$_2$-C$_6$ haloalkylcarbonyl or C$_1$-C$_6$ alkoxy;

each R$^{12a}$ and R$^{12b}$ is independently C$_1$-C$_5$ alkyl, C$_2$-C$_5$ alkenyl, C$_2$-C$_5$ alkynyl, C$_3$-C$_8$ cycloalkyl, C$_3$-C$_6$ halocycloalkyl, C$_4$-C$_{10}$ cycloalkylalkyl, C$_4$-C$_7$ alkylcycloalkyl, C$_5$-C$_8$ alkylcycloalkylalkyl, C$_1$-C$_5$ haloalkyl, C$_1$-C$_5$ alkoxy or C$_1$-C$_5$ haloalkoxy;

each R$^{13}$ is independently halogen, C$_1$-C$_6$ alkyl, C$_2$-C$_6$ alkenyl, C$_2$-C$_6$ alkynyl, C$_3$-C$_6$ cycloalkyl, C$_3$-C$_6$ halocycloalkyl, C$_4$-C$_7$ alkylcycloalkyl, C$_1$-C$_6$ haloalkyl, C$_2$-C$_6$ haloalkenyl, cyano, nitro, C$_1$-C$_6$ alkoxy, C$_1$-C$_6$ haloalkoxy, C$_1$-C$_6$ alkylthio, C$_1$-C$_6$ alkylsulfinyl, C$_1$-C$_6$ alkylsulfonyl, C$_1$-C$_6$ haloalkylthio, C$_1$-C$_6$ haloalkylsulfinyl, C$_1$-C$_6$ haloalkylsulfonyl, C$_1$-C$_6$ alkylamino, C$_2$-C$_6$ dialkylamino, C$_2$-C$_6$ alkylcarbonyl, C$_2$-C$_6$ alkoxycarbonyl, C$_2$-C$_6$ alkylaminocarbonyl, C$_3$-C$_6$ dialkylaminocarbonyl, C$_3$-C$_{15}$ trialkylsilyl or C$_3$-C$_{15}$ halotrialkylsilyl;

p and q are independently an integer from 0 to 5; provided that when p is 0, then X is other than O or NR$^{11}$; and u and z in each instance of S(=O)$_u$(=NR$^{11}$)$_z$ are independently 0, 1 or 2, provided that the sum of u and z in each instance of S(=O)$_u$(=NR$^{11}$)$_z$ is 0, 1 or 2.

2. A compound of claim 1 wherein:
R$^1$ is halogen, CN, C$_1$-C$_2$ alkyl, C$_1$-C$_2$ alkoxy, C$_1$-C$_2$ haloalkyl, or C$_1$-C$_2$ haloalkoxy;
R$^2$ is H, halogen, CN, methyl or trifluoromethyl;
V is NR$^3$;
R$^3$ is H, C$_1$-C$_2$ alkyl, C$_1$-C$_2$ haloalkyl, C$_2$-C$_3$ alkylcarbonyl or C$_2$-C$_3$ haloalkylcarbonyl;
R$^4$ is C$_1$-C$_2$ alkoxy, C$_1$-C$_2$ haloalkoxy, C$_1$-C$_2$ alkylamino or C$_2$-C$_4$ dialkylamino;
W is O; and
R$^5$ is C$_1$-C$_3$ alkyl or C$_1$-C$_3$ haloalkyl.

3. A compound of claim 2 wherein:
R$^1$ is F, Cl, Br, CN, methyl or C$_1$ haloalkyl;
R$^2$ is H, F or Cl;
R$^3$ is H, C$_1$-C$_2$ alkyl or C$_1$-C$_2$ haloalkyl;
R$^4$ is C$_1$-C$_2$ alkoxy or C$_1$-C$_2$ haloalkoxy;
R$^5$ is C$_1$-C$_3$ alkyl;
p is 0; and
X is direct bond.

4. A compound of claim 1 which is selected from the group consisting of:
methyl N-[[2-chloro-5-[1-[[2-(trimethylsilyl)ethoxy]imino]ethyl]phenyl]-methyl]carbamate;
methyl N-[[2-chloro-5-[1-[[2-(trimethylsilyl)propoxy]imino]ethyl]phenyl]-methyl]carbamate;
methyl N-[[2-chloro-5-[1-[[(trimethylsilyl)methoxy]imino]ethyl]phenyl]-methyl]carbamate; and
methyl N-[[2-chloro-5-[1-[[(ethyldimethylsilyl)methoxy]imino]ethyl]phenyl]-methyl]carbamate.

5. A fungicidal composition comprising (a) a compound of claim 1; and (b) at least one fungicide.

6. A fungicidal composition comprising (1) a fungicidally effective amount of a compound of claim 1; and (2) at least one additional component selected from the group consisting of surfactants, solid diluents and liquid diluents.

7. A method for controlling plant diseases caused by fungal plant pathogens comprising applying to the plant or portion thereof, or to the plant seed, a fungicidally effective amount of a compound of claim 1.

8. The fungicidal composition of claim 5 wherein component (b) comprises at least one compound selected from the group consisting of acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, captafol, captan, carbendazim, carboxin, carpropamid, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dichloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, guazatine, hexaconazole, hymexazol, imazalil, imibenconazole, iminoctadine albesilate, iminoctadine triacetate, iodocarb, ipconazole, iprobenfos, iprodione, iprovalicarb, isoprothiolane, isotianil, kasugamycin, kresoxim-methyl, mancozeb, mandipropamid, maneb, mepanipyrim, mepronil, meptyldinocap, metalaxyl, metalaxyl-M, metconazole, methasulfocarb, metiram, metominostrobin, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, pefurazoate, penconazole, pencycuron, penthiopyrad, phosphorous acid and salts, phthalide, picobenzamid, picoxystrobin, piperalin, polyoxin, probenazole, prochloraz, procymidone, propamocarb, propamocarb-hydrochloride, propiconazole, propineb, proquinazid, prothiocarb, prothioconazole, pryazophos, pyraclostrobin, pyribencarb, pyributicarb, pyrifenox, pyrimethanil, pyrrolnitrin, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolyfluanid, triadimefon, triadimenol, triazoxide, tricyclazole, tridemorph, trifloxystrobin, triflumizole, triforine, triticonazole, uniconazole, validamycin, valiphenal, vinclozolin, zineb, ziram, zoxamide, N-[2-(1,3-dimethylbutyl)phenyl]-5-fluoro-1,3-dimethyl-1H-pyrazol-4-carboxamide, N-[2-(1S,2R)-[1,1'-bicyclopropyl]-2-ylphenyl]-3-(difluoromethyl)-1-methyl-1H-pyrazole-4-carboxamide, α-[methoxyimino]-N-methyl-2-[[[1-[3-(trifluoromethyl)-phenyl]-ethoxy]imino]methyl]benzeneacetamide, 2-[[[3-(2,6-dichlorophenyl)-1-methyl-2-propen-1-ylidene]amino]oxy]methyl]-α-(methoxyimino)-N-methylbenzeneacetamide, N-[2-[4-[[3-(4-chlorophenyl)-2-propyn-1-yl]oxy]-3-methoxy phenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]-methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3 difluorophenyl]methylene]benzeneacetamide, N'-[4-[4-chloro-3-(trifluoromethyl)phenoxy]-2,5-dimethylphenyl]-N-ethyl-N-methylmethanimidamide, and 1-[(2-propenylthio)carbonyl]-2-(1-methylethyl)-4-(2-methylphenyl)-5-amino-1H-pyrazol-3-one.

9. The fungicidal composition of claim 5 wherein component (b) comprises at least one compound selected from the group consisting of azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, uniconazole, clotrimazole, imazalil, oxpoconazole, prochloraz, pefurazoate, triflumizole, fenarimol, nuarimol, triforine and pyrifenox.

10. The fungicidal composition of claim 5 wherein component (b) comprises at least one compound selected from the group consisting of benodanil, flutolanil, mepronil, fenfuram, carboxin, oxycarboxin, thifluzamide, furametpyr, penthiopyrad, bixafen, N-[2-(1S,2R)-[1,1'-bicyclopropyl]-2-ylphenyl]-3-(difluoromethyl)-1-methyl-1H-pyrazole-4-carboxamide, N-[2-(1,3-dimethylbutyl)phenyl]-5-fluoro-1,3-dimethyl-1H-pyrazole-4-carboxamide and boscalid.

11. The fungicidal composition of claim 5 wherein component (b) comprises at least one compound selected from the group consisting of azoxystrobin, enestroburin, picoxystrobin, pyraclostrobin, kresoxim-methyl, trifloxystrobin, dimoxystrobin, metominostrobin, orysastrobin, α-[methoxyimino]-N-methyl-2-[[[1-[3-(trifluoromethyl)phenyl]-ethoxy]imino]methyl]benzeneacetamide, 2-[[[3-(2,6-dichlorophenyl)-1-methyl-2-propen-1-ylidene]amino]oxy]methyl]-α-(methoxyimino)-N-methylbenzeneacetamide, famoxadone, fluoxastrobin, fenamidone and pyribencarb.

12. The fungicidal composition of claim 5 wherein component (b) comprises at least one compound selected from the group consisting of copper oxychloride, copper sulfate, copper hydroxide, Bordeaux mixture, elemental sulfur, mancozeb, metiram, propineb, ferbam, maneb, thiram, zineb, ziram, folpet, captan, captafol, chlorothalonil, dichlofluanid, tolyfluanid, dodine, guazatine, iminoctadine albesilate, iminoctadine triacetate, anilazine and dithianon.

* * * * *